(12) United States Patent
Kaiser et al.

(10) Patent No.: US 8,633,134 B2
(45) Date of Patent: Jan. 21, 2014

(54) SUBSTITUTED AMIDINE COMPOUNDS FOR COMBATING ANIMAL PESTS

(75) Inventors: Florian Kaiser, Mannheim (DE); Karsten Koerber, Eppelheim (DE); Matthias Pohlman, Freinsheim (DE); Steffen Gross, Ludwigshafen (DE); Prashant Deshmukh, Mannheim (DE); Joachim Dickhaut, Heidelberg (DE); Nina Gertrud Bandur, Mannheim (DE); Wolfgang von Deyn, Neustadt (DE); Deborah L. Culbertson, Fuquay Varina, NC (US); Douglas D. Anspaugh, Apex, NC (US); Franz-Josef Braun, Durham, NC (US); Cecille Ebuenga, Los Banos (PH)

(73) Assignee: BASF SE, Ludwigshafen (DE)

( * ) Notice: Subject to any disclaimer, the term of this patent is extended or adjusted under 35 U.S.C. 154(b) by 48 days.

(21) Appl. No.: 13/141,264

(22) PCT Filed: Dec. 14, 2009

(86) PCT No.: PCT/EP2009/067037
§ 371 (c)(1),
(2), (4) Date: Jun. 21, 2011

(87) PCT Pub. No.: WO2010/072602
PCT Pub. Date: Jul. 1, 2010

(65) Prior Publication Data
US 2011/0257011 A1    Oct. 20, 2011

Related U.S. Application Data

(60) Provisional application No. 61/140,363, filed on Dec. 23, 2008.

(51) Int. Cl.
| | | |
|---|---|---|
| *A01N 43/836* | (2006.01) | |
| *A01N 43/40* | (2006.01) | |
| *A01N 43/80* | (2006.01) | |
| *A61P 33/00* | (2006.01) | |
| *A61K 31/4245* | (2006.01) | |
| *A61K 31/4439* | (2006.01) | |
| *A61K 31/42* | (2006.01) | |
| *A61K 31/444* | (2006.01) | |
| *C07D 261/04* | (2006.01) | |
| *C07D 413/04* | (2006.01) | |
| *C07D 413/10* | (2006.01) | |
| *C07D 413/14* | (2006.01) | |

(52) U.S. Cl.
USPC ........... 504/100; 514/333; 514/340; 514/364; 514/378; 546/256; 546/272.1; 548/131; 548/240

(58) Field of Classification Search
None
See application file for complete search history.

(56) References Cited

U.S. PATENT DOCUMENTS

| | | |
|---|---|---|
| 3,917,698 A | 11/1975 | Breslow |
| 6,313,344 B1 | 11/2001 | Trah et al. |
| 6,521,643 B1 | 2/2003 | Tomishima et al. |
| 2003/0119806 A1 | 6/2003 | Lindell et al. |
| 2004/0014801 A1 | 1/2004 | Cohen et al. |
| 2004/0110637 A1 | 6/2004 | Ziemer et al. |
| 2007/0066617 A1 | 3/2007 | Mita et al. |
| 2008/0262057 A1 | 10/2008 | Tisdell et al. |
| 2009/0023923 A1 | 1/2009 | Mizukoshi et al. |
| 2009/0156643 A1 | 6/2009 | Mita et al. |
| 2010/0144797 A1 | 6/2010 | Mita et al. |
| 2010/0144808 A1 | 6/2010 | Mita et al. |
| 2010/0160683 A1 | 6/2010 | Matoba et al. |
| 2010/0286175 A1 | 11/2010 | Grammenos et al. |
| 2011/0172414 A1 | 7/2011 | Mita et al. |

FOREIGN PATENT DOCUMENTS

| | | |
|---|---|---|
| CA | 2 547 744 | 12/2006 |
| CH | 577487 | 7/1976 |
| CH | 595365 | 2/1978 |
| CH | 608011 | 12/1978 |

(Continued)

OTHER PUBLICATIONS

Belen'Kii et al, Database: Beilstein, XP002580907 database accession No. 1988095, Russian Chem. Bull., (1997), pp. 101-104, vol. 46, No. 1.

(Continued)

*Primary Examiner* — Joseph McKane
*Assistant Examiner* — Alicia L Otton
(74) *Attorney, Agent, or Firm* — Brinks Gilson & Lione

(57) ABSTRACT

The invention relates to substituted amidine compounds of formula (I), to the enantiomers, diastereomers and salts thereof and to compositions comprising such compounds. The invention also relates to the use of the substituted amidine compounds, of their salts or of compositions comprising them for combating animal pests. Furthermore the invention relates also to methods of applying such substituted amidine compounds.
The substituted amidine compounds of the present invention are defined by the following formula I:

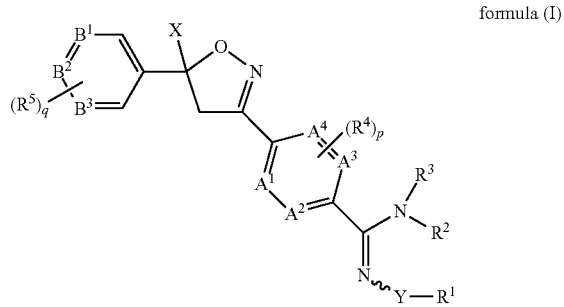

formula (I)

wherein $A^1$ to $A^4$, $B^1$ to $B^3$, $R^1$ to $R^3$, $(R^4)_p$, $(R^5)_q$, X and Y are defined as in the description.

26 Claims, No Drawings

(56) References Cited

FOREIGN PATENT DOCUMENTS

| | | |
|---|---|---|
| CN | 1 927 860 | 3/2007 |
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1 932 836 | 6/2008 |
| EP | 1 997 813 | 12/2008 |
| EP | 2 151 437 | 2/2010 |
| EP | 2 186 804 | 5/2010 |
| EP | 2199287 | 6/2010 |
| JP | 2007-016017 | 1/2007 |
| JP | 2007-106756 | 4/2007 |
| JP | 2007 308471 | 11/2007 |
| JP | 2008-239611 | 10/2008 |
| JP | 2009 108046 | 5/2009 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/060371 | 7/2004 |
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO 2007/079162 | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 2008/154528 | 12/2008 |
| WO | WO 2009/002809 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/077197 | 6/2009 |
| WO | WO 2009/112275 | 9/2009 |
| WO | WO 2009/126668 | 10/2009 |
| WO | WO 2010/003877 | 1/2010 |
| WO | WO 2010/003923 | 1/2010 |
| WO | WO 2010/020521 | 2/2010 |
| WO | WO 2010/020522 | 2/2010 |
| WO | WO 2010/072781 | 7/2010 |
| WO | WO 2010/112545 | 10/2010 |
| WO | WO 2011/073444 | 6/2011 |

OTHER PUBLICATIONS

Wierenga, J. et al., "Insecticidal activity of N-arylalkylbenzhydrolpiperidines", Pest Management Science, (2002), pp. 1266-1272, vol. 58.

International Search Report prepared in International Application No. PCT/EP2009/067037, filed Dec. 14, 2009.

International Preliminary Report on Patentability from corresponding International Application No. PCT/EP2009/067037, filed Dec. 14, 2009.

"DMP 754 Roxifiban Acetate", Drugs of the Future, (1998), pp. 707-711, vol. 23(7).

Hosking, M., et al., "Roxifiban DuPont", Current Opinion in Cardiovascular, Pulmonary & Renal Investigational Drugs, (2000), pp. 165-171, vol. 2(2).

Kaugars, G. et al., "Miticidal activity of benzoyl chloride phenylhydrazones", Journal of Agriculture and Food Chem., (1973), pp. 647-650, vol. 21, No. 4.

Kiriyama, K. et al., "Insecticidal and Neuroblocking Activities of Acetamiprid and Related Compounds", Journal of Pesticide Science, (2003), pp. 8-17, vol. 28.

Office Action dated Jun. 6, 2013, from U.S. Appl. No. 13/140,989.

Walters, Matthew J. et al., "The preparation of 5-Aryl-5-methyl-4,5-dihydroisoxazoles from dilithiated $C(\alpha)$, $O$-oximes and Select Acetyl Ketones", Synthetic Communications, 2003, p. 4163-4171, vol. 33, No. 23.

Office Action dated Dec. 5, 2012, from U.S. Appl. No. 13/003,037.

Office Action dated Oct. 24, 2012, from U.S. Appl. No. 13/003,032.

SUBSTITUTED AMIDINE COMPOUNDS FOR COMBATING ANIMAL PESTS

This application is a National Stage application of International Application No. PCT/EP2009/067037, filed Dec. 14, 2009, which claims the benefit of U.S. Provisional Application No. 61/140,363 filed Dec. 23, 2008, the entire contents of which are hereby incorporated herein by reference.

The present invention relates to substituted amidine compounds, to the enantiomers, diastereomers and salts thereof and to compositions comprising such compounds. The invention also relates to the use of the substituted amidine compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by substituted amidine derivatives of the general formula I:

Substituted amidine compounds of the general formula (I)

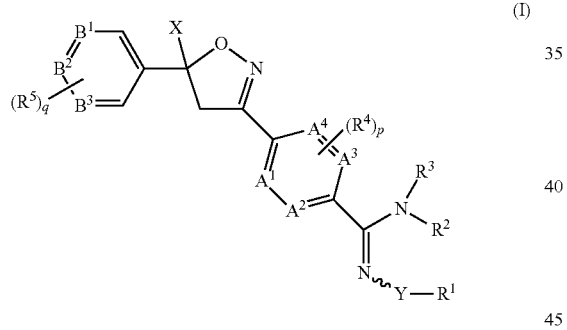

wherein
$A^1, A^2, A^3$ and $A^4$ are N or C, wherein the carbon atom my optionally be substituted with $R^4$, and with the proviso that no more than two nitrogen are present in the ring
$B^1, B^2, B^3$ are N or C, wherein the carbon atom my optionally be substituted with $R^5$, and with the proviso that no more than two nitrogen are present in the ring
X is selected from the group consisting of $C_1$-$C_4$ alkyl, $C_1$-$C_4$ haloalkyl, $C_1$-$C_4$ alkoxyalky, $C_1$-$C_4$ haloalkoxyalkyl, $C_2$-$C_4$ alkenyl, $C_2$-$C_4$ haloalkenyl, $C_2$-$C_4$ alkinyl, $C_2$-$C_4$ haloalkinyl, $C_3$-$C_6$ cycloalkyl, $C_3$-$C_8$ halocycloalkyl;
Y is O, N—$R^8$ or a chemical bond
p is 0, 1, 2, 3 or 4
q is 0, 1, 2, 3, 4 or 5
$R^1$ is selected from the group consisting of hydrogen, cyano, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $S(O)_nR^7$, $S(O)_nNR^{9a}R^{9b}$, $C(=O)R^6$, $C(=O)NR^{9a}R^{9b}$, $C(=O)OR^7$, $C(=S)R^6$, $C(=S)NR^{9a}R^{9b}$, $C(=S)OR^7$, $C(=S)SR^7$, phenyl, optionally substituted with one or more substituents $R^{10}$, which are independently selected from one another, a 3-, 4-, 5-, 6- or 7-membered saturated, partly saturated or unsaturated aromatic heterocyclic ring, comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or $R^1$ may be together with $R^2$ a $CH_2CH_2$ or $CH_2$ bridge, forming a 5-membered or 6-membered heterocyclic ring together with the substituted amidine unit they are bond to;

$R^2$, $R^3$ are selected independent of each other from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^8$, which are independently selected from one another, $NR^{9a}R^{9b}$, $Si(R^{11})_2R^{12}$, $OR^7$, $S(O)_nR^7$, $C(=O)R^6$, $C(=O)NR^{9a}R^{9b}$, $C(=O)OR^7$, $C(=S)R^6$, $C(=S)NR^{9a}R^{9b}$, $C(=S)SR^7$, $C(=NR^{9a})R^6$;

phenyl, optionally substituted with one or more substituents from $R^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

with the proviso that $R^2$ and $R^3$ are not both hydrogen at the same time;

or $R^2$ and $R^3$ together may be $=CR^{13}R^{14}$; $=S(O)_nR^7$; $=S(O)_nNR^{9a}R^{9b}$, $=NR^{9a}$ or $=NOR^7$;

or $R^2$ and $R^3$ may be together a $C_2$-$C_7$ alkylene chain, forming a 3- to 8-membered saturated, partly saturated or unsaturated aromatic heterocyclic ring together with the nitrogen atom they are bond to, wherein the alkylene chain may further contain 1 or 2 oxygen atoms, sulfur atoms or nitrogen atoms, and
wherein the alkylene chain may optionally be substituted with halogen, $C_1$-$C_8$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^4$ is selected independently from p from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $OR^7$, —$OS(O)_nR^7$, $S(O)_nR^7$, $NR^{9a}R^{9b}$, $N(R^{9a})C(=O)R^6$, $C(=O)R^6$, —$C(=O)OR^7$, $C(=NR^{9a})R^6$, $C(=S)R^6$, phenyl, optionally substituted with one or more substituents independently selected from $R^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or, when p is 2 or more and two of $R^4$ are adjacent, the two adjacent $R^4$ may be a bridge selected from the group consisting of $CH_2CH_2CH_2CH_2$, $CH=CH$—$CH=CH$, $N=CH$—$CH=CH$, $CH=N$—$CH=CH$, $N=CH$—$N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{9a}$, $CH_2CH=N$, $OCH=N$, $SCH=N$, $CH=CH$—$NR^{9a}$; which bridge may form together with carbon atoms to which the two adjacent $R^4$ are bonded to a 5-membered or 6-membered partly saturated or unsaturated aromatic carbocyclic or heterocyclic ring, wherein the carbon atoms of the bridge may optionally be substituted with one or two substituents selected from the group consisting of =O, OH, $CH_3$, $OCH_3$, halogen, halomethyl or halomethoxy;

$R^5$ is selected independently from q from the group consisting of hydrogen, halogen, cyano, azido, nitro, SCN, $SF_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $Si(R^{12})_2R^{13}$, $OR^7$, —$OS(O)_nR^7$, $S(O)_nR^7$, $NR^{9a}R^{9b}$, $N(=R^{9a})C(=O)R^6$, $C(=O)R^6$, $C(=O)OR^7$, $C(=NR^{9a})R^6$, $C(=S)R^6$, phenyl, optionally substituted with one or more substituents $R^{10}$; which are independently selected from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^6$ is selected from the group consisting of hydrogen, halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $Si(R^{12})_2R^{13}$, $OR^{16}$, $OSO_2R^{16}$, $S(O)_nR^{16}$, $S(O)_nNR^{17a}R^{17b}_2$, $NR^{17a}R^{17b}$, $C(=O)NR^{17a}R^{17b}$, $C(=S)NR^{17a}R^{17b}$, $C(=O)OR^{16}$, phenyl, optionally substituted with one or more substituents $R^{18}$, which are independently selected from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized, or two $R^6$ present on one carbon atom may together form =O, =$CR^{13}R^{14}$; =$S(O)_nR^{16}$; =$S(O)_nNR^{17a}R^{17b}$, =$NR^{17a}$, =$NOR^{16}$; =$NNR^{17a}$; or two $R^6$ may form a 3-, 4-, 5-, 6-, 7- or 8-membered saturated or partly unsaturated carbocyclic or heterocyclic ring together with the carbon atoms to which the two $R^6$ are bonded to;

$R^7$ is, independent from each other, selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, —$Si(R^{11})_2R^{12}$, $S(O)_nR^{16}$, —$S(O)_nNR^{17a}R^{17b}$, $NR^{17a}R^{17b}$, —$N=CR^{13}R^{14}$, —$C(=O)R^{16}$, $C(=O)NR^{17a}R^{17b}$, $C(=S)NR^{17a}R^{17b}$, —$C(=O)OR^{16}$, phenyl, optionally substituted with one or more substituents $R^{18}$; which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^8$ is selected from the group consisting of hydrogen, cyano, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another, $NR^{17a}R^{17b}$, $Si(R^{11})_2R^{12}$, $OR^{16}$, $S(O)_nR^{16}$, $S(O)_nNR^{17a}R^{17b}$, $C(=O)R^{15}$, —$C(=O)OR^{16}$, $C(=O)NR^{17a}R^{17b}$, $C(=S)R^{15}$, $C(=S)SR^{16}$, $C(=S)NR^{17a}R^{17b}$; $C(=NR^{17a})R^{15}$;

phenyl, optionally substituted with one or more substituents $R^{18}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, independently selected from one another, and wherein the nitrogen and/or the sulfur atom(s) of the heterocyclic ring may optionally be oxidized;

$R^8$ and $R^1$ may be together a $C_2$-$C_7$ alkylene chain, forming a 3-, 4-, 5-, 6-, 7- or 8-membered saturated, partly saturated or unsaturated aromatic heterocyclic ring together with the nitrogen atom they are bond to, wherein the alkylene chain may further contain 1 or 2 oxygen atoms, sulfur atoms or nitrogen atoms, and wherein the alkylene chain may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^{9a}$, $R^{9b}$ are selected independent from one another from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $S(O)_nR^{16}$, —$S(O)_nNR^{17a}R^{17b}$, $C(=O)R^{15}$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17a})R^{15}$;

phenyl, optionally substituted with one or more substituents $R^{18}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteratoms selected from oxygen, sulfur or nitrogen, and may optionally be substituted with halogen, $C_1$-$C_8$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally substituted with one or more substituents $R^{18}$; which are selected independently from one another, a 3-, 4-, 5-, 6,- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^{10}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another, $Si(R^{11})_2R^{12}$, $OR^{16}$, $OS(O)_nR^{16}$, —$S(O)_nR^{16}$, $S(O)_nNR^{17a}R^{17b}$, $NR^{17a}R^{17b}$, $C(=O)R^{15}$, $C(=O)OR^{16}$, —$C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents selected independently from one another from halogen, cyano, $NO_2$, $C_1$-$C_6$-alkyl, $C_1$-$C_6$-haloalkyl, $C_1$-$C_6$-alkoxy or $C_1$-$C_6$-haloalkoxy, and wherein the nitrogen and/or the sulfur atom(s) of the heterocyclic ring may optionally be oxidized;

or two $R^{10}$ present together on one atom of a partly saturated heterocyclic may be =O, =$CR^{13}R^{14}$; =$S(O)_nR^{18}$; =$S(O)_nNR^{17a}R^{17b}$, =$NR^{17a}$, =$NOR^{16}$ or =$NNR^{17a}$, or, two $R^{10}$ on adjacent carbon atoms may be a bridge selected from $CH_2CH_2CH_2CH_2$, CH=CH—CH=CH, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, $C(=S)SCH_2$, $S(CH_2)S$, $CH_2CH_2NR^8$, $CH_2CH=N$, CH=CH—$NR^{9a}$, OCH=N, SCH=N and form together with the carbon atoms to which the two $R^{10}$ are bonded to a 5-membered or 6-membered partly saturated or unsaturated, aromatic carbocyclic or heteocyclic ring, wherein the ring may optionally be substituted with one or two substituents selected from =O, OH, $CH^3$, $OCH_3$, halogen, halomethyl or halomethoxy;

$R^{11}$, $R^{12}$ are selected independent from one another from the group consisting of hydrogen, halogen, $C_1$-$C_6$ alkyl, $C_1$-$C_5$ haloalkyl, $C_1$-$C_6$ alkoxyalkyl, $C_2$-$C_6$ alkenyl, $C_2$-$C_6$ haloalkenyl, $C_2$-$C_6$ alkinyl, $C_2$-$C_6$ haloalkinyl, $C_3$-$C_8$ cycloalkyl, $C_3$-$C_8$ halocycloalkyl, $C_1$-$C_6$ alkoxyalkyl, $C_1$-$C_6$ haloalkoxyalkyl, phenyl, optionally substituted with one or more substituents $R^{18}$; which are selected independently from one another, a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^{13}$, $R^{14}$ are selected independent from one another from $C_1$-$C_4$ alkyl, $C_1$-$C_6$ cycloalkyl, $C_1$-$C_4$ alkoxyalkyl, phenyl or benzyl;

$R^{15}$ is selected from the group consisting of hydrogen, halogen, cyano, azido, nitro, OH, SH, SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$ alkoxy, phenyl, benzyl, pyridyl, phenoxy, wherein the last four radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino, or two $R^{15}$ present on the same carbon atom may together be =O, =CH($C_1$-$C_4$), =C($C_1$-$C_4$-alkyl)$C_1$-$C_4$-alkyl, =N($C_1$-$C_6$-alkyl) or =NO($C_1$-$C_6$-alkyl);

$R^{16}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxygenated and/or may carry 1 or 2 radicals selected from $C_1$-$C_4$ alkoxy, phenyl, benzyl, pyridyl, phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl;

$R^{17a}$, $R^{17b}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl, or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

$R^{18}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy); ($C_1$-$C_6$-alkoxy)carbonyl, or two $R^{18}$ present together on one atom of a partly saturated atom may be =O, =N($C_1$-$C_6$-alkyl), =NO ($C_1$-$C_6$-alkyl), =CH($C_1$-$C_4$-alkyl) or =C($C_1$-$C_4$-alkyl)$C_1$-$C_4$-alkyl or, two $R^{18}$ on two adjacent carbon atoms may be together a $C_2$-$C_6$ alkylene chain, which form together with the carbon atom they are bonded to a 3-, 4-, 5-, 6- or 7-membered saturated, partly saturated or unsaturated aromatic, wherein the alkylene chain may contain 1 or 2 heteroatoms selected from oxygen, sulfur or nitrogen; and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

n is 0, 1 or 2;

k is an integer selected from 0 to 10;

or an enantiomer, diastereomer and salt thereof.

Aryl isoxazolines in general have been previously described. Insecticidal aryl isoxazolines of the following formula

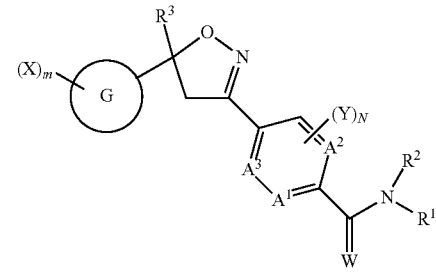

wherein, inter alia, each of $A^1$, $A^2$ and $A^3$ are independently carbon or nitrogen, G is a benzene ring, and W being defined as oxygen or sulfur are disclosed in WO 2005/085216 (corresponding US 20070066617). Similar aryl isoxazoline to those used in pesticidal mixtures have been described in JP 2009-108046 and unpublished international appplications PCT/EP2009/058517 and PCT/EP2009/058334. These documents do not disclose isoxazolins that incorporate a substituted aryl amidine group according to the present invention.

Related insecticidal aryl isoxazolines are further described in JP 2007-016017, WO 2007/026965, JP 2007-106756, WO 2007/070606, WO 2007/075459, WO 2007/079162, WO 2007/105814, WO 2007/125984, WO 2008/012027, WO 2008/019760, WO 2008/108448, JP 2008-239611, WO 2008/122375, WO 2008/130651, WO 2007/026965, WO 2009/126668, WO2009/051956, WO 2009/080250 and US 20080262057. None of these documents discloses isoxazolines incorporating a substituted aryl amidine group according to the present invention.

Insecticidal aryl amidoximes are disclosed in JP 1988158393, U.S. Pat. Nos. 4,268,525 and 3,717,690. These documents do not disclose aryl amidoximes that incorporate an isoxazoline-group according to the present invention.

Insecticidal aryl amidrazones are disclosed in JP 1996-123496; WO 9703976; EP 643040 and the Journal of Agricultural and Food Chemistry 1997, 21, 647-650. These documents do not disclose aryl amidrazones that incorporate an isoxazoline group according to the present invention.

Insecticidal aryl amidine are disclosed in WO 2007/131680, US 2002-331211, WO 2003/016300, EP 223141, EP 5944, U.S. Pat. No. 4,200,653 and the Journal of Pesticide Science 2003, 28, 8-17. These documents do not disclose aryl amidines that incorporate an isoxazoline group according to the present invention.

Various 4-(5-substituted carbamoylmethyl-4,5-dihydroisoxazole-3-yl)benz-amidine compounds like the compound known as "Roxifiban" have been described to have platelet glycoprotein IIb/IIIa fibrinogen receptor complex competition activity, or factor Xa inhibition activity, and can be used as a thrombolysis agent or as a therapeutic agent of thrombo-embolic disorder etc, and are disclosed in, for example, WO 9514682, WO 96038426, WO 2000029406, Drugs of the Future 1998, 23, 707-711, Current Opinion in Cardiovascular, Pulmonary & Renal Investigational Drugs 2000, 2, 165-171. However, these documents do not disclose N-substituted 4-(5-aryl-substituted 5-substituted aryl-4,5-dihydroisoxazole-3-yl) aryl amidine compounds according to the present invention. Further, the usefulness thereof as a pesticide is neither disclosed.

However, the compounds of formula I of the present invention are also new in view of intermediately published WO 2009/049846, which describes similar isoxazoline derivatives for pesticidal uses.

The substituted amidine compounds of the formula I, and their agriculturally acceptable salts are highly active against animal pest, i.e. harmful arthropodes and nematodes, especially against difficult to control insects and acaridae.

Accordingly, the present invention relates to substituted amidine compounds of the general formula I, to their agriculturally or veterinarily useful salts, their enantiomers or diasteromers.

Moreover, the present invention relates to and includes the following embodiments:

agricultural and veterinary compositions comprising an amount of at least one compound of the formula I or an enantiomer, diasteromer or salt thereof;

the use of a compound of formula I or an enantiomer, diasteromer or salt thereof for combating animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I or an enantiomer, diasteromer or salt thereof;

a method for protecting crops from attack or infestation by animal pests, which comprises contacting a crop with a pesticidally effective amount of at least one compound of the formula I or an enantiomer, diasteromer or salt thereof;

a method for the protection of seeds from soil insects and of the seedlings' roots and shoots from soil and foliar insects comprising contacting the seeds before sowing and/or after pregermination with at least one compound of the formula I, or the enantiomers, diastereomers or salts thereof;

seeds comprising a compound of the formula I or an enantiomer, diasteromer or salt thereof;

the use of compounds of formula I or the enantiomers, diastereomers or veterinary acceptable salts thereof for combating parasites in and on animals.

a method for treating, controlling, preventing or protecting animals against infestation or infection by parasites which comprises orally, topically or parenterally administering or applying to the animals a parasiticidally effective amount of a compound of formula I or the enantiomers, diastereomers and/or veterinary acceptable salt thereof;

a process for the preparation of a composition for treating, controlling, preventing or protecting animals against infestation or infection by parasites which comprises a parasiticidally effective amount of a compound of formula I or the enantiomers, diastereomers and/or veterinary acceptable salt thereof;

the use of a compound of formula I or the enantiomers, diastereomers and/or veterinary acceptable salt thereof for the preparation of a medicament for treating, controlling, preventing or protecting animals against infestation or infection by parasites;

The present invention also relates to plant propagation materials, in particular seed, comprising at least one compound of formula I and/or an agriculturally acceptable salt thereof.

The present invention relates to every possible stereoisomer of the compounds of formula I, i.e. to single enantiomers or diastereomers, as well as to mixtures thereof.

The compounds of the present invention may be amorphous or may exist in one or more different crystalline states (polymorphs) or modifications which may have a different macroscopic properties such as stability or show different biological properties such as activities. The present invention includes both amorphous and crystalline cornpounds of the formula I, mixtures of different crystalline states or modifications of the respective compound I, as well as amorphous or crystalline salts thereof.

Salts of the compounds of the formula I are preferably agriculturally and/or veterinary acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-aralkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroetlylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms or heteroatom groups selected from N, O, S, NO, SO and SO2, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include:

Oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 2,3-dihydrooxazol-3-yl, 3,4-dihydrooxazol-4-yl, 3,4 dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro [1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1, 4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 5-pyrazolyl, 2-oxazolyl, 4-oxazolyl, 5-oxazolyl, 2-thiazolyl, 4 thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

$C_2$-$C_7$-alkylene is divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$ Preferences Embodiments and preferred compounds of the present invention are outlined in the following paragraphs.

The remarks made below concerning preferred embodiments of the variables of the compounds of formula I, especially with respect to their substituents X, Y, $A^1$, $A^2$, $A^3$, $A^4$, $B^1$, $B^2$, $B^3$, $R^1$, $R^2$, $R^3$, $R^4$, $R^5$, p and q, the features of the use and method according to the invention and of the composition of the invention are valid both on their own and, in particular, in every possible combination with each other.

As a matter of course, the q radicals $R^5$ replace a hydrogen atom on a carbon ring atom. For instance, if $B^1$, $B^2$ or $B^3$ is defined to be CH and if this position is to be substituted by a radical $R^5$, then $B^1$, $B^2$ and/or $B^3$ are/is C—$R^5$. If there is more than one radical $R^5$, these can be the same or different.

As a matter of course, the p radicals $R^4$ replace a hydrogen atom on a carbon ring atom. For instance, if $A^1$, $A^2$, $A^3$ or $A^4$ is defined to be CH and if this position is to be substituted by a radical $R^4$, then $A^1$, $A^2$, $A^3$ and/or $A^4$ are/is C—$R^4$. If there is more than one radical $R^4$, these can be the same or different.

Preferably, at most two of $A^1$, $A^2$, $A^3$ and $A^4$ are N. In one embodiment, $A^1$, $A^2$, $A^3$ and $A^4$ are CH. In an alternative embodiment, $A^1$, $A^3$ and $A^4$ are CH and $A^2$ is N. In an alternative embodiment, $A^1$ and $A^4$ are CH and $A^2$ and $A^3$ are N. In an alternative embodiment, $A^1$ and $A^2$ are CH and $A^3$ and $A^4$ are N. In an alternative embodiment, $A^2$ and $A^4$ are CH and $A^1$ and $A^3$ are N.

More preferably, $A^4$ is CH.
More preferably, $A^1$ and $A^3$ are CH.
Even more preferably, $A^1$, $A^3$ and $A^4$ are CH and $A^2$ is CH or N and in particular CH.

In a preferred embodiment, the ring comprising the groups $A^1$, $A^2$, $A^3$ or $A^4$ as ring members carries 0, 1 or 2, preferably 0 or 1 and in particular 1 substituent $R^4$. In other words, p is preferably 0, 1 or 2, more preferably 0 or 1 and in particular 1. In case $A^2$ is CH and p is 1, the substituent $R^4$ is preferably bound on the position of $A^2$. In other words, $A^2$ is in this case preferably C—$R^4$. In case $A^2$ is N and p is 1, the substituent $R^4$ is preferably bound on the position of $A^3$. In other words, $A^3$ is in this case preferably C—$R^4$.

In case p is 2, two substituents $R^4$ bound on adjacent carbon atoms preferably form together a group selected from —CH$_2$CH$_2$CH$_2$CH$_2$— and —CH=CH—CH=CH— and more preferably —CH=CH—CH=CH—, thus yielding a fused phenyl ring.

Preferably, at most one of $B^1$, $B^2$ and $B^3$ is N. More preferably, $B^1$, $B^2$ and $B^3$ are CH or $B^1$ and $B^2$ are CH and $B^3$ is N.

q is preferably 0, 1, 2 or 3, more preferably 1, 2 or 3, even more preferably 2 or 3 and in particular 2. If q is 3 and $B^1$, $B^2$ and $B^3$ are CH, then the three substituents $R^5$ are preferably bound in the positions of $B^1$, $B^2$ and $B^3$; $B^1$, $B^2$ and $B^3$ thus being C—$R^5$. If q is 2 and $B^1$, $B^2$ and $B^3$ are CH, then the two substituents $R^5$ are preferably bound in the positions of $B^1$ and $B^3$; $B^1$ and $B^3$ thus being C—$R^5$. $B^2$ in this case is preferably CH. In case $B^1$ and $B^2$ are CH and $B^3$ is N, q is preferably 1. In this case, $R^5$ is preferably bound in the position of $B^1$, $B^1$ thus being C—$R^5$.

X is preferably selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl and $C_3$-$C_6$-halocycloalkyl. More preferably, X is selected from the group consisting of $C_1$-$C_4$-alkyl, $C_1$-$C_4$-haloalkyl, $C_3$-$C_6$-cycloalkyl and $C_3$-$C_6$-halocycloalkyl. Even more preferably, X is selected from the group consisting of $C_1$-$C_4$-alkyl and $C_1$-$C_4$-haloalkyl. In particular, X is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Preferred are substituted amidine compounds of the following formula (I-2):

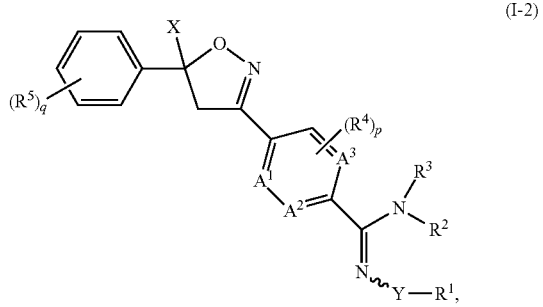

wherein

X is selected from the group consisting of $C_1$-$C_4$ alkyl, $C_1$-$C_4$ haloalkyl, $C_1$-$C_4$ alkoxyalkyl, $C_1$-$C_4$ haloalkoxyalkyl, $C_3$-$C_6$ cycloalkyl and $C_3$-$C_6$ halocycloalkyl.

Preferred are substituted amidine compounds of the following formula (I-3):

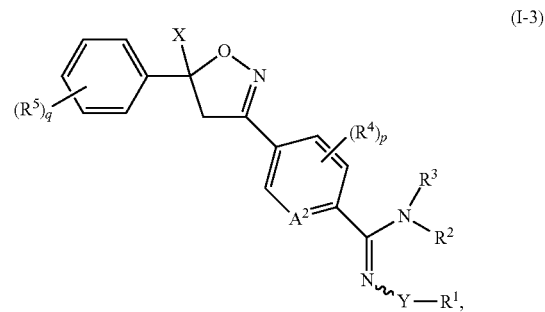

wherein

X is selected from the group consisting of $C_1$-$C_4$ alkyl, $C_1$-$C_4$ haloalkyl, $C_1$-$C_4$ alkoxyalky, $C_1$-$C_4$ haloalkoxyalkyl, $C_3$-$C_6$ cycloalkyl and $C_3$-$C_6$ halocycloalkyl.

Preferred are substituted amidine compounds of the following formula (I-4):

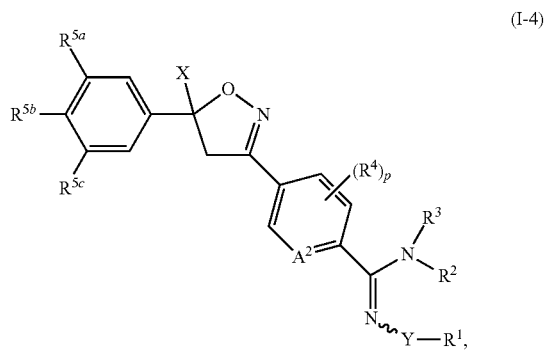

wherein

X is selected from $C_1$-$C_4$ alkyl, $C_1$-$C_4$ haloalkyl, $C_3$-$C_6$ cycloalkyl or $C_3$-$C_6$ halocycloalkyl;

p is 0, 1 or 2;

$R^4$ is selected independently from p from the group consisting of hydrogen, halogen, cyano, azido, nitro, —SCN, SF$_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, Si(R$^{11}$)$_2$R$^{12}$, OR$^7$, —OS(O)$_n$R$^7$, S(O)$_n$R', NR$^{9a}$R$^{9b}$, N(R$^{9a}$)C(=O)R$^6$, C(=O)R$^6$, C(=O)OR$^7$, C(=NR$^{9a}$)R$^6$, C(=S)R$^6$, phenyl, optionally substituted with one or more substituents independently selected from R$^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized, or, when p is 2 and two of R$^4$ are adjacent, the two adjacent R$^4$ may be a bridge selected from the group consisting of CH$_2$CH$_2$CH$_2$CH$_2$, CH=CH—CH=CH, N=CH—CH=CH, CH=N—CH=CH, N=CH—N=CH, OCH$_2$CH$_2$CH$_2$, OCH=CHCH$_2$, CH$_2$OCH$_2$CH$_2$, OCH$_2$CH$_2$O, OCH$_2$OCH$_2$, CH$_2$CH$_2$CH$_2$, CH=CHCH$_2$, CH$_2$CH$_2$O, CH=CHO, CH$_2$OCH$_2$, CH$_2$C(=O)O, C(=O)OCH$_2$, O(CH$_2$)O, SCH$_2$CH$_2$CH$_2$, SCH=CHCH$_2$, CH$_2$SCH$_2$CH$_2$, SCH$_2$CH$_2$S, SCH$_2$SCH$_2$, CH$_2$CH$_2$S, CH=CHS, CH$_2$SCH$_2$, CH$_2$C(=S)S, C(=S)SCH$_2$, S(CH$_2$)S, CH$_2$CH$_2$NR$^{9a}$, CH$_2$CH=N, CH=CH—NR$^{9a}$, OCH=N, SCH=N;

R$^{5a}$ and R$^{5c}$ are selected independently from one another from the group consisting of hydrogen, halogen, cyano, nitro, SCN, SF$_5$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another, OR$^7$, S(O)$_n$R$^7$, NR$^{9a}$R$^{9b}$, C(=O)R$^6$, —C(=O)OR$^7$, C(=NR$^9$)R$^6$, C(=S)NR$^6$;

and

R$^{5b}$ is selected from the group consisting of hydrogen, halogen, cyano, nitro, —SCN, SF$_5$, C$_1$-C$_6$-alkyl, C$_1$-C$_6$-alkyl, C$_3$-C$_8$-cycloalkyl, C$_2$-C$_6$-alkenyl, C$_2$-C$_6$-alkinyl, wherein the five last aliphatic and cyclo-aliphatic radicals may optionally be substituted with one or more R$^6$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, CHO, C(=O)R$^6$, C(=O)OR$^7$, C(=NR$^9$)R$^6$, C(=S)NR$^6$, phenyl, optionally substituted with one or more substituents R$^{10}$, which are selected independently from one another;

a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized.

Preferred are substituted amidine compounds of the following formula (I-5):

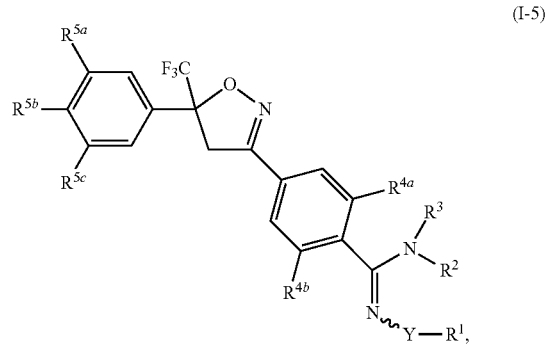

(I-5)

wherein

R$^{4a}$, R$^{4b}$ are selected independently from one another from the group consisting of hydrogen, halogen, cyano, azido, nitro, —SCN, SF$_5$, C$_1$-C$_6$-alkyl, C$_3$-C$_8$-cycloalkyl, wherein the carbon atoms of the last two aliphatic and cyclo-aliphatic radicals may optionally be, substituted with one or more R$^6$, which are independently selected from one another, OR$^7$, —OS(O)$_n$R$^7$, S(O)nR$^7$, NR$^{9a}$R$^{9b}$, N(R$^{9a}$)C(=O)R$^6$, CHO, C(=O)R$^6$, —C(=O)OR$^7$, C(=NR$^{9a}$)R$^6$, C(=S)R$^6$, phenyl, optionally substituted with one or more substituents independently selected from R$^{10}$, which are selected independently from one another, a 3-, 4-, 5-, 6- or 7-membered saturated, partly saturated or unsaturated aromatic heterocyclic ring;

R$^{5a}$ and R$^{5c}$ are selected independently from one another from the group consisting of hydrogen, halogen, cyano, nitro, SCN, SF$_5$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another, OR$^7$, S(O)$_n$R$^7$, NR$^{9a}$R$^{9b}$, C(=O)R$^6$, —C(=O)OR$^7$, C(=NR$^8$)R$^6$, C(=S)NR$^6$;

and

R$^{5b}$ is selected from the group consisting of hydrogen, halogen, cyano, nitro, —SCN, SF$_5$, C$_1$-C$_6$-alkyl, C$_1$-C$_6$-alkyl, C$_3$-C$_8$-cycloalkyl, C$_2$-C$_6$-alkenyl, C$_2$-C$_6$-alkinyl, wherein the aliphatic chains of the five last radicals may optionally be substituted with one or more R$^6$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, C(=O)R$^6$, C(=O)OR$^7$, C(=NR$^{9a}$)R$^6$, C(=S)NR$^6$, phenyl, optionally substituted with one or more substituents R$^{10}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized.

Especially preferred substituted amidine compounds of formula (I-5) are those, wherein R$^1$ is selected from the group consisting of hydrogen, cyano, C$_1$-C$_6$-alkyl, C$_3$-C$_8$-cycloalkyl, C$_2$-C$_6$-alkenyl, C$_2$-C$_6$-alkinyl, wherein the carbon atoms of the aforementioned aliphatic and cyclo-aliphatic radicals may optionally be substituted with one or more R$^6$, which are independently selected from one another, Si(R$^{11}$)$_2$R$^{12}$, —S(O)$_n$R$^7$, —S(O)$_n$NR$^{9a}$R$^{9b}$, C(=O)R$^6$, C(=O)NR$^{9a}$R$^{9b}$, C(=O)OR$^7$, —C(=S)R$^6$, C(=S)NR$^{9a}$R$^{9b}$, C(=S)OR$^7$, —C(=S)SR$^7$, phenyl, optionally substituted with one or more substituents R$^{10}$, which are independently selected from one another, a 5- or 6-membered saturated, partly saturated or unsaturated aromatic heterocyclic ring, comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized;

R$^{4a}$, R$^{4b}$ are selected independently from one another from the group consisting of hydrogen, halogen, cyano, nitro, SCN, C$_1$-C$_6$-alkyl, C$_3$-C$_8$-cycloalkyl, wherein the carbon atoms of the of the last two aliphatic and cyclo-aliphatic radicals may optionally be substituted with one or more R$^6$, which are independently selected from one another, OR$^7$, —OS(O)$_n$R$^7$, S(O)$_n$R$^7$, NR$^{9a}$R$^{9b}$, N(R$^{9a}$)C(=O)R$^6$, C(=O)R$^6$, —C(=O)OR$^7$, C(=NR$^{9a}$)R$^6$, C(=S)R$^6$;

R$^{5a}$ and R$^{5c}$ are selected independently from one another from the group consisting of hydrogen, halogen, cyano, OR$^7$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another;

and

R$^{5b}$ is selected from the group consisting of hydrogen, halogen, cyano, C$_1$-C$_6$-alkyl, C$_1$-C$_6$-alkyl, C$_3$-C$_8$-cycloalkyl, wherein the five last aliphatic and cyclo-aliphatic radicals may optionally be substituted with one or more R$^{15}$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, C(=O)R$^6$, C(=O)OR$^7$, C(=NR$^{9a}$)R$^6$ and C(=S)R$^6$.

Preferred are substituted amidine compounds as of formula (I), (I-2), (I-3), (I-4) or (I-5), wherein Y is oxygen.

Preferred are substituted amidine compounds as of formula (I), (I-2), (I-3), (I-4) or (I-5), wherein Y is a chemical bond.

Preferred are substituted amidine compounds as of formula (I), (I-2), (I-3), (I-4) or (I-5), wherein Y is NR$^8$.

Preferred are S-configured enantiomers of substituted amidine compounds of formula (I-S)

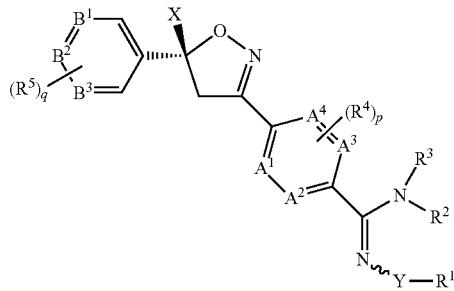

(I-S)

More preferred are enantiomers of formula (I-S), wherein the variables corresponds to the definitions as given for formula (I-2), (I-3), (I-4) or (I-5).

Preferred are R-configured enantiomers of substituted amidine compounds of formula (I-R)

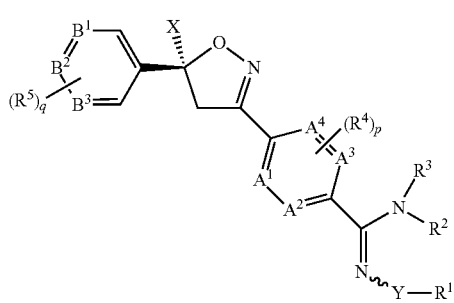

(I-R)

More preferred are enantiomers of formula (I-R), wherein the variables corresponds to the definitions as given for formula (I-2), (I-3), (I-4) or (I-5).

Preferred are substituted amidine compounds as of formula (I), (I-2), (I-3), (I-4) or (I-5),
wherein
R$^2$ and R$^3$ are selected independent of each other from the group consisting of hydrogen, cyano, C$_1$-C$_6$-alkyl, C$_3$-C$_8$-cycloalkyl, C$_2$-C$_6$-alkenyl, C$_2$-C$_6$-alkinyl, wherein the carbon atoms of the aforementioned aliphatic and cyclo-aliphatic radicals may optionally be substituted with one or more R$^6$, which are independently selected from one another,
NR$^{9a}$R$^{9b}$, S(O)$_n$R$^7$, C(=O)R$^6$, C(=O)NR$^{9a}$R$^{9b}$, C(=O)OR$^7$, C(=S)R$^6$, C(=O)NR$^{9a}$R$^{9b}$, C(=S)SR$^7$, C(=NR$^{9a}$)R$^6$, phenyl, optionally substituted with one or more substituents from R$^{10}$, which are selected independently from one another, a 5- or 6-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized, and with the proviso that R$^2$ and R$^3$ are not both hydrogen at the same time.

Preferred are substituted amidine compounds as of formula (I), (I-2), (I-3), (I-4) or (I-5),
wherein R$^2$ and R$^3$ may be together a C$_4$- or C$_5$ alkylene chain, forming a 5- to 6-membered saturated, partly saturated or unsaturated aromatic heterocyclic ring together with the nitrogen atom they are bond to,
wherein the alkylene chain may further contain 1 oxygen atom, sulfur atom or nitrogen atom, and wherein the alkylene chain may optionally be substituted with
halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkinyl, C$_2$-C$_6$ haloalkinyl, phenyl, optionally be substituted with one or more substituents R$^{10}$ which are selected independently from one another, a 5 or 6-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized;

As noted above, some of the variables of formula (I), (I-2), (I-3), (I-4) or (I-5) may optionally be further substituted by an unsaturated (aromatic), partly saturated or saturated 3-7 membered heterocyclic ring, which may arbitrarily be substituted with k substituents R$^{10}$, selected independently from the integer of k.

Preferred examples of a 6-membered unsaturated (aromatic) heterocyclic ring, optionally substituted with k substituents R$^{10}$, selected independently from the interger of K, include the rings D-1 through D-14:

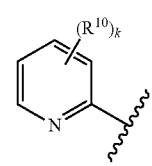

D-1

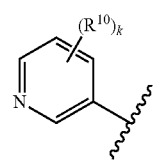

D-2

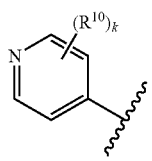 D-3
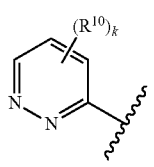 D-4
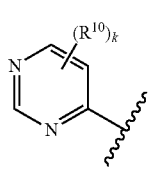 D-5
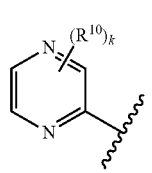 D-6
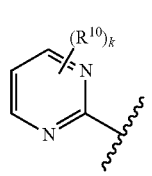 D-7
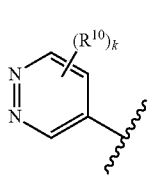 D-8
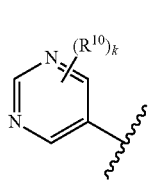 D-9
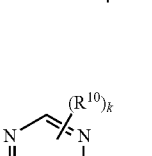 D-10
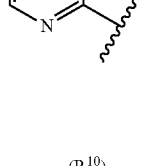 D-11
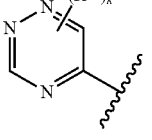
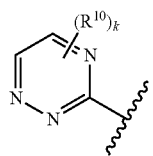 D-12
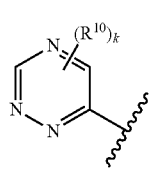 D-13
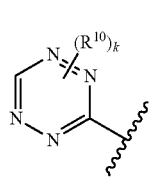 D-14
Preferred examples of a 5-membered unsaturated (aromatic) heterocyclic ring, optionally substituted with k substituents $R^{10}$, selected independently from the integer of k, include the rings D-15 through D-65:
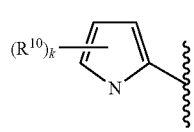 D-15
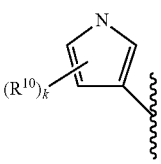 D-16
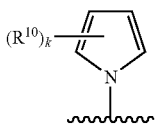 D-17
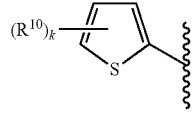 D-18
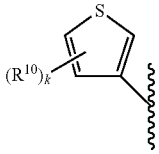 D-19
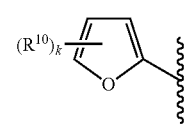 D-20

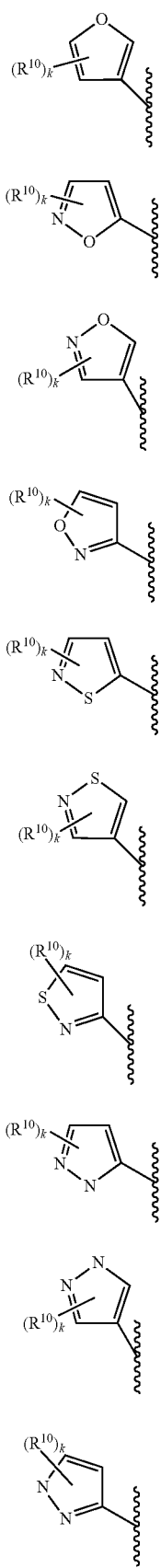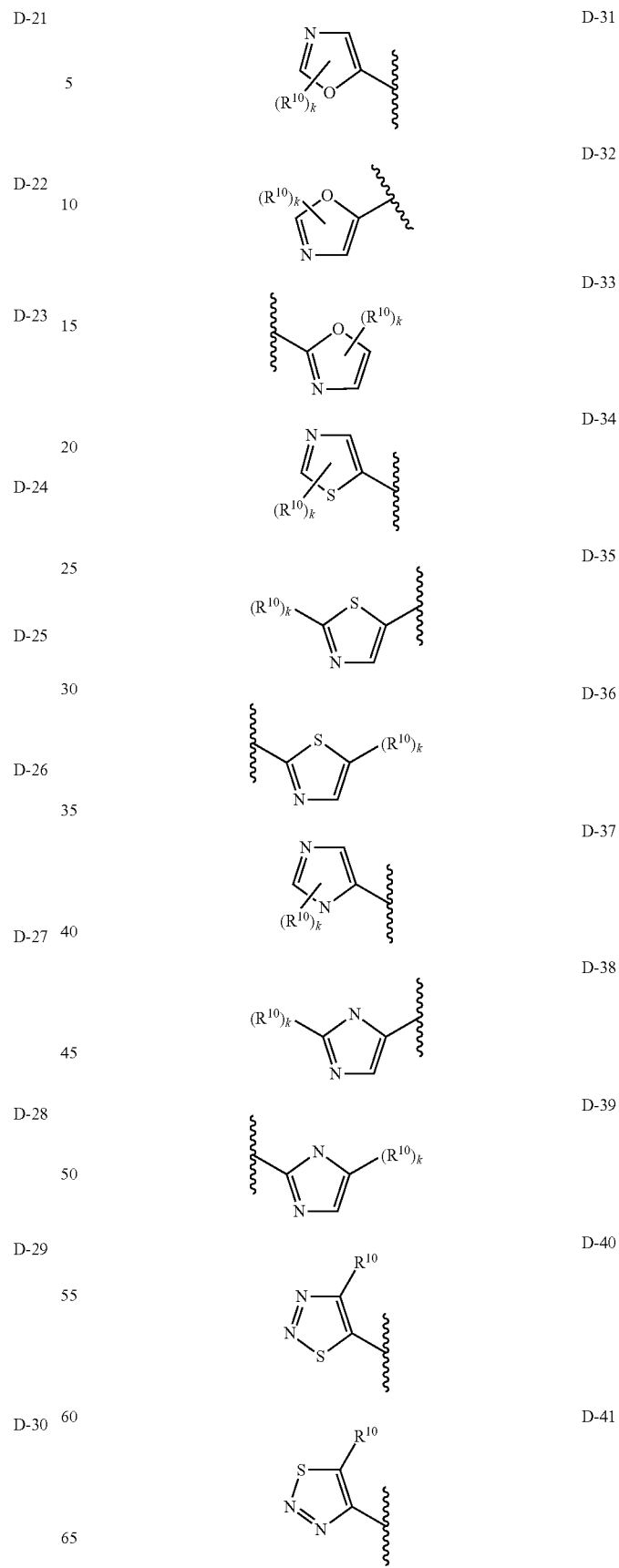

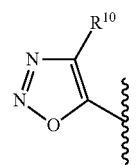 D-42
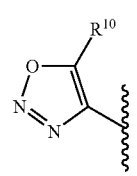 D-43
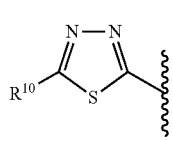 D-44
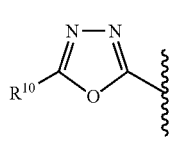 D-45
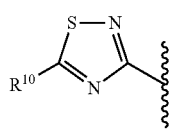 D-46
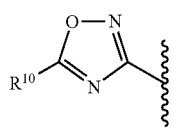 D-47
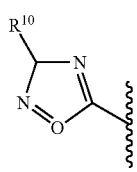 D-48
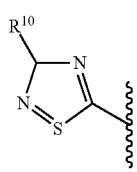 D-49
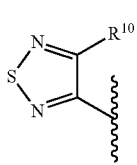 D-50
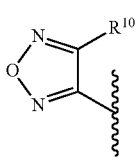 D-51
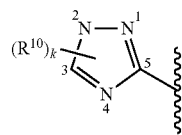 D-52
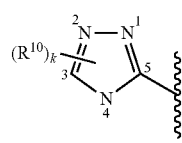 D-53
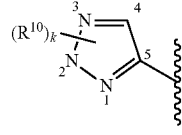 D-54
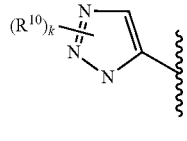 D-55
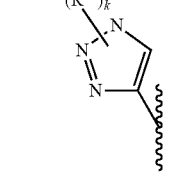 D-56
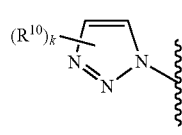 D-57
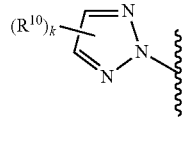 D-58
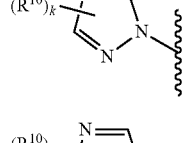 D-59
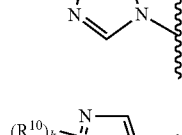 D-60
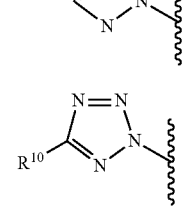 D-61
D-62

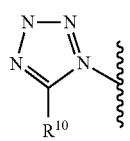
D-63
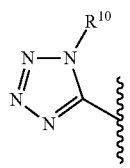
D-64
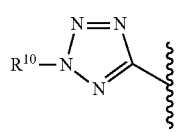
D-65
Preferred examples of a 3-7-membered saturated heterocyclic ring, optionally substituted with k substituents $R^{10}$, selected independently from the integer of k, include the rings D-66 through D-120:
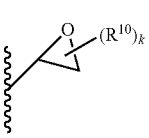
D-66
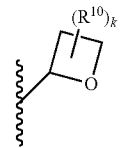
D-67
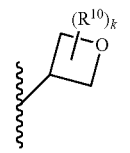
D-68
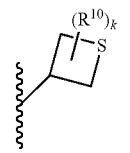
D-69
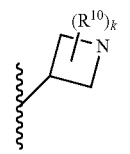
D-70
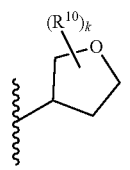
D-71
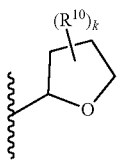
D-72
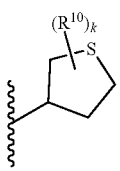
D-73
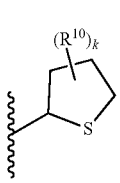
D-74
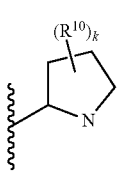
D-75
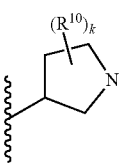
D-76
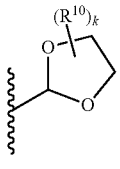
D-77
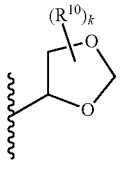
D-78
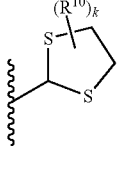
D-79
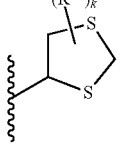
D-80

| | | | |
|---|---|---|---|
| 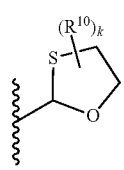 | D-81 | 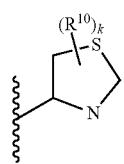 | D-90 |
| 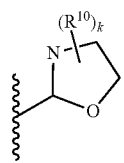 | D-82 | 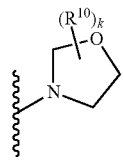 | D-91 |
| 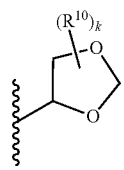 | D-83 | 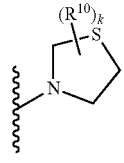 | D-92 |
| 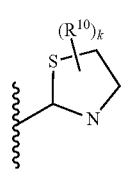 | D-84 | 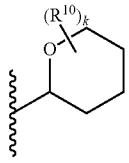 | D-93 |
| 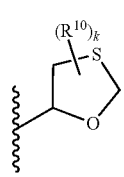 | D-85 | 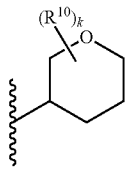 | D-94 |
| 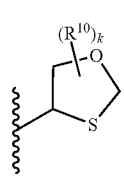 | D-86 | 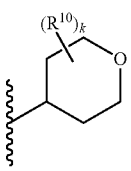 | D-95 |
| 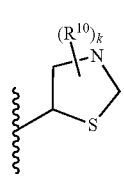 | D-87 | 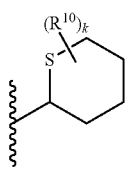 | D-96 |
| 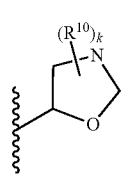 | D-88 | 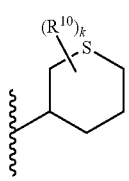 | D-97 |
| 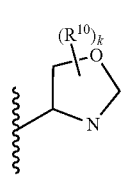 | D-89 | 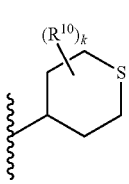 | D-98 |

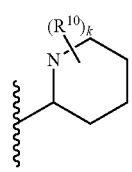 D-99
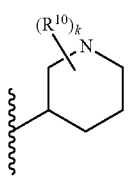 D-100
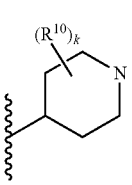 D-101
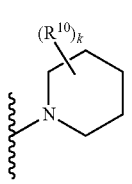 D-102
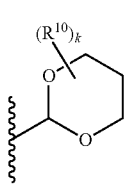 D-103
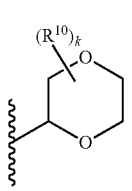 D-104
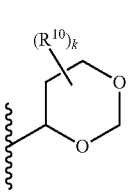 D-105
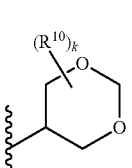 D-106
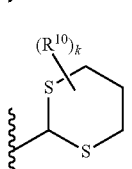 D-107
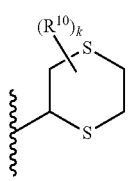 D-108
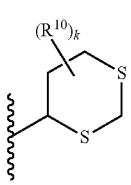 D-109
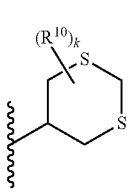 D-110
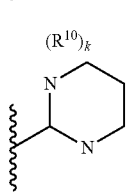 D-111
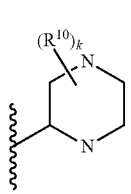 D-112
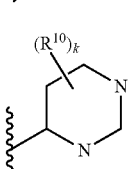 D-113
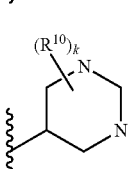 D-114
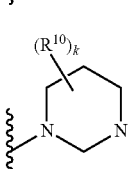 D-115
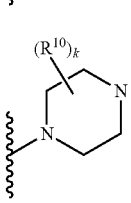 D-116

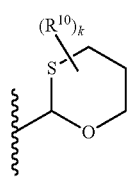 D-117
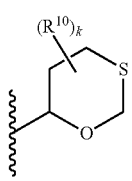 D-118
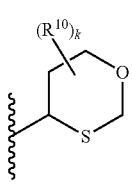 D-119
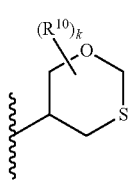 D-120
Preferred examples of a 5-7-membered, partly saturated heterocyclic ring, optionally substituted with k substituents R$^{10}$, selected independently from the integer of k, include the rings D-121 through D-169:
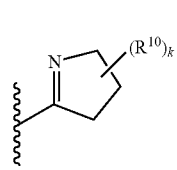 D-121
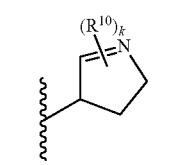 D-122
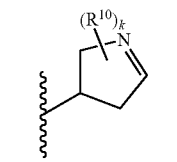 D-123
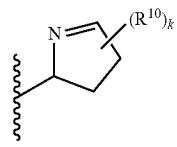 D-124
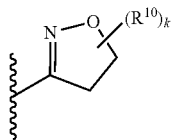 D-125
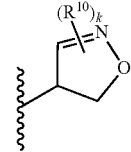 D-126
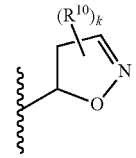 D-127
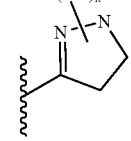 D-128
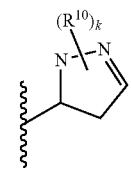 D-129
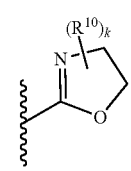 D-130
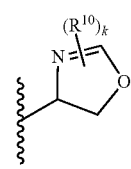 D-131
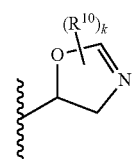 D-132
D-133

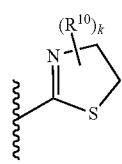 D-134
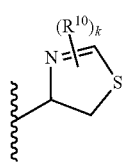 D-135
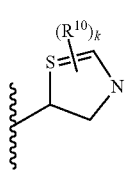 D-136
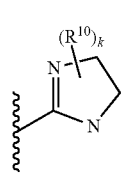 D-137
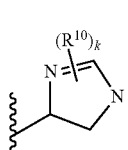 D-138
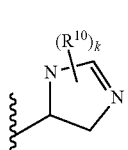 D-139
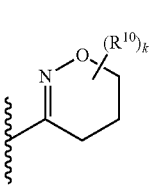 D-140
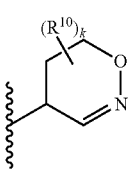 D-141
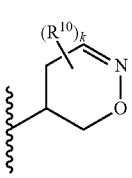 D-142
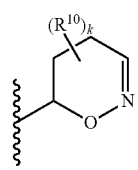 D-143
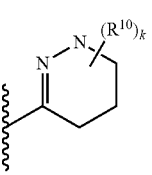 D-144
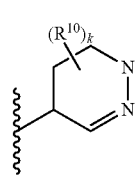 D-145
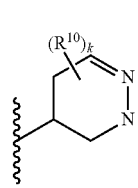 D-146
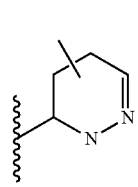 D-147
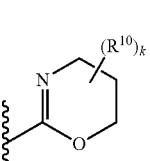 D-148
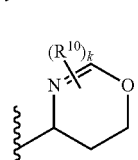 D-149
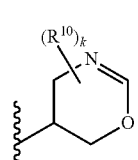 D-150
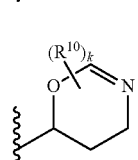 D-151

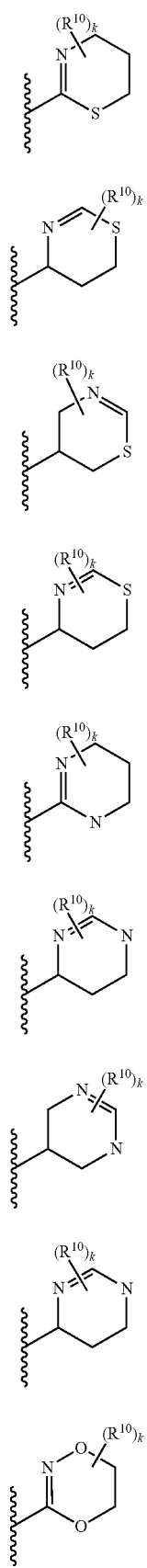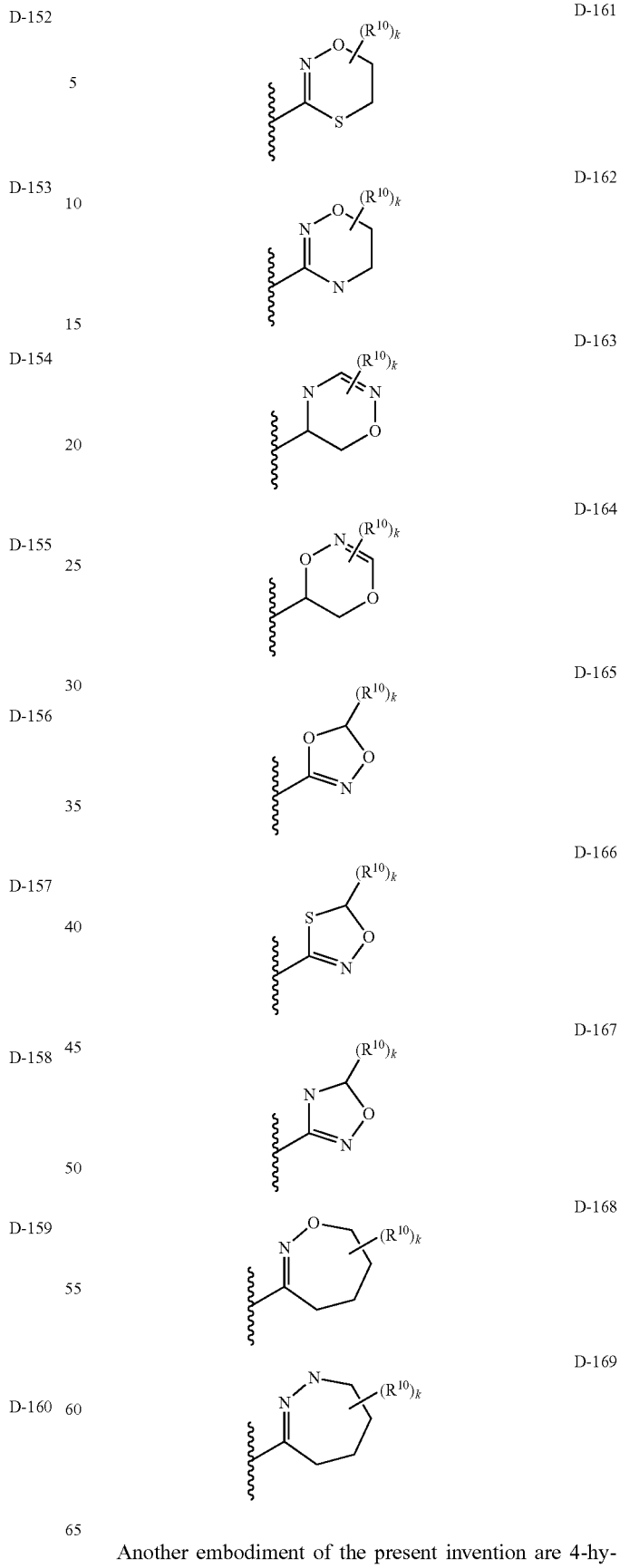
Another embodiment of the present invention are 4-hydroxyiminomethyl substituted amidine compounds of the general formulae (II-A) and (II-B), wherein the 4-hydroxyiminomethyl substituted amidine compound of the general formula (II-A) is

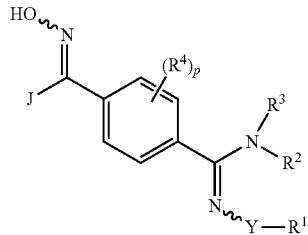
(II-A)

wherein

J is hydrogen or halogen;

and wherein Y, $R^1$, $R^2$, $R^3$, $R^4$ and p are defined as for compounds of formula (I); and the 4-hydroxyiminomethyl substituted amidine compound of the general formula (II-B) is

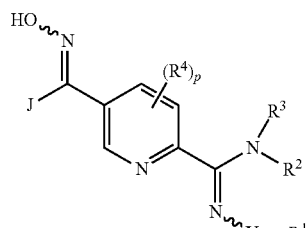
(II-B)

wherein

J is hydrogen or halogen;

and wherein Y, $R^1$, $R^2$, $R^3$, $R^4$ and p are defined as for compounds of formula (I).

Examples of Preferred Compounds

Examples of preferred compounds of the present invention are described in the following without imposing any limitation to the invention.

Preferred are compounds of the following 52 formulae I-a to I-zz, wherein the variables have one of the general or preferred meanings given above. Each of the given formulae I-a to Izz represents both respective isomer in regard of the N to Y bond.

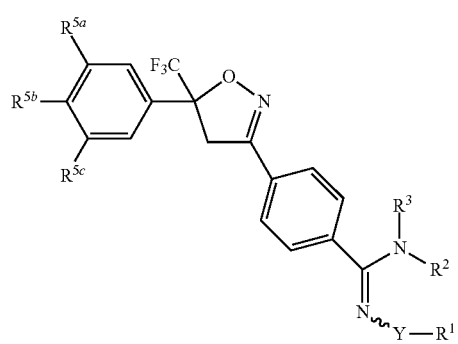
(I-a)

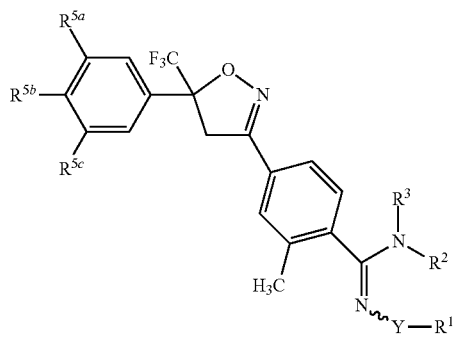
(I-b)

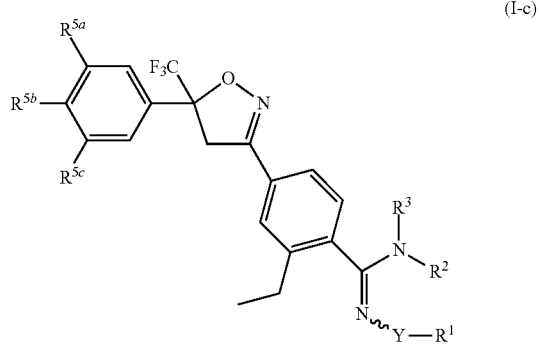
(I-c)

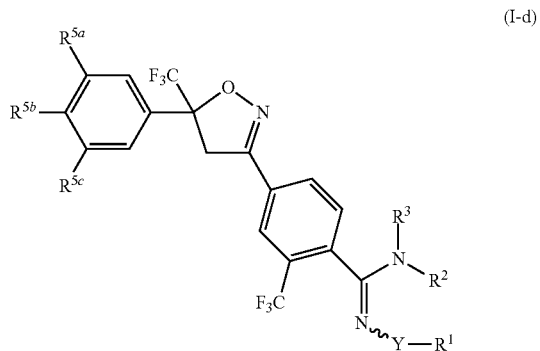
(I-d)

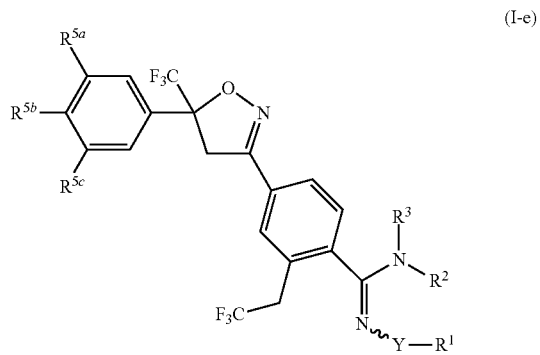
(I-e)

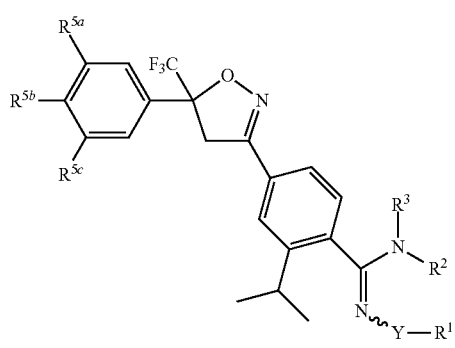
(I-f)
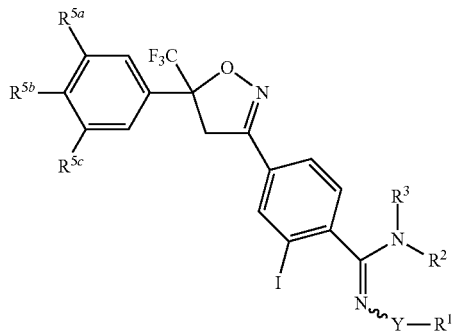
(I-j)
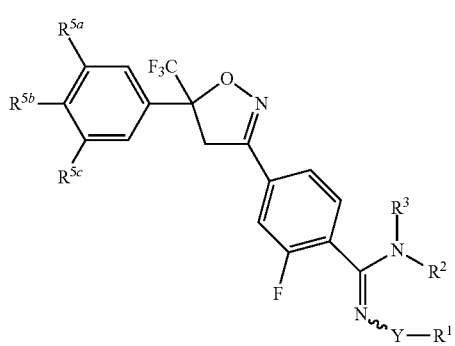
(I-g)
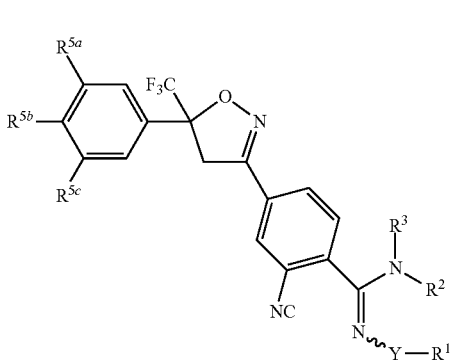
(I-k)
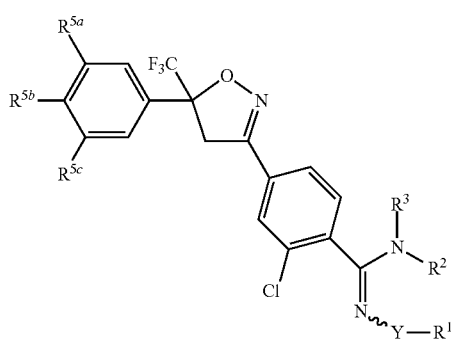
(I-h)
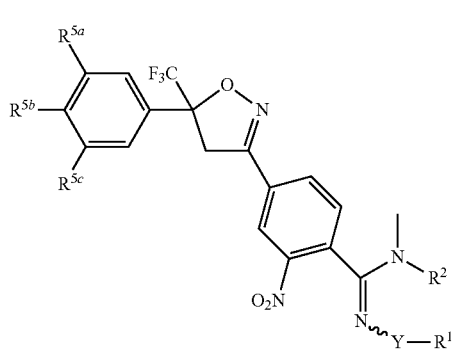
(I-l)
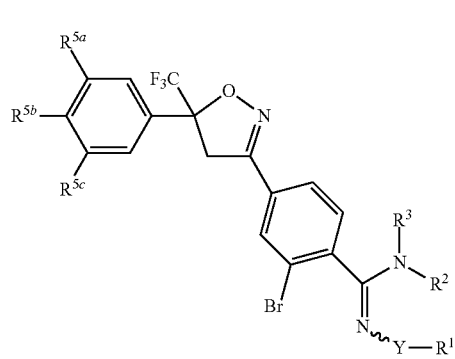
(I-i)
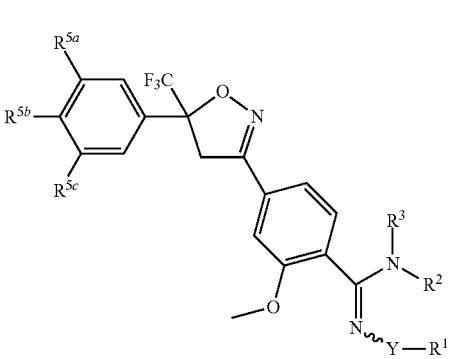
(I-m)

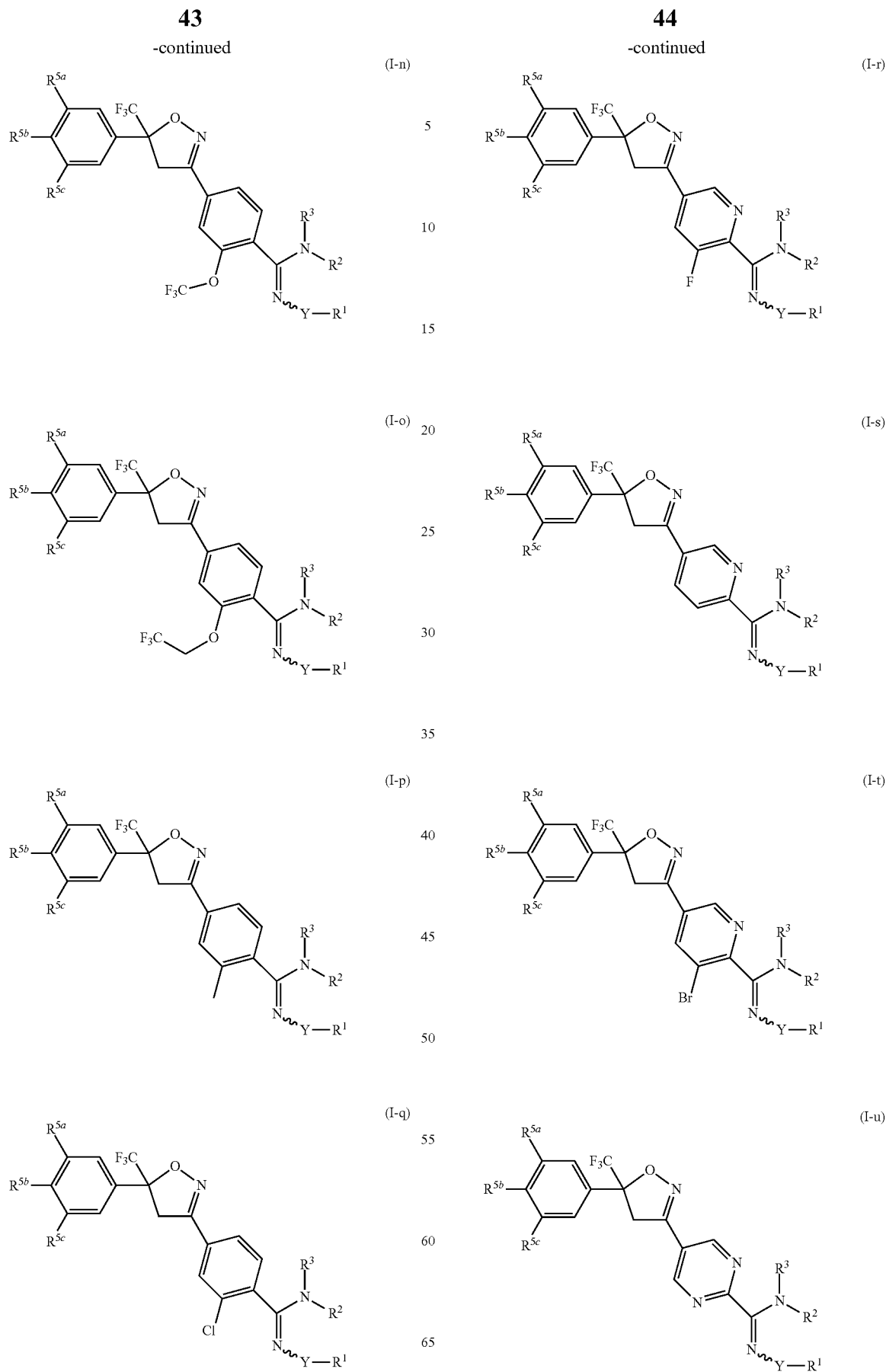

-continued
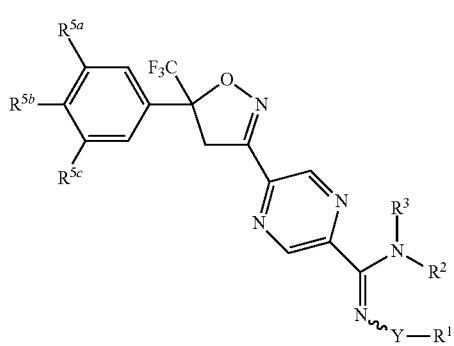
(I-v)
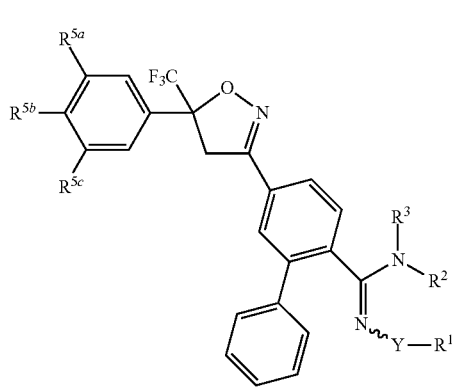
(I-z)
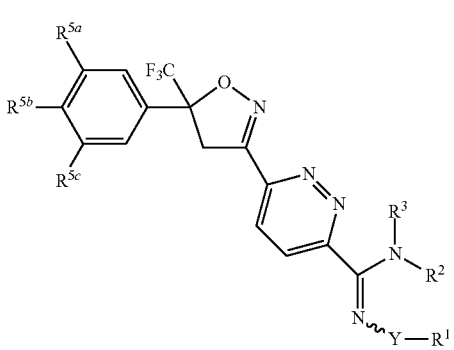
(I-w)
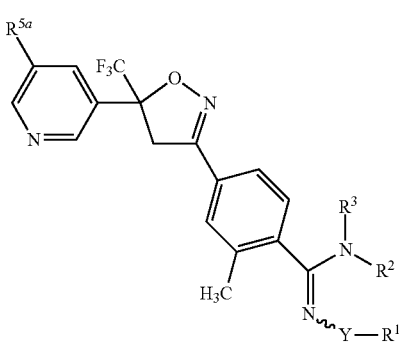
(I-aa)
(I-x)
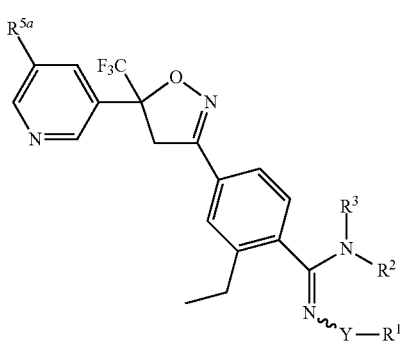
(I-bb)
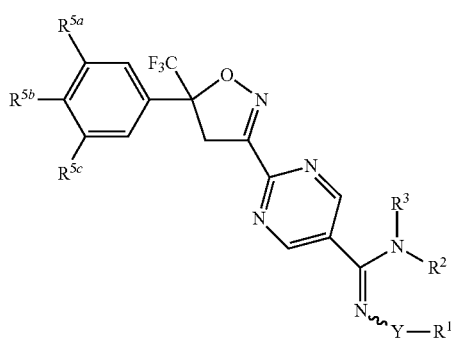
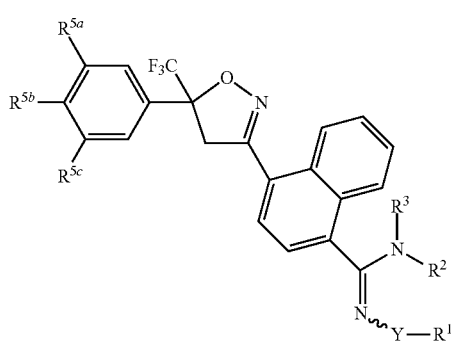
(I-y)
(I-cc)

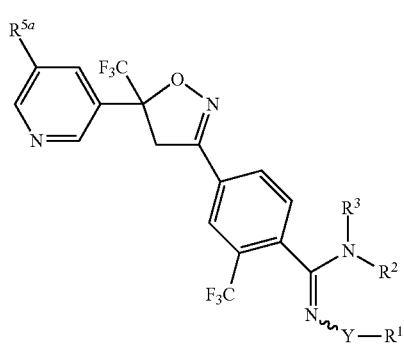 (I-dd)
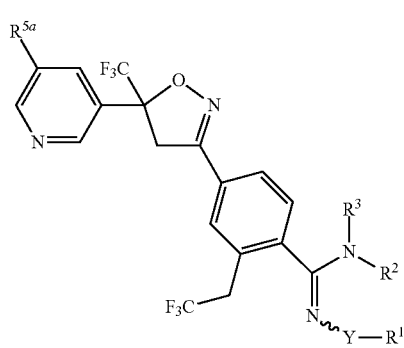 (I-ee)
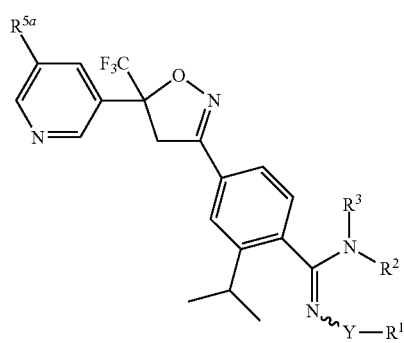 (I-ff)
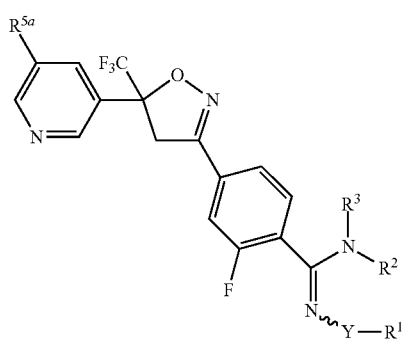 (I-gg)
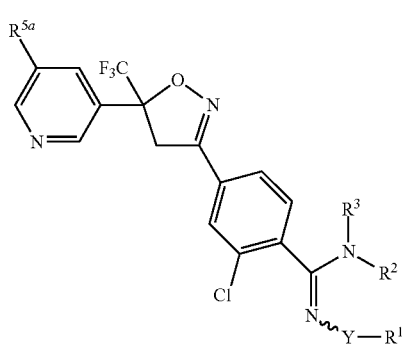 (I-hh)
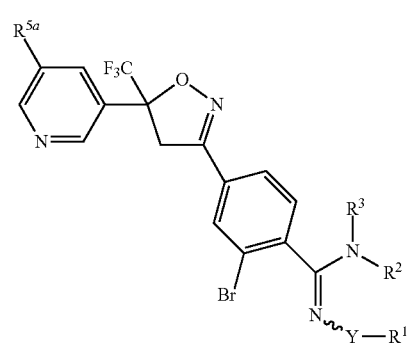 (I-ii)
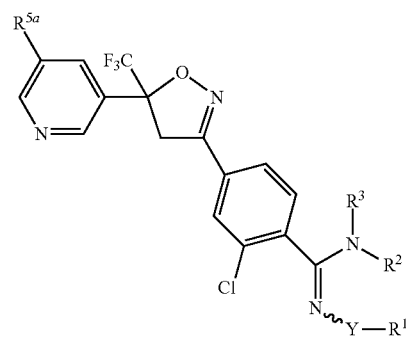 (I-jj)
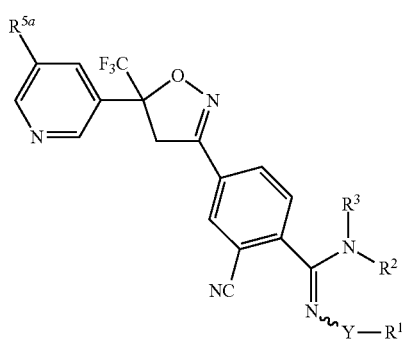 (I-kk)

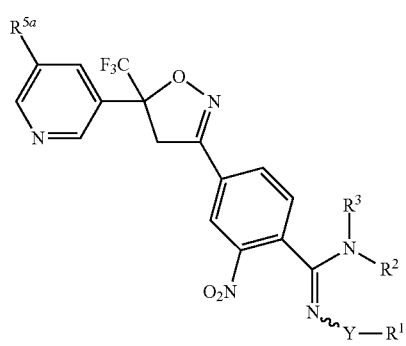
(I-ll)
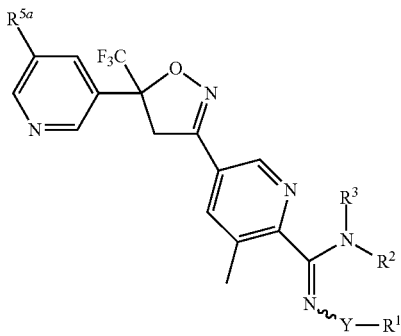
(I-pp)
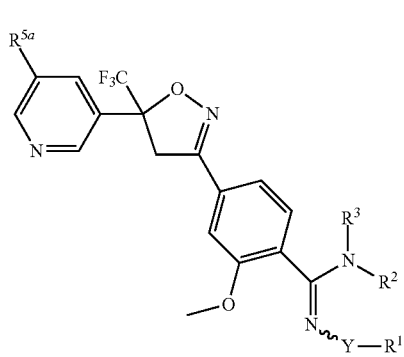
(I-mm)
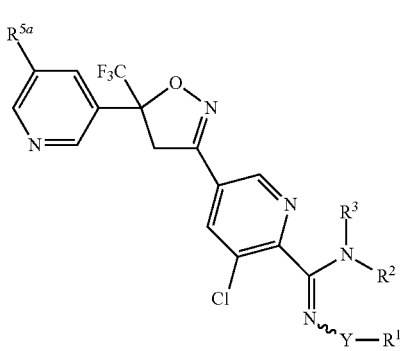
(I-qq)
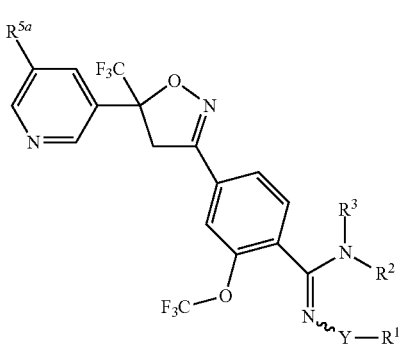
(I-nn)
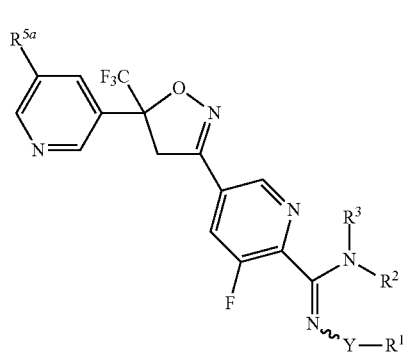
(I-rr)
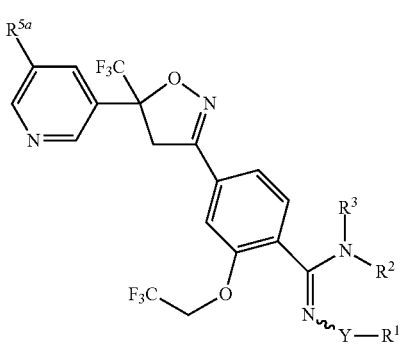
(I-oo)
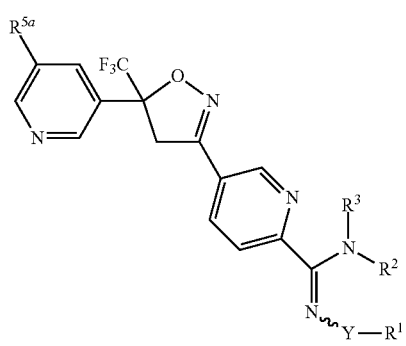
(I-ss)

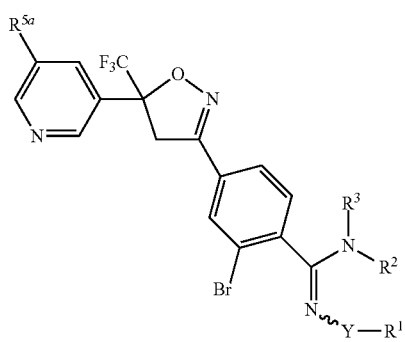 (I-tt)

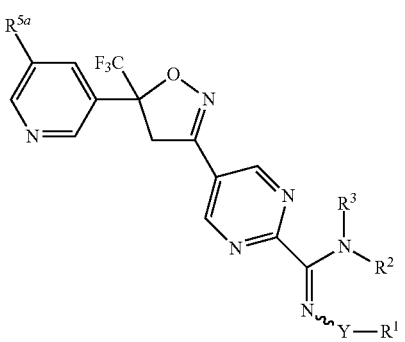 (I-uu)

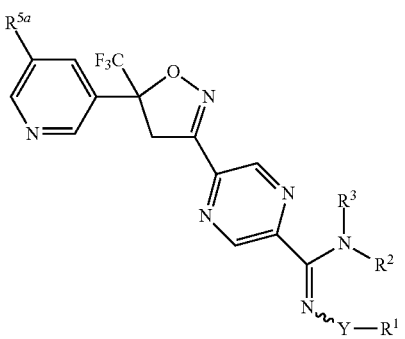 (I-vv)

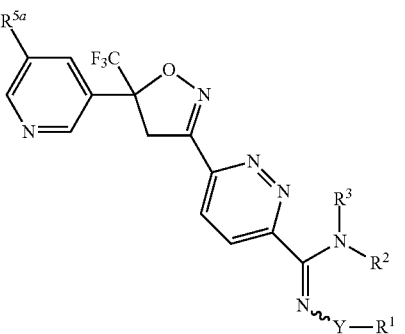 (I-ww)

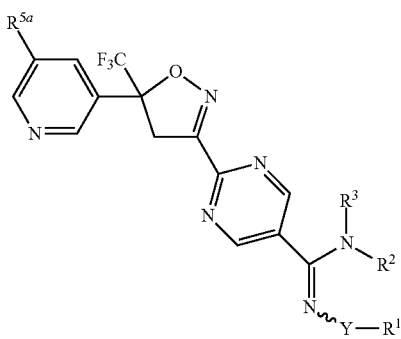 (I-xx)

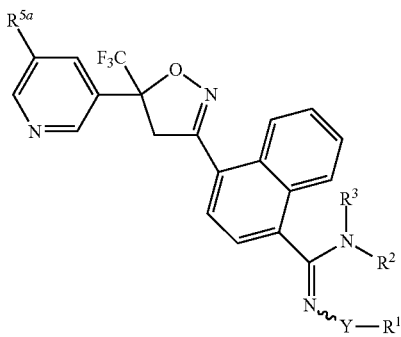 (I-yy)

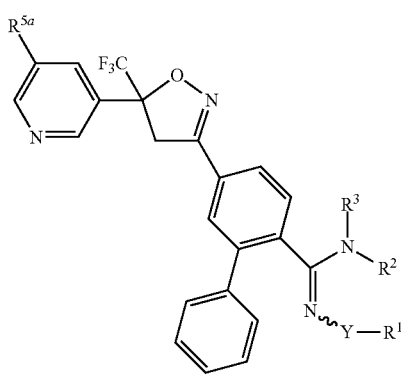 (I-zz)

Examples of more preferred compounds are represented by the formulae Ia to Izz, and the individual compounds are compiled in the tables thereafter. The meaning of the respective individual variables $R^{5a}$, $R^{5b}$ and $R^{5c}$ are defined therein, the sequence of Y and $R^1$ is individually identified as outlined in table Z and the meaning of the variables $R^2$ and $R^3$ are defined by their combination as given in one row of table Q. Moreover, the meanings mentioned for the individual variables in the tables are per se, independently of the combination in which they are mentioned, a particularly preferred embodiment of the substituents in question.

TABLES

Table 1
Compounds of the formula I-a in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 2
Compounds of the formula I-a in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 3
Compounds of the formula I-a in which $R^{5a}$ and $R^{5c}$ are fluorine, $R^{5b}$ is H, the sequence of Y and $R^1$ is Z.1 as defined in table Z and the combination of $R^2$ and $R^3$ for a cornpound corresponds in each case to one row of Table Q.

Table 4
Compounds of the formula I-a in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 5
Compounds of the formula I-a in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 6
Compounds of the formula I-a in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 7
Compounds of the formula I-a in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 8
Compounds of the formula I-a in which $R^{5a}$ is $CF_3$, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 9
Compounds of the formula I-a in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 10
Compounds of the formula I-a in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 11
Compounds of the formula I-a in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 12
Compounds of the formula I-b in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 13
Compounds of the formula I-b in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 14
Compounds of the formula I-b in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 15
Compounds of the formula I-b in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 16
Compounds of the formula I-b in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 17
Compounds of the formula I-b in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 18
Compounds of the formula I-b in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 19
Compounds of the formula I-b in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 20
Compounds of the formula I-b in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 21
Compounds of the formula I-b in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 22
Compounds of the formula I-b in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 23
Compounds of the formula I-c in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 24
Compounds of the formula I-c in which $R^{5a}$ and $R^{5c}$ are bromine, $R^{5b}$ is H, the sequence of Y and $R^1$ is Z.1 as defined in table Z and the combination of $R^2$ and $R^3$ for a cornpound corresponds in each case to one row of Table Q.

Table 25
Compounds of the formula I-c in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 26
Compounds of the formula I-c in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 27
Compounds of the formula I-c in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 28
Compounds of the formula I-c in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 29
Compounds of the formula I-c in which $R^{5a}$ and $R^{5b}$ are methyl, $R^{5a}$ is H, the sequence of Y and $R^1$ is Z.1 as defined in table Z and the combination of $R^2$ and $R^3$ for a compound corresponds in each case to one row of Table Q.

Table 30
Compounds of the formula I-c in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 31
Compounds of the formula I-c in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 32
Compounds of the formula I-c in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 33
Compounds of the formula I-c in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 34
Compounds of the formula I-d in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 35
Compounds of the formula I-d in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 36
Compounds of the formula I-d in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 37
Compounds of the formula I-d in which $R^{5a}$ and $R^{5c}$ are methyl, $R^{5b}$ is H, the sequence of Y and $R^1$ is Z.1 as defined in table Z and the combination of $R^2$ and $R^3$ for a cornpound corresponds in each case to one row of Table Q.

Table 38
Compounds of the formula I-d in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 39
Compounds of the formula I-d in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 40
Compounds of the formula I-d in which $R^{5a}$ and $R^{5b}$ are methyl, $R^{5c}$ is H, the sequence of Y and $R^1$ is Z.1 as defined in table Z and the combination of $R^2$ and $R^3$ for a cornpound corresponds in each case to one row of Table Q.

Table 41
Compounds of the formula I-d in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 42
Compounds of the formula I-d in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 43
Compounds of the formula I-d in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 44
Compounds of the formula I-d in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 45
Compounds of the formula I-e in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 46
Compounds of the formula I-e in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 47
Compounds of the formula I-e in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 48
Compounds of the formula I-e in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 49
Compounds of the formula I-e in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 50
Compounds of the formula I-e in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 51
Compounds of the formula I-e in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 52
Compounds of the formula I-e in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 53
Compounds of the formula I-e in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 54
Compounds of the formula I-e in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 55
Compounds of the formula I-e in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 56
Compounds of the formula I-f in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 57
Compounds of the formula I-f in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 58
Compounds of the formula I-f in which $R^{5a}$ and $R^{5c}$ are fluorine, $R^{5b}$ is H, the sequence of Y and $R^1$ is Z.1 as defined in table Z and the combination of $R^2$ and $R^3$ for a cornpound corresponds in each case to one row of Table Q.

Table 59
Compounds of the formula I-f in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 60
Compounds of the formula I-f in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 61
Compounds of the formula I-f in which $R^{5a}$ and $R^{5b}$ are chlorine, $R^{5c}$ is H, the sequence of Y and $R^1$ is Z.1 as defined in table Z and the combination of $R^2$ and $R^3$ for a cornpound corresponds in each case to one row of Table Q.

Table 62
Compounds of the formula I-f in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 63
Compounds of the formula I-f in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 64
Compounds of the formula I-f in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 65
Compounds of the formula I-f in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 66
Compounds of the formula I-f in which $R^{5a}$, $R^{5b}$ and $R^{5c}$ are methyl, the sequence of Y and $R^1$, is Z.1 as defined in table Z and the combination of $R^2$ and $R^3$ for a compound corresponds in each case to one row of Table Q.

Table 67
Compounds of the formula I-g in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 68
Compounds of the formula I-g in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 69
Compounds of the formula I-g in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 70
Compounds of the formula I-g in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 71
Compounds of the formula I-g in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 72
Compounds of the formula I-g in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 73
Compounds of the formula I-g in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 74
Compounds of the formula I-g in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 75
Compounds of the formula I-g in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 76
Compounds of the formula I-g in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 77
Compounds of the formula I-g in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 78
Compounds of the formula I-h in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 79
Compounds of the formula I-h in which $R^{5a}$ and $R^{5c}$ are bromine, $R^{5b}$ is H, the sequence of Y and $R^1$ is Z.1 as defined in table Z and the combination of $R^2$ and $R^3$ for a cornpound corresponds in each case to one row of Table Q.

Table 80
Compounds of the formula I-h in which $R^{5a}$ and $R^{5b}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 81
Compounds of the formula I-h in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 82
Compounds of the formula I-h in which $R^{5a}$ and $R^{5b}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 83
Compounds of the formula I-h in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 84
Compounds of the formula I-h in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 85
Compounds of the formula I-h in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 86
Compounds of the formula I-h in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 87
Compounds of the formula I-h in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 88
Compounds of the formula I-h in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 89
Compounds of the formula I-i in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 90
Compounds of the formula I-i in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 91
Compounds of the formula I-i in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 92
Compounds of the formula I-i in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 93
Compounds of the formula I-i in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 94
Compounds of the formula I-i in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 95
Compounds of the formula I-i in which $R^{5a}$ and $R^{5b}$ are methyl, $R^{5c}$ is H, the sequence of Y and $R^1$ is Z.1 as defined in table Z and the combination of $R^2$ and $R^3$ for a cornpound corresponds in each case to one row of Table Q.

Table 96
Compounds of the formula I-i in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 97
Compounds of the formula I-i in which $R^{5a}$, $R^{5b}$ and $R^{5c}$ are chlorine, the sequence of Y and $R^1$ is 11 as defined in table Z and the combination of $R^2$ and $R^3$ for a compound corresponds in each case to one row of Table Q.

Table 98
Compounds of the formula I-i in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 99
Compounds of the formula I-i in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 100
Compounds of the formula I-j in which $R^{5a}$ and $R^{5c}$ are chlorine, $R^{5b}$ is H, the sequence of Y and $R^1$ is Z.1 as defined in table Z and the combination of $R^2$ and $R^3$ for a cornpound corresponds in each case to one row of Table Q.

Table 101
Compounds of the formula I-j in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 102
Compounds of the formula I-j in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 103
Compounds of the formula H in which $R^{5a}$ and $R^{5c}$ are methyl, $R^{5b}$ is H, the sequence of Y and $R^1$ is Z.1 as defined in table Z and the combination of $R^2$ and $R^3$ for a cornpound corresponds in each case to one row of Table Q.

Table 104
Compounds of the formula II in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 105
Compounds of the formula I-j in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 106
Compounds of the formula I-j in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 107
Compounds of the formula I-j in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 108
Compounds of the formula II in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 109
Compounds of the formula I-j in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 110
Compounds of the formula I-j in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 111
Compounds of the formula I-k in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 112
Compounds of the formula I-k in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 113
Compounds of the formula I-k in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 114
Compounds of the formula I-k in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 115
Compounds of the formula I-k in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 116
Compounds of the formula I-k in which $R^{5a}$ and $R^{5b}$ are chlorine, $R^{5c}$ is H, the sequence of Y and $R^1$ is Z.1 as defined in table Z and the combination of $R^2$ and $R^3$ for a cornpound corresponds in each case to one row of Table Q.

Table 117
Compounds of the formula I-k in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 118
Compounds of the formula I-k in which Rya is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 119
Compounds of the formula I-k in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 120
Compounds of the formula I-k in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 121
Compounds of the formula I-k in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 122
Compounds of the formula I-l in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 123
Compounds of the formula I-l in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 124
Compounds of the formula I-l in which $R^{5a}$ and $R^{5c}$ are fluorine, $R^{5b}$ is H, the sequence of Y and $R^1$ is Z.1 as defined in table Z and the combination of $R^2$ and $R^3$ for a cornpound corresponds in each case to one row of Table Q.

Table 125
Compounds of the formula I-l in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 126
Compounds of the formula I-l in which $R^{5a}$ and $R^{5b}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 127
Compounds of the formula I-l in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 128
Compounds of the formula I-l in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 129
Compounds of the formula I-l in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 130
Compounds of the formula I-l in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 131
Compounds of the formula I-l in which $R^{5a}$, $R^{5b}$ and $R^{56}$ are fluorine, the sequence of Y and $R^1$ is Z.1 as defined in table Z and the combination of $R^2$ and $R^3$ for a compound corresponds in each case to one row of Table Q.

Table 132
Compounds of the formula I-l in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 133
Compounds of the formula I-m in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 134
Compounds of the formula I-m in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 135
Compounds of the formula I-m in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 136
Compounds of the formula I-m in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 137
Compounds of the formula I-m in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 138
Compounds of the formula I-m in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 139
Compounds of the formula I-m in which $R^{5a}$ and $R^{5b}$ are methyl, $R^{c0}$ is H, the sequence of Y and $R^1$ is Z.1 as defined in table Z and the combination of $R^2$ and $R^3$ for a compound corresponds in each case to one row of Table Q.

Table 140
Compounds of the formula I-m in which Rya is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 141
Compounds of the formula I-m in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 142
Compounds of the formula I-m in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 143
Compounds of the formula I-m in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 144
Compounds of the formula I-n in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 145
Compounds of the formula I-n in which $R^{5a}$ and $R^{5c}$ are bromine, $R^{5b}$ is H, the sequence of Y and $R^1$ is Z.1 as defined in table Z and the combination of $R^2$ and $R^3$ for a cornpound corresponds in each case to one row of Table Q.

Table 146
Compounds of the formula I-n in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 147
Compounds of the formula I-n in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 148
Compounds of the formula I-n in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 149
Compounds of the formula I-n in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 150
Compounds of the formula I-n in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 151
Compounds of the formula I-n in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 152
Compounds of the formula I-n in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 153
Compounds of the formula I-n in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 154
Compounds of the formula I-n in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 155
Compounds of the formula I-o in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 156
Compounds of the formula I-o in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 157
Compounds of the formula I-o in which $R^{5a}$ and $R^{5c}$ are fluorine, $R^{5b}$ is H, the sequence of Y and $R^1$ is L1 as defined in table Z and the combination of $R^2$ and $R^3$ for a compound corresponds in each case to one row of Table Q.

Table 158
Compounds of the formula I-o in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 159
Compounds of the formula I-o in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 160
Compounds of the formula I-o in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 161
Compounds of the formula I-o in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 162
Compounds of the formula I-o in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 163
Compounds of the formula I-o in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 164
Compounds of the formula I-o in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 165
Compounds of the formula I-o in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 166
Compounds of the formula I-p in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 167
Compounds of the formula I-p in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 168
Compounds of the formula I-p in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 169
Compounds of the formula I-p in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 170
Compounds of the formula I-p in which $R^{5a}$ and $R^{5c}$ are CF$_3$, $R^{5b}$ is H, the sequence of Y and $R^1$ is Z.1 as defined in table Z and the combination of $R^2$ and $R^3$ for a compound corresponds in each case to one row of Table Q.

Table 171
Compounds of the formula I-p in which $R^{5a}$ and $R^{5b}$ are chlorine, $R^{5c}$ is H, the sequence of Y and $R^1$ is Z.1 as defined in table Z and the combination of $R^2$ and $R^3$ for a cornpound corresponds in each case to one row of Table Q.

Table 172
Compounds of the formula I-p in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 173
Compounds of the formula I-p in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 174
Compounds of the formula I-p in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 175
Compounds of the formula I-p in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 176
Compounds of the formula I-p in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 177
Compounds of the formula I-q in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 178
Compounds of the formula I-q in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 179
Compounds of the formula I-q in which $R^{5a}$ and $R^{5c}$ are fluorine, $R^{5b}$ is H, the sequence of Y and $R^1$ is Z.1 as defined in table Z and the combination of $R^2$ and $R^3$ for a cornpound corresponds in each case to one row of Table Q.

Table 180
Compounds of the formula I-q in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 181
Compounds of the formula I-q in which $R^{5a}$ and $R^{5b}$ are CF$_3$, $R^{5c}$ is H, the sequence of Y and $R^1$ is Z.1 as defined in table Z and the combination of $R^2$ and $R^3$ for a compound corresponds in each case to one row of Table Q.

Table 182
Compounds of the formula I-q in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 183
Compounds of the formula I-q in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 184
Compounds of the formula I-q in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 185
Compounds of the formula I-q in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 186
Compounds of the formula I-q in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 187
Compounds of the formula I-q in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 188
Compounds of the formula I-r in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 189
Compounds of the formula I-r in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 190
Compounds of the formula I-r in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 191
Compounds of the formula I-r in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 192
Compounds of the formula I-r in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 193
Compounds of the formula I-r in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 194
Compounds of the formula I-r in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 195
Compounds of the formula I-r in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 196
Compounds of the formula I-r in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 197
Compounds of the formula I-r in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 198
Compounds of the formula I-r in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 199
Compounds of the formula I-s in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 200
Compounds of the formula I-s in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 201
Compounds of the formula I-s in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 202
Compounds of the formula I-s in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 203
Compounds of the formula I-s in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 204
Compounds of the formula I-s in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 205
Compounds of the formula I-s in which $R^{5a}$ and $R^{5b}$ are methyl, $R^{5c}$ is H, the sequence of Y and $R^1$ is Z.1 as defined in table Z and the combination of $R^2$ and $R^3$ for a cornpound corresponds in each case to one row of Table Q.

Table 206
Compounds of the formula I-s in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 207
Compounds of the formula I-s in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 208
Compounds of the formula I-s in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 209
Compounds of the formula I-s in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 210
Compounds of the formula I-t in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 211
Compounds of the formula I-t in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 212
Compounds of the formula I-t in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 213
Compounds of the formula I-t in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 214
Compounds of the formula I-t in which $R^{5a}$ and $R^{5c}$ are $CF_3$, $R^{5b}$ is H, the sequence of Y and $R^1$ is Z.1 as defined in Table 215
Compounds of the formula I-t in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 216
Compounds of the formula I-t in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 217
Compounds of the formula I-t in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 218
Compounds of the formula I-t in which $R^{5a}$, $R^{5b}$ and $R^{5b}$ are chlorine, the sequence of Y and $R^1$ is Z.1 as defined in table Z and the combination of $R^2$ and $R^3$ for a compound corresponds in each case to one row of Table Q.

Table 219
Compounds of the formula I-t in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 220
Compounds of the formula I-t in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 221
Compounds of the formula I-u in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 222
Compounds of the formula I-u in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 223
Compounds of the formula I-u in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 224
Compounds of the formula I-u in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 225
Compounds of the formula I-u in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 226
Compounds of the formula I-u in which $R^{5a}$ and $R^{5b}$ are chlorine, $R^{5c}$ is H, the sequence of Y and $R^1$ is Z.1 as defined in table Z and the combination of $R^2$ and $R^3$ for a cornpound corresponds in each case to one row of Table Q.

Table 227
Compounds of the formula I-u in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 228
Compounds of the formula I-u in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 229
Compounds of the formula I-u in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 230
Compounds of the formula I-u in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 231
Compounds of the formula I-u in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 232
Compounds of the formula I-v in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 233
Compounds of the formula I-v in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 234
Compounds of the formula I-v in which $R^{5a}$ and $R^{5c}$ are fluorine, $R^{5b}$ is H, the sequence of Y and $R^1$ is 11 as defined in table Z and the combination of $R^2$ and $R^3$ for a compound corresponds in each case to one row of Table Q.

Table 235
Compounds of the formula I-v in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 236
Compounds of the formula I-v in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 237
Compounds of the formula I-v in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 238
Compounds of the formula I-v in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 239
Compounds of the formula I-v in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 240
Compounds of the formula I-v in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 241
Compounds of the formula I-v in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 242
Compounds of the formula I-v in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 243
Compounds of the formula I-w in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 244
Compounds of the formula I-w in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 245
Compounds of the formula I-w in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 246
Compounds of the formula I-w in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 247
Compounds of the formula I-w in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 248
Compounds of the formula I-w in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 249
Compounds of the formula I-w in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 250
Compounds of the formula I-w in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 251
Compounds of the formula I-w in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 252
Compounds of the formula I-w in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 253
Compounds of the formula I-w in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 254
Compounds of the formula I-x in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 255
Compounds of the formula I-x in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 256
Compounds of the formula I-x in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 257
Compounds of the formula I-x in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 258
Compounds of the formula I-x in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 259
Compounds of the formula I-x in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 260
Compounds of the formula I-x in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 261
Compounds of the formula I-x in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 262
Compounds of the formula I-x in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 263
Compounds of the formula I-x in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 264
Compounds of the formula I-x in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 265
Compounds of the formula I-y in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 266
Compounds of the formula I-y in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 267
Compounds of the formula I-y in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 268
Compounds of the formula I-y in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 269
Compounds of the formula I-y in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 270
Compounds of the formula I-y in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 271
Compounds of the formula I-y in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 272
Compounds of the formula I-y in which $R^{52}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 273
Compounds of the formula I-y in which $R^{52}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 274
Compounds of the formula I-y in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 275
Compounds of the formula I-y in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 276
Compounds of the formula I-z in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 277
Compounds of the formula I-z in which $R^{5a}$ and $R^{5b}$ are bromine, $R^{5b}$ is H, the sequence of Y and $R^1$ is Z.1 as defined in table Z and the combination of $R^2$ and $R^3$ for a compound corresponds in each case to one row of Table Q.

Table 278
Compounds of the formula I-z in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 279
Compounds of the formula I-z in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 280
Compounds of the formula I-z in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 281
Compounds of the formula I-z in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 282
Compounds of the formula I-z in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 283
Compounds of the formula I-z in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 284
Compounds of the formula I-z in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 285
Compounds of the formula I-z in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 286
Compounds of the formula I-z in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 287
Compounds of the formula I-aa in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 288
Compounds of the formula I-aa in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 289
Compounds of the formula I-aa in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 290
Compounds of the formula I-aa in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 291
Compounds of the formula I-aa in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 292
Compounds of the formula I-aa in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 293
Compounds of the formula I-aa in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 294
Compounds of the formula I-aa in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 295
Compounds of the formula I-aa in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 296
Compounds of the formula I-aa in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 297
Compounds of the formula I-aa in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 298
Compounds of the formula I-bb in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 299
Compounds of the formula I-bb in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 300
Compounds of the formula I-bb in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 301
Compounds of the formula I-bb in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 302
Compounds of the formula I-bb in which $R^{5a}$ and $R^{5c}$ are CF3, $R^{5b}$ is H, the sequence of Y and $R^1$ is Z.1 as defined in table Z and the combination of $R^2$ and $R^3$ for a compound corresponds in each case to one row of Table Q.

Table 303
Compounds of the formula I-bb in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 304
Compounds of the formula I-bb in which $R^{5a}$ and $R^{5b}$ are methyl, $R^{5c}$ is H, the sequence of Y and $R^1$ is L1 as defined in table Z and the combination of $R^2$ and $R^3$ for a compound corresponds in each case to one row of Table Q.

Table 305
Compounds of the formula I-bb in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 306
Compounds of the formula I-bb in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 307
Compounds of the formula I-bb in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 308
Compounds of the formula I-bb in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 309
Compounds of the formula I-cc in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 310
Compounds of the formula I-cc in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 311
Compounds of the formula I-cc in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 312
Compounds of the formula I-cc in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 313
Compounds of the formula I-cc in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 314
Compounds of the formula I-cc in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 315
Compounds of the formula I-cc in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 316
Compounds of the formula I-cc in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 317
Compounds of the formula I-cc in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 318
Compounds of the formula I-cc in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 319
Compounds of the formula I-cc in which $R^{5a}$, $R^{5b}$ and $R^{5c}$ are methyl, the sequence of Y and $R^1$ is 11 as defined in table Z and the combination of $R^2$ and $R^3$ for a compound corresponds in each case to one row of Table Q.

Table 320
Compounds of the formula I-dd in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 321
Compounds of the formula I-dd in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 322
Compounds of the formula I-dd in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 323
Compounds of the formula I-dd in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 324
Compounds of the formula I-dd in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 325
Compounds of the formula I-dd in which $R^{5a}$ and $R^{5b}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 326
Compounds of the formula I-dd in which $R^{5a}$ and $R^{5b}$ are methyl, $R^{5b}$ is H, the sequence of Y and $R^1$ is Z.1 as defined in table Z and the combination of $R^2$ and $R^3$ for a compound corresponds in each case to one row of Table Q.

Table 327
Compounds of the formula I-dd in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 328
Compounds of the formula I-dd in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 329
Compounds of the formula I-dd in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 330
Compounds of the formula I-dd in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 331
Compounds of the formula I-ee in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 332
Compounds of the formula I-ee in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 333
Compounds of the formula I-ee in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 334
Compounds of the formula I-ee in which $R^{5a}$ and $R^{5c}$ are methyl, $R^{5b}$ is H, the sequence of Y and $R^1$ is Z.1 as defined in table Z and the combination of $R^2$ and $R^3$ for a cornpound corresponds in each case to one row of Table Q.

Table 335
Compounds of the formula I-ee in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 336
Compounds of the formula I-ee in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 337
Compounds of the formula I-ee in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 338
Compounds of the formula I-ee in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 339
Compounds of the formula I-ee in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 340
Compounds of the formula I-ee in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 341
Compounds of the formula I-ee in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 342
Compounds of the formula I-ff in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 343
Compounds of the formula I-ff in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 344
Compounds of the formula I-ff in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 345
Compounds of the formula I-ff in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 346
Compounds of the formula I-ff in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 347
Compounds of the formula I-ff in which $R^{5a}$ and $R^{5b}$ are chlorine, $R^{5b}$ is H, the sequence of Y and $R^1$ is Z.1 as defined in table Z and the combination of $R^2$ and $R^3$ for a cornpound corresponds in each case to one row of Table Q.

Table 348
Compounds of the formula I-ff in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 349
Compounds of the formula I-ff in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 350
Compounds of the formula I-ff in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 351
Compounds of the formula I-ff in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 352
Compounds of the formula I-ff in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 353
Compounds of the formula I-gg in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 354
Compounds of the formula I-gg in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 355
Compounds of the formula I-gg in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 356
Compounds of the formula I-gg in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 357
Compounds of the formula I-gg in which $R^{5a}$ and $R^{5c}$ are CF$_3$, $R^{5b}$ is H, the sequence of Y and $R^1$ is Z.1 as defined in table Z and the combination of $R^2$ and $R^3$ for a compound corresponds in each case to one row of Table Q.

Table 358
Compounds of the formula I-gg in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 359
Compounds of the formula I-gg in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 360
Compounds of the formula I-gg in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 361
Compounds of the formula I-gg in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 362
Compounds of the formula I-gg in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 363
Compounds of the formula I-gg in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 364
Compounds of the formula I-hh in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 365
Compounds of the formula I-hh in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 366
Compounds of the formula I-hh in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 367
Compounds of the formula I-hh in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 368
Compounds of the formula I-hh in which $R^{5a}$ and $R^{5c}$ are CF$_3$, $R^{5b}$ is H, the sequence of Y and $R^1$ is Z.1 as defined in table Z and the combination of $R^2$ and $R^3$ for a compound corresponds in each case to one row of Table Q.

Table 369
Compounds of the formula I-hh in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 370
Compounds of the formula I-hh in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 371
Compounds of the formula I-hh in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 372
Compounds of the formula I-hh in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 373
Compounds of the formula I-hh in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 374
Compounds of the formula I-hh in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 375
Compounds of the formula I-ii in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 376
Compounds of the formula I-ii in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 377
Compounds of the formula I-ii in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 378
Compounds of the formula I-ii in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 379
Compounds of the formula I-ii in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 380
Compounds of the formula I-ii in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 381
Compounds of the formula I-ii in which $R^{5a}$ and $R^{5b}$ are methyl, $R^{5c}$ is H, the sequence of Y and $R^1$ is Z.1 as defined in table Z and the combination of $R^2$ and $R^3$ for a cornpound corresponds in each case to one row of Table Q.

Table 382
Compounds of the formula I-ii in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 383
Compounds of the formula I-ii in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 384
Compounds of the formula I-ii in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 385
Compounds of the formula I-ii in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 386
Compounds of the formula I-jj in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 387
Compounds of the formula I-jj in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 388
Compounds of the formula I-jj in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 389
Compounds of the formula I-jj in which $R^{5a}$ and $R^{5c}$ are methyl, $R^{5b}$ is H, the sequence of Y and $R^1$ is Z.1 as defined in table Z and the combination of $R^2$ and $R^3$ for a cornpound corresponds in each case to one row of Table Q.

Table 390
Compounds of the formula I-jj in which $R^{5a}$ and $R^{5b}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 391
Compounds of the formula I-jj in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 392
Compounds of the formula I-jj in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 393
Compounds of the formula I-jj in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 394
Compounds of the formula I-jj in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 395
Compounds of the formula I-jj in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 396
Compounds of the formula I-jj in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 397
Compounds of the formula I-kk in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 398
Compounds of the formula I-kk in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 399
Compounds of the formula I-kk in which $R^{5a}$ and $R^{5c}$ are fluorine, $R^{5b}$ is H, the sequence of Y and $R^1$ is Z.1 as defined Table 400
Compounds of the formula I-kk in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 401
Compounds of the formula I-kk in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 402
Compounds of the formula I-kk in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 403
Compounds of the formula I-kk in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 404
Compounds of the formula I-kk in which Rya is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 405
Compounds of the formula I-kk in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 406
Compounds of the formula I-kk in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 407
Compounds of the formula I-kk in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 408
Compounds of the formula I-ll in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 409
Compounds of the formula I-ll in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 410
Compounds of the formula I-ll in which $R^{5a}$ and $R^{5c}$ are fluorine, $R^{5b}$ is H, the sequence of Y and $R^1$ is Z.1 as defined in table Z and the combination of $R^2$ and $R^3$ for a cornpound corresponds in each case to one row of Table Q.

Table 411
Compounds of the formula I-ll in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 412
Compounds of the formula I-ll in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 413
Compounds of the formula I-ll in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 414
Compounds of the formula I-ll in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 415
Compounds of the formula I-ll in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 416
Compounds of the formula I-ll in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 417
Compounds of the formula I-ll in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 418
Compounds of the formula I-ll in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 419
Compounds of the formula I-mm in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 420
Compounds of the formula I-mm in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 421
Compounds of the formula I-mm in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 422
Compounds of the formula I-mm in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 423
Compounds of the formula I-mm in which $R^{5a}$ and $R^{5c}$ are $CF_3$, $R^{5b}$ is H, the sequence of Y and $R^1$ is Z.1 as defined in table Z and the combination of $R^2$ and $R^3$ for a cornpound corresponds in each case to one row of Table Q.

Table 424
Compounds of the formula I-mm in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 425
Compounds of the formula I-mm in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 426
Compounds of the formula I-mm in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 427
Compounds of the formula I-mm in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 428
Compounds of the formula I-mm in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 429
Compounds of the formula I-mm in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 430
Compounds of the formula I-nn in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 431
Compounds of the formula I-nn in which $R^{5a}$ and $R^{5c}$ are bromine, $R^{5c}$ is H, the sequence of Y and $R^1$ is Z.1 as defined in table Z and the combination of $R^2$ and $R^3$ for a compound corresponds in each case to one row of Table Q.

Table 432
Compounds of the formula I-nn in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 433
Compounds of the formula I-nn in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 434
Compounds of the formula I-nn in which $R^{5a}$ and $R^{5c}$ are CF3, $R^{5b}$ is H, the sequence of Y and $R^1$ is Z.1 as defined in table Z and the combination of $R^2$ and $R^3$ for a compound corresponds in each case to one row of Table Q.

Table 435
Compounds of the formula I-nn in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 436
Compounds of the formula I-nn in which $R^{5a}$ and $R^{5b}$ are methyl, $R^{5c}$ is H, the sequence of Y and $R^1$ is Z.1 as defined in table Z and the combination of $R^2$ and $R^3$ for a cornpound corresponds in each case to one row of Table Q.

Table 437
Compounds of the formula I-nn in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 438
Compounds of the formula I-nn in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 439
Compounds of the formula I-nn in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 440
Compounds of the formula I-nn in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 441
Compounds of the formula I-oo in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 442
Compounds of the formula I-oo in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 443
Compounds of the formula I-oo in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 444
Compounds of the formula I-oo in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 445
Compounds of the formula I-oo in which $R^{5a}$ and $R^{5c}$ are CF3, $R^{5b}$ is H, the sequence of Y and $R^1$ is Z.1 as defined in table Z and the combination of $R^2$ and $R^3$ for a compound corresponds in each case to one row of Table Q.

Table 446
Compounds of the formula I-oo in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 447
Compounds of the formula I-oo in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 448
Compounds of the formula I-oo in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 449
Compounds of the formula I-oo in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 450
Compounds of the formula I-oo in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 451
Compounds of the formula I-oo in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 452
Compounds of the formula I-pp in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 453
Compounds of the formula I-pp in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 454
Compounds of the formula I-pp in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 455
Compounds of the formula I-pp in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 456
Compounds of the formula I-pp in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 457
Compounds of the formula I-pp in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 458
Compounds of the formula I-pp in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 459
Compounds of the formula I-pp in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 460
Compounds of the formula I-pp in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 461
Compounds of the formula I-pp in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 462
Compounds of the formula I-pp in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 463
Compounds of the formula I-qq in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 464
Compounds of the formula I-qq in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 465
Compounds of the formula I-qq in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 466
Compounds of the formula I-qq in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 467
Compounds of the formula I-qq in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 468
Compounds of the formula I-qq in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 469
Compounds of the formula I-qq in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 470
Compounds of the formula I-qq in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 471
Compounds of the formula I-qq in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 472
Compounds of the formula I-qq in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 473
Compounds of the formula I-qq in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 474
Compounds of the formula I-rr in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 475
Compounds of the formula I-rr in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 476
Compounds of the formula I-rr in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 477
Compounds of the formula I-rr in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 478
Compounds of the formula I-rr in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 479
Compounds of the formula I-rr in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 480
Compounds of the formula I-rr in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 481
Compounds of the formula I-rr in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 482
Compounds of the formula I-rr in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 483
Compounds of the formula I-rr in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 484
Compounds of the formula I-rr in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 485
Compounds of the formula I-ss in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 486
Compounds of the formula I-ss in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 487
Compounds of the formula I-ss in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 488
Compounds of the formula I-ss in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 489
Compounds of the formula I-ss in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 490
Compounds of the formula I-ss in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 491
Compounds of the formula I-ss in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 492
Compounds of the formula I-ss in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 493
Compounds of the formula I-ss in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 494
Compounds of the formula I-ss in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 495
Compounds of the formula I-ss in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 496
Compounds of the formula I-tt in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 497
Compounds of the formula I-tt in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 498
Compounds of the formula I-tt in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 499
Compounds of the formula I-tt in which $R^{5a}$ and $R^{5c}$ are methyl, $R^{5b}$ is H, the sequence of Y and $R^1$ is Z.1 as defined in table Z and the combination of $R^2$ and $R^3$ for a cornpound corresponds in each case to one row of Table Q.

Table 500
Compounds of the formula I-tt in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 501
Compounds of the formula I-tt in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 502
Compounds of the formula I-tt in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 503
Compounds of the formula I-tt in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 504
Compounds of the formula I-tt in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 505
Compounds of the formula I-tt in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 506
Compounds of the formula I-tt in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 507
Compounds of the formula I-uu in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 508
Compounds of the formula I-uu in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 509
Compounds of the formula I-uu in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 510
Compounds of the formula I-uu in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 511
Compounds of the formula I-uu in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 512
Compounds of the formula I-uu in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 513
Compounds of the formula I-uu in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 514
Compounds of the formula I-uu in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 515
Compounds of the formula I-uu in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 516
Compounds of the formula I-uu in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 517
Compounds of the formula I-uu in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 518
Compounds of the formula I-vv in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 519
Compounds of the formula I-vv in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 520
Compounds of the formula I-vv in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 521
Compounds of the formula I-vv in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 522
Compounds of the formula I-vv in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 523
Compounds of the formula I-w in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 524
Compounds of the formula I-vv in which $R^{58}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 525
Compounds of the formula I-vv in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 526
Compounds of the formula I-vv in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 527
Compounds of the formula I-vv in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 528
Compounds of the formula I-ww in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 529
Compounds of the formula I-ww in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 530
Compounds of the formula I-ww in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 531
Compounds of the formula I-ww in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 532
Compounds of the formula I-ww in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 533
Compounds of the formula I-ww in which $R^{5a}$ and $R^{5b}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 534
Compounds of the formula I-ww in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 535
Compounds of the formula I-ww in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 536
Compounds of the formula I-ww in which $R^{5a}$ is CF3, $R^{5b}$ and $R^{5c}$ are H, the sequence of Y and $R^1$ is Z.1 as defined in table Z and the combination of $R^2$ and $R^3$ for a cornpound corresponds in each case to one row of Table Q.

Table 537
Compounds of the formula I-ww in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 538
Compounds of the formula I-ww in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 539
Compounds of the formula I-ww in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 540
Compounds of the formula I-xx in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 541
Compounds of the formula I-xx in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 542
Compounds of the formula I-xx in which $R^{5a}$ and $R^{5b}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 543
Compounds of the formula I-xx in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 544
Compounds of the formula I-xx in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 545
Compounds of the formula I-xx in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 546
Compounds of the formula I-xx in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 547
Compounds of the formula I-xx in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 548
Compounds of the formula I-xx in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 549
Compounds of the formula I-xx in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 550
Compounds of the formula I-xx in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 551
Compounds of the formula I-yy in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 552
Compounds of the formula I-yy in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 553
Compounds of the formula I-yy in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 554
Compounds of the formula I-yy in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 555
Compounds of the formula I-yy in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 556
Compounds of the formula I-yy in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 557
Compounds of the formula I-yy in which $R^{5a}$ and $R^{5b}$ are methyl, MC is H, the sequence of Y and $R^1$ is Z.1 as defined in table Z and the combination of $R^2$ and $R^3$ for a cornpound corresponds in each case to one row of Table Q.

Table 558
Compounds of the formula I-yy in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 559

Compounds of the formula I-yy in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 560

Compounds of the formula I-yy in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 561

Compounds of the formula I-yy in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Table 562

Compounds of the formula I-zz in which $R^{5a}$ and $R^{5c}$ are chlorine, $R^{5b}$ is H, the sequence of Y and $R^1$ is Z.1 as defined in table Z and the combination of $R^2$ and $R^3$ for a compound corresponds in each case to one row of Table Q.

Table 563

Compounds of the formula I-zz in which $R^{5a}$ and $R^{5c}$ are bromine, $R^{5b}$ is H, the sequence of Y and $R^1$ is Z.1 as defined in table Z and the combination of $R^2$ and $R^3$ for a compound corresponds in each case to one row of Table Q.

Table 564

Compounds of the formula I-zz in which $R^{5a}$ and $R^{5c}$ are fluorine, $R^{5b}$ is H, the sequence of Y and $R^1$ is Z.1 as defined in table Z and the combination of $R^2$ and $R^3$ for a compound corresponds in each case to one row of Table Q.

Table 565

Compounds of the formula I-zz in which $R^{5a}$ and $R^{5c}$ are methyl, $R^{5b}$ is H, the sequence of Y and $R^1$ is Z.1 as defined in table Z and the combination of $R^2$ and $R^3$ for a compound corresponds in each case to one row of Table Q.

Table 566

Compounds of the formula I-zz in which $R^{5a}$ and $R^{5c}$ are $CF_3$, $R^{5b}$ is H, the sequence of Y and $R^1$ is Z.1 as defined in table Z and the combination of $R^2$ and $R^3$ for a compound corresponds in each case to one row of Table Q.

Table 567

Compounds of the formula I-zz in which $R^{5a}$ and $R^{5b}$ are chlorine, $R^{5c}$ is H, the sequence of Y and $R^1$ is Z.1 as defined in table Z and the combination of $R^2$ and $R^3$ for a compound corresponds in each case to one row of Table Q.

Table 568

Compounds of the formula I-zz in which $R^{5a}$ and $R^{5b}$ are methyl, $R^{5c}$ is H, the sequence of Y and $R^1$ is Z.1 as defined in table Z and the combination of $R^2$ and $R^3$ for a compound corresponds in each case to one row of Table Q.

Table 569

Compounds of the formula I-zz in which $R^{5a}$ is CF3, $R^{5b}$ and $R^{5c}$ are H, the sequence of Y and $R^1$ is Z.1 as defined in table Z and the combination of $R^2$ and $R^3$ for a compound corresponds in each case to one row of Table Q.

Table 570

Compounds of the formula I-zz in which $R^{5a}$, $R^{5b}$ and $R^{5c}$ are chlorine, the sequence of Y and $R^1$ is Z.1 as defined in table Z and the combination of $R^2$ and $R^3$ for a compound corresponds in each case to one row of Table Q.

Table 571

Compounds of the formula I-zz in which $R^{5a}$, $R^{5b}$ and $R^{5c}$ are fluorine, the sequence of Y and $R^1$ is Z.1 as defined in table Z and the combination of $R^2$ and $R^3$ for a compound corresponds in each case to one row of Table Q.

Table 572

Compounds of the formula I-zz in which $R^{5a}$, $R^{5b}$ and $R^{5c}$ are methyl, the sequence of Y and $R^1$ is Z.1 as defined in table Z and the combination of $R^2$ and $R^3$ for a compound corresponds in each case to one row of Table Q.

Tables 573-1144

Compounds as defined in table 1 to table 572, but wherein the sequence of Y and $R^1$ is Z.2 as defined in table Z instead of being Z.1.

Tables 1145-1716

Compounds as defined in table 1 to table 572, but wherein the sequence of Y and $R^1$ is Z.3 as defined in table Z instead of being Z.1.

Tables 1717-2288

Compounds as defined in table 1 to table 572, but wherein the sequence of Y and $R^1$ is Z.4 as defined in table Z instead of being Z.1.

Tables 2289-2860

Compounds as defined in table 1 to table 572, but wherein the sequence of Y and $R^1$ is Z.5 as defined in table Z instead of being Z.1.

Tables 2861-3432

Compounds as defined in table 1 to table 572, but wherein the sequence of Y and $R^1$ is Z.6 as defined in table Z instead of being Z.1.

Tables 3433-4004

Compounds as defined in table 1 to table 572, but wherein the sequence of Y and $R^1$ is Z.7 as defined in table Z instead of being Z.1.

Tables 4005-4576

Compounds as defined in table 1 to table 572, but wherein the sequence of Y and $R^1$ is Z.8 as defined in table Z instead of being Z.1.

Tables 4577-5148

Compounds as defined in table 1 to table 572, but wherein the sequence of Y and $R^1$ is Z.9 as defined in table Z instead of being Z.1.

Tables 5149-5720

Compounds as defined in table 1 to table 572, but wherein the sequence of Y and $R^1$ is Z.10 as defined in table Z instead of being Z.1.

Tables 5721-6292

Compounds as defined in table 1 to table 572, but wherein the sequence of Y and $R^1$ is Z.11 as defined in table Z instead of being Z.1.

Tables 6293-6864

Compounds as defined in table 1 to table 572, but wherein the sequence of Y and $R^1$ is Z.12 as defined in table Z instead of being Z.1.

Tables 6865-7436

Compounds as defined in table 1 to table 572, but wherein the sequence of Y and $R^1$ is Z.13 as defined in table Z instead of being Z.1.

Tables 7437-8008

Compounds as defined in table 1 to table 572, but wherein the sequence of Y and $R^1$ is Z.14 as defined in table Z instead of being Z.1.

Tables 8009-8580

Compounds as defined in table 1 to table 572, but wherein the sequence of Y and $R^1$ is Z.15 as defined in table Z instead of being Z.1.

Tables 8581-9152

Compounds as defined in table 1 to table 572, but wherein the sequence of Y and $R^1$ is Z.16 as defined in table Z instead of being Z.1.

Tables 9153-9724
Compounds as defined in table 1 to table 572, but wherein the sequence of Y and $R^1$ is Z.17 as defined in table Z instead of being Z.1.

Tables 9725-10296
Compounds as defined in table 1 to table 572, but wherein the sequence of Y and $R^1$ is Z.18 as defined in table Z instead of being Z.1.

Tables 10297-10868
Compounds as defined in table 1 to table 572, but wherein the sequence of Y and $R^1$ is Z.19 as defined in table Z instead of being Z.1.

Tables 10869-11440
Compounds as defined in table 1 to table 572, but wherein the sequence of Y and $R^1$ is Z.20 as defined in table Z instead of being Z.1.

Tables 11441-12012
Compounds as defined in table 1 to table 572, but wherein the sequence of Y and $R^1$ is Z.21 as defined in table Z instead of being Z.1.

Tables 12013-12584
Compounds as defined in table 1 to table 572, but wherein the sequence of Y and $R^1$ is Z.22 as defined in table Z instead of being Z.1.

Tables 12585-13156
Compounds as defined in table 1 to table 572, but wherein the sequence of Y and $R^1$ is Z.23 as defined in table Z instead of being Z.1.

Tables 13157-13728
Compounds as defined in table 1 to table 572, but wherein the sequence of Y and $R^1$ is Z.24 as defined in table Z instead of being Z.1.

Tables 13729-14300
Compounds as defined in table 1 to table 572, but wherein the sequence of Y and $R^1$ is Z.25 as defined in table Z instead of being Z.1.

Tables 14301-14872
Compounds as defined in table 1 to table 572, but wherein the sequence of Y and $R^1$ is Z.26 as defined in table Z instead of being Z.1.

Tables 14873-15444
Compounds as defined in table 1 to table 572, but wherein the sequence of Y and $R^1$ is Z.27 as defined in table Z instead of being Z.1.

Tables 15445-16016
Compounds as defined in table 1 to table 572, but wherein the sequence of Y and $R^1$ is Z.28 as defined in table Z instead of being 11.

Tables 16017-16588
Compounds as defined in table 1 to table 572, but wherein the sequence of Y and $R^1$ is Z.29 as defined in table Z instead of being Z.1.

Tables 16589-17160
Compounds as defined in table 1 to table 572, but wherein the sequence of Y and $R^1$ is Z.30 as defined in table Z instead of being Z.1.

Tables 17161-17732
Compounds as defined in table 1 to table 572, but wherein the sequence of Y and $R^1$ is Z.31 as defined in table Z instead of being Z.1.

Tables 17733-18304
Compounds as defined in table 1 to table 572, but wherein the sequence of Y and $R^1$ is Z.32 as defined in table Z instead of being Z.1.

Tables 18305-18876
Compounds as defined in table 1 to table 572, but wherein the sequence of Y and $R^1$ is Z.33 as defined in table Z instead of being Z.1.

Tables 18877-19448
Compounds as defined in table 1 to table 572, but wherein the sequence of Y and $R^1$ is 134 as defined in table Z instead of being Z.1.

Tables 19449-20020
Compounds as defined in table 1 to table 572, but wherein the sequence of Y and $R^1$ is Z.35 as defined in table Z instead of being Z.1.

Tables 20021-20592
Compounds as defined in table 1 to table 572, but wherein the sequence of Y and $R^1$ is Z.36 as defined in table Z instead of being Z.1.

Tables 20593-21164
Compounds as defined in table 1 to table 572, but wherein the sequence of Y and $R^1$ is Z.37 as defined in table Z instead of being Z.1.

Tables 21165-21736
Compounds as defined in table 1 to table 572, but wherein the sequence of Y and $R^1$ is Z.38 as defined in table Z instead of being Z.1.

Tables 21737-22308
Compounds as defined in table 1 to table 572, but wherein the sequence of Y and $R^1$ is Z.39 as defined in table Z instead of being Z.1.

Tables 22309-22880
Compounds as defined in table 1 to table 572, but wherein the sequence of Y and $R^1$ is 140 as defined in table Z instead of being Z.1.

Tables 22881-23452
Compounds as defined in table 1 to table 572, but wherein the sequence of Y and $R^1$ is Z.41 as defined in table Z instead of being Z.1.

Tables 23453-24024
Compounds as defined in table 1 to table 572, but wherein the sequence of Y and $R^1$ is Z.42 as defined in table Z instead of being Z.1.

Tables 24025-24596
Compounds as defined in table 1 to table 572, but wherein the sequence of Y and $R^1$ is Z.43 as defined in table Z instead of being Z.1.

Tables 24597-25168
Compounds as defined in table 1 to table 572, but wherein the sequence of Y and $R^1$ is Z.44 as defined in table Z instead of being Z.1.

Tables 25169-25740
Compounds as defined in table 1 to table 572, but wherein the sequence of Y and $R^1$ is Z.45 as defined in table Z instead of being Z.1.

Tables 25741-26312
Compounds as defined in table 1 to table 572, but wherein the sequence of Y and $R^1$ is Z.46 as defined in table Z instead of being Z.1.

Tables 26313-26884
Compounds as defined in table 1 to table 572, but wherein the sequence of Y and $R^1$ is Z.47 as defined in table Z instead of being Z.1.

Tables 26885-27456
Compounds as defined in table 1 to table 572, but wherein the sequence of Y and $R^1$ is Z.48 as defined in table Z instead of being Z.1.

Tables 27456-28028
Compounds as defined in table 1 to table 572, but wherein the sequence of Y and $R^1$ is Z.49 as defined in table Z instead of being Z.1.

Tables 28029-28600
Compounds as defined in table 1 to table 572, but wherein the sequence of Y and $R^1$ is Z.50 as defined in table Z instead of being Z.1.

Tables 28601-29172
Compounds as defined in table 1 to table 572, but wherein the sequence of Y and $R^1$ is Z.51 as defined in table Z instead of being Z.1.

Tables 29173-29744
Compounds as defined in table 1 to table 572, but wherein the sequence of Y and $R^1$ is Z.52 as defined in table Z instead of being Z.1.

Tables 29745-30316
Compounds as defined in table 1 to table 572, but wherein the sequence of Y and $R^1$ is Z.53 as defined in table Z instead of being Z.1.

Tables 30317-30888
Compounds as defined in table 1 to table 572, but wherein the sequence of Y and $R^1$ is Z.54 as defined in table Z instead of being Z.1.

Tables 30889-31460
Compounds as defined in table 1 to table 572, but wherein the sequence of Y and $R^1$ is Z.55 as defined in table Z instead of being Z.1.

Tables 31461-32032
Compounds as defined in table 1 to table 572, but wherein the sequence of Y and $R^1$ is Z.56 as defined in table Z instead of being Z.1.

Tables 32033-32604
Compounds as defined in table 1 to table 572, but wherein the sequence of Y and $R^1$ is Z.57 as defined in table Z instead of being Z.1.

Tables 32605-33176
Compounds as defined in table 1 to table 572, but wherein the sequence of Y and $R^1$ is Z.58 as defined in table Z instead of being Z.1.

Tables 33177-33748
Compounds as defined in table 1 to table 572, but wherein the sequence of Y and $R^1$ is Z.59 as defined in table Z instead of being Z.1.

Tables 33749-34320
Compounds as defined in table 1 to table 572, but wherein the sequence of Y and $R^1$ is Z.60 as defined in table Z instead of being Z.1.

Tables 34321-34892
Compounds as defined in table 1 to table 572, but wherein the sequence of Y and $R^1$ is Z.61 as defined in table Z instead of being Z.1.

Tables 34893-35464
Compounds as defined in table 1 to table 572, but wherein the sequence of Y and $R^1$ is Z.62 as defined in table Z instead of being Z.1.

Tables 35465-36036
Compounds as defined in table 1 to table 572, but wherein the sequence of Y and $R^1$ is Z.63 as defined in table Z instead of being Z.1.

Tables 36037-36608
Compounds as defined in table 1 to table 572, but wherein the sequence of Y and $R^1$ is Z.64 as defined in table Z instead of being Z.1.

Tables 36609-37180
Compounds as defined in table 1 to table 572, but wherein the sequence of Y and $R^1$ is Z.65 as defined in table Z instead of being Z.1.

Tables 37181-37752
Compounds as defined in table 1 to table 572, but wherein the sequence of Y and $R^1$ is 166 as defined in table Z instead of being Z.1.

Tables 37753-38324
Compounds as defined in table 1 to table 572, but wherein the sequence of Y and $R^1$ is Z.67 as defined in table Z instead of being Z.1.

Tables 38325-38896
Compounds as defined in table 1 to table 572, but wherein the sequence of Y and $R^1$ is Z.68 as defined in table Z instead of being Z.1.

Tables 38897-39468
Compounds as defined in table 1 to table 572, but wherein the sequence of Y and $R^1$ is Z.69 as defined in table Z instead of being Z.1.

Tables 39469-40040
Compounds as defined in table 1 to table 572, but wherein the sequence of Y and $R^1$ is Z.70 as defined in table Z instead of being Z.1.

Tables 40041-40612
Compounds as defined in table 1 to table 572, but wherein the sequence of Y and $R^1$ is Z.71 as defined in table Z instead of being Z.1.

Tables 40613-41184
Compounds as defined in table 1 to table 572, but wherein the sequence of Y and $R^1$ is Z.72 as defined in table Z instead of being Z.1.

Tables 41185-41756
Compounds as defined in table 1 to table 572, but wherein the sequence of Y and $R^1$ is Z.73 as defined in table Z instead of being Z.1.

Tables 41757-42328
Compounds as defined in table 1 to table 572, but wherein the sequence of Y and $R^1$ is Z.74 as defined in table Z instead of being Z.1.

Tables 42329-42900
Compounds as defined in table 1 to table 572, but wherein the sequence of Y and $R^1$ is Z.75 as defined in table Z instead of being Z.1.

Tables 42901-43472
Compounds as defined in table 1 to table 572, but wherein the sequence of Y and $R^1$ is Z.76 as defined in table Z instead of being Z.1.

Tables 43473-44044
Compounds as defined in table 1 to table 572, but wherein the sequence of Y and $R^1$ is Z.77 as defined in table Z instead of being Z.1.

Tables 44045-44616
Compounds as defined in table 1 to table 572, but wherein the sequence of Y and $R^1$ is Z.78 as defined in table Z instead of being Z.1.

Tables 44617-45188
Compounds as defined in table 1 to table 572, but wherein the sequence of Y and $R^1$ is Z.79 as defined in table Z instead of being Z.1.

Tables 45189-45760
Compounds as defined in table 1 to table 572, but wherein the sequence of Y and $R^1$ is Z.80 as defined in table Z instead of being Z.1.

Tables 45761-46332
Compounds as defined in table 1 to table 572, but wherein the sequence of Y and $R^1$ is Z.81 as defined in table Z instead of being Z.1.

Tables 46333-46904
Compounds as defined in table 1 to table 572, but wherein the sequence of Y and $R^1$ is Z.82 as defined in table Z instead of being Z.1.

Tables 46905-47476
Compounds as defined in table 1 to table 572, but wherein the sequence of Y and $R^1$ is Z.83 as defined in table Z instead of being Z.1.
Tables 47477-48048
Compounds as defined in table 1 to table 572, but wherein the sequence of Y and $R^1$ is Z.84 as defined in table Z instead of being Z.1.
Tables 48049-48620
Compounds as defined in table 1 to table 572, but wherein the sequence of Y and $R^1$ is Z.85 as defined in table Z instead of being Z.1.
Tables 48621-49192
Compounds as defined in table 1 to table 572, but wherein the sequence of Y and $R^1$ is Z.86 as defined in table Z instead of being Z.1.
Tables 49193-49764
Compounds as defined in table 1 to table 572, but wherein the sequence of Y and $R^1$ is Z.87 as defined in table Z instead of being Z.1.
Tables 49765-50336
Compounds as defined in table 1 to table 572, but wherein the sequence of Y and $R^1$ is Z.88 as defined in table Z instead of being Z.1.
Tables 50337-50908
Compounds as defined in table 1 to table 572, but wherein the sequence of Y and $R^1$ is Z.89 as defined in table Z instead of being Z.1.
Tables 50909-51480
Compounds as defined in table 1 to table 572, but wherein the sequence of Y and $R^1$ is 190 as defined in table Z instead of being Z.1.
Tables 51481-52052
Compounds as defined in table 1 to table 572, but wherein the sequence of Y and $R^1$ is Z.91 as defined in table Z instead of being Z.1.
Tables 52053-52624
Compounds as defined in table 1 to table 572, but wherein the sequence of Y and $R^1$ is Z.92 as defined in table Z instead of being Z.1.
Tables 52625-53196
Compounds as defined in table 1 to table 572, but wherein the sequence of Y and $R^1$ is Z.93 as defined in table Z instead of being Z.1.
Tables 53197-53768
Compounds as defined in table 1 to table 572, but wherein the sequence of Y and $R^1$ is Z.94 as defined in table Z instead of being Z.1.
Tables 53769-54340
Compounds as defined in table 1 to table 572, but wherein the sequence of Y and $R^1$ is Z.95 as defined in table Z instead of being Z.1.
Tables 54341-54912
Compounds as defined in table 1 to table 572, but wherein the sequence of Y and $R^1$ is Z.96 as defined in table Z instead of being Z.1.
Tables 54913-55484
Compounds as defined in table 1 to table 572, but wherein the sequence of Y and $R^1$ is Z.97 as defined in table Z instead of being Z.1.
Tables 55485-56056
Compounds as defined in table 1 to table 572, but wherein the sequence of Y and $R^1$ is Z.98 as defined in table Z instead of being Z.1.
Tables 56057-56628
Compounds as defined in table 1 to table 572, but wherein the sequence of Y and $R^1$ is Z.99 as defined in table Z instead of being Z.1.
Tables 56629-57200
Compounds as defined in table 1 to table 572, but wherein the sequence of Y and $R^1$ is Z.100 as defined in table Z instead of being Z.1.
Tables 57201-57772
Compounds as defined in table 1 to table 572, but wherein the sequence of Y and $R^1$ is Z.101 as defined in table Z instead of being Z.1.
Tables 57773-58344
Compounds as defined in table 1 to table 572, but wherein the sequence of Y and $R^1$ is Z.102 as defined in table Z instead of being Z.1.
Tables 58345-58916
Compounds as defined in table 1 to table 572, but wherein the sequence of Y and $R^1$ is Z.103 as defined in table Z instead of being Z.1.
Tables 58917-59488
Compounds as defined in table 1 to table 572, but wherein the sequence of Y and $R^1$ is Z.104 as defined in table Z instead of being Z.1.
Tables 59489-60060
Compounds as defined in table 1 to table 572, but wherein the sequence of Y and $R^1$ is Z.105 as defined in table Z instead of being Z.1.
Tables 60061-60632
Compounds as defined in table 1 to table 572, but wherein the sequence of Y and $R^1$ is Z.106 as defined in table Z instead of being Z.1.
Tables 60633-61204
Compounds as defined in table 1 to table 572, but wherein the sequence of Y and $R^1$ is Z.107 as defined in table Z instead of being Z.1.
Tables 61205-61776
Compounds as defined in table 1 to table 572, but wherein the sequence of Y and $R^1$ is Z.108 as defined in table Z instead of being Z.1.
Tables 61777-62348
Compounds as defined in table 1 to table 572, but wherein the sequence of Y and $R^1$ is Z.109 as defined in table Z instead of being Z.1.
Tables 62349-62920
Compounds as defined in table 1 to table 572, but wherein the sequence of Y and $R^1$ is Z.110 as defined in table Z instead of being Z.1.
Tables 62921-63492
Compounds as defined in table 1 to table 572, but wherein the sequence of Y and $R^1$ is Z.111 as defined in table Z instead of being Z.1.
Tables 63493-64064
Compounds as defined in table 1 to table 572, but wherein the sequence of Y and $R^1$ is Z.112 as defined in table Z instead of being Z.1.
Tables 64065-64636
Compounds as defined in table 1 to table 572, but wherein the sequence of Y and $R^1$ is Z.113 as defined in table Z instead of being Z.1.
Tables 64637-65208
Compounds as defined in table 1 to table 572, but wherein the sequence of Y and $R^1$ is Z.114 as defined in table Z instead of being Z.1.
Tables 65209-65780
Compounds as defined in table 1 to table 572, but wherein the sequence of Y and $R^1$ is Z.115 as defined in table Z instead of being Z.1.

Tables 65781-66352
Compounds as defined in table 1 to table 572, but wherein the sequence of Y and R$^1$ is Z.116 as defined in table Z instead of being Z.1.
Tables 66353-66924
Compounds as defined in table 1 to table 572, but wherein the sequence of Y and R$^1$ is Z.117 as defined in table Z instead of being Z.1.
Tables 66925-67496
Compounds as defined in table 1 to table 572, but wherein the sequence of Y and R$^1$ is Z.118 as defined in table Z instead of being Z.1.
Tables 67497-68068
Compounds as defined in table 1 to table 572, but wherein the sequence of Y and R$^1$ is Z.119 as defined in table Z instead of being Z.1.
Tables 68069-68640
Compounds as defined in table 1 to table 572, but wherein the sequence of Y and R$^1$ is Z.120 as defined in table Z instead of being Z.1.
Tables 68641-69212
Compounds as defined in table 1 to table 572, but wherein the sequence of Y and R$^1$ is Z.121 as defined in table Z instead of being Z.1.
Tables 69213-69784
Compounds as defined in table 1 to table 572, but wherein the sequence of Y and R$^1$ is Z.122 as defined in table Z instead of being 11.
Tables 69785-70356
Compounds as defined in table 1 to table 572, but wherein the sequence of Y and R$^1$ is Z.123 as defined in table Z instead of being Z.1.
Tables 70357-70928
Compounds as defined in table 1 to table 572, but wherein the sequence of Y and R$^1$ is Z.124 as defined in table Z instead of being Z.1.
Tables 70929-71500
Compounds as defined in table 1 to table 572, but wherein the sequence of Y and R$^1$ is 1125 as defined in table Z instead of being Z.1.
Tables 71501-72072
Compounds as defined in table 1 to table 572, but wherein the sequence of Y and R$^1$ is Z.126 as defined in table Z instead of being Z.1.
Tables 72073-72644
Compounds as defined in table 1 to table 572, but wherein the sequence of Y and R$^1$ is Z.127 as defined in table Z instead of being Z.1.
Tables 72645-73216
Compounds as defined in table 1 to table 572, but wherein the sequence of Y and R$^1$ is Z.128 as defined in table Z instead of being Z.1.
Tables 73217-73788
Compounds as defined in table 1 to table 572, but wherein the sequence of Y and R$^1$ is Z.129 as defined in table Z instead of being Z.1.
Tables 73789-74360
Compounds as defined in table 1 to table 572, but wherein the sequence of Y and R$^1$ is Z.130 as defined in table Z instead of being Z.1.
Tables 74361-74932
Compounds as defined in table 1 to table 572, but wherein the sequence of Y and R$^1$ is 1131 as defined in table Z instead of being Z.1.
Tables 74933-75504
Compounds as defined in table 1 to table 572, but wherein the sequence of Y and R$^1$ is Z.132 as defined in table Z instead of being Z.1.
Tables 75505-76076
Compounds as defined in table 1 to table 572, but wherein the sequence of Y and R$^1$ is Z.133 as defined in table Z instead of being Z.1.
Tables 76077-76648
Compounds as defined in table 1 to table 572, but wherein the sequence of Y and R$^1$ is Z.134 as defined in table Z instead of being Z.1.
Tables 76649-77220
Compounds as defined in table 1 to table 572, but wherein the sequence of Y and R$^1$ is Z.135 as defined in table Z instead of being Z.1.
Tables 77221-77792
Compounds as defined in table 1 to table 572, but wherein the sequence of Y and R$^1$ is Z.136 as defined in table Z instead of being Z.1.
Tables 77793-78364
Compounds as defined in table 1 to table 572, but wherein the sequence of Y and R$^1$ is Z.137 as defined in table Z instead of being Z.1.
Tables 78365-78936
Compounds as defined in table 1 to table 572, but wherein the sequence of Y and R$^1$ is Z.138 as defined in table Z instead of being Z.1.
Tables 78937-79508
Compounds as defined in table 1 to table 572, but wherein the sequence of Y and R$^1$ is Z.139 as defined in table Z instead of being Z.1.
Tables 79509-80080
Compounds as defined in table 1 to table 572, but wherein the sequence of Y and R$^1$ is Z.140 as defined in table Z instead of being Z.1.
Tables 80081-80652
Compounds as defined in table 1 to table 572, but wherein the sequence of Y and R$^1$ is Z.141 as defined in table Z instead of being Z.1.
Tables 80653-81224
Compounds as defined in table 1 to table 572, but wherein the sequence of Y and R$^1$ is Z.142 as defined in table Z instead of being Z.1.
Tables 81225-81796
Compounds as defined in table 1 to table 572, but wherein the sequence of Y and R$^1$ is Z.143 as defined in table Z instead of being Z.1.
Tables 81797-82368
Compounds as defined in table 1 to table 572, but wherein the sequence of Y and R$^1$ is Z.144 as defined in table Z instead of being Z.1.
Tables 82369-82940
Compounds as defined in table 1 to table 572, but wherein the sequence of Y and R$^1$ is Z.145 as defined in table Z instead of being Z.1.
Tables 82941-83512
Compounds as defined in table 1 to table 572, but wherein the sequence of Y and R$^1$ is Z.146 as defined in table Z instead of being 11.
Tables 83513-84084
Compounds as defined in table 1 to table 572, but wherein the sequence of Y and R$^1$ is Z.147 as defined in table Z instead of being Z.1.
Tables 84085-84656
Compounds as defined in table 1 to table 572, but wherein the sequence of Y and R$^1$ is Z.148 as defined in table Z instead of being Z.1.

Tables 84657-85228
Compounds as defined in table 1 to table 572, but wherein the sequence of Y and R$^1$ is Z.149 as defined in table Z instead of being Z.1.
Tables 85229-85800
Compounds as defined in table 1 to table 572, but wherein the sequence of Y and R$^1$ is Z.150 as defined in table Z instead of being Z.1.
Tables 85801-86372
Compounds as defined in table 1 to table 572, but wherein the sequence of Y and R$^1$ is Z.151 as defined in table Z instead of being Z.1.
Tables 86373-86944
Compounds as defined in table 1 to table 572, but wherein the sequence of Y and R$^1$ is Z.152 as defined in table Z instead of being Z.1.
Tables 86945-87516
Compounds as defined in table 1 to table 572, but wherein the sequence of Y and R$^1$ is Z.153 as defined in table Z instead of being Z.1.
Tables 87517-88088
Compounds as defined in table 1 to table 572, but wherein the sequence of Y and R$^1$ is Z.154 as defined in table Z instead of being Z.1.
Tables 88089-88660
Compounds as defined in table 1 to table 572, but wherein the sequence of Y and R$^1$ is Z.155 as defined in table Z instead of being Z.1.
Tables 88661-89232
Compounds as defined in table 1 to table 572, but wherein the sequence of Y and R$^1$ is Z.156 as defined in table Z instead of being Z.1.
Tables 89233-89804
Compounds as defined in table 1 to table 572, but wherein the sequence of Y and R$^1$ is Z.157 as defined in table Z instead of being Z.1.
Tables 89805-90376
Compounds as defined in table 1 to table 572, but wherein the sequence of Y and R$^1$ is Z.158 as defined in table Z instead of being Z.1.
Tables 90377-90948
Compounds as defined in table 1 to table 572, but wherein the sequence of Y and R$^1$ is Z.159 as defined in table Z instead of being Z.1.
Tables 90949-91520
Compounds as defined in table 1 to table 572, but wherein the sequence of Y and R$^1$ is Z.160 as defined in table Z instead of being Z.1.
Tables 91521-92092
Compounds as defined in table 1 to table 572, but wherein the sequence of Y and R$^1$ is Z.161 as defined in table Z instead of being Z.1.
Tables 92093-92664
Compounds as defined in table 1 to table 572, but wherein the sequence of Y and R$^1$ is Z.162 as defined in table Z instead of being Z.1.
Tables 92665-93236
Compounds as defined in table 1 to table 572, but wherein the sequence of Y and R$^1$ is Z.163 as defined in table Z instead of being Z.1.
Tables 93237-93808
Compounds as defined in table 1 to table 572, but wherein the sequence of Y and R$^1$ is Z.164 as defined in table Z instead of being Z.1.
Tables 93809-94380
Compounds as defined in table 1 to table 572, but wherein the sequence of Y and R$^1$ is Z.165 as defined in table Z instead of being 11.
Tables 94381-94952
Compounds as defined in table 1 to table 572, but wherein the sequence of Y and R$^1$ is Z.166 as defined in table Z instead of being Z.1.
Tables 94953-95524
Compounds as defined in table 1 to table 572, but wherein the sequence of Y and R$^1$ is Z.167 as defined in table Z instead of being Z.1.
Tables 95525-96096
Compounds as defined in table 1 to table 572, but wherein the sequence of Y and R$^1$ is Z.168 as defined in table Z instead of being Z.1.
Tables 96097-96668
Compounds as defined in table 1 to table 572, but wherein the sequence of Y and R$^1$ is Z.169 as defined in table Z instead of being Z.1.
Tables 96669-97240
Compounds as defined in table 1 to table 572, but wherein the sequence of Y and R$^1$ is Z.170 as defined in table Z instead of being Z.1.
Tables 97241-97812
Compounds as defined in table 1 to table 572, but wherein the sequence of Y and R$^1$ is Z.171 as defined in table Z instead of being Z.1.
Tables 97813-98384
Compounds as defined in table 1 to table 572, but wherein the sequence of Y and R$^1$ is Z.172 as defined in table Z instead of being Z.1.
Tables 98385-98956
Compounds as defined in table 1 to table 572, but wherein the sequence of Y and R$^1$ is Z.173 as defined in table Z instead of being Z.1.
Tables 98957-99528
Compounds as defined in table 1 to table 572, but wherein the sequence of Y and R$^1$ is Z.174 as defined in table Z instead of being Z.1.
Tables 99528-100100
Compounds as defined in table 1 to table 572, but wherein the sequence of Y and R$^1$ is Z.175 as defined in table Z instead of being Z.1.
Tables 100101-100672
Compounds as defined in table 1 to table 572, but wherein the sequence of Y and R$^1$ is Z.176 as defined in table Z instead of being Z.1.
Tables 100673-101244
Compounds as defined in table 1 to table 572, but wherein the sequence of Y and R$^1$ is Z.177 as defined in table Z instead of being Z.1.
Tables 101245-101816
Compounds as defined in table 1 to table 572, but wherein the sequence of Y and R$^1$ is Z.178 as defined in table Z instead of being Z.1.
Tables 101817-102388
Compounds as defined in table 1 to table 572, but wherein the sequence of Y and R$^1$ is Z.179 as defined in table Z instead of being Z.1.
Tables 102389-102960
Compounds as defined in table 1 to table 572, but wherein the sequence of Y and R$^1$ is Z.180 as defined in table Z instead of being Z.1.
Tables 102961-103532
Compounds as defined in table 1 to table 572, but wherein the sequence of Y and R$^1$ is Z.181 as defined in table Z instead of being Z.1.

Tables 103533-104104
Compounds as defined in table 1 to table 572, but wherein the sequence of Y and $R^1$ is Z.182 as defined in table Z instead of being Z.1.

Tables 104105-104676
Compounds as defined in table 1 to table 572, but wherein the sequence of Y and $R^1$ is Z.183 as defined in table Z instead of being Z.1.

Tables 104677-105248
Compounds as defined in table 1 to table 572, but wherein the sequence of Y and $R^1$ is Z.184 as defined in table Z instead of being Z.1.

Tables 105249-105820
Compounds as defined in table 1 to table 572, but wherein the sequence of Y and $R^1$ is Z.185 as defined in table Z instead of being Z.1.

Tables 105821-106392
Compounds as defined in table 1 to table 572, but wherein the sequence of Y and $R^1$ is Z.186 as defined in table Z instead of being Z.1.

Tables 106393-106964
Compounds as defined in table 1 to table 572, but wherein the sequence of Y and $R^1$ is Z.187 as defined in table Z instead of being Z.1.

Tables 106965-107536
Compounds as defined in table 1 to table 572, but wherein the sequence of Y and $R^1$ is Z.188 as defined in table Z instead of being Z.1.

Tables 107537-108108
Compounds as defined in table 1 to table 572, but wherein the sequence of Y and $R^1$ is Z.189 as defined in table Z instead of being Z.1.

Tables 108109-108680
Compounds as defined in table 1 to table 572, but wherein the sequence of Y and $R^1$ is Z.190 as defined in table Z instead of being Z.1.

Tables 108681-109252
Compounds as defined in table 1 to table 572, but wherein the sequence of Y and $R^1$ is Z.191 as defined in table Z instead of being Z.1.

Tables 109253-109824
Compounds as defined in table 1 to table 572, but wherein the sequence of Y and $R^1$ is Z.192 as defined in table Z instead of being Z.1.

Tables 109825-110396
Compounds as defined in table 1 to table 572, but wherein the sequence of Y and $R^1$ is Z.193 as defined in table Z instead of being Z.1.

Tables 110397-110968
Compounds as defined in table 1 to table 572, but wherein the sequence of Y and $R^1$ is Z.194 as defined in table Z instead of being Z.1.

Tables 110969-111540
Compounds as defined in table 1 to table 572, but wherein the sequence of Y and $R^1$ is Z.195 as defined in table Z instead of being Z.1.

Tables 111541-112112
Compounds as defined in table 1 to table 572, but wherein the sequence of Y and $R^1$ is Z.196 as defined in table Z instead of being Z.1.

Tables 112113-112684
Compounds as defined in table 1 to table 572, but wherein the sequence of Y and $R^1$ is Z.197 as defined in table Z instead of being Z.1.

Tables 112685-113256
Compounds as defined in table 1 to table 572, but wherein the sequence of Y and $R^1$ is Z.198 as defined in table Z instead of being Z.1.

Tables 113257-113828
Compounds as defined in table 1 to table 572, but wherein the sequence of Y and $R^1$ is Z.199 as defined in table Z instead of being Z.1.

Tables 113829-114400
Compounds as defined in table 1 to table 572, but wherein the sequence of Y and $R^1$ is Z.200 as defined in table Z instead of being Z.1.

Tables 114400-114972
Compounds as defined in table 1 to table 572, but wherein the sequence of Y and $R^1$ is Z.201 as defined in table Z instead of being Z.1.

Tables 114973-115544
Compounds as defined in table 1 to table 572, but wherein the sequence of Y and $R^1$ is Z.202 as defined in table Z instead of being Z.1.

Tables 115545-116116
Compounds as defined in table 1 to table 572, but wherein the sequence of Y and $R^1$ is Z.203 as defined in table Z instead of being Z.1.

Tables 116117-116688
Compounds as defined in table 1 to table 572, but wherein the sequence of Y and $R^1$ is Z.204 as defined in table Z instead of being Z.1.

Tables 116689-117260
Compounds as defined in table 1 to table 572, but wherein the sequence of Y and $R^1$ is Z.205 as defined in table Z instead of being Z.1.

Tables 117261-117832
Compounds as defined in table 1 to table 572, but wherein the sequence of Y and $R^1$ is Z.206 as defined in table Z instead of being Z.1.

Tables 117833-118404
Compounds as defined in table 1 to table 572, but wherein the sequence of Y and $R^1$ is Z.207 as defined in table Z instead of being Z.1.

Tables 118405-118976
Compounds as defined in table 1 to table 572, but wherein the sequence of Y and $R^1$ is Z.208 as defined in table Z instead of being Z.1.

Tables 118977-119548
Compounds as defined in table 1 to table 572, but wherein the sequence of Y and $R^1$ is Z.209 as defined in table Z instead of being Z.1.

Tables 119549-120120
Compounds as defined in table 1 to table 572, but wherein the sequence of Y and $R^1$ is Z.210 as defined in table Z instead of being Z.1.

Tables 120121-120692
Compounds as defined in table 1 to table 572, but wherein the sequence of Y and $R^1$ is Z.211 as defined in table Z instead of being Z.1.

Tables 120693-121264
Compounds as defined in table 1 to table 572, but wherein the sequence of Y and $R^1$ is Z.212 as defined in table Z instead of being Z.1.

Tables 121265-121836
Compounds as defined in table 1 to table 572, but wherein the sequence of Y and $R^1$ is Z.213 as defined in table Z instead of being Z.1.

Tables 121837-122408
Compounds as defined in table 1 to table 572, but wherein the sequence of Y and $R^1$ is Z.214 as defined in table Z instead of being Z.1.

Tables 122409-122980
Compounds as defined in table 1 to table 572, but wherein the sequence of Y and $R^1$ is Z.215 as defined in table Z instead of being Z.1.

Tables 122981-123552
Compounds as defined in table 1 to table 572, but wherein the sequence of Y and $R^1$ is Z.216 as defined in table Z instead of being Z.1.

Tables 123553124124
Compounds as defined in table 1 to table 572, but wherein the sequence of Y and $R^1$ is Z.217 as defined in table Z instead of being Z.1.

Tables 124125-124696
Compounds as defined in table 1 to table 572, but wherein the sequence of Y and $R^1$ is Z.218 as defined in table Z instead of being Z.1.

Tables 124697-125268
Compounds as defined in table 1 to table 572, but wherein the sequence of Y and $R^1$ is Z.219 as defined in table Z instead of being Z.1.

Tables 125269-125840
Compounds as defined in table 1 to table 572, but wherein the sequence of Y and $R^1$ is Z.220 as defined in table Z instead of being Z.1.

Tables 125841-126412
Compounds as defined in table 1 to table 572, but wherein the sequence of Y and $R^1$ is Z.221 as defined in table Z instead of being Z.1.

Tables 126413-126984
Compounds as defined in table 1 to table 572, but wherein the sequence of Y and $R^1$ is Z.222 as defined in table Z instead of being Z.1.

Tables 126985-127556
Compounds as defined in table 1 to table 572, but wherein the sequence of Y and $R^1$ is Z.223 as defined in table Z instead of being Z.1.

Tables 127557-128128
Compounds as defined in table 1 to table 572, but wherein the sequence of Y and $R^1$ is Z.224 as defined in table Z instead of being Z.1.

Tables 128129-128700
Compounds as defined in table 1 to table 572, but wherein the sequence of Y and $R^1$ is Z.225 as defined in table Z instead of being Z.1.

Tables 128701-129272
Compounds as defined in table 1 to table 572, but wherein the sequence of Y and $R^1$ is Z.226 as defined in table Z instead of being Z.1.

Tables 129273-129844
Compounds as defined in table 1 to table 572, but wherein the sequence of Y and $R^1$ is Z.227 as defined in table Z instead of being Z.1.

Tables 129845-130416
Compounds as defined in table 1 to table 572, but wherein the sequence of Y and $R^1$ is Z.228 as defined in table Z instead of being Z.1.

Tables 130417-130988
Compounds as defined in table 1 to table 572, but wherein the sequence of Y and $R^1$ is Z.229 as defined in table Z instead of being Z.1.

Tables 130989-131560
Compounds as defined in table 1 to table 572, but wherein the sequence of Y and $R^1$ is Z.230 as defined in table Z instead of being Z.1.

Tables 131561-132132
Compounds as defined in table 1 to table 572, but wherein the sequence of Y and $R^1$ is Z.231 as defined in table Z instead of being Z.1.

Tables 132133-132704
Compounds as defined in table 1 to table 572, but wherein the sequence of Y and $R^1$ is Z.232 as defined in table Z instead of being Z.1.

Tables 132705-133276
Compounds as defined in table 1 to table 572, but wherein the sequence of Y and $R^1$ is Z.233 as defined in table Z instead of being Z.1.

Tables 133277-133848
Compounds as defined in table 1 to table 572, but wherein the sequence of Y and $R^1$ is Z.234 as defined in table Z instead of being Z.1.

Tables 133849-134420
Compounds as defined in table 1 to table 572, but wherein the sequence of Y and $R^1$ is Z.235 as defined in table Z instead of being Z.1.

Tables 134421-134992
Compounds as defined in table 1 to table 572, but wherein the sequence of Y and $R^1$ is Z.236 as defined in table Z instead of being Z.1.

Tables 134993-135564
Compounds as defined in table 1 to table 572, but wherein the sequence of Y and $R^1$ is Z.237 as defined in table Z instead of being Z.1.

Tables 135565-136136
Compounds as defined in table 1 to table 572, but wherein the sequence of Y and $R^1$ is Z.238 as defined in table Z instead of being Z.1.

Tables 136137-136708
Compounds as defined in table 1 to table 572, but wherein the sequence of Y and $R^1$ is Z.239 as defined in table Z instead of being Z.1.

Tables 136709-137280
Compounds as defined in table 1 to table 572, but wherein the sequence of Y and $R^1$ is Z.240 as defined in table Z instead of being Z.1.

Tables 137281-137852
Compounds as defined in table 1 to table 572, but wherein the sequence of Y and $R^1$ is Z.241 as defined in table Z instead of being Z.1.

Tables 137853-138424
Compounds as defined in table 1 to table 572, but wherein the sequence of Y and $R^1$ is Z.242 as defined in table Z instead of being Z.1.

Tables 138425-138996
Compounds as defined in table 1 to table 572, but wherein the sequence of Y and $R^1$ is Z.243 as defined in table Z instead of being Z.1.

Tables 138997-139568
Compounds as defined in table 1 to table 572, but wherein the sequence of Y and $R^1$ is Z.244 as defined in table Z instead of being Z.1.

Tables 139569-140140
Compounds as defined in table 1 to table 572, but wherein the sequence of Y and $R^1$ is Z.245 as defined in table Z instead of being Z.1.

Tables 140141-140712
Compounds as defined in table 1 to table 572, but wherein the sequence of Y and $R^1$ is Z.246 as defined in table Z instead of being Z.1.

Tables 140712-141284
Compounds as defined in table 1 to table 572, but wherein the sequence of Y and $R^1$ is Z.247 as defined in table Z instead of being Z.1.

Tables 141285-141856
Compounds as defined in table 1 to table 572, but wherein the sequence of Y and R$^1$ is Z.248 as defined in table Z instead of being Z.1.
Tables 141857-142428
Compounds as defined in table 1 to table 572, but wherein the sequence of Y and R$^1$ is Z.249 as defined in table Z instead of being Z.1.
Tables 142429-143000
Compounds as defined in table 1 to table 572, but wherein the sequence of Y and R$^1$ is Z.250 as defined in table Z instead of being Z.1.
Tables 143001-143572
Compounds as defined in table 1 to table 572, but wherein the sequence of Y and R$^1$ is Z.251 as defined in table Z instead of being Z.1.
Tables 143573-144144
Compounds as defined in table 1 to table 572, but wherein the sequence of Y and R$^1$ is Z.252 as defined in table Z instead of being Z.1.
Tables 144145-144716
Compounds as defined in table 1 to table 572, but wherein the sequence of Y and R$^1$ is Z.253 as defined in table Z instead of being Z.1.
Tables 144717-145288
Compounds as defined in table 1 to table 572, but wherein the sequence of Y and R$^1$ is Z.254 as defined in table Z instead of being Z.1.
Tables 145289-145860
Compounds as defined in table 1 to table 572, but wherein the sequence of Y and R$^1$ is Z.255 as defined in table Z instead of being Z.1.
Tables 145861-146432
Compounds as defined in table 1 to table 572, but wherein the sequence of Y and R$^1$ is Z.256 as defined in table Z instead of being Z.1.
Tables 146433-147004
Compounds as defined in table 1 to table 572, but wherein the sequence of Y and R$^1$ is Z.257 as defined in table Z instead of being Z.1.
Tables 147005-147576
Compounds as defined in table 1 to table 572, but wherein the sequence of Y and R$^1$ is Z.258 as defined in table Z instead of being Z.1.
Tables 147577-148148
Compounds as defined in table 1 to table 572, but wherein the sequence of Y and R$^1$ is Z.259 as defined in table Z instead of being Z.1.
Tables 148149-148720
Compounds as defined in table 1 to table 572, but wherein the sequence of Y and R$^1$ is Z.260 as defined in table Z instead of being Z.1.
Tables 148721-149292
Compounds as defined in table 1 to table 572, but wherein the sequence of Y and R$^1$ is Z.261 as defined in table Z instead of being Z.1.
Tables 149293-149864
Compounds as defined in table 1 to table 572, but wherein the sequence of Y and R$^1$ is Z.262 as defined in table Z instead of being Z.1.
Tables 149865-150436
Compounds as defined in table 1 to table 572, but wherein the sequence of Y and R$^1$ is Z.263 as defined in table Z instead of being Z.1.
Tables 150437-151008
Compounds as defined in table 1 to table 572, but wherein the sequence of Y and R$^1$ is Z.264 as defined in table Z instead of being Z.1.
Tables 151009-151580
Compounds as defined in table 1 to table 572, but wherein the sequence of Y and R$^1$ is Z.265 as defined in table Z instead of being Z.1.
Tables 151581-152152
Compounds as defined in table 1 to table 572, but wherein the sequence of Y and R$^1$ is Z.266 as defined in table Z instead of being Z.1.
Tables 152153-152724
Compounds as defined in table 1 to table 572, but wherein the sequence of Y and R$^1$ is Z.267 as defined in table Z instead of being Z.1.
Tables 152725-153296
Compounds as defined in table 1 to table 572, but wherein the sequence of Y and R$^1$ is Z.268 as defined in table Z instead of being Z.1.
Tables 153297153868
Compounds as defined in table 1 to table 572, but wherein the sequence of Y and R$^1$ is Z.269 as defined in table Z instead of being Z.1.
Tables 153869-154440
Compounds as defined in table 1 to table 572, but wherein the sequence of Y and R$^1$ is Z.270 as defined in table Z instead of being Z.1.
Tables 154441-155012
Compounds as defined in table 1 to table 572, but wherein the sequence of Y and R$^1$ is Z.271 as defined in table Z instead of being Z.1.
Tables 155013-155584
Compounds as defined in table 1 to table 572, but wherein the sequence of Y and R$^1$ is Z.272 as defined in table Z instead of being Z.1.
Tables 155585-156156
Compounds as defined in table 1 to table 572, but wherein the sequence of Y and R$^1$ is Z.273 as defined in table Z instead of being Z.1.
Tables 156157-156728
Compounds as defined in table 1 to table 572, but wherein the sequence of Y and R$^1$ is Z.274 as defined in table Z instead of being Z.1.
Tables 156729-157300
Compounds as defined in table 1 to table 572, but wherein the sequence of Y and R$^1$ is Z.275 as defined in table Z instead of being Z.1.
Tables 157301-157872
Compounds as defined in table 1 to table 572, but wherein the sequence of Y and R$^1$ is Z.276 as defined in table Z instead of being Z.1.
Tables 157873-158444
Compounds as defined in table 1 to table 572, but wherein the sequence of Y and R$^1$ is Z.277 as defined in table Z instead of being Z.1.
Tables 158445-159016
Compounds as defined in table 1 to table 572, but wherein the sequence of Y and R$^1$ is Z.278 as defined in table Z instead of being Z.1.
Tables 159017-159588
Compounds as defined in table 1 to table 572, but wherein the sequence of Y and R$^1$ is Z.279 as defined in table Z instead of being Z.1.
Tables 159589-160160
Compounds as defined in table 1 to table 572, but wherein the sequence of Y and R$^1$ is Z.280 as defined in table Z instead of being Z.1.

Tables 160161-160732
Compounds as defined in table 1 to table 572, but wherein the sequence of Y and R$^1$ is Z.281 as defined in table Z instead of being 11.
Tables 160733-161304
Compounds as defined in table 1 to table 572, but wherein the sequence of Y and R$^1$ is Z.282 as defined in table Z instead of being Z.1.
Tables 161305-161876
Compounds as defined in table 1 to table 572, but wherein the sequence of Y and R$^1$ is Z.283 as defined in table Z instead of being Z.1.
Tables 161877-162448
Compounds as defined in table 1 to table 572, but wherein the sequence of Y and R$^1$ is Z.284 as defined in table Z instead of being Z.1.
Tables 162449-163020
Compounds as defined in table 1 to table 572, but wherein the sequence of Y and R$^1$ is Z.285 as defined in table Z instead of being Z.1.
Tables 1163021-163592
Compounds as defined in table 1 to table 572, but wherein the sequence of Y and R$^1$ is Z.286 as defined in table Z instead of being Z.1.
Tables 163593-164164
Compounds as defined in table 1 to table 572, but wherein the sequence of Y and R$^1$ is Z.287 as defined in table Z instead of being Z.1.
Tables 164165-164736
Compounds as defined in table 1 to table 572, but wherein the sequence of Y and R$^1$ is Z.288 as defined in table Z instead of being Z.1.
Tables 164737-165308
Compounds as defined in table 1 to table 572, but wherein the sequence of Y and R$^1$ is Z.289 as defined in table Z instead of being Z.1.
Tables 165309-165880
Compounds as defined in table 1 to table 572, but wherein the sequence of Y and R$^1$ is Z.290 as defined in table Z instead of being Z.1.
Tables 165881-166452
Compounds as defined in table 1 to table 572, but wherein the sequence of Y and R$^1$ is Z.291 as defined in table Z instead of being Z.1.
Tables 166453-167024
Compounds as defined in table 1 to table 572, but wherein the sequence of Y and R$^1$ is Z.292 as defined in table Z instead of being Z.1.
Tables 167025-167596
Compounds as defined in table 1 to table 572, but wherein the sequence of Y and R$^1$ is Z.293 as defined in table Z instead of being L1.
Tables 167597-168168
Compounds as defined in table 1 to table 572, but wherein the sequence of Y and R$^1$ is Z.294 as defined in table Z instead of being Z.1.
Tables 168169-168740
Compounds as defined in table 1 to table 572, but wherein the sequence of Y and R$^1$ is Z.295 as defined in table Z instead of being Z.1.
Tables 168741-169312
Compounds as defined in table 1 to table 572, but wherein the sequence of Y and R$^1$ is Z.296 as defined in table Z instead of being Z.1.
Tables 169313-169884
Compounds as defined in table 1 to table 572, but wherein the sequence of Y and R$^1$ is Z.297 as defined in table Z instead of being L1.
Tables 169885-170456
Compounds as defined in table 1 to table 572, but wherein the sequence of Y and R$^1$ is Z.298 as defined in table Z instead of being Z.1.
Tables 170457-171028
Compounds as defined in table 1 to table 572, but wherein the sequence of Y and R$^1$ is Z.299 as defined in table Z instead of being Z.1.
Tables 171029-171600
Compounds as defined in table 1 to table 572, but wherein the sequence of Y and R$^1$ is Z.300 as defined in table Z instead of being Z.1.
Tables 171601-172172
Compounds as defined in table 1 to table 572, but wherein the sequence of Y and R$^1$ is Z.301 as defined in table Z instead of being Z.1.
Tables 172173-172744
Compounds as defined in table 1 to table 572, but wherein the sequence of Y and R$^1$ is Z.302 as defined in table Z instead of being Z.1.
Tables 172745-173316
Compounds as defined in table 1 to table 572, but wherein the sequence of Y and R$^1$ is Z.303 as defined in table Z instead of being 11.
Tables 173317-173888
Compounds as defined in table 1 to table 572, but wherein the sequence of Y and R$^1$ is Z.304 as defined in table Z instead of being Z.1.
Tables 173889-174460
Compounds as defined in table 1 to table 572, but wherein the sequence of Y and R$^1$ is Z.305 as defined in table Z instead of being Z.1.
Tables 174461-175032
Compounds as defined in table 1 to table 572, but wherein the sequence of Y and R$^1$ is Z.306 as defined in table Z instead of being Z.1.
Tables 175033-175604
Compounds as defined in table 1 to table 572, but wherein the sequence of Y and R$^1$ is Z.307 as defined in table Z instead of being Z.1.
Tables 175605-176176
Compounds as defined in table 1 to table 572, but wherein the sequence of Y and R$^1$ is Z.308 as defined in table Z instead of being Z.1.
Tables 176177-176748
Compounds as defined in table 1 to table 572, but wherein the sequence of Y and R$^1$ is Z.309 as defined in table Z instead of being Z.1.
Tables 176749-177320
Compounds as defined in table 1 to table 572, but wherein the sequence of Y and R$^1$ is Z.310 as defined in table Z instead of being 11.
Tables 177321-177892
Compounds as defined in table 1 to table 572, but wherein the sequence of Y and R$^1$ is Z.311 as defined in table Z instead of being Z.1.
Tables 177893-178464
Compounds as defined in table 1 to table 572, but wherein the sequence of Y and R$^1$ is Z.312 as defined in table Z instead of being Z.1.
Tables 178465-179036
Compounds as defined in table 1 to table 572, but wherein the sequence of Y and R$^1$ is Z.313 as defined in table Z instead of being Z.1.

Tables 179037-179608
Compounds as defined in table 1 to table 572, but wherein the sequence of Y and $R^1$ is Z.314 as defined in table Z instead of being Z.1.
Tables 179609-180180
Compounds as defined in table 1 to table 572, but wherein the sequence of Y and $R^1$ is Z.315 as defined in table Z instead of being Z.1.
Tables 180181-108752
Compounds as defined in table 1 to table 572, but wherein the sequence of Y and $R^1$ is Z.316 as defined in table Z instead of being Z.1.
Tables 108753-181324
Compounds as defined in table 1 to table 572, but wherein the sequence of Y and $R^1$ is Z.317 as defined in table Z instead of being Z.1.
Tables 181325-181896
Compounds as defined in table 1 to table 572, but wherein the sequence of Y and $R^1$ is Z.318 as defined in table Z instead of being Z.1.
Tables 181897-182468
Compounds as defined in table 1 to table 572, but wherein the sequence of Y and $R^1$ is Z.319 as defined in table Z instead of being Z.1.
Tables 1182469-183040
Compounds as defined in table 1 to table 572, but wherein the sequence of Y and $R^1$ is Z.320 as defined in table Z instead of being Z.1.
Tables 183041-183612
Compounds as defined in table 1 to table 572, but wherein the sequence of Y and $R^1$ is Z.321 as defined in table Z instead of being Z.1.
Tables 183613-184184
Compounds as defined in table 1 to table 572, but wherein the sequence of Y and $R^1$ is Z.322 as defined in table Z instead of being Z.1.
Tables 184185-184756
Compounds as defined in table 1 to table 572, but wherein the sequence of Y and $R^1$ is Z.323 as defined in table Z instead of being Z.1.
Tables 184757-185328
Compounds as defined in table 1 to table 572, but wherein the sequence of Y and $R^1$ is Z.324 as defined in table Z instead of being Z.1.
Tables 185329-185900
Compounds as defined in table 1 to table 572, but wherein the sequence of Y and $R^1$ is Z.325 as defined in table Z instead of being Z.1.
Tables 185901-186472
Compounds as defined in table 1 to table 572, but wherein the sequence of Y and $R^1$ is Z.326 as defined in table Z instead of being Z.1.
Tables 186473-187044
Compounds as defined in table 1 to table 572, but wherein the sequence of Y and $R^1$ is Z.327 as defined in table Z instead of being Z.1.
Tables 187045-187616
Compounds as defined in table 1 to table 572, but wherein the sequence of Y and $R^1$ is Z.328 as defined in table Z instead of being Z.1.
Tables 187617-188188
Compounds as defined in table 1 to table 572, but wherein the sequence of Y and $R^1$ is Z.329 as defined in table Z instead of being Z.1.
Tables 188189-188760
Compounds as defined in table 1 to table 572, but wherein the sequence of Y and $R^1$ is Z.330 as defined in table Z instead of being Z.1.
Tables 188761-189332
Compounds as defined in table 1 to table 572, but wherein the sequence of Y and $R^1$ is Z.331 as defined in table Z instead of being Z.1.
Tables 189333-189904
Compounds as defined in table 1 to table 572, but wherein the sequence of Y and $R^1$ is Z.332 as defined in table Z instead of being Z.1.
Tables 189905-190476
Compounds as defined in table 1 to table 572, but wherein the sequence of Y and $R^1$ is Z.333 as defined in table Z instead of being Z.1.
Tables 190477-191048
Compounds as defined in table 1 to table 572, but wherein the sequence of Y and $R^1$ is Z.334 as defined in table Z instead of being Z.1.
Tables 191049-191620
Compounds as defined in table 1 to table 572, but wherein the sequence of Y and $R^1$ is Z.335 as defined in table Z instead of being Z.1.
Tables 191621-192192
Compounds as defined in table 1 to table 572, but wherein the sequence of Y and $R^1$ is Z.336 as defined in table Z instead of being Z.1.
Tables 192193-192764
Compounds as defined in table 1 to table 572, but wherein the sequence of Y and $R^1$ is Z.337 as defined in table Z instead of being Z.1.
Tables 192765-193336
Compounds as defined in table 1 to table 572, but wherein the sequence of Y and $R^1$ is Z.338 as defined in table Z instead of being Z.1.
Tables 193337-193908
Compounds as defined in table 1 to table 572, but wherein the sequence of Y and $R^1$ is Z.339 as defined in table Z instead of being Z.1.
Tables 193909-194480
Compounds as defined in table 1 to table 572, but wherein the sequence of Y and $R^1$ is Z.340 as defined in table Z instead of being Z.1.
Tables 194481-195052
Compounds as defined in table 1 to table 572, but wherein the sequence of Y and $R^1$ is Z.341 as defined in table Z instead of being Z.1.
Tables 195053-195624
Compounds as defined in table 1 to table 572, but wherein the sequence of Y and $R^1$ is Z.342 as defined in table Z instead of being Z.1.
Tables 195625-196196
Compounds as defined in table 1 to table 572, but wherein the sequence of Y and $R^1$ is Z.343 as defined in table Z instead of being Z.1.
Tables 196197-196768
Compounds as defined in table 1 to table 572, but wherein the sequence of Y and $R^1$ is Z.344 as defined in table Z instead of being Z.1.
Tables 196769-197340
Compounds as defined in table 1 to table 572, but wherein the sequence of Y and $R^1$ is Z.345 as defined in table Z instead of being Z.1.
Tables 197341-197912
Compounds as defined in table 1 to table 572, but wherein the sequence of Y and $R^1$ is Z.346 as defined in table Z instead of being 11.

Tables 197912-198484
Compounds as defined in table 1 to table 572, but wherein the sequence of Y and R$^1$ is Z.347 as defined in table Z instead of being Z.1.
Tables 198485-199056
Compounds as defined in table 1 to table 572, but wherein the sequence of Y and R$^1$ is Z.348 as defined in table Z instead of being Z.1.
Tables 199057-199628
Compounds as defined in table 1 to table 572, but wherein the sequence of Y and R$^1$ is Z.349 as defined in table Z instead of being Z.1.
Tables 199628-200200
Compounds as defined in table 1 to table 572, but wherein the sequence of Y and R$^1$ is Z.350 as defined in table Z instead of being Z.1.
Tables 200201-200772
Compounds as defined in table 1 to table 572, but wherein the sequence of Y and R$^1$ is Z.351 as defined in table Z instead of being Z.1.
Tables 200773-201344
Compounds as defined in table 1 to table 572, but wherein the sequence of Y and R$^1$ is Z.352 as defined in table Z instead of being Z.1.
Tables 201345-201916
Compounds as defined in table 1 to table 572, but wherein the sequence of Y and R$^1$ is Z.353 as defined in table Z instead of being Z.1.
Tables 201917-202488
Compounds as defined in table 1 to table 572, but wherein the sequence of Y and R$^1$ is Z.354 as defined in table Z instead of being Z.1.
Tables 202489-203060
Compounds as defined in table 1 to table 572, but wherein the sequence of Y and R$^1$ is Z.355 as defined in table Z instead of being Z.1.
Tables 203061-203632
Compounds as defined in table 1 to table 572, but wherein the sequence of Y and R$^1$ is Z.356 as defined in table Z instead of being Z.1.
Tables 203633-204204
Compounds as defined in table 1 to table 572, but wherein the sequence of Y and R$^1$ is Z.357 as defined in table Z instead of being Z.1.
Tables 204205-204776
Compounds as defined in table 1 to table 572, but wherein the sequence of Y and R$^1$ is Z.358 as defined in table Z instead of being 11.
Tables 204777-205348
Compounds as defined in table 1 to table 572, but wherein the sequence of Y and R$^1$ is Z.359 as defined in table Z instead of being Z.1.
Tables 205349-205920
Compounds as defined in table 1 to table 572, but wherein the sequence of Y and R$^1$ is Z.360 as defined in table Z instead of being Z.1.
Tables 2059231-206492
Compounds as defined in table 1 to table 572, but wherein the sequence of Y and R$^1$ is Z.361 as defined in table Z instead of being Z.1.
Tables 206493-207064
Compounds as defined in table 1 to table 572, but wherein the sequence of Y and R$^1$ is Z.362 as defined in table Z instead of being Z.1.
Tables 207065-207636
Compounds as defined in table 1 to table 572, but wherein the sequence of Y and R$^1$ is Z.363 as defined in table Z instead of being Z.1.
Tables 207637-208208
Compounds as defined in table 1 to table 572, but wherein the sequence of Y and R$^1$ is Z.364 as defined in table Z instead of being Z.1.
Tables 208029-208780
Compounds as defined in table 1 to table 572, but wherein the sequence of Y and R$^1$ is Z.365 as defined in table Z instead of being Z.1.
Tables 208781-209352
Compounds as defined in table 1 to table 572, but wherein the sequence of Y and R$^1$ is Z.366 as defined in table Z instead of being Z.1.
Tables 209353-209924
Compounds as defined in table 1 to table 572, but wherein the sequence of Y and R$^1$ is Z.367 as defined in table Z instead of being Z.1.
Tables 209925-210496
Compounds as defined in table 1 to table 572, but wherein the sequence of Y and R$^1$ is Z.368 as defined in table Z instead of being Z.1.
Tables 210497-211068
Compounds as defined in table 1 to table 572, but wherein the sequence of Y and R$^1$ is Z.369 as defined in table Z instead of being Z.1.
Tables 211069-211640
Compounds as defined in table 1 to table 572, but wherein the sequence of Y and R$^1$ is Z.370 as defined in table Z instead of being Z.1.
Tables 211641-212212
Compounds as defined in table 1 to table 572, but wherein the sequence of Y and R$^1$ is Z.371 as defined in table Z instead of being Z.1.
Tables 212213-212784
Compounds as defined in table 1 to table 572, but wherein the sequence of Y and R$^1$ is Z.372 as defined in table Z instead of being Z.1.
Tables 212785-213356
Compounds as defined in table 1 to table 572, but wherein the sequence of Y and R$^1$ is Z.373 as defined in table Z instead of being Z.1.
Tables 213357-213928
Compounds as defined in table 1 to table 572, but wherein the sequence of Y and R$^1$ is Z.374 as defined in table Z instead of being Z.1.
Tables 213929-214500
Compounds as defined in table 1 to table 572, but wherein the sequence of Y and R$^1$ is Z.375 as defined in table Z instead of being Z.1.
Tables 214501-215072
Compounds as defined in table 1 to table 572, but wherein the sequence of Y and R$^1$ is Z.376 as defined in table Z instead of being Z.1.
Tables 215073-215644
Compounds as defined in table 1 to table 572, but wherein the sequence of Y and R$^1$ is Z.377 as defined in table Z instead of being Z.1.
Tables 215645-216216
Compounds as defined in table 1 to table 572, but wherein the sequence of Y and R$^1$ is Z.378 as defined in table Z instead of being Z.1.
Tables 216217-216788
Compounds as defined in table 1 to table 572, but wherein the sequence of Y and R$^1$ is Z.379 as defined in table Z instead of being Z.1.

Tables 216789-217360
Compounds as defined in table 1 to table 572, but wherein the sequence of Y and $R^1$ is Z.380 as defined in table Z instead of being Z.1.
Tables 217361-217932
Compounds as defined in table 1 to table 572, but wherein the sequence of Y and $R^1$ is Z.381 as defined in table Z instead of being L1.
Tables 217933-218504
Compounds as defined in table 1 to table 572, but wherein the sequence of Y and $R^1$ is Z.382 as defined in table Z instead of being Z.1.
Tables 218505-219076
Compounds as defined in table 1 to table 572, but wherein the sequence of Y and $R^1$ is Z.383 as defined in table Z instead of being Z.1.
Tables 219077-219648
Compounds as defined in table 1 to table 572, but wherein the sequence of Y and $R^1$ is Z.384 as defined in table Z instead of being Z.1.
Tables 219649-220220
Compounds as defined in table 1 to table 572, but wherein the sequence of Y and $R^1$ is Z.385 as defined in table Z instead of being Z.1.
Tables 220221-220792
Compounds as defined in table 1 to table 572, but wherein the sequence of Y and $R^1$ is Z.386 as defined in table Z instead of being Z.1.
Tables 220793-221364
Compounds as defined in table 1 to table 572, but wherein the sequence of Y and $R^1$ is Z.387 as defined in table Z instead of being Z.1.
Tables 221364-221936
Compounds as defined in table 1 to table 572, but wherein the sequence of Y and $R^1$ is Z.388 as defined in table Z instead of being Z.1.
Tables 221937-222508
Compounds as defined in table 1 to table 572, but wherein the sequence of Y and $R^1$ is Z.389 as defined in table Z instead of being Z.1.
Tables 222509-223080
Compounds as defined in table 1 to table 572, but wherein the sequence of Y and $R^1$ is Z.390 as defined in table Z instead of being Z.1.
Tables 223081-223652
Compounds as defined in table 1 to table 572, but wherein the sequence of Y and $R^1$ is Z.391 as defined in table Z instead of being Z.1.
Tables 223653-224224
Compounds as defined in table 1 to table 572, but wherein the sequence of Y and $R^1$ is Z.392 as defined in table Z instead of being Z.1.
Tables 224225-224796
Compounds as defined in table 1 to table 572, but wherein the sequence of Y and $R^1$ is Z.393 as defined in table Z instead of being Z.1.
Tables 224797-225368
Compounds as defined in table 1 to table 572, but wherein the sequence of Y and $R^1$ is Z.394 as defined in table Z instead of being Z.1.
Tables 225369-225940
Compounds as defined in table 1 to table 572, but wherein the sequence of Y and $R^1$ is Z.395 as defined in table Z instead of being Z.1.
Tables 225941-226512
Compounds as defined in table 1 to table 572, but wherein the sequence of Y and $R^1$ is Z.396 as defined in table Z instead of being Z.1.
Tables 226513-227084
Compounds as defined in table 1 to table 572, but wherein the sequence of Y and $R^1$ is Z.397 as defined in table Z instead of being Z.1.
Tables 227085-227656
Compounds as defined in table 1 to table 572, but wherein the sequence of Y and $R^1$ is Z.398 as defined in table Z instead of being Z.1.
Tables 227657-228228
Compounds as defined in table 1 to table 572, but wherein the sequence of Y and $R^1$ is Z.399 as defined in table Z instead of being Z.1.
Tables 228229-228800
Compounds as defined in table 1 to table 572, but wherein the sequence of Y and $R^1$ is Z.400 as defined in table Z instead of being Z.1.
Tables 228801-229372
Compounds as defined in table 1 to table 572, but wherein the sequence of Y and $R^1$ is Z.401 as defined in table Z instead of being Z.1.
Tables 229373-229944
Compounds as defined in table 1 to table 572, but wherein the sequence of Y and $R^1$ is Z.402 as defined in table Z instead of being Z.1.
Tables 229945-230516
Compounds as defined in table 1 to table 572, but wherein the sequence of Y and $R^1$ is Z.403 as defined in table Z instead of being Z.1.
Tables 230517-231088
Compounds as defined in table 1 to table 572, but wherein the sequence of Y and $R^1$ is Z.404 as defined in table Z instead of being Z.1.
Tables 231089-231660
Compounds as defined in table 1 to table 572, but wherein the sequence of Y and $R^1$ is Z.405 as defined in table Z instead of being Z.1.
Tables 231661-232232
Compounds as defined in table 1 to table 572, but wherein the sequence of Y and $R^1$ is 1406 as defined in table Z instead of being Z.1.
Tables 232233-232804
Compounds as defined in table 1 to table 572, but wherein the sequence of Y and $R^1$ is Z.407 as defined in table Z instead of being Z.1.
Tables 232805-233376
Compounds as defined in table 1 to table 572, but wherein the sequence of Y and $R^1$ is 1408 as defined in table Z instead of being Z.1.
Tables 233377-233948
Compounds as defined in table 1 to table 572, but wherein the sequence of Y and $R^1$ is Z.409 as defined in table Z instead of being Z.1.
Tables 233949-234520
Compounds as defined in table 1 to table 572, but wherein the sequence of Y and $R^1$ is Z.410 as defined in table Z instead of being Z.1.
Tables 234521-235092
Compounds as defined in table 1 to table 572, but wherein the sequence of Y and $R^1$ is Z.411 as defined in table Z instead of being Z.1.
Tables 235093-235664
Compounds as defined in table 1 to table 572, but wherein the sequence of Y and $R^1$ is Z.412 as defined in table Z instead of being Z.1.

Tables 235665-236236
Compounds as defined in table 1 to table 572, but wherein the sequence of Y and $R^1$ is Z.413 as defined in table Z instead of being Z.1.
Tables 236237-236808
Compounds as defined in table 1 to table 572, but wherein the sequence of Y and $R^1$ is Z.414 as defined in table Z instead of being Z.1.
Tables 236809-237380
Compounds as defined in table 1 to table 572, but wherein the sequence of Y and $R^1$ is Z.415 as defined in table Z instead of being Z.1.
Tables 237381-237952
Compounds as defined in table 1 to table 572, but wherein the sequence of Y and $R^1$ is Z.416 as defined in table Z instead of being Z.1.
Tables 237953-238524
Compounds as defined in table 1 to table 572, but wherein the sequence of Y and $R^1$ is Z.417 as defined in table Z instead of being Z.1.
Tables 238525-239096
Compounds as defined in table 1 to table 572, but wherein the sequence of Y and $R^1$ is 1418 as defined in table Z instead of being Z.1.
Tables 239097-239668
Compounds as defined in table 1 to table 572, but wherein the sequence of Y and $R^1$ is Z.419 as defined in table Z instead of being Z.1.
Tables 239669-240240
Compounds as defined in table 1 to table 572, but wherein the sequence of Y and $R^1$ is Z.420 as defined in table Z instead of being Z.1.
Tables 240241-240812
Compounds as defined in table 1 to table 572, but wherein the sequence of Y and $R^1$ is Z.421 as defined in table Z instead of being Z.1.
Tables 240813-241384
Compounds as defined in table 1 to table 572, but wherein the sequence of Y and $R^1$ is Z.422 as defined in table Z instead of being Z.1.
Tables 241385-241956
Compounds as defined in table 1 to table 572, but wherein the sequence of Y and $R^1$ is Z.423 as defined in table Z instead of being Z.1.
Tables 241957-242528
Compounds as defined in table 1 to table 572, but wherein the sequence of Y and $R^1$ is Z.424 as defined in table Z instead of being Z.1.
Tables 242529-243100
Compounds as defined in table 1 to table 572, but wherein the sequence of Y and $R^1$ is Z.425 as defined in table Z instead of being Z.1.
Tables 243101-243672
Compounds as defined in table 1 to table 572, but wherein the sequence of Y and $R^1$ is Z.426 as defined in table Z instead of being Z.1.
Tables 243673-244244
Compounds as defined in table 1 to table 572, but wherein the sequence of Y and $R^1$ is Z.427 as defined in table Z instead of being Z.1.
Tables 244245-244816
Compounds as defined in table 1 to table 572, but wherein the sequence of Y and $R^1$ is Z.428 as defined in table Z instead of being Z.1.
Tables 244817-245388
Compounds as defined in table 1 to table 572, but wherein the sequence of Y and $R^1$ is Z.429 as defined in table Z instead of being Z.1.
Tables 245389-245960
Compounds as defined in table 1 to table 572, but wherein the sequence of Y and $R^1$ is Z.430 as defined in table Z instead of being Z.1.
Tables 245961-246532
Compounds as defined in table 1 to table 572, but wherein the sequence of Y and $R^1$ is Z.431 as defined in table Z instead of being Z.1.
Tables 246533-247104
Compounds as defined in table 1 to table 572, but wherein the sequence of Y and $R^1$ is Z.432 as defined in table Z instead of being 11.
Tables 247105-247676
Compounds as defined in table 1 to table 572, but wherein the sequence of Y and $R^1$ is Z.433 as defined in table Z instead of being Z.1.
Tables 247677-248248
Compounds as defined in table 1 to table 572, but wherein the sequence of Y and $R^1$ is Z.434 as defined in table Z instead of being 11.
Tables 248249-248820
Compounds as defined in table 1 to table 572, but wherein the sequence of Y and $R^1$ is Z.435 as defined in table Z instead of being Z.1.
Tables 248821-249392
Compounds as defined in table 1 to table 572, but wherein the sequence of Y and $R^1$ is Z.436 as defined in table Z instead of being Z.1.
Tables 249393-249964
Compounds as defined in table 1 to table 572, but wherein the sequence of Y and $R^1$ is Z.437 as defined in table Z instead of being Z.1.
Tables 249965-250536
Compounds as defined in table 1 to table 572, but wherein the sequence of Y and $R^1$ is Z.438 as defined in table Z instead of being Z.1.
Tables 250537-251108
Compounds as defined in table 1 to table 572, but wherein the sequence of Y and $R^1$ is Z.439 as defined in table Z instead of being Z.1.
Tables 251109-251680
Compounds as defined in table 1 to table 572, but wherein the sequence of Y and $R^1$ is Z.440 as defined in table Z instead of being Z.1.
Tables 251681-252252
Compounds as defined in table 1 to table 572, but wherein the sequence of Y and $R^1$ is Z.441 as defined in table Z instead of being Z.1.
Tables 252253-252824
Compounds as defined in table 1 to table 572, but wherein the sequence of Y and $R^1$ is Z.442 as defined in table Z instead of being Z.1.
Tables 252825-253396
Compounds as defined in table 1 to table 572, but wherein the sequence of Y and $R^1$ is Z.443 as defined in table Z instead of being Z.1.
Tables 253397-25396
Compounds as defined in table 1 to table 572, but wherein the sequence of Y and $R^1$ is Z.444 as defined in table Z instead of being Z.1.
Tables 253969-254540
Compounds as defined in table 1 to table 572, but wherein the sequence of Y and $R^1$ is Z.445 as defined in table Z instead of being Z.1.

Tables 254541-255112
Compounds as defined in table 1 to table 572, but wherein the sequence of Y and $R^1$ is Z.446 as defined in table Z instead of being Z.1.

Tables 255113-255684
Compounds as defined in table 1 to table 572, but wherein the sequence of Y and $R^1$ is Z.447 as defined in table Z instead of being Z.1.

Tables 255685-256256
Compounds as defined in table 1 to table 572, but wherein the sequence of Y and $R^1$ is Z.448 as defined in table Z instead of being Z.1.

Tables 256257-256828
Compounds as defined in table 1 to table 572, but wherein the sequence of Y and $R^1$ is Z.449 as defined in table Z instead of being Z.1.

Tables 256829-257400
Compounds as defined in table 1 to table 572, but wherein the sequence of Y and $R^1$ is Z.450 as defined in table Z instead of being Z.1.

Tables 257401-257972
Compounds as defined in table 1 to table 572, but wherein the sequence of Y and $R^1$ is Z.451 as defined in table Z instead of being Z.1.

Tables 257973-258544
Compounds as defined in table 1 to table 572, but wherein the sequence of Y and $R^1$ is Z.452 as defined in table Z instead of being Z.1.

Tables 258545-259116
Compounds as defined in table 1 to table 572, but wherein the sequence of Y and $R^1$ is Z.453 as defined in table Z instead of being Z.1.

Tables 259117-259688
Compounds as defined in table 1 to table 572, but wherein the sequence of Y and $R^1$ is Z.454 as defined in table Z instead of being Z.1.

Tables 259689-260260
Compounds as defined in table 1 to table 572, but wherein the sequence of Y and $R^1$ is Z.455 as defined in table Z instead of being Z.1.

Tables 260261-260832
Compounds as defined in table 1 to table 572, but wherein the sequence of Y and $R^1$ is Z.456 as defined in table Z instead of being Z.1.

Tables 260833-261404
Compounds as defined in table 1 to table 572, but wherein the sequence of Y and $R^1$ is Z.457 as defined in table Z instead of being Z.1.

Tables 261405-261976
Compounds as defined in table 1 to table 572, but wherein the sequence of Y and $R^1$ is Z.458 as defined in table Z instead of being Z.1.

Tables 261977-262548
Compounds as defined in table 1 to table 572, but wherein the sequence of Y and $R^1$ is Z.459 as defined in table Z instead of being Z.1.

Tables 262549-263120
Compounds as defined in table 1 to table 572, but wherein the sequence of Y and $R^1$ is Z.460 as defined in table Z instead of being Z.1.

Tables 263121-263692
Compounds as defined in table 1 to table 572, but wherein the sequence of Y and $R^1$ is Z.461 as defined in table Z instead of being Z.1.

Tables 263693-264264
Compounds as defined in table 1 to table 572, but wherein the sequence of Y and $R^1$ is Z.462 as defined in table Z instead of being Z.1.

Tables 264265-264836
Compounds as defined in table 1 to table 572, but wherein the sequence of Y and $R^1$ is Z.463 as defined in table Z instead of being Z.1.

Tables 264837-265408
Compounds as defined in table 1 to table 572, but wherein the sequence of Y and $R^1$ is Z.464 as defined in table Z instead of being Z.1.

Tables 265409-265980
Compounds as defined in table 1 to table 572, but wherein the sequence of Y and $R^1$ is Z.465 as defined in table Z instead of being Z.1.

Tables 265981-266552
Compounds as defined in table 1 to table 572, but wherein the sequence of Y and $R^1$ is Z.466 as defined in table Z instead of being Z.1.

Tables 266553-267124
Compounds as defined in table 1 to table 572, but wherein the sequence of Y and $R^1$ is Z.467 as defined in table Z instead of being Z.1.

Tables 267125-267696
Compounds as defined in table 1 to table 572, but wherein the sequence of Y and $R^1$ is Z.468 as defined in table Z instead of being Z.1.

Tables 267697-268268
Compounds as defined in table 1 to table 572, but wherein the sequence of Y and $R^1$ is Z.469 as defined in table Z instead of being Z.1.

Tables 268269-268840
Compounds as defined in table 1 to table 572, but wherein the sequence of Y and $R^1$ is Z.470 as defined in table Z instead of being Z.1.

Tables 268841-269412
Compounds as defined in table 1 to table 572, but wherein the sequence of Y and $R^1$ is Z.471 as defined in table Z instead of being Z.1.

Tables 269413-269984
Compounds as defined in table 1 to table 572, but wherein the sequence of Y and $R^1$ is Z.472 as defined in table Z instead of being Z.1.

Tables 269985-270556
Compounds as defined in table 1 to table 572, but wherein the sequence of Y and $R^1$ is Z.473 as defined in table Z instead of being Z.1.

Tables 270557-271128
Compounds as defined in table 1 to table 572, but wherein the sequence of Y and $R^1$ is Z.474 as defined in table Z instead of being Z.1.

Tables 271129-271700
Compounds as defined in table 1 to table 572, but wherein the sequence of Y and $R^1$ is Z.475 as defined in table Z instead of being Z.1.

Tables 271701-272272
Compounds as defined in table 1 to table 572, but wherein the sequence of Y and $R^1$ is Z.476 as defined in table Z instead of being Z.1.

Tables 272273-272844
Compounds as defined in table 1 to table 572, but wherein the sequence of Y and $R^1$ is 1477 as defined in table Z instead of being Z.1.

Tables 272845-273416
Compounds as defined in table 1 to table 572, but wherein the sequence of Y and $R^1$ is Z.478 as defined in table Z instead of being Z.1.

Tables 273417-273988
Compounds as defined in table 1 to table 572, but wherein the sequence of Y and R$^1$ is Z.479 as defined in table Z instead of being Z.1.
Tables 273989-274560
Compounds as defined in table 1 to table 572, but wherein the sequence of Y and R$^1$ is Z.480 as defined in table Z instead of being Z.1.
Tables 274561-275132
Compounds as defined in table 1 to table 572, but wherein the sequence of Y and R$^1$ is Z.481 as defined in table Z instead of being Z.1.
Tables 275133-275704
Compounds as defined in table 1 to table 572, but wherein the sequence of Y and R$^1$ is Z.482 as defined in table Z instead of being Z.1.
Tables 275705-276276
Compounds as defined in table 1 to table 572, but wherein the sequence of Y and R$^1$ is Z.483 as defined in table Z instead of being Z.1.
Tables 276277-276848
Compounds as defined in table 1 to table 572, but wherein the sequence of Y and R$^1$ is Z.484 as defined in table Z instead of being Z.1.
Tables 276849-277420
Compounds as defined in table 1 to table 572, but wherein the sequence of Y and R$^1$ is Z.485 as defined in table Z instead of being Z.1.
Tables 277421-277992
Compounds as defined in table 1 to table 572, but wherein the sequence of Y and R$^1$ is Z.486 as defined in table Z instead of being Z.1.
Tables 277993-278564
Compounds as defined in table 1 to table 572, but wherein the sequence of Y and R$^1$ is Z.487 as defined in table Z instead of being Z.1.
Tables 278565-279136
Compounds as defined in table 1 to table 572, but wherein the sequence of Y and R$^1$ is Z.488 as defined in table Z instead of being Z.1.
Tables 279137-279708
Compounds as defined in table 1 to table 572, but wherein the sequence of Y and R$^1$ is Z.489 as defined in table Z instead of being Z.1.
Tables 279709-280280
Compounds as defined in table 1 to table 572, but wherein the sequence of Y and R$^1$ is Z.490 as defined in table Z instead of being Z.1.
Tables 280281-280852
Compounds as defined in table 1 to table 572, but wherein the sequence of Y and R$^1$ is Z.491 as defined in table Z instead of being Z.1.
Tables 280853-281424
Compounds as defined in table 1 to table 572, but wherein the sequence of Y and R$^1$ is Z.492 as defined in table Z instead of being Z.1.
Tables 281425-281996
Compounds as defined in table 1 to table 572, but wherein the sequence of Y and R$^1$ is 1493 as defined in table Z instead of being Z.1.
Tables 281997-282568
Compounds as defined in table 1 to table 572, but wherein the sequence of Y and R$^1$ is Z.494 as defined in table Z instead of being Z.1.
Tables 282569-283140
Compounds as defined in table 1 to table 572, but wherein the sequence of Y and R$^1$ is Z.495 as defined in table Z instead of being Z.1.
Tables 283141-283712
Compounds as defined in table 1 to table 572, but wherein the sequence of Y and R$^1$ is Z.496 as defined in table Z instead of being Z.1.
Tables 283713-284284
Compounds as defined in table 1 to table 572, but wherein the sequence of Y and R$^1$ is Z.497 as defined in table Z instead of being Z.1.
Tables 284285-284856
Compounds as defined in table 1 to table 572, but wherein the sequence of Y and R$^1$ is Z.498 as defined in table Z instead of being Z.1.
Tables 284857-285428
Compounds as defined in table 1 to table 572, but wherein the sequence of Y and R$^1$ is Z.499 as defined in table Z instead of being Z.1.
Tables 285428-286000
Compounds as defined in table 1 to table 572, but wherein the sequence of Y and R$^1$ is Z.500 as defined in table Z instead of being Z.1.
Tables 286001-286572
Compounds as defined in table 1 to table 572, but wherein the sequence of Y and R$^1$ is Z.501 as defined in table Z instead of being Z.1.
Tables 286573-287144
Compounds as defined in table 1 to table 572, but wherein the sequence of Y and R$^1$ is Z.502 as defined in table Z instead of being Z.1.
Tables 287145-287716
Compounds as defined in table 1 to table 572, but wherein the sequence of Y and R$^1$ is Z.503 as defined in table Z instead of being Z.1.
Tables 287717-288288
Compounds as defined in table 1 to table 572, but wherein the sequence of Y and R$^1$ is Z.504 as defined in table Z instead of being Z.1.
Tables 288289-288860
Compounds as defined in table 1 to table 572, but wherein the sequence of Y and R$^1$ is Z.505 as defined in table Z instead of being Z.1.
Tables 288861-289432
Compounds as defined in table 1 to table 572, but wherein the sequence of Y and R$^1$ is Z.506 as defined in table Z instead of being 11.
Tables 289433-290004
Compounds as defined in table 1 to table 572, but wherein the sequence of Y and R$^1$ is Z.507 as defined in table Z instead of being Z.1.
Tables 290005-290576
Compounds as defined in table 1 to table 572, but wherein the sequence of Y and R$^1$ is Z.508 as defined in table Z instead of being Z.1.
Tables 290577-291148
Compounds as defined in table 1 to table 572, but wherein the sequence of Y and R$^1$ is Z.509 as defined in table Z instead of being Z.1.
Tables 291149-291720
Compounds as defined in table 1 to table 572, but wherein the sequence of Y and R$^1$ is 1510 as defined in table Z instead of being Z.1.
Tables 291721-292292
Compounds as defined in table 1 to table 572, but wherein the sequence of Y and R$^1$ is Z.511 as defined in table Z instead of being Z.1.

Tables 292293-292864
Compounds as defined in table 1 to table 572, but wherein the sequence of Y and $R^1$ is Z.512 as defined in table Z instead of being Z.1.
Tables 292865-293436
Compounds as defined in table 1 to table 572, but wherein the sequence of Y and $R^1$ is Z.513 as defined in table Z instead of being Z.1.
Tables 293437-294008
Compounds as defined in table 1 to table 572, but wherein the sequence of Y and $R^1$ is Z.514 as defined in table Z instead of being Z.1.
Tables 294009-294580
Compounds as defined in table 1 to table 572, but wherein the sequence of Y and $R^1$ is Z.515 as defined in table Z instead of being Z.1.
Tables 294581-295152
Compounds as defined in table 1 to table 572, but wherein the sequence of Y and $R^1$ is Z.516 as defined in table Z instead of being Z.1.
Tables 295153-295724
Compounds as defined in table 1 to table 572, but wherein the sequence of Y and $R^1$ is Z.517 as defined in table Z instead of being Z.1.
Tables 295725-296296
Compounds as defined in table 1 to table 572, but wherein the sequence of Y and $R^1$ is Z.518 as defined in table Z instead of being Z.1.
Tables 296297-296868
Compounds as defined in table 1 to table 572, but wherein the sequence of Y and $R^1$ is Z.519 as defined in table Z instead of being Z.1.
Tables 296869-297440
Compounds as defined in table 1 to table 572, but wherein the sequence of Y and $R^1$ is Z.520 as defined in table Z instead of being Z.1.
Tables 297441-298012
Compounds as defined in table 1 to table 572, but wherein the sequence of Y and $R^1$ is 1521 as defined in table Z instead of being Z.1.
Tables 298013-298584
Compounds as defined in table 1 to table 572, but wherein the sequence of Y and $R^1$ is Z.522 as defined in table Z instead of being Z.1.
Tables 298585-299156
Compounds as defined in table 1 to table 572, but wherein the sequence of Y and $R^1$ is Z.523 as defined in table Z instead of being Z.1.
Tables 299157-299728
Compounds as defined in table 1 to table 572, but wherein the sequence of Y and $R^1$ is Z.524 as defined in table Z instead of being Z.1.
Tables 299729-300300
Compounds as defined in table 1 to table 572, but wherein the sequence of Y and $R^1$ is Z.525 as defined in table Z instead of being Z.1.
Tables 300301-300872
Compounds as defined in table 1 to table 572, but wherein the sequence of Y and $R^1$ is Z.526 as defined in table Z instead of being Z.1.
Tables 300873-301444
Compounds as defined in table 1 to table 572, but wherein the sequence of Y and $R^1$ is Z.527 as defined in table Z instead of being Z.1.
Tables 301445-302016
Compounds as defined in table 1 to table 572, but wherein the sequence of Y and $R^1$ is Z.528 as defined in table Z instead of being Z.1.
Tables 302017-302588
Compounds as defined in table 1 to table 572, but wherein the sequence of Y and $R^1$ is Z.529 as defined in table Z instead of being Z.1.
Tables 302589-303160
Compounds as defined in table 1 to table 572, but wherein the sequence of Y and $R^1$ is Z.530 as defined in table Z instead of being Z.1.
Tables 303161-303732
Compounds as defined in table 1 to table 572, but wherein the sequence of Y and $R^1$ is Z.531 as defined in table Z instead of being Z.1.
Tables 303733-304304
Compounds as defined in table 1 to table 572, but wherein the sequence of Y and $R^1$ is Z.532 as defined in table Z instead of being Z.1.
Tables 304305-304876
Compounds as defined in table 1 to table 572, but wherein the sequence of Y and $R^1$ is Z.533 as defined in table Z instead of being 11.
Tables 304877-305448
Compounds as defined in table 1 to table 572, but wherein the sequence of Y and $R^1$ is Z.534 as defined in table Z instead of being Z.1.
Tables 305449-306020
Compounds as defined in table 1 to table 572, but wherein the sequence of Y and $R^1$ is Z.535 as defined in table Z instead of being Z.1.
Tables 306021-306592
Compounds as defined in table 1 to table 572, but wherein the sequence of Y and $R^1$ is Z.536 as defined in table Z instead of being Z.1.
Tables 306593-307164
Compounds as defined in table 1 to table 572, but wherein the sequence of Y and $R^1$ is Z.537 as defined in table Z instead of being Z.1.
Tables 307165-307736
Compounds as defined in table 1 to table 572, but wherein the sequence of Y and $R^1$ is Z.538 as defined in table Z instead of being Z.1.
Tables 307737-308308
Compounds as defined in table 1 to table 572, but wherein the sequence of Y and $R^1$ is Z.539 as defined in table Z instead of being Z.1.
Tables 308309-308880
Compounds as defined in table 1 to table 572, but wherein the sequence of Y and $R^1$ is Z.540 as defined in table Z instead of being Z.1.
Tables 308881-309452
Compounds as defined in table 1 to table 572, but wherein the sequence of Y and $R^1$ is Z.541 as defined in table Z instead of being Z.1.
Tables 309453-310024
Compounds as defined in table 1 to table 572, but wherein the sequence of Y and $R^1$ is Z.542 as defined in table Z instead of being Z.1.
Tables 310025-310596
Compounds as defined in table 1 to table 572, but wherein the sequence of Y and $R^1$ is Z.543 as defined in table Z instead of being Z.1.
Tables 310597-311168
Compounds as defined in table 1 to table 572, but wherein the sequence of Y and $R^1$ is Z.544 as defined in table Z instead of being Z.1.

Tables 311169-311740
Compounds as defined in table 1 to table 572, but wherein the sequence of Y and $R^1$ is Z.545 as defined in table Z instead of being Z.1.

Tables 311741-312312
Compounds as defined in table 1 to table 572, but wherein the sequence of Y and $R^1$ is Z.546 as defined in table Z instead of being Z.1.

Tables 312313-312884
Compounds as defined in table 1 to table 572, but wherein the sequence of Y and $R^1$ is Z.547 as defined in table Z instead of being Z.1.

Tables 312885-313456
Compounds as defined in table 1 to table 572, but wherein the sequence of Y and $R^1$ is Z.548 as defined in table Z instead of being Z.1.

Tables 313457-314028
Compounds as defined in table 1 to table 572, but wherein the sequence of Y and $R^1$ is Z.549 as defined in table Z instead of being Z.1.

Tables 314029-314600
Compounds as defined in table 1 to table 572, but wherein the sequence of Y and $R^1$ is Z.550 as defined in table Z instead of being Z.1.

Tables 314601-315172
Compounds as defined in table 1 to table 572, but wherein the sequence of Y and $R^1$ is Z.551 as defined in table Z instead of being Z.1.

Tables 315173-315744
Compounds as defined in table 1 to table 572, but wherein the sequence of Y and $R^1$ is Z.552 as defined in table Z instead of being Z.1.

Tables 315745-316316
Compounds as defined in table 1 to table 572, but wherein the sequence of Y and $R^1$ is Z.553 as defined in table Z instead of being Z.1.

Tables 316317-316888
Compounds as defined in table 1 to table 572, but wherein the sequence of Y and $R^1$ is Z.554 as defined in table Z instead of being Z.1.

Tables 316889-317460
Compounds as defined in table 1 to table 572, but wherein the sequence of Y and $R^1$ is Z.555 as defined in table Z instead of being Z.1.

Tables 317461-318032
Compounds as defined in table 1 to table 572, but wherein the sequence of Y and $R^1$ is Z.556 as defined in table Z instead of being Z.1.

Tables 318033-318604
Compounds as defined in table 1 to table 572, but wherein the sequence of Y and $R^1$ is Z.557 as defined in table Z instead of being Z.1.

Tables 318605-319176
Compounds as defined in table 1 to table 572, but wherein the sequence of Y and $R^1$ is Z.558 as defined in table Z instead of being Z.1.

Tables 319177-319748
Compounds as defined in table 1 to table 572, but wherein the sequence of Y and $R^1$ is Z.559 as defined in table Z instead of being Z.1.

Tables 319749-320320
Compounds as defined in table 1 to table 572, but wherein the sequence of Y and $R^1$ is Z.560 as defined in table Z instead of being Z.1.

Tables 320321-320892
Compounds as defined in table 1 to table 572, but wherein the sequence of Y and $R^1$ is Z.561 as defined in table Z instead of being Z.1.

Tables 320893-321464
Compounds as defined in table 1 to table 572, but wherein the sequence of Y and $R^1$ is Z.562 as defined in table Z instead of being Z.1.

Tables 321465-322036
Compounds as defined in table 1 to table 572, but wherein the sequence of Y and $R^1$ is Z.563 as defined in table Z instead of being 11.

Tables 322037-322608
Compounds as defined in table 1 to table 572, but wherein the sequence of Y and $R^1$ is Z.564 as defined in table Z instead of being Z.1.

Tables 322609-323180
Compounds as defined in table 1 to table 572, but wherein the sequence of Y and $R^1$ is Z.565 as defined in table Z instead of being Z.1.

Tables 323181-323752
Compounds as defined in table 1 to table 572, but wherein the sequence of Y and $R^1$ is Z.566 as defined in table Z instead of being Z.1.

Tables 323753-324324
Compounds as defined in table 1 to table 572, but wherein the sequence of Y and $R^1$ is Z.567 as defined in table Z instead of being Z.1.

Tables 324325-324896
Compounds as defined in table 1 to table 572, but wherein the sequence of Y and $R^1$ is Z.568 as defined in table Z instead of being 11.

Tables 324897-325468
Compounds as defined in table 1 to table 572, but wherein the sequence of Y and $R^1$ is Z.569 as defined in table Z instead of being Z.1.

Tables 325469-326040
Compounds as defined in table 1 to table 572, but wherein the sequence of Y and $R^1$ is Z.570 as defined in table Z instead of being Z.1.

Tables 326041-326612
Compounds as defined in table 1 to table 572, but wherein the sequence of Y and $R^1$ is Z.571 as defined in table Z instead of being Z.1.

Tables 326613-327184
Compounds as defined in table 1 to table 572, but wherein the sequence of Y and $R^1$ is Z.572 as defined in table Z instead of being Z.1.

Tables 327185-327756
Compounds as defined in table 1 to table 572, but wherein the sequence of Y and $R^1$ is Z.573 as defined in table Z instead of being Z.1.

Tables 327757-328328
Compounds as defined in table 1 to table 572, but wherein the sequence of Y and $R^1$ is Z.574 as defined in table Z instead of being Z.1.

Tables 328329-328900
Compounds as defined in table 1 to table 572, but wherein the sequence of Y and $R^1$ is Z.575 as defined in table Z instead of being Z.1.

Tables 328901-329472
Compounds as defined in table 1 to table 572, but wherein the sequence of Y and $R^1$ is Z.576 as defined in table Z instead of being Z.1.

Tables 329473-330044
Compounds as defined in table 1 to table 572, but wherein the sequence of Y and $R^1$ is Z.577 as defined in table Z instead of being Z.1.

Tables 330045-330616
Compounds as defined in table 1 to table 572, but wherein the sequence of Y and $R^1$ is Z.578 as defined in table Z instead of being Z.1.
Tables 330617-331188
Compounds as defined in table 1 to table 572, but wherein the sequence of Y and $R^1$ is Z.579 as defined in table Z instead of being Z.1.
Tables 331189-331760
Compounds as defined in table 1 to table 572, but wherein the sequence of Y and $R^1$ is Z.580 as defined in table Z instead of being Z.1.
Tables 331761-332332
Compounds as defined in table 1 to table 572, but wherein the sequence of Y and $R^1$ is Z.581 as defined in table Z instead of being Z.1.
Tables 332333-332904
Compounds as defined in table 1 to table 572, but wherein the sequence of Y and $R^1$ is Z.582 as defined in table Z instead of being Z.1.
Tables 332905-333476
Compounds as defined in table 1 to table 572, but wherein the sequence of Y and $R^1$ is Z.583 as defined in table Z instead of being Z.1.
Tables 333477-334048
Compounds as defined in table 1 to table 572, but wherein the sequence of Y and $R^1$ is 1584 as defined in table Z instead of being Z.1.
Tables 334049-334620
Compounds as defined in table 1 to table 572, but wherein the sequence of Y and $R^1$ is Z.585 as defined in table Z instead of being Z.1.
Tables 334621-335192
Compounds as defined in table 1 to table 572, but wherein the sequence of Y and $R^1$ is Z.586 as defined in table Z instead of being Z.1.
Tables 335193-335764
Compounds as defined in table 1 to table 572, but wherein the sequence of Y and $R^1$ is Z.587 as defined in table Z instead of being Z.1.
Tables 335765-336336
Compounds as defined in table 1 to table 572, but wherein the sequence of Y and $R^1$ is 1588 as defined in table Z instead of being Z.1.
Tables 336337-336908
Compounds as defined in table 1 to table 572, but wherein the sequence of Y and $R^1$ is Z.589 as defined in table Z instead of being Z.1.
Tables 336909-337480
Compounds as defined in table 1 to table 572, but wherein the sequence of Y and $R^1$ is Z.590 as defined in table Z instead of being Z.1.
Tables 337481-338052
Compounds as defined in table 1 to table 572, but wherein the sequence of Y and $R^1$ is Z.591 as defined in table Z instead of being Z.1.
Tables 338053-338624
Compounds as defined in table 1 to table 572, but wherein the sequence of Y and $R^1$ is Z.592 as defined in table Z instead of being Z.1.
Tables 338625-339196
Compounds as defined in table 1 to table 572, but wherein the sequence of Y and $R^1$ is Z.593 as defined in table Z instead of being Z.1.
Tables 339197-339768
Compounds as defined in table 1 to table 572, but wherein the sequence of Y and $R^1$ is 1594 as defined in table Z instead of being Z.1.
Tables 339769-340340
Compounds as defined in table 1 to table 572, but wherein the sequence of Y and $R^1$ is Z.595 as defined in table Z instead of being Z.1.
Tables 340341-340912
Compounds as defined in table 1 to table 572, but wherein the sequence of Y and $R^1$ is Z.596 as defined in table Z instead of being Z.1.
Tables 340913-341484
Compounds as defined in table 1 to table 572, but wherein the sequence of Y and $R^1$ is Z.597 as defined in table Z instead of being Z.1.
Tables 341485-342056
Compounds as defined in table 1 to table 572, but wherein the sequence of Y and $R^1$ is Z.598 as defined in table Z instead of being Z.1.
Tables 342057-342628
Compounds as defined in table 1 to table 572, but wherein the sequence of Y and $R^1$ is Z.599 as defined in table Z instead of being Z.1.
Tables 342629-343200
Compounds as defined in table 1 to table 572, but wherein the sequence of Y and $R^1$ is Z.600 as defined in table Z instead of being Z.1.
Tables 343201-343772
Compounds as defined in table 1 to table 572, but wherein the sequence of Y and $R^1$ is Z.601 as defined in table Z instead of being Z.1.

TABLE Z

| Z | Y | $R^1$ |
|---|---|---|
| Z.1. | O | H |
| Z.2. | O | $CH_3$ |
| Z.3. | O | $CF_3$ |
| Z.4. | O | $CH_2CH_3$ |
| Z.5. | O | $CH_2CF_3$ |
| Z.6. | O | $CH_2CH_2CH_3$ |
| Z.7. | O | $CH(CH_3)_2$ |
| Z.8. | O | $(CH_2)_3CH_3$ |
| Z.9. | O | $C_6H_5$ |
| Z.10. | O | 2-Cl—$C_6H_4$ |
| Z.11. | O | 3-Cl—$C_6H_4$ |
| Z.12. | O | 4-Cl—$C_6H_4$ |
| Z.13. | O | $C(=O)CH_3$ |
| Z.14. | O | $C(=O)CH_2CH_3$ |
| Z.15. | O | $C(=O)CH_2OCH_3$ |
| Z.16. | O | $C(=O)(CH_2)_2CH_3$ |
| Z.17. | O | $C(=O)CH(CH_3)_2$ |
| Z.18. | O | $C(=O)C_6H_5$ |
| Z.19. | O | $C(=O)$-2-Cl—$C_6H_4$ |
| Z.20. | O | $C(=O)$-3-Cl—$C_6H_4$ |
| Z.21. | O | $C(=O)$-4-Cl—$C_6H_4$ |
| Z.22. | O | $C(=O)CH_2CF_3$ |
| Z.23. | O | $C(=O)CH_2CCl_3$ |
| Z.24. | O | $C(=O)OCH_2Cl_3$ |
| Z.25. | O | $CH_2C_6H_5$ |
| Z.26. | O | $CH_2CH_2C_6H_5$ |
| Z.27. | O | $CH_2$-2-Cl—$C_6H_4$ |
| Z.28. | O | $CH_2$-4-Cl—$C_6H_4$ |
| Z.29. | O | A-1 |
| Z.30. | O | A-2 |
| Z.31. | O | A-10 |
| Z.32. | O | A-11 |
| Z.33. | O | $CH_2$-A-1 |
| Z.34. | O | $CH_2$-A-2 |
| Z.35. | O | $CH_2$-A-3 |
| Z.36. | O | $CH_2$-A-4 |
| Z.37. | O | $CH_2$-A-5 |
| Z.38. | O | $CH_2$-A-6 |

TABLE Z-continued

| Z | Y | R¹ |
|---|---|---|
| Z.39. | O | $CH_2$-A-7 |
| Z.40. | O | $CH_2$-A-8 |
| Z.41. | O | $CH_2$-A-9 |
| Z.42. | O | $CH_2$-A-10 |
| Z.43. | O | $CH_2$-A-11 |
| Z.44. | O | $CH_2$-A-12 |
| Z.45. | O | $CH_2$-A-13 |
| Z.46. | O | $CH_2$-A-14 |
| Z.47. | O | $CH_2$-A-15 |
| Z.48. | O | $CH_2$-A-16 |
| Z.49. | O | $CH_2$-A-17 |
| Z.50. | O | $CH_2$-A-18 |
| Z.51. | O | $CH_2$-A-19 |
| Z.52. | O | $CH_2$-A-20 |
| Z.53. | O | $CH_2$-A-21 |
| Z.54. | O | $CH_2$-A-22 |
| Z.55. | O | $CH_2$-A-23 |
| Z.56. | O | $CH_2$-A-24 |
| Z.57. | O | $CH_2$-A-25 |
| Z.58. | O | $CH_2$-A-26 |
| Z.59. | O | $CH_2$-A-27 |
| Z.60. | O | $CH_2$-A-28 |
| Z.61. | O | C(=O)-A-2 |
| Z.62. | O | C(=O)-A-3 |
| Z.63. | O | C(=O)-A-4 |
| Z.64. | O | C(=O)-A-5 |
| Z.65. | chemical bond | H |
| Z.66. | chemical bond | $CH_3$ |
| Z.67. | chemical bond | $CF_3$ |
| Z.68. | chemical bond | $CH_2CH_3$ |
| Z.69. | chemical bond | $CH_2CF_3$ |
| Z.70. | chemical bond | $CH_2CH_2CH_3$ |
| Z.71. | chemical bond | $CH(CH_3)_2$ |
| Z.72. | chemical bond | $(CH_2)_3CH_3$ |
| Z.73. | chemical bond | $C_6H_5$ |
| Z.74. | chemical bond | 2-Cl—$C_6H_4$ |
| Z.75. | chemical bond | 3-Cl—$C_6H_4$ |
| Z.76. | chemical bond | 4-Cl—$C_6H_4$ |
| Z.77. | chemical bond | C(=O)$CH_3$ |
| Z.78. | chemical bond | C(=O)$CH_2CH_3$ |
| Z.79. | chemical bond | C(=O)$CH_2OCH_3$ |
| Z.80. | chemical bond | C(=O)$(CH_2)_2CH_3$ |
| Z.81. | chemical bond | C(=O)$CH(CH_3)_2$ |
| Z.82. | chemical bond | C(=O)$C_6H_5$ |
| Z.83. | chemical bond | C(=O)-2-Cl—$C_6H_4$ |
| Z.84. | chemical bond | C(=O)-3-Cl—$C_6H_4$ |
| Z.85. | chemical bond | C(=O)-4-Cl—$C_6H_4$ |
| Z.86. | chemical bond | C(=O)$CH_2CF_3$ |
| Z.87. | chemical bond | C(=O)$CH_2CCl_3$ |
| Z.88. | chemical bond | C(=O)O$CH_2Cl_3$ |
| Z.89. | chemical bond | $CH_2C_6H_5$ |
| Z.90. | chemical bond | $CH_2CH_2C_6H_5$ |
| Z.91. | chemical bond | $CH_2$-2-Cl—$C_6H_4$ |
| Z.92. | chemical bond | $CH_2$-4-Cl—$C_6H_4$ |
| Z.93. | chemical bond | A-1 |
| Z.94. | chemical bond | A-2 |
| Z.95. | chemical bond | A-10 |
| Z.96. | chemical bond | A-11 |
| Z.97. | chemical bond | $CH_2$-A-1 |
| Z.98. | chemical bond | $CH_2$-A-2 |
| Z.99. | chemical bond | $CH_2$-A-3 |
| Z.100. | chemical bond | $CH_2$-A-4 |
| Z.101. | chemical bond | $CH_2$-A-5 |
| Z.102. | chemical bond | $CH_2$-A-6 |
| Z.103. | chemical bond | $CH_2$-A-7 |
| Z.104. | chemical bond | $CH_2$-A-8 |
| Z.105. | chemical bond | $CH_2$-A-9 |
| Z.106. | chemical bond | $CH_2$-A-10 |
| Z.107. | chemical bond | $CH_2$-A-11 |
| Z.108. | chemical bond | $CH_2$-A-12 |
| Z.109. | chemical bond | $CH_2$-A-13 |
| Z.110. | chemical bond | $CH_2$-A-14 |
| Z.111. | chemical bond | $CH_2$-A-15 |
| Z.112. | chemical bond | $CH_2$-A-16 |
| Z.113. | chemical bond | $CH_2$-A-17 |
| Z.114. | chemical bond | $CH_2$-A-18 |
| Z.115. | chemical bond | $CH_2$-A-19 |
| Z.116. | chemical bond | $CH_2$-A-20 |
| Z.117. | chemical bond | $CH_2$-A-21 |
| Z.118. | chemical bond | $CH_2$-A-22 |
| Z.119. | chemical bond | $CH_2$-A-23 |
| Z.120. | chemical bond | $CH_2$-A-24 |
| Z.121. | chemical bond | $CH_2$-A-25 |
| Z.122. | chemical bond | $CH_2$-A-26 |
| Z.123. | chemical bond | $CH_2$-A-27 |
| Z.124. | chemical bond | $CH_2$-A-28 |
| Z.125. | chemical bond | C(=O)-A-2 |
| Z.126. | chemical bond | C(=O)-A-3 |
| Z.127. | chemical bond | C(=O)-A-4 |
| Z.128. | chemical bond | C(=O)-A-5 |
| Z.129. | NH | H |
| Z.130. | NH | $CH_3$ |
| Z.131. | NH | $CF_3$ |
| Z.132. | NH | $CH_2CH_3$ |
| Z.133. | NH | $CH_2CF_3$ |
| Z.134. | NH | $CH_2CH_2CH_3$ |
| Z.135. | NH | $CH(CH_3)_2$ |
| Z.136. | NH | $(CH_2)_3CH_3$ |
| Z.137. | NH | $C_6H_5$ |
| Z.138. | NH | 2-Cl—$C_6H_4$ |
| Z.139. | NH | 3-Cl—$C_6H_4$ |
| Z.140. | NH | 4-Cl—$C_6H_4$ |
| Z.141. | NH | C(=O)$CH_3$ |
| Z.142. | NH | C(=O)$CH_2CH_3$ |
| Z.143. | NH | C(=O)$CH_2OCH_3$ |
| Z.144. | NH | C(=O)$(CH_2)_2CH_3$ |
| Z.145. | NH | C(=O)$CH(CH_3)_2$ |
| Z.146. | NH | C(=O)$C_6H_5$ |
| Z.147. | NH | C(=O)-2-Cl—$C_6H_4$ |
| Z.148. | NH | C(=O)-3-Cl—$C_6H_4$ |
| Z.149. | NH | C(=O)-4-Cl—$C_6H_4$ |
| Z.150. | NH | C(=O)$CH_2CF_3$ |
| Z.151. | NH | C(=O)$CH_2CCl_3$ |
| Z.152. | NH | C(=O)O$CH_2Cl_3$ |
| Z.153. | NH | $CH_2C_6H_5$ |
| Z.154. | NH | $CH_2CH_2C_6H_5$ |
| Z.155. | NH | $CH_2$-2-Cl—$C_6H_4$ |
| Z.156. | NH | $CH_2$-4-Cl—$C_6H_4$ |
| Z.157. | NH | A-1 |
| Z.158. | NH | A-2 |
| Z.159. | NH | A-10 |
| Z.160. | NH | A-11 |
| Z.161. | NH | $CH_2$-A-1 |
| Z.162. | NH | $CH_2$-A-2 |
| Z.163. | NH | $CH_2$-A-3 |
| Z.164. | NH | $CH_2$-A-4 |
| Z.165. | NH | $CH_2$-A-5 |
| Z.166. | NH | $CH_2$-A-6 |
| Z.167. | NH | $CH_2$-A-7 |
| Z.168. | NH | $CH_2$-A-8 |
| Z.169. | NH | $CH_2$-A-9 |
| Z.170. | NH | $CH_2$-A-10 |
| Z.171. | NH | $CH_2$-A-11 |
| Z.172. | NH | $CH_2$-A-12 |
| Z.173. | NH | $CH_2$-A-13 |
| Z.174. | NH | $CH_2$-A-14 |
| Z.175. | NH | $CH_2$-A-15 |
| Z.176. | NH | $CH_2$-A-16 |
| Z.177. | NH | $CH_2$-A-17 |
| Z.178. | NH | $CH_2$-A-18 |
| Z.179. | NH | $CH_2$-A-19 |
| Z.180. | NH | $CH_2$-A-20 |
| Z.181. | NH | $CH_2$-A-21 |
| Z.182. | NH | $CH_2$-A-22 |
| Z.183. | NH | $CH_2$-A-23 |
| Z.184. | NH | $CH_2$-A-24 |
| Z.185. | NH | $CH_2$-A-25 |
| Z.186. | NH | $CH_2$-A-26 |
| Z.187. | NH | $CH_2$-A-27 |
| Z.188. | NH | $CH_2$-A-28 |
| Z.189. | NH | C(=O)-A-2 |
| Z.190. | NH | C(=O)-A-3 |
| Z.191. | NH | C(=O)-A-4 |
| Z.192. | NH | C(=O)-A-5 |
| Z.193. | $NCH_3$ | H |
| Z.194. | $NCH_3$ | $CH_3$ |

TABLE Z-continued

| Z | Y | R¹ |
|---|---|---|
| Z.195. | NCH$_3$ | CF$_3$ |
| Z.196. | NCH$_3$ | CH$_2$CH$_3$ |
| Z.197. | NCH$_3$ | CH$_2$CF$_3$ |
| Z.198. | NCH$_3$ | CH$_2$CH$_2$CH$_3$ |
| Z.199. | NCH$_3$ | CH$_2$CH$_2$CF$_3$ |
| Z.200. | NCH$_3$ | CH$_2$CF$_2$CF$_3$ |
| Z.201. | NCH$_3$ | CH(CH$_3$)$_2$ |
| Z.202. | NCH$_3$ | (CH$_2$)$_3$CH$_3$ |
| Z.203. | NCH$_3$ | (CH$_2$)$_3$CF$_3$ |
| Z.204. | NCH$_3$ | CH$_2$-°propyl |
| Z.205. | NCH$_3$ | CH(CH$_3$)-°propyl |
| Z.206. | NCH$_3$ | C$_6$H$_5$ |
| Z.207. | NCH$_3$ | 2-F—C$_6$H$_4$ |
| Z.208. | NCH$_3$ | 3-F—C$_6$H$_4$ |
| Z.209. | NCH$_3$ | 4-F—C$_6$H$_4$ |
| Z.210. | NCH$_3$ | 2-Cl—C$_6$H$_4$ |
| Z.211. | NCH$_3$ | 3-Cl—C$_6$H$_4$ |
| Z.212. | NCH$_3$ | 4-Cl—C$_6$H$_4$ |
| Z.213. | NCH$_3$ | 2-Br—C$_6$H$_4$ |
| Z.214. | NCH$_3$ | 3-Br—C$_6$H$_4$ |
| Z.215. | NCH$_3$ | 4-Br—C$_6$H$_4$ |
| Z.216. | NCH$_3$ | C(=O)CH$_3$ |
| Z.217. | NCH$_3$ | C(=O)CH$_2$CH$_3$ |
| Z.218. | NCH$_3$ | C(=O)CH$_2$OCH$_3$ |
| Z.219. | NCH$_3$ | C(=O)(CH$_2$)$_2$CH$_3$ |
| Z.220. | NCH$_3$ | C(=O)CH(CH$_3$)$_2$ |
| Z.221. | NCH$_3$ | C(=O)C$_6$H$_5$ |
| Z.222. | NCH$_3$ | C(=O)-2-F—C$_6$H$_4$ |
| Z.223. | NCH$_3$ | C(=O)-3-F—C$_6$H$_4$ |
| Z.224. | NCH$_3$ | C(=O)-4-F—C$_6$H$_4$ |
| Z.225. | NCH$_3$ | C(=O)-2-Cl—C$_6$H$_4$ |
| Z.226. | NCH$_3$ | C(=O)-3-Cl—C$_6$H$_4$ |
| Z.227. | NCH$_3$ | C(=O)-4-Cl—C$_6$H$_4$ |
| Z.228. | NCH$_3$ | C(=O)-2-Br—C$_6$H$_4$ |
| Z.229. | NCH$_3$ | C(=O)-3-Br—C$_6$H$_4$ |
| Z.230. | NCH$_3$ | C(=O)-4-Br—C$_6$H$_4$ |
| Z.231. | NCH$_3$ | C(=O)CH$_2$CF$_3$ |
| Z.232. | NCH$_3$ | C(=O)CH$_2$CCl$_3$ |
| Z.233. | NCH$_3$ | C(=O)OCH$_2$CCl$_3$ |
| Z.234. | NCH$_3$ | CH$_2$C$_6$H$_5$ |
| Z.235. | NCH$_3$ | CH$_2$CH$_2$C$_6$H$_5$ |
| Z.236. | NCH$_3$ | CH$_2$-2-F—C$_6$H$_4$ |
| 2.237. | NCH$_3$ | CH$_2$-3-F—C$_6$H$_4$ |
| Z.238. | NCH$_3$ | CH$_2$-4-F—C$_6$H$_4$ |
| Z.239. | NCH$_3$ | CH$_2$-2-Cl—C$_6$H$_4$ |
| Z.240. | NCH$_3$ | CH$_2$-3-Cl—C$_6$H$_4$ |
| Z.241. | NCH$_3$ | CH$_2$-4-Cl—C$_6$H$_4$ |
| Z.242. | NCH$_3$ | CH$_2$-2-Br—C$_6$H$_4$ |
| Z.243. | NCH$_3$ | CH$_2$-3-Br—C$_6$H$_4$ |
| Z.244. | NCH$_3$ | CH$_2$-4-Br—C$_6$H$_4$ |
| Z.245. | NCH$_3$ | CH$_2$-2-MeO—C$_6$H$_4$ |
| Z.246. | NCH$_3$ | CH$_2$-3-MeO—C$_6$H$_4$ |
| Z.247. | NCH$_3$ | CH$_2$-4-MeO—C$_6$H$_4$ |
| Z.248. | NCH$_3$ | CH$_2$-2-F—C$_6$H$_4$ |
| Z.249. | NCH$_3$ | CH$_2$-3-F—C$_6$H$_4$ |
| Z.250. | NCH$_3$ | CH$_2$-4-F—C$_6$H$_4$ |
| Z.251. | NCH$_3$ | A-1 |
| Z.252. | NCH$_3$ | A-2 |
| Z.253. | NCH$_3$ | A-3 |
| Z.254. | NCH$_3$ | A-4 |
| Z.255. | NCH$_3$ | A-5 |
| Z.256. | NCH$_3$ | A-6 |
| Z.257. | NCH$_3$ | A-7 |
| Z.258. | NCH$_3$ | A-8 |
| Z.259. | NCH$_3$ | A-9 |
| Z.260. | NCH$_3$ | A-10 |
| Z.261. | NCH$_3$ | A-11 |
| Z.262. | NCH$_3$ | A-12 |
| Z.263. | NCH$_3$ | A-13 |
| Z.264. | NCH$_3$ | A-14 |
| Z.265. | NCH$_3$ | A-15 |
| Z.266. | NCH$_3$ | A-16 |
| Z.267. | NCH$_3$ | A-17 |
| Z.268. | NCH$_3$ | A-18 |
| Z.269. | NCH$_3$ | A-19 |
| Z.270. | NCH$_3$ | A-20 |
| Z.271. | NCH$_3$ | A-21 |
| Z.272. | NCH$_3$ | A-22 |
| Z.273. | NCH$_3$ | A-23 |
| Z.274. | NCH$_3$ | A-24 |
| Z.275. | NCH$_3$ | A-25 |
| Z.276. | NCH$_3$ | A-26 |
| Z.277. | NCH$_3$ | A-27 |
| Z.278. | NCH$_3$ | A-28 |
| Z.279. | NCH$_3$ | CH$_2$-A-1 |
| Z.280. | NCH$_3$ | CH$_2$-A-2 |
| Z.281. | NCH$_3$ | CH$_2$-A-3 |
| Z.282. | NCH$_3$ | CH$_2$-A-4 |
| Z.283. | NCH$_3$ | CH$_2$-A-5 |
| Z.284. | NCH$_3$ | CH$_2$-A-6 |
| Z.285. | NCH$_3$ | CH$_2$-A-7 |
| Z.286. | NCH$_3$ | CH$_2$-A-8 |
| Z.287. | NCH$_3$ | CH$_2$-A-9 |
| Z.288. | NCH$_3$ | CH$_2$-A-10 |
| Z.289. | NCH$_3$ | CH$_2$-A-11 |
| Z.290. | NCH$_3$ | CH$_2$-A-12 |
| Z.291. | NCH$_3$ | CH$_2$-A-13 |
| Z.292. | NCH$_3$ | CH$_2$-A-14 |
| Z.293. | NCH$_3$ | CH$_2$-A-15 |
| Z.294. | NCH$_3$ | CH$_2$-A-16 |
| Z.295. | NCH$_3$ | CH$_2$-A-17 |
| Z.296. | NCH$_3$ | CH$_2$-A-18 |
| Z.297. | NCH$_3$ | CH$_2$-A-19 |
| Z.298. | NCH$_3$ | CH$_2$-A-20 |
| Z.299. | NCH$_3$ | CH$_2$-A-21 |
| Z.300. | NCH$_3$ | CH$_2$-A-22 |
| Z.301. | NCH$_3$ | CH$_2$-A-23 |
| Z.302. | NCH$_3$ | CH$_2$-A-24 |
| Z.303. | NCH$_3$ | CH$_2$-A-25 |
| Z.304. | NCH$_3$ | CH$_2$-A-26 |
| Z.305. | NCH$_3$ | CH$_2$-A-27 |
| Z.306. | NCH$_3$ | CH$_2$-A-28 |
| Z.307. | NCH$_3$ | C(=O)-A-1 |
| Z.308. | NCH$_3$ | C(=O)-A-2 |
| Z.309. | NCH$_3$ | C(=O)-A-3 |
| Z.310. | NCH$_3$ | C(=O)-A-4 |
| Z.311. | NCH$_3$ | C(=O)-A-5 |
| Z.312. | NCH$_3$ | C(=O)-A-6 |
| Z.313. | NCH$_3$ | C(=O)-A-7 |
| Z.314. | NCH$_3$ | C(=O)-A-8 |
| Z.315. | NCH$_3$ | C(=O)-A-9 |
| Z.316. | NCH$_3$ | C(=O)-A-10 |
| Z.317. | NCH$_3$ | C(=O)-A-11 |
| Z.318. | NCH$_3$ | C(=O)-A-12 |
| Z.319. | NCH$_3$ | C(=O)-A-13 |
| Z.320. | NCH$_3$ | C(=O)-A-14 |
| Z.321. | NCH$_3$ | C(=O)-A-15 |
| Z.322. | NCH$_3$ | C(=O)-A-16 |
| Z.323. | NCH$_3$ | C(=O)-A-17 |
| Z.324. | NCH$_3$ | C(=O)-A-18 |
| Z.325. | NCH$_3$ | C(=O)-A-19 |
| Z.326. | NCH$_3$ | C(=O)-A-20 |
| Z.327. | NCH$_3$ | C(=O)-A-21 |
| Z.328. | NCH$_3$ | C(=O)-A-22 |
| Z.329. | NCH$_3$ | C(=O)-A-23 |
| Z.330. | NCH$_3$ | C(=O)-A-24 |
| Z.331. | NCH$_3$ | C(=O)-A-25 |
| Z.332. | NCH$_3$ | C(=O)-A-26 |
| Z.333. | NCH$_3$ | C(=O)-A-27 |
| Z.334. | NCH$_3$ | C(=O)-A-28 |
| Z.335. | NCH$_2$CN | H |
| Z.336. | NCH$_2$CN | CH$_3$ |
| Z.337. | NCH$_2$CN | CF$_3$ |
| Z.338. | NCH$_2$CN | CH$_2$CH$_3$ |
| Z.339. | NCH$_2$CN | CH$_2$CF$_3$ |
| Z.340. | NCH$_2$CN | CH(CH$_3$)$_2$ |
| Z.341. | NCH$_2$CN | (CH$_2$)$_3$CH$_3$ |
| Z.342. | NCH$_2$CN | C$_6$H$_5$ |
| Z.343. | NCH$_2$CN | C(=O)CH$_3$ |
| Z.344. | NCH$_2$CN | CH$_2$C$_6$H$_5$ |
| Z.345. | NCH$_2$CH$_3$ | H |
| Z.346. | NCH$_2$CH$_3$ | CH$_3$ |
| Z.347. | NCH$_2$CH$_3$ | CF$_3$ |
| Z.348. | NCH$_2$CH$_3$ | CH$_2$CH$_3$ |
| Z.349. | NCH$_2$CH$_3$ | CH$_2$CF$_3$ |

TABLE Z-continued

| Z | Y | R¹ |
|---|---|---|
| Z.350. | NCH₂CH₃ | CH₂CH₂CH₃ |
| Z.351. | NCH₂CH₃ | CH₂CH₂CF₃ |
| Z.352. | NCH₂CH₃ | CH₂CF₂CF₃ |
| Z.353. | NCH₂CH₃ | CH(CH₃)₂ |
| Z.354. | NCH₂CH₃ | (CH₂)₃CH₃ |
| Z.355. | NCH₂CH₃ | C₆H₅ |
| Z.356. | NCH₂CH₃ | C(=O)CH₃ |
| Z.357. | NCH₂CH₃ | C(=O)CH₂CH₃ |
| Z.358. | NCH₂CH₃ | C(=O)CH₂OCH₃ |
| Z.359. | NCH₂CH₃ | C(=O)(CH₂)₂CH₃ |
| Z.360. | NCH₂CH₃ | C(=O)CH(CH₃)₂ |
| Z.361. | NCH₂CH₃ | C(=O)C₆H₅ |
| Z.362. | NCH₂CH₃ | CH₂C₆H₅ |
| Z.363. | NCH₂CH₃ | CH₂-A-1 |
| Z.364. | NCH₂CH₃ | CH₂-A-2 |
| Z.365. | NCH₂CH₃ | CH₂-A-3 |
| Z.366. | NCH₂CH₃ | CH₂-A-4 |
| Z.367. | NCH₂CH₃ | CH₂-A-5 |
| Z.368. | NCH₂CH₃ | CH₂-A-6 |
| Z.369. | NCH₂CH₃ | CH₂-A-7 |
| Z.370. | NCH₂CH₃ | CH₂-A-8 |
| Z.371. | NCH₂CH₃ | CH₂-A-9 |
| Z.372. | NCH₂CH₃ | CH₂-A-10 |
| Z.373. | NCH₂CH₃ | CH₂-A-11 |
| Z.374. | NCH₂CH₃ | CH₂-A-12 |
| Z.375. | NCH₂CH₃ | CH₂-A-13 |
| Z.376. | NCH₂CH₃ | CH₂-A-14 |
| Z.377. | NCH₂CH₃ | CH₂-A-15 |
| Z.378. | NCH₂CH₃ | CH₂-A-16 |
| Z.379. | NCH₂CH₃ | CH₂-A-17 |
| Z.380. | NCH₂CH₃ | CH₂-A-18 |
| Z.381. | NCH₂CH₃ | CH₂-A-19 |
| Z.382. | NCH₂CH₃ | CH₂-A-20 |
| Z.383. | NCH₂CH₃ | CH₂-A-21 |
| Z.384. | NCH₂CH₃ | CH₂-A-22 |
| Z.385. | NCH₂CH₃ | CH₂-A-23 |
| Z.386. | NCH₂CH₃ | CH₂-A-24 |
| Z.387. | NCH₂CH₃ | CH₂-A-25 |
| Z.388. | NCH₂CH₃ | CH₂-A-26 |
| Z.389. | NCH₂CH₃ | CH₂-A-27 |
| Z.390. | NCH₂CH₃ | CH₂-A-28 |
| Z.391. | NCH₂CF₃ | H |
| Z.392. | NCH₂CF₃ | CH₃ |
| Z.393. | NCH₂CH₂CH₃ | H |
| Z.394. | NCH₂CH₂CH₃ | CH₃ |
| Z.395. | NCH₂CH₂CH₃ | CF₃ |
| Z.396. | NCH₂CH₂CH₃ | CH₂CH₃ |
| Z.397. | NCH₂CH₂CH₃ | CH₂CF₃ |
| Z.398. | NCH₂CH₂CH₃ | CH₂CH₂CH₃ |
| Z.399. | NCH₂CH₂CH₃ | CH(CH₃)₂ |
| Z.400. | NCH₂CH₂CH₃ | (CH₂)₃CH₃ |
| Z.401. | NCH₂CH₂CH₃ | C₆H₅ |
| Z.402. | NCH₂CH₂CH₃ | C(=O)CH₃ |
| Z.403. | NCH₂CF₂CF₃ | H |
| Z.404. | NCH₂CF₂CF₃ | CH₃ |
| Z.405. | N(CH₂)₃CH₃ | H |
| Z.406. | N(CH₂)₃CH₃ | CH₃ |
| Z.407. | NCH₂-cyclopropyl | H |
| Z.408. | NCH₂-cyclopropyl | CH₃ |
| Z.409. | NCH₂-cyclopropyl | CF₃ |
| Z.410. | NCH₂-cyclopropyl | CH₂CH₃ |
| Z.411. | NCH₂-cyclopropyl | CH₂CH₂CH₃ |
| Z.412. | NCH₂-cyclopropyl | CH(CH₃)₂ |
| Z.413. | NCH₂-cyclopropyl | (CH₂)₃CH₃ |
| Z.414. | NCH₂-cyclopropyl | C₆H₅ |
| Z.415. | NCH₂-cyclopropyl | C(=O)CH₃ |
| Z.416. | NCH₂OCH₃ | H |
| Z.417. | NCH₂OCH₃ | CH₃ |
| Z.418. | NCH₂OCH₃ | CF₃ |
| Z.419. | NCH₂OCH₃ | CH₂CH₃ |
| Z.420. | NCH₂OCH₃ | CH₂CF₃ |
| Z.421. | NCH₂OCH₃ | CH₂CH₂CH₃ |
| Z.422. | NCH₂OCH₃ | CH₂CH₂CF₃ |
| Z.423. | NCH₂OCH₃ | CH₂CF₂CF₃ |
| Z.424. | NCH₂OCH₃ | CH(CH₃)₂ |
| Z.425. | NCH₂OCH₃ | (CH₂)₃CH₃ |
| Z.426. | NCH₂OCH₃ | C₆H₅ |
| Z.427. | NCH₂OCH₃ | C(=O)CH₃ |
| Z.428. | NCH₂OCH₃ | C(=O)CH₂CH₃ |
| Z.429. | NCH₂OCH₃ | C(=O)CH₂OCH₃ |
| Z.430. | NCH₂OCH₃ | C(=O)(CH₂)₂CH₃ |
| Z.431. | NCH₂OCH₃ | C(=O)CH(CH₃)₂ |
| Z.432. | NCH₂OCH₃ | C(=O)C₆H₅ |
| Z.433. | NCH₂OCH₃ | CH₂C₆H₅ |
| Z.434. | NCH₂OCF₃ | H |
| Z.435. | NCH₂OCF₃ | CH₃ |
| Z.436. | NCH₂OCF₃ | CF₃ |
| Z.437. | NCH₂OCF₃ | CH₂CH₃ |
| Z.438. | NCH₂OCF₃ | C₆H₅ |
| Z.439. | NCH₂OCF₃ | CH₂C₆H₅ |
| Z.440. | NCH₂OCH₂CH₃ | H |
| Z.441. | NCH₂OCH₂CH₃ | CH₃ |
| Z.442. | NCH₂OCH₂CH₃ | CF₃ |
| Z.443. | NCH₂OCH₂CH₃ | CH₂CH₃ |
| Z.444. | NCH₂OCH₂CH₃ | CH(CH₃)₂ |
| Z.445. | NCH₂OCH₂CH₃ | (CH₂)₃CH₃ |
| Z.446. | NCH₂OCH₂CH₃ | C₆H₅ |
| Z.447. | NCH₂OCH₂CH₃ | CH₂C₆H₅ |
| Z.448. | NCH₂OCH₂CF₃ | H |
| Z.449. | NCH₂OCH₂CF₃ | CH₃ |
| Z.450. | NCH₂OCH₂CF₃ | C₆H₅ |
| Z.451. | NCH₂SCH₃ | H |
| Z.452. | NCH₂SCH₃ | CH₃ |
| Z.453. | NCH₂SCF₃ | H |
| Z.454. | NCH₂SCF₃ | CH₃ |
| Z.455. | NCH₂SCH₂CH₃ | H |
| Z.456. | NCH₂SCH₂CH₃ | CH₃ |
| Z.457. | NCH₂SCH₂CF₃ | H |
| Z.458. | NCH₂SCH₂CF₃ | CH₃ |
| Z.459. | NCH₂CH₂OCH₃ | H |
| Z.460. | NCH₂CH₂OCH₃ | CH₃ |
| Z.461. | NCH₂CH₂OCH₃ | CH₂CH₃ |
| Z.462. | NCH₂CH₂OCH₃ | CH₂CF₃ |
| Z.463. | NCH₂CH₂OCH₃ | CH₂CH₂CH₃ |
| Z.464. | NCH₂CH₂OCH₃ | CH(CH₃)₂ |
| Z.465. | NCH₂CH₂OCH₃ | (CH₂)₃CH₃ |
| Z.466. | NCH₂CH₂OCH₃ | (CH₂)₃CF₃ |
| Z.467. | NCH₂CH₂OCH₃ | C₆H₅ |
| Z.468. | NCH₂CH₂OCH₃ | C(=O)CH₃ |
| Z.469. | NCH₂CH₂OCH₃ | CH₂C₆H₅ |
| Z.470. | NCH₂CH₂OCF₃ | H |
| Z.471. | NCH₂CH₂OCF₃ | CH₃ |
| Z.472. | N(CH₂)₂OCH₂CH₃ | H |
| Z.473. | N(CH₂)₂OCH₂CH₃ | CH₃ |
| Z.474. | N(CH₂)₂OCH₂CH₃ | CF₃ |
| Z.475. | N(CH₂)₂OCH₂CH₃ | C₆H₅ |
| Z.476. | NCH=CHOCH₃ | H |
| Z.477. | NCH=CHOCH₃ | CH₃ |
| Z.478. | NCH₂-A1 | H |
| Z.479. | NCH₂-A1 | CH₃ |
| Z.480. | NCH₂-A20 | H |
| Z.481. | NCH₂-A20 | CH₃ |
| Z.482. | NCH₂-A20 | C₆H₅ |
| Z.483. | NCH₂-A20 | C(=O)CH₃ |
| Z.484. | NCH₂-A20 | C(=O)CH(CH₃)₂ |
| Z.485. | NCH₂-A20 | C(=O)C₆H₅ |
| Z.486. | NCH₂-A20 | CH₂C₆H₅ |
| Z.487. | NC(=O)CH₃ | H |
| Z.488. | NC(=O)CH₃ | CH₃ |
| Z.489. | NC(=O)CH₃ | CF₃ |
| Z.490. | NC(=O)CH₃ | CH₂CH₃ |
| Z.491. | NC(=O)CH₃ | CH₂CF₃ |
| Z.492. | NC(=O)CH₃ | CH₂CH₂CH₃ |
| Z.493. | NC(=O)CH₃ | CH₂CH₂CF₃ |
| Z.494. | NC(=O)CH₃ | CH₂CF₂CF₃ |
| Z.495. | NC(=O)CH₃ | CH(CH₃)₂ |
| Z.496. | NC(=O)CH₃ | (CH₂)₃CH₃ |

TABLE Z-continued

| Z | Y | R¹ |
|---|---|---|
| Z.497. | NC(=O)CH₃ | (CH₂)₃CF₃ |
| Z.498. | NC(=O)CH₃ | CH₂-ᶜpropyl |
| Z.499. | NC(=O)CH₃ | CH(CH₃)-ᶜpropyl |
| Z.500. | NC(=O)CH₃ | C₆H₅ |
| Z.501. | NC(=O)CH₃ | 2-Cl—C₆H₄ |
| Z.502. | NC(=O)CH₃ | 3-Cl—C₆H₄ |
| Z.503. | NC(=O)CH₃ | 4-Cl—C₆H₄ |
| Z.504. | NC(=O)CH₃ | C(=O)CH₃ |
| Z.505. | NC(=O)CH₃ | CH₂C₆H₅ |
| Z.506. | NC(=O)CH₃ | A-1 |
| Z.507. | NC(=O)CH₃ | A-2 |
| Z.508. | NC(=O)CH₃ | A-3 |
| Z.509. | NC(=O)CH₃ | A-4 |
| Z.510. | NC(=O)CH₃ | A-5 |
| Z.511. | NC(=O)CH₃ | A-6 |
| Z.512. | NC(=O)CH₃ | A-7 |
| Z.513. | NC(=O)CH₃ | A-8 |
| Z.514. | NC(=O)CH₃ | A-9 |
| Z.515. | NC(=O)CH₃ | A-10 |
| Z.516. | NC(=O)CH₃ | A-11 |
| Z.517. | NC(=O)CH₃ | A-12 |
| Z.518. | NC(=O)CH₃ | A-15 |
| Z.519. | NC(=O)CH₃ | A-16 |
| Z.520. | NC(=O)CH₃ | A-20 |
| Z.521. | NC(=O)CH₃ | CH₂-A-1 |
| Z.522. | NC(=O)CH₃ | CH₂-A-2 |
| Z.523. | NC(=O)CH₃ | CH₂-A-3 |
| Z.524. | NC(=O)CH₃ | CH₂-A-4 |
| Z.525. | NC(=O)CH₃ | CH₂-A-5 |
| Z.526. | NC(=O)CH₃ | CH₂-A-6 |
| Z.527. | NC(=O)CH₃ | CH₂-A-7 |
| Z.528. | NC(=O)CH₃ | CH₂-A-8 |
| Z.529. | NC(=O)CH₃ | CH₂-A-9 |
| Z.530. | NC(=O)CH₃ | CH₂-A-10 |
| Z.531. | NC(=O)CH₃ | CH₂-A-11 |
| Z.532. | NC(=O)CH₃ | CH₂-A-12 |
| Z.533. | NC(=O)CH₃ | CH₂-A-13 |
| Z.534. | NC(=O)CH₃ | CH₂-A-14 |
| Z.535. | NC(=O)CH₃ | CH₂-A-15 |
| Z.536. | NC(=O)CH₃ | CH₂-A-16 |
| Z.537. | NC(=O)CH₃ | CH₂-A-17 |
| Z.538. | NC(=O)CH₃ | CH₂-A-18 |
| Z.539. | NC(=O)CH₃ | CH₂-A-19 |
| Z.540. | NC(=O)CH₃ | CH₂-A-20 |
| Z.541. | NC(=O)CH₃ | CH₂-A-21 |
| Z.542. | NC(=O)CH₃ | CH₂-A-22 |
| Z.543. | NC(=O)CH₃ | CH₂-A-23 |
| Z.544. | NC(=O)CH₃ | CH₂-A-24 |
| Z.545. | NC(=O)CH₃ | CH₂-A-25 |
| Z.546. | NC(=O)CH₃ | CH₂-A-26 |
| Z.547. | NC(=O)CH₃ | CH₂-A-27 |
| Z.548. | NC(=O)CH₃ | CH₂-A-28 |
| Z.549. | NC(=O)CF₃ | H |
| Z.550. | NC(=O)CF₃ | CH₃ |
| Z.551. | NC(=O)CF₃ | CF₃ |
| Z.552. | NC(=O)CF₃ | CH₂CH₃ |
| Z.553. | NC(=O)CF₃ | CH(CH₃)₂ |
| Z.554. | NC(=O)CF₃ | (CH₂)₃CH₃ |
| Z.555. | NC(=O)CF₃ | C₆H₅ |
| Z.556. | NC(=O)CH₂CH₃ | H |
| Z.557. | NC(=O)CH₂CH₃ | CH₃ |
| Z.558. | NC(=O)CH₂CF₃ | H |
| Z.559. | NC(=O)CH₂CF₃ | CH₃ |
| Z.560. | NC(=O)(CH₂)₂CH₃ | H |
| Z.561. | NC(=O)(CH₂)₂CH₃ | CH₃ |
| Z.562. | NC(=O)OCH₃ | H |
| Z.563. | NC(=O)OCH₃ | CH₃ |
| Z.564. | NC(=O)OCH₂CCl₃ | H |
| Z.565. | NC(=O)OCH₂CCl₃ | CH₃ |
| Z.566. | NC(=O)NH₂ | H |
| Z.567. | NC(=O)NH₂ | CH₃ |
| Z.568. | NC(=O)NH₂ | CF₃ |
| Z.569. | NC(=O)NH₂ | CH₂CH₃ |
| Z.570. | NC(=O)NH₂ | CH₂CF₃ |
| Z.571. | NC(=O)NH₂ | CH₂CH₂CH₃ |
| Z.572. | NC(=O)NH₂ | CH(CH₃)₂ |
| Z.573. | NC(=O)NH₂ | (CH₂)₃CH₃ |
| Z.574. | NC(=O)NH₂ | C₆H₅ |
| Z.575. | NC(=O)NH₂ | C(=O)CH₃ |
| Z.576. | NC(=O)NH₂ | C(=O)CH₂CH₃ |
| Z.577. | NC(=O)NH₂ | C(=O)CH₂OCH₃ |
| Z.578. | NC(=O)NH₂ | C(=O)(CH₂)₂CH₃ |
| Z.579. | NC(=O)NH₂ | C(=O)CH(CH₃)₂ |
| Z.580. | NC(=O)NH₂ | C(=O)C₆H₅ |
| Z.581. | NC(=O)NH₂ | CH₂C₆H₅ |
| Z.582. | NC(=O)NHCH₃ | H |
| Z.583. | NC(=O)NHCH₃ | CH₃ |
| Z.584. | NC(=O)NHCH₃ | CF₃ |
| Z.585. | NC(=O)NHCH₃ | CH₂CH₃ |
| Z.586. | NC(=O)NHCH₃ | CH₂CF₃ |
| Z.587. | NC(=O)NHCH₃ | CH₂CH₂CH₃ |
| Z.588. | NC(=O)NHCH₃ | CH(CH₃)₂ |
| Z.589. | NC(=O)NHCH₃ | C₆H₅ |
| Z.590. | NC(=O)NHCH₃ | C(=O)CH₃ |
| Z.591. | NC(=O)NHCH₃ | C(=O)C₆H₅ |
| Z.592. | NC(=O)NHCH₃ | CH₂C₆H₅ |
| Z.593. | NC(=O)N(CH₃)₂ | H |
| Z.594. | NC(=O)N(CH₃)₂ | CH₃ |
| Z.595. | NC(=O)N(CH₃)₂ | CF₃ |
| Z.596. | NC(=O)N(CH₃)₂ | CH₂CH₃ |
| Z.597. | NC(=O)N(CH₃)₂ | CH(CH₃)₂ |
| Z.598. | NC(=O)N(CH₃)₂ | (CH₂)₃CH₃ |
| Z.599. | NC(=O)N(CH₃)₂ | (CH₂)₃CF₃ |
| Z.600. | NC(=O)N(CH₃)₂ | C₆H₅ |
| Z.601. | NC(=O)N(CH₃)₂ | C(=O)CH₃ | and wherein the variables A in table Z have the following meaning:

A-1: 2,2-dichlorocyclopropyl

A-2: pyridin-2-yl

A-3: pyrimidin-2-yl

A-4: 6-chloropyridin-2-yl

A-5: 5-chloropyridin-2-yl

A-6: 4-chloropyridin-2-yl

-continued
A-7 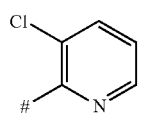
A-8 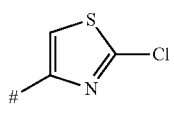
A-9 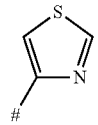
A-10 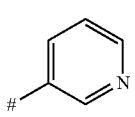
A-11 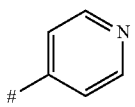
A-12 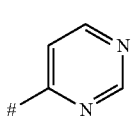
A-13 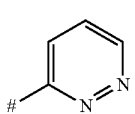
A-14 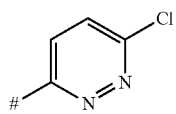
A-15 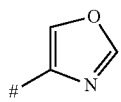
A-16 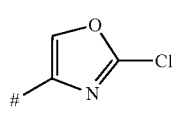
A-17 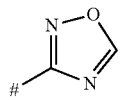
A-18 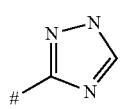
A-19 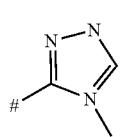
-continued
A-20 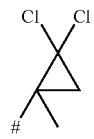
A-21 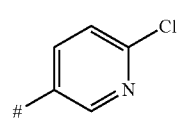
A-22 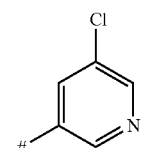
A-23 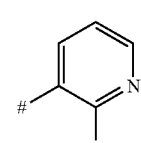
A-24 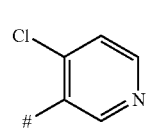
A-25 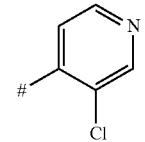
A-26 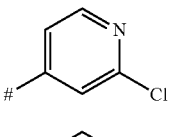
A-27 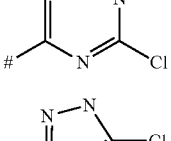
A-28 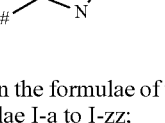
wherein the "#" in the formulae of variables A indicate the bond to formulae I-a to I-zz;
TABLE Q
| Q | $R^2$ | $R^3$ |
|---|---|---|
| Q.1. | | —CH$_2$—CH$_2$—CH$_2$—CH$_2$— |
| Q.2. | | —CH$_2$—CH$_2$—CH$_2$—CH$_2$—CH$_2$— |
| Q.3. | | —CH$_2$—S—CH$_2$—CH$_2$— |
| Q.4. | | —CH$_2$—O—CH$_2$—CH$_2$— |
| Q.5. | | —CH$_2$—CH$_2$—O—CH$_2$—CH$_2$— |
| Q.6. | | —CH$_2$—CH$_2$—S—CH$_2$—CH$_2$— |
| Q.7. | | —CH$_2$—CH$_2$—NH—CH$_2$—CH$_2$— |
| Q.8. | | —CH$_2$—CH$_2$—N(CH$_3$)—CH$_2$—CH$_2$— |
| Q.9. | | —CH$_2$—CH$_2$—CH$_2$— |
| Q.10. | H | F$_3$C |
| Q.11. | H | Cl$_3$C |

TABLE Q-continued

| Q | R² | R³ |
|---|---|---|
| Q.12. | H | Cl₂CH |
| Q.13. | H | ClCH₂ |
| Q.14. | H | CH₃ |
| Q.15. | H | CH₃CH₂ |
| Q.16. | H | (CH₃)₂CH |
| Q.17. | H | (CH₃)₃C |
| Q.18. | H | CH₃CH₂CH₂ |
| Q.19. | H | CH₃CH₂CH₂CH₂ |
| Q.20. | H | (CH₃)₃CCH₂ |
| Q.21. | H | CH₃O |
| Q.22. | H | CH₃CH₂O |
| Q.23. | H | F₃CCH₂O |
| Q.24. | H | CH₃NH |
| Q.25. | H | CH₃CH₂NH |
| Q.26. | H | (CH₃)₂N |
| Q.27. | H | (CH₃CH₂)₂N |
| Q.28. | H | (CH₃CH₂)CH₃N |
| Q.29. | H | C₆H₅NH |
| Q.30. | H | (C₆H₅)CH₃N |
| Q.31. | H | (2,6-F₂C₆H₃)NH |
| Q.32. | H | (2,6-F₂C₆H₃)CH₃N |
| Q.33. | H | cyclopropyl |
| Q.34. | H | cyclobutyl |
| Q.35. | H | cyclopentyl |
| Q.36. | H | cyclohexyl |
| Q.37. | H | CNCH₂ |
| Q.38. | H | CH₃OCH₂ |
| Q.39. | H | CH₃CH₂OCH₂ |
| Q.40. | H | CH₃OCH₂CH₂ |
| Q.41. | H | F₃CCH₂ |
| Q.42. | H | CH₃OCOCH₂ |
| Q.43. | H | CH₃SCH₂ |
| Q.44. | H | CH₃CH₂SCH₂ |
| Q.45. | H | CH₃SCH₂CH₂ |
| Q.46. | H | C₆H₅CH₂ |
| Q.47. | H | CH₂=CHCH₂ |
| Q.48. | H | CH₂=CH |
| Q.49. | H | CH₃CH=CH |
| Q.50. | H | C₆H₅ |
| Q.51. | H | 2-F—C₆H₄ |
| Q.52. | H | 3-F—C₆H₄ |
| Q.53. | H | 4-F—C₆H₄ |
| Q.54. | H | 2-Cl—C₆H₄ |
| Q.55. | H | 3-Cl—C₆H₄ |
| Q.56. | H | 4-Cl—C₆H₄ |
| Q.57. | H | 2-CH₃—C₆H₄ |
| Q.58. | H | 3-CH₃—C₆H₄ |
| Q.59. | H | 4-CH₃—C₆H₄ |
| Q.60. | H | 2-CH₃O—C₆H₄ |
| Q.61. | H | 3-CH₃O—C₆H₄ |
| Q.62. | H | 4-CH₃O—C₆H₄ |
| Q.63. | H | 2-F₃C—C₆H₄ |
| Q.64. | H | 3-F₃C—C₆H₄ |
| Q.65. | H | 4-F₃C—C₆H₄ |
| Q.66. | H | 2-Br—C₆H₄ |
| Q.67. | H | 3-Br—C₆H₄ |
| Q.68. | H | 4-Br—C₆H₄ |
| Q.69. | H | 3-CN—C₆H₄ |
| Q.70. | H | 4-CN—C₆H₄ |
| Q.71. | H | pyridin-2-yl |
| Q.72. | H | pyridin-3-yl |
| Q.73. | H | pyridin-4-yl |
| Q.74. | H | 2-methyl-pyridin-5-yl |
| Q.75. | H | 3-methyl-pyridin-2-yl |
| Q.76. | H | 2-chloro-pyridin-3-yl |
| Q.77. | H | 2-chloro-pyridin-4-yl |
| Q.78. | H | 2-chloro-pyridin-5-yl |
| Q.79. | H | 2-chloro-pyridin-6-yl |
| Q.80 | H | 2-chloro-pyridin-6-yl |
| Q.81. | H | 4-trifluoromethyl-pyridin-3-yl |
| Q.82. | H | 3-methylthio-pyridin-3-yl |
| Q.83. | H | 2,3-dichloro-pyridin-5-yl |
| Q.84. | H | 2,5-dichloro-pyridin-3-yl |
| Q.85. | H | 2,6-dichloro-pyridin-3-yl |
| Q.86. | H | 3,5-dichloro-pyridin-4-yl |
| Q.87. | H | N-methyl-pyrrol-2-yl |
| Q.88. | H | pyrazin-2-yl |
| Q.89. | H | 4-trifluoromethyl-pyrimidin-5-yl |
| Q.90. | H | furan-2-yl |
| Q.91. | H | furan-3-yl |
| Q.92. | H | 2-tetrahydrofuranyl |
| Q.93. | H | 3-tetrahydrofuranyl |
| Q.94. | H | thiophen-2-yl |
| Q.95. | H | thiophen-3-yl |
| Q.96. | H | 1-methyl-3-trifluoro-methyl-1H-pyrazol-4-yl |
| Q.97. | H | 1-methyl-5-trifluoro-methyl-1H-pyrazol-4-yl |
| Q.98. | H | isoxazol-5-yl |
| Q.99. | H | 2,4-dimethyl-thiazol-5-yl |
| Q.100 | H | 4-trifluoromethyl-thiazol-5-yl |
| Q.101 | H | 3-methyl-isothiazol-5-yl |
| Q.102 | H | 3,4-dichloro-isothiazol-5-yl |
| Q.103 | H | C(=O)CH₃ |
| Q.104 | H | C(=O)CH₂CH₃ |
| Q.105 | H | C(=O)CH₂OCH₃ |
| Q.106 | H | C(=O)(CH₂)₂CH₃ |
| Q.107 | H | C(=O)CH(CH₃)₂ |
| Q.108 | H | C(=O)C₆H₅ |
| Q.109 | H | C(=O)-2-Cl—C₆H₄ |
| Q.110 | H | C(=O)-3-Cl—C₆H₄ |
| Q.111 | H | C(=O)-4-Cl—C₆H₄ |
| Q.112 | H | C(=O)CH₂CF₃ |
| Q.113 | H | C(=O)CH₂CCl₃ |
| Q.114 | H | C(=O)OCH₂Cl₃ |
| Q.115 | H | C(=O)N(CH₃)₂ |
| Q.116 | H | C(=O)N(CH₂CH₃)₂ |
| Q.117 | H | C(=S)CH₃ |
| Q.118 | H | C(=S)CH₂CH₃ |
| Q.119 | H | C(=O)-pyridin-2-yl |
| Q.120 | H | C(=O)-pyridin-3-yl |
| Q.121 | H | C(=O)-pyridin-4-yl |
| Q.122 | H | CH₂-A-1 |
| Q.123 | H | CH₂-A-2 |
| Q.124 | H | CH₂-A-3 |
| Q.125 | H | CH₂-A-4 |
| Q.126 | H | CH₂-A-5 |
| Q.127 | H | CH₂-A-6 |
| Q.128 | H | CH₂-A-7 |
| Q.129 | H | CH₂-A-8 |
| Q.130 | H | CH₂-A-9 |
| Q.131 | H | CH₂-A-10 |
| Q.132 | H | CH₂-A-11 |
| Q.133 | H | CH₂-A-12 |
| Q.134 | H | CH₂-A-13 |
| Q.135 | H | CH₂-A-14 |
| Q.136 | H | CH₂-A-15 |
| Q.137 | H | CH₂-A-16 |

TABLE Q-continued

| Q | R² | R³ |
|---|----|----|
| Q.138 | H | CH₂-A-17 |
| Q.139 | H | CH₂-A-18 |
| Q.140 | H | CH₂-A-19 |
| Q.141 | H | CH₂-A-20 |
| Q.142 | H | CH₂-A-21 |
| Q.143 | H | CH₂-A-22 |
| Q.144 | H | CH₂-A-23 |
| Q.145 | H | CH₂-A-24 |
| Q.146 | H | CH₂-A-25 |
| Q.147 | H | CH₂-A-26 |
| Q.148 | H | CH₂-A-27 |
| Q.149 | H | CH₂-A-28 |
| Q.150 | H | A-1 |
| Q.151 | H | A-20 |
| Q.152 | CH₃ | H |
| Q.153 | CH₃ | F₃C |
| Q.154 | CH₃ | Cl₃C |
| Q.155 | CH₃ | Cl₂CH |
| Q.156 | CH₃ | ClCH₂ |
| Q.157 | CH₃ | CH₃ |
| Q.158 | CH₃ | CH₃CH₂ |
| Q.159 | CH₃ | (CH₃)₂CH |
| Q.160 | CH₃ | (CH₃)₃C |
| Q.161 | CH₃ | CH₃CH₂CH₂ |
| Q.162 | CH₃ | CH₃CH₂CH₂CH₂ |
| Q.163 | CH₃ | (CH₃)₃CCH₂ |
| Q.164 | CH₃ | CH₃O |
| Q.165 | CH₃ | CH₃CH₂O |
| Q.166 | CH₃ | F₃CCH₂O |
| Q.167 | CH₃ | CH₃NH |
| Q.168 | CH₃ | CH₃CH₂NH |
| Q.169 | CH₃ | (CH₃)₂N |
| Q.170 | CH₃ | (CH₃CH₂)₂N |
| Q.171 | CH₃ | (CH₃CH₂)CH₃N |
| Q.172 | CH₃ | C₆H₅NH |
| Q.173 | CH₃ | (C₆H₅)CH₃N |
| Q.174 | CH₃ | (2,6-F₂C₆H₃)NH |
| Q.175 | CH₃ | (2,6-F₂C₆H₃)CH₃N |
| Q.176 | CH₃ | cyclopropyl |
| Q.177 | CH₃ | cyclobutyl |
| Q.178 | CH₃ | cyclopentyl |
| Q.179 | CH₃ | cyclohexyl |
| Q.180 | CH₃ | CNCH₂ |
| Q.181 | CH₃ | CH₃OCH₂ |
| Q.182 | CH₃ | CH₃CH₂OCH₂ |
| Q.183 | CH₃ | CH₃OCH₂CH₂ |
| Q.184 | CH₃ | F₃CCH₂ |
| Q.185 | CH₃ | CH₃OCOCH₂ |
| Q.186 | CH₃ | CH₃SCH₂ |
| Q.187 | CH₃ | CH₃CH₂SCH₂ |
| Q.188 | CH₃ | CH₃SCH₂CH₂ |
| Q.189 | CH₃ | C₆H₅CH₂ |
| Q.190 | CH₃ | CH₂=CHCH₂ |
| Q.191 | CH₃ | CH₂=CH |
| Q.192 | CH₃ | CH₃CH=CH |
| Q.193 | CH₃ | C₆H₅ |
| Q.194 | CH₃ | 2-F—C₆H₄ |
| Q.195 | CH₃ | 3-F—C₆H₄ |
| Q.196 | CH₃ | 4-F—C₆H₄ |
| Q.197 | CH₃ | 2-Cl—C₆H₄ |
| Q.198 | CH₃ | 3-Cl—C₆H₄ |
| Q.199 | CH₃ | 4-Cl—C₆H₄ |
| Q.200 | CH₃ | 2-CH₃—C₆H₄ |
| Q.201 | CH₃ | 3-CH₃—C₆H₄ |
| Q.202 | CH₃ | 4-CH₃—C₆H₄ |
| Q.203 | CH₃ | 2-CH₃O—C₆H₄ |
| Q.204 | CH₃ | 3-CH₃O—C₆H₄ |
| Q.205 | CH₃ | 4-CH₃O—C₆H₄ |
| Q.206 | CH₃ | 2-F₃C—C₆H₄ |
| Q.207 | CH₃ | 3-F₃C—C₆H₄ |
| Q.208 | CH₃ | 4-F₃C—C₆H₄ |
| Q.209 | CH₃ | 2-Br—C₆H₄ |
| Q.210 | CH₃ | 3-Br—C₆H₄ |
| Q.211 | CH₃ | 4-Br—C₆H₄ |
| Q.212 | CH₃ | 3-CN—C₆H₄ |
| Q.213 | CH₃ | 4-CN—C₆H₄ |
| Q.214 | CH₃ | pyridin-2-yl |
| Q.215 | CH₃ | pyridin-3-yl |
| Q.216 | CH₃ | pyridin-4-yl |
| Q.217 | CH₃ | 2-methyl-pyridin-5-yl |
| Q.218 | CH₃ | 3-methyl-pyridin-2-yl |
| Q.219 | CH₃ | 2-chloro-pyridin-3-yl |
| Q.220 | CH₃ | 2-chloro-pyridin-4-yl |
| Q.221 | CH₃ | 2-chloro-pyridin-5-yl |
| Q.222 | CH₃ | 2-chloro-pyridin-6-yl |
| Q.223 | CH₃ | 2-chloro-pyridin-6-yl |
| Q.224 | CH₃ | 4-trifluoromethyl-pyridin-3-yl |
| Q.225 | CH₃ | 3-methylthio-pyridin-3-yl |
| Q.226 | CH₃ | 2,3-dichloro-pyridin-5-yl |
| Q.227 | CH₃ | 2,5-dichloro-pyridin-3-yl |
| Q.228 | CH₃ | 2,6-dichloro-pyridin-3-yl |
| Q.229 | CH₃ | 3,5-dichloro-pyridin-4-yl |
| Q.230 | CH₃ | N-methyl-pyrrol-2-yl |
| Q.231 | CH₃ | pyrazin-2-yl |
| Q.232 | CH₃ | 4-trifluoromethyl-pyrimidin-5-yl |
| Q.233 | CH₃ | furan-2-yl |
| Q.234 | CH₃ | furan-3-yl |
| Q.235 | CH₃ | 2-tetrahydrofuranyl |
| Q.236 | CH₃ | 3-tetrahydrofuranyl |
| Q.237 | CH₃ | thiophen-2-yl |
| Q.238 | CH₃ | thiophen-3-yl |
| Q.239 | CH₃ | 1-methyl-3-trifluoro-methyl-1H-pyrazol-4-yl |
| Q.240 | CH₃ | 1-methyl-5-trifluoro-methyl-1H-pyrazol-4-yl |
| Q.241 | CH₃ | isoxazol-5-yl |
| Q.242 | CH₃ | 2,4-dimethyl-thiazol-5-yl |
| Q.243 | CH₃ | 4-trifluoromethyl-thiazol-5-yl |
| Q.244 | CH₃ | 3-methyl-isothiazol-5-yl |
| Q.245 | CH₃ | 3,4-dichloro-isothiazol-5-yl |
| Q.246 | CH₃ | C(=O)CH₃ |
| Q.247 | CH₃ | C(=O)CH₂CH₃ |
| Q.248 | CH₃ | C(=O)CH₂OCH₃ |
| Q.249 | CH₃ | C(=O)(CH₂)₂CH₃ |
| Q.250 | CH₃ | C(=O)CH(CH₃)₂ |
| Q.251 | CH₃ | C(=O)C₆H₅ |
| Q.252 | CH₃ | C(=O)-2-Cl—C₆H₄ |
| Q.253 | CH₃ | C(=O)-3-Cl—C₆H₄ |
| Q.254 | CH₃ | C(=O)-4-Cl—C₆H₄ |
| Q.255 | CH₃ | C(=O)CH₂CF₃ |
| Q.256 | CH₃ | C(=O)CH₂CCl₃ |
| Q.257 | CH₃ | C(=O)OCH₂Cl₃ |
| Q.258 | CH₃ | C(=O)N(CH₃)₂ |
| Q.259 | CH₃ | C(=O)N(CH₂CH₃)₂ |
| Q.260 | CH₃ | C(=S)CH₃ |
| Q.261 | CH₃ | C(=S)CH₂CH₃ |
| Q.262 | CH₃ | C(=O)-pyridin-2-yl |
| Q.263 | CH₃ | C(=O)-pyridin-3-yl |
| Q.264 | CH₃ | C(=O)-pyridin-4-yl |

TABLE Q-continued

| Q | R² | R³ |
|---|---|---|
| Q.265 | CH₃ | CH₂-A-1 |
| Q.266 | CH₃ | CH₂-A-2 |
| Q.267 | CH₃ | CH₂-A-3 |
| Q.268 | CH₃ | CH₂-A-4 |
| Q.269 | CH₃ | CH₂-A-5 |
| Q.270 | CH₃ | CH₂-A-6 |
| Q.271 | CH₃ | CH₂-A-7 |
| Q.272 | CH₃ | CH₂-A-8 |
| Q.273 | CH₃ | CH₂-A-9 |
| Q.274 | CH₃ | CH₂-A-10 |
| Q.275 | CH₃ | CH₂-A-11 |
| Q.276 | CH₃ | CH₂-A-12 |
| Q.277 | CH₃ | CH₂-A-13 |
| Q.278 | CH₃ | CH₂-A-14 |
| Q.279 | CH₃ | CH₂-A-15 |
| Q.280 | CH₃ | CH₂-A-16 |
| Q.281 | CH₃ | CH₂-A-17 |
| Q.282 | CH₃ | CH₂-A-18 |
| Q.283 | CH₃ | CH₂-A-19 |
| Q.284 | CH₃ | CH₂-A-20 |
| Q.285 | CH₃ | CH₂-A-21 |
| Q.286 | CH₃ | CH₂-A-22 |
| Q.287 | CH₃ | CH₂-A-23 |
| Q.288 | CH₃ | CH₂-A-24 |
| Q.289 | CH₃ | CH₂-A-25 |
| Q.290 | CH₃ | CH₂-A-26 |
| Q.291 | CH₃ | CH₂-A-27 |
| Q.292 | CH₃ | CH₂-A-28 |
| Q.293 | CH₃ | A-1 |
| Q.294 | CH₃ | A-20 |
| Q.295 | CH₃CH₂ | H |
| Q.296 | CH₃CH₂ | F₃C |
| Q.297 | CH₃CH₂ | Cl₃C |
| Q.298 | CH₃CH₂ | Cl₂CH |
| Q.299 | CH₃CH₂ | ClCH₂ |
| Q.300 | CH₃CH₂ | CH₃ |
| Q.301 | CH₃CH₂ | CH₃CH₂ |
| Q.302 | CH₃CH₂ | (CH₃)₂CH |
| Q.303 | CH₃CH₂ | (CH₃)₃C |
| Q.304 | CH₃CH₂ | CH₃CH₂CH₂ |
| Q.305 | CH₃CH₂ | CH₃CH₂CH₂CH₂ |
| Q.306 | CH₃CH₂ | (CH₃)₃CCH₂ |
| Q.307 | CH₃CH₂ | CH₃O |
| Q.308 | CH₃CH₂ | CH₃CH₂O |
| Q.309 | CH₃CH₂ | F₃CCH₂O |
| Q.310 | CH₃CH₂ | CH₃NH |
| Q.311 | CH₃CH₂ | CH₃CH₂NH |
| Q.312 | CH₃CH₂ | (CH₃)₂N |
| Q.313 | CH₃CH₂ | (CH₃CH₂)₂N |
| Q.314 | CH₃CH₂ | (CH₃CH₂)CH₃N |
| Q.315 | CH₃CH₂ | C₆H₅ NH |
| Q.316 | CH₃CH₂ | (C₆H₅)CH₃N |
| Q.317 | CH₃CH₂ | (2,6-F₂C₆H₃) NH |
| Q.318 | CH₃CH₂ | (2,6-F₂C₆H₃)CH₃N |
| Q.319 | CH₃CH₂ | cyclopropyl |
| Q.320 | CH₃CH₂ | cyclobutyl |
| Q.321 | CH₃CH₂ | cyclopentyl |
| Q.322 | CH₃CH₂ | cyclohexyl |
| Q.323 | CH₃CH₂ | CNCH₂ |
| Q.324 | CH₃CH₂ | CH₃OCH₂ |
| Q.325 | CH₃CH₂ | CH₃CH₂OCH₂ |
| Q.326 | CH₃CH₂ | CH₃OCH₂CH₂ |
| Q.327 | CH₃CH₂ | F₃C CH₂ |
| Q.328 | CH₃CH₂ | CH₃OCOCH₂ |
| Q.329 | CH₃CH₂ | CH₃SCH₂ |
| Q.330 | CH₃CH₂ | CH₃CH₂SCH₂ |
| Q.331 | CH₃CH₂ | CH₃SCH₂CH₂ |
| Q.332 | CH₃CH₂ | C₆H₅CH₂ |
| Q.333 | CH₃CH₂ | CH₂=CHCH₂ |
| Q.334 | CH₃CH₂ | CH₂=CH |
| Q.335 | CH₃CH₂ | CH₃CH=CH |
| Q.336 | CH₃CH₂ | C₆H₅ |
| Q.337 | CH₃CH₂ | 2-F—C₆H₄ |
| Q.338 | CH₃CH₂ | 3-F—C₆H₄ |
| Q.339 | CH₃CH₂ | 4-F—C₆H₄ |
| Q.340 | CH₃CH₂ | 2-Cl—C₆H₄ |
| Q.341 | CH₃CH₂ | 3-Cl—C₆H₄ |
| Q.342 | CH₃CH₂ | 4-Cl—C₆H₄ |
| Q.343 | CH₃CH₂ | 2-CH₃—C₆H₄ |
| Q.344 | CH₃CH₂ | 3-CH₃—C₆H₄ |
| Q.345 | CH₃CH₂ | 4-CH₃—C₆H₄ |
| Q.346 | CH₃CH₂ | 2-CH₃O—C₆H₄ |
| Q.347 | CH₃CH₂ | 3-CH₃O—C₆H₄ |
| Q.348 | CH₃CH₂ | 4-CH₃O—C₆H₄ |
| Q.349 | CH₃CH₂ | 2-F₃C—C₆H₄ |
| Q.350 | CH₃CH₂ | 3-F₃C—C₆H₄ |
| Q.351 | CH₃CH₂ | 4-F₃C—C₆H₄ |
| Q.352 | CH₃CH₂ | 2-Br—C₆H₄ |
| Q.353 | CH₃CH₂ | 3-Br—C₆H₄ |
| Q.354 | CH₃CH₂ | 4-Br—C₆H₄ |
| Q.355 | CH₃CH₂ | 3-CN—C₆H₄ |
| Q.356 | CH₃CH₂ | 4-CN—C₆H₄ |
| Q.357 | CH₃CH₂ | pyridin-2-yl |
| Q.358 | CH₃CH₂ | pyridin-3-yl |
| Q.359 | CH₃CH₂ | pyridin-4-yl |
| Q.360 | CH₃CH₂ | 2-methyl-pyridin-5-yl |
| Q.361 | CH₃CH₂ | 3-methyl-pyridin-2-yl |
| Q.362 | CH₃CH₂ | 2-chloro-pyridin-3-yl |
| Q.363 | CH₃CH₂ | 2-chloro-pyridin-4-yl |
| Q.364 | CH₃CH₂ | 2-chloro-pyridin-5-yl |
| Q.365 | CH₃CH₂ | 2-chloro-pyridin-6-yl |
| Q.366 | CH₃CH₂ | 2-chloro-pyridin-6-yl |
| Q.367 | CH₃CH₂ | 4-trifluoromethyl-pyridin-3-yl |
| Q.368 | CH₃CH₂ | 3-methylthio-pyridin-3-yl |
| Q.369 | CH₃CH₂ | 2,3-dichloro-pyridin-5-yl |
| Q.370 | CH₃CH₂ | 2,5-dichloro-pyridin-3-yl |
| Q.371 | CH₃CH₂ | 2,6-dichloro-pyridin-3-yl |
| Q.372 | CH₃CH₂ | 3,5-dichloro-pyridin-4-yl |
| Q.373 | CH₃CH₂ | N-methypyrrol-2-yl |
| Q.374 | CH₃CH₂ | pyrazin-2-yl |
| Q.375 | CH₃CH₂ | 4-trifluoromethyl-pyrimidin-5-yl |
| Q.376 | CH₃CH₂ | furan-2-yl |
| Q.377 | CH₃CH₂ | furan-3-yl |
| Q.378 | CH₃CH₂ | 2-tetrahydrofuranyl |
| Q.379 | CH₃CH₂ | 3-tetrahydrofuranyl |
| Q.380 | CH₃CH₂ | thiophen-2-yl |
| Q.381 | CH₃CH₂ | thiophen-3-yl |
| Q.382 | CH₃CH₂ | 1-methyl-3-trifluoro-methyl-1H-pyrazol-4-yl |
| Q.383 | CH₃CH₂ | 1-methyl-5-trifluoro-methyl-1H-pyrazol-4-yl |
| Q.384 | CH₃CH₂ | isoxazol-5-yl |
| Q.385 | CH₃CH₂ | 2,4-dimethyl-thiazol-5-yl |
| Q.386 | CH₃CH₂ | 4-trifluoromethyl-thiazol-5-yl |
| Q.387 | CH₃CH₂ | 3-methyl-isothiazol-5-yl |
| Q.388 | CH₃CH₂ | 3,4-dichloro-isothiazol-5-yl |
| Q.389 | CH₃CH₂ | CH₂-A-1 |
| Q.390 | CH₃CH₂ | CH₂-A-2 |
| Q.391 | CH₃CH₂ | CH₂-A-3 |
| Q.392 | CH₃CH₂ | CH₂-A-4 |
| Q.393 | CH₃CH₂ | CH₂-A-5 |
| Q.394 | CH₃CH₂ | CH₂-A-6 |

TABLE Q-continued

| Q | R² | R³ |
|---|---|---|
| Q.395 | CH₃CH₂ | CH₂-A-7 |
| Q.396 | CH₃CH₂ | CH₂-A-8 |
| Q.397 | CH₃CH₂ | CH₂-A-9 |
| Q.398 | CH₃CH₂ | CH₂-A-10 |
| Q.399 | CH₃CH₂ | CH₂-A-11 |
| Q.400 | CH₃CH₂ | CH₂-A-15 |
| Q.401 | CH₃CH₂ | CH₂-A-16 |
| Q.402 | CH₃CH₂ | CH₂-A-17 |
| Q.403 | CH₃CH₂ | CH₂-A-18 |
| Q.404 | CH₃CH₂ | CH₂-A-19 |
| Q.405 | CH₃CH₂ | CH₂-A-20 |
| Q.406 | CH₃CH₂ | CH₂-A-21 |
| Q.407 | CH₃CH₂ | CH₂-A-22 |
| Q.408 | CH₃CH₂ | CH₂-A-23 |
| Q.409 | CH₃CH₂ | CH₂-A-24 |
| Q.410 | CH₃CH₂ | CH₂-A-25 |
| Q.411 | CH₃CH₂ | CH₂-A-26 |
| Q.412 | CH₃CH₂ | A-1 |
| Q.413 | CH₃CH₂ | A-20 |
| Q.414 | CH₃CH₂CH₂ | H |
| Q.415 | CH₃CH₂CH₂ | F₃C |
| Q.416 | CH₃CH₂CH₂ | Cl₃C |
| Q.417 | CH₃CH₂CH₂ | Cl₂CH |
| Q.418 | CH₃CH₂CH₂ | ClCH₂ |
| Q.419 | CH₃CH₂CH₂ | CH₃ |
| Q.420 | CH₃CH₂CH₂ | CH₃CH₂ |
| Q.421 | CH₃CH₂CH₂ | (CH₃)₂CH |
| Q.422 | CH₃CH₂CH₂ | (CH₃)₃C |
| Q.423 | CH₃CH₂CH₂ | CH₃CH₂CH₂ |
| Q.424 | CH₃CH₂CH₂ | CH₃CH₂CH₂CH₂ |
| Q.425 | CH₃CH₂CH₂ | (CH₃)₃CCH₂ |
| Q.426 | CH₃CH₂CH₂ | CH₃O |
| Q.427 | CH₃CH₂CH₂ | CH₃CH₂O |
| Q.428 | CH₃CH₂CH₂ | F₃CCH₂O |
| Q.429 | CH₃CH₂CH₂ | CH₃NH |
| Q.430 | CH₃CH₂CH₂ | CH₃CH₂NH |
| Q.431 | CH₃CH₂CH₂ | (CH₃)₂N |
| Q.432 | CH₃CH₂CH₂ | (CH₃CH₂)₂N |
| Q.433 | CH₃CH₂CH₂ | (CH₃CH₂)CH₃N |
| Q.434 | CH₃CH₂CH₂ | C₆H₅NH |
| Q.435 | CH₃CH₂CH₂ | (C₆H₅)CH₃N |
| Q.436 | CH₃CH₂CH₂ | (2,6-F₂C₆H₃)NH |
| Q.437 | CH₃CH₂CH₂ | (2,6-F₂C₆H₃)CH₃N |
| Q.438 | CH₃CH₂CH₂ | cyclopropyl |
| Q.439 | CH₃CH₂CH₂ | cyclobutyl |
| Q.440 | CH₃CH₂CH₂ | cyclopentyl |
| Q.441 | CH₃CH₂CH₂ | cyclohexyl |
| Q.442 | CH₃CH₂CH₂ | CNCH₂ |
| Q.443 | CH₃CH₂CH₂ | CH₃OCH₂ |
| Q.444 | CH₃CH₂CH₂ | CH₃CH₂OCH₂ |
| Q.445 | CH₃CH₂CH₂ | CH₃OCH₂CH₂ |
| Q.446 | CH₃CH₂CH₂ | F₃CCH₂ |
| Q.447 | CH₃CH₂CH₂ | CH₃OCOCH₂ |
| Q.448 | CH₃CH₂CH₂ | CH₃SCH₂ |
| Q.449 | CH₃CH₂CH₂ | CH₃CH₂SCH₂ |
| Q.450 | CH₃CH₂CH₂ | CH₃SCH₂CH₂ |
| Q.451 | CH₃CH₂CH₂ | C₆H₅CH₂ |
| Q.452 | CH₃CH₂CH₂ | CH₂=CHCH₂ |
| Q.453 | CH₃CH₂CH₂ | CH₂=CH |
| Q.454 | CH₃CH₂CH₂ | CH₃CH=CH |
| Q.455 | CH₃CH₂CH₂ | C₆H₅ |
| Q.456 | CH₃CH₂CH₂ | 2-F—C₆H₄ |
| Q.457 | CH₃CH₂CH₂ | 3-F—C₆H₄ |
| Q.458 | CH₃CH₂CH₂ | 4-F—C₆H₄ |
| Q.459 | CH₃CH₂CH₂ | 2-Cl—C₆H₄ |
| Q.460 | CH₃CH₂CH₂ | 3-Cl—C₆H₄ |
| Q.461 | CH₃CH₂CH₂ | 4-Cl—C₆H₄ |
| Q.462 | CH₃CH₂CH₂ | 2-CH₃—C₆H₄ |
| Q.463 | CH₃CH₂CH₂ | 3-CH₃—C₆H₄ |
| Q.464 | CH₃CH₂CH₂ | 4-CH₃—C₆H₄ |
| Q.465 | CH₃CH₂CH₂ | 2-CH₃O—C₆H₄ |
| Q.466 | CH₃CH₂CH₂ | 3-CH₃O—C₆H₄ |
| Q.467 | CH₃CH₂CH₂ | 4-CH₃O—C₆H₄ |
| Q.468 | CH₃CH₂CH₂ | 2-F₃C—C₆H₄ |
| Q.469 | CH₃CH₂CH₂ | 3-F₃C—C₆H₄ |
| Q.470 | CH₃CH₂CH₂ | 4-F₃C—C₆H₄ |
| Q.471 | CH₃CH₂CH₂ | 2-Br—C₆H₄ |
| Q.472 | CH₃CH₂CH₂ | 3-Br—C₆H₄ |
| Q.473 | CH₃CH₂CH₂ | 4-Br—C₆H₄ |
| Q.474 | CH₃CH₂CH₂ | 3-CN—C₆H₄ |
| Q.475 | CH₃CH₂CH₂ | 4-CN—C₆H₄ |
| Q.476 | CH₃CH₂CH₂ | pyridin-2-yl |
| Q.477 | CH₃CH₂CH₂ | pyridin-3-yl |
| Q.478 | CH₃CH₂CH₂ | pyridin-4-yl |
| Q.479 | CH₃CH₂CH₂ | 2-methyl-pyridin-5-yl |
| Q.480 | CH₃CH₂CH₂ | 3-methyl-pyridin-2-yl |
| Q.481 | CH₃CH₂CH₂ | 2-chloro-pyridin-3-yl |
| Q.482 | CH₃CH₂CH₂ | 2-chloro-pyridin-4-yl |
| Q.483 | CH₃CH₂CH₂ | 2-chloro-pyridin-5-yl |
| Q.484 | CH₃CH₂CH₂ | 2-chloro-pyridin-6-yl |
| Q.485 | CH₃CH₂CH₂ | 2-chloro-pyridin-6-yl |
| Q.486 | CH₃CH₂CH₂ | 4-trifluoromethyl-pyridin-3-yl |
| Q.487 | CH₃CH₂CH₂ | 3-methylthio-pyridin-3-yl |
| Q.488 | CH₃CH₂CH₂ | 2,3-dichloro-pyridin-5-yl |
| Q.489 | CH₃CH₂CH₂ | 2,5-dichloro-pyridin-3-yl |
| Q.490 | CH₃CH₂CH₂ | 2,6-dichloro-pyridin-3-yl |
| Q.491 | CH₃CH₂CH₂ | 3,5-dichloro-pyridin-4-yl |
| Q.492 | CH₃CH₂CH₂ | N-methy-pyrrol-2-yl |
| Q.493 | CH₃CH₂CH₂ | pyrazin-2-yl |
| Q.494 | CH₃CH₂CH₂ | 4-trifluoromethyl-pyrimidin-5-yl |
| Q.495 | CH₃CH₂CH₂ | furan-2-yl |
| Q.496 | CH₃CH₂CH₂ | furan-3-yl |
| Q.497 | CH₃CH₂CH₂ | 2-tetrahydrofuranyl |
| Q.498 | CH₃CH₂CH₂ | 3-tetrahydrofuranyl |
| Q.499 | CH₃CH₂CH₂ | thiophen-2-yl |
| Q.500 | CH₃CH₂CH₂ | thiophen-3-yl |
| Q.501 | CH₃CH₂CH₂ | 1-methyl-3-trifluoro-methyl-1H-pyrazol-4-yl |
| Q.502 | CH₃CH₂CH₂ | 1-methyl-5-trifluoro-methyl-1H-pyrazol-4-yl |
| Q.503 | CH₃CH₂CH₂ | isoxazol-5-yl |
| Q.504 | CH₃CH₂CH₂ | 2,4-dimethyl-thiazol-5-yl |
| Q.505 | CH₃CH₂CH₂ | 4-trifluoromethyl-thiazol-5-yl |
| Q.506 | CH₃CH₂CH₂ | 3-methyl-isothiazol-5-yl |
| Q.507 | CH₃CH₂CH₂ | 3,4-dichloro-isothiazol-5-yl |
| Q.508 | (C=O)CH₃ | H |
| Q.509 | (C=O)CH₃ | F₃C |
| Q.510 | (C=O)CH₃ | Cl₃C |
| Q.511 | (C=O)CH₃ | Cl₂CH |
| Q.512 | (C=O)CH₃ | ClCH₂ |
| Q.513 | (C=O)CH₃ | CH₃ |
| Q.514 | (C=O)CH₃ | CH₃CH₂ |
| Q.515 | (C=O)CH₃ | (CH₃)₂CH |
| Q.516 | (C=O)CH₃ | (CH₃)₃C |
| Q.517 | (C=O)CH₃ | CH₃CH₂CH₂ |
| Q.518 | (C=O)CH₃ | CH₃CH₂CH₂CH₂ |
| Q.519 | (C=O)CH₃ | (CH₃)₃CCH₂ |
| Q.520 | (C=O)CH₃ | CH₃O |
| Q.521 | (C=O)CH₃ | CH₃CH₂O |
| Q.522 | (C=O)CH₃ | F₃CCH₂O |
| Q.523 | (C=O)CH₃ | CH₃NH |
| Q.524 | (C=O)CH₃ | CH₃CH₂NH |

TABLE Q-continued

| Q | R² | R³ |
|---|---|---|
| Q.525 | (C=O)CH₃ | (CH₃)₂N |
| Q.526 | (C=O)CH₃ | (CH₃CH₂)₂N |
| Q.527 | (C=O)CH₃ | (CH₃CH₂)CH₃N |
| Q.528 | (C=O)CH₃ | C₆H₅ NH |
| Q.529 | (C=O)CH₃ | (C₆H₅)CH₃N |
| Q.530 | (C=O)CH₃ | (2,6-F₂C₆H₃) NH |
| Q.531 | (C=O)CH₃ | (2,6-F₂C₆H₃)CH₃N |
| Q.532 | (C=O)CH₃ | cyclopropyl |
| Q.533 | (C=O)CH₃ | cyclobutyl |
| Q.534 | (C=O)CH₃ | cyclopentyl |
| Q.535 | (C=O)CH₃ | cyclohexyl |
| Q.536 | (C=O)CH₃ | CNCH₂ |
| Q.537 | (C=O)CH₃ | CH₃OCH₂ |
| Q.538 | (C=O)CH₃ | CH₃CH₂OCH₂ |
| Q.539 | (C=O)CH₃ | CH₃OCH₂CH₂ |
| Q.540 | (C=O)CH₃ | F₃C CH₂ |
| Q.541 | (C=O)CH₃ | CH₃OCOCH₂ |
| Q.542 | (C=O)CH₃ | CH₃SCH₂ |
| Q.543 | (C=O)CH₃ | CH₃CH₂SCH₂ |
| Q.544 | (C=O)CH₃ | CH₃SCH₂CH₂ |
| Q.545 | (C=O)CH₃ | C₆H₅CH₂ |
| Q.546 | (C=O)CH₃ | CH₂=CHCH₂ |
| Q.547 | (C=O)CH₃ | CH₂=CH |
| Q.548 | (C=O)CH₃ | CH₃CH=CH |
| Q.549 | (C=O)CH₃ | C₆H₅ |
| Q.550 | (C=O)CH₃ | 2-F—C₆H₄ |
| Q.551 | (C=O)CH₃ | 3-F—C₆H₄ |
| Q.552 | (C=O)CH₃ | 4-F—C₆H₄ |
| Q.553 | (C=O)CH₃ | 2-Cl—C₆H₄ |
| Q.554 | (C=O)CH₃ | 3-Cl—C₆H₄ |
| Q.555 | (C=O)CH₃ | 4-Cl—C₆H₄ |
| Q.556 | (C=O)CH₃ | 2-CH₃—C₆H₄ |
| Q.557 | (C=O)CH₃ | 3-CH₃—C₆H₄ |
| Q.558 | (C=O)CH₃ | 4-CH₃—C₆H₄ |
| Q.559 | (C=O)CH₃ | 2-CH₃O—C₆H₄ |
| Q.560 | (C=O)CH₃ | 3-CH₃O—C₆H₄ |
| Q.561 | (C=O)CH₃ | 4-CH₃O—C₆H₄ |
| Q.562 | (C=O)CH₃ | 2-F₃C—C₆H₄ |
| Q.563 | (C=O)CH₃ | 3-F₃C—C₆H₄ |
| Q.564 | (C=O)CH₃ | 4-F₃C—C₆H₄ |
| Q.565 | (C=O)CH₃ | 2-Br—C₆H₄ |
| Q.566 | (C=O)CH₃ | 3-Br—C₆H₄ |
| Q.567 | (C=O)CH₃ | 4-Br—C₆H₄ |
| Q.568 | (C=O)CH₃ | 3-CN—C₆H₄ |
| Q.569 | (C=O)CH₃ | 4-CN—C₆H₄ |
| Q.570 | (C=O)CH₃ | pyridin-2-yl |
| Q.571 | (C=O)CH₃ | pyridin-3-yl |
| Q.572 | (C=O)CH₃ | pyridin-4-yl |
| Q.573 | (C=O)CH₃ | 2-methyl-pyridin-5-yl |
| Q.574 | (C=O)CH₃ | 3-methyl-pyridin-2-yl |
| Q.575 | (C=O)CH₃ | 2-chloro-pyridin-3-yl |
| Q.576 | (C=O)CH₃ | 2-chloro-pyridin-4-yl |
| Q.577 | (C=O)CH₃ | 2-chloro-pyridin-5-yl |
| Q.578 | (C=O)CH₃ | 2-chloro-pyridin-6-yl |
| Q.579 | (C=O)CH₃ | 2-chloro-pyridin-6-yl |
| Q.580 | (C=O)CH₃ | 4-trifluoromethyl-pyridin-3-yl |
| Q.581 | (C=O)CH₃ | 3-methylthio-pyridin-3-yl |
| Q.582 | (C=O)CH₃ | 2,3-dichloro-pyridin-5-yl |
| Q.583 | (C=O)CH₃ | 2,5-dichloro-pyridin-3-yl |
| Q.584 | (C=O)CH₃ | 2,6-dichloro-pyridin-3-yl |
| Q.585 | (C=O)CH₃ | 3,5-dichloro-pyridin-4-yl |
| Q.586 | (C=O)CH₃ | N-methyl-pyrrol-2-yl |
| Q.587 | (C=O)CH₃ | pyrazin-2-yl |
| Q.588 | (C=O)CH₃ | 4-trifluoromethyl-pyrimidin-5-yl |
| Q.589 | (C=O)CH₃ | furan-2-yl |
| Q.590 | (C=O)CH₃ | furan-3-yl |
| Q.591 | (C=O)CH₃ | 2-tetrahydrofuranyl |
| Q.592 | (C=O)CH₃ | 3-tetrahydrofuranyl |
| Q.593 | (C=O)CH₃ | thiophen-2-yl |
| Q.594 | (C=O)CH₃ | thiophen-3-yl |
| Q.595 | (C=O)CH₃ | 1-methyl-3-trifluoro-methyl-1H-pyrazol-4-yl |
| Q.596 | (C=O)CH₃ | 1-methyl-5-trifluoro-methyl-1H-pyrazol-4-yl |
| Q.597 | (C=O)CH₃ | isoxazol-5-yl |
| Q.598 | (C=O)CH₃ | 2,4-dimethyl-thiazol-5-yl |
| Q.599 | (C=O)CH₃ | 4-trifluoromethyl-thiazol-5-yl |
| Q.600 | (C=O)CH₃ | 3-methyl-isothiazol-5-yl |
| Q.601 | (C=O)CH₃ | 3,4-dichloro-isothiazol-5-yl |
| Q.602 | (C=O)CH₃ | CH₂-A-1 |
| Q.603 | (C=O)CH₃ | CH₂-A-2 |
| Q.604 | (C=O)CH₃ | CH₂-A-3 |
| Q.605 | (C=O)CH₃ | CH₂-A-4 |
| Q.606 | (C=O)CH₃ | CH₂-A-5 |
| Q.607 | (C=O)CH₃ | CH₂-A-6 |
| Q.608 | (C=O)CH₃ | CH₂-A-7 |
| Q.609 | (C=O)CH₃ | CH₂-A-8 |
| Q.610 | (C=O)CH₃ | CH₂-A-9 |
| Q.611 | (C=O)CH₃ | CH₂-A-10 |
| Q.612 | (C=O)CH₃ | CH₂-A-11 |
| Q.613 | (C=O)CH₃ | CH₂-A-12 |
| Q.614 | (C=O)CH₃ | CH₂-A-13 |
| Q.615 | (C=O)CH₃ | CH₂-A-14 |
| Q.616 | (C=O)CH₃ | CH₂-A-15 |
| Q.617 | (C=O)CH₃ | CH₂-A-16 |
| Q.618 | (C=O)CH₃ | CH₂-A-17 |
| Q.619 | (C=O)CH₃ | CH₂-A-18 |
| Q.620 | (C=O)CH₃ | CH₂-A-19 |
| Q.621 | (C=O)CH₃ | CH₂-A-20 |
| Q.622 | (C=O)CH₃ | CH₂-A-21 |
| Q.623 | (C=O)CH₃ | CH₂-A-22 |
| Q.624 | (C=O)CH₃ | CH₂-A-23 |
| Q.625 | (C=O)CH₃ | CH₂-A-24 |
| Q.626 | (C=O)CH₃ | CH₂-A-25 |
| Q.627 | (C=O)CH₃ | CH₂-A-26 |
| Q.628 | (C=O)CH₃ | CH₂-A-27 |
| Q.629 | (C=O)CH₃ | CH₂-A-28 |
| Q.630 | (C=O)CH₃ | A-1 |
| Q.631 | (C=O)CH₃ | A-20 |
| Q.632 | CNCH₂ | F₃C |
| Q.633 | CNCH₂ | Cl₃C |
| Q.634 | CNCH₂ | Cl₂CH |
| Q.635 | CNCH₂ | ClCH₂ |
| Q.636 | CNCH₂ | CH₃ |
| Q.637 | CNCH₂ | CH₃CH₂ |
| Q.638 | CNCH₂ | (CH₃)₂CH |
| Q.639 | CNCH₂ | (CH₃)₃C |
| Q.640 | CNCH₂ | CH₃CH₂CH₂ |
| Q.641 | CNCH₂ | CH₃CH₂CH₂CH₂ |
| Q.642 | CNCH₂ | (CH₃)₃CCH₂ |
| Q.643 | CNCH₂ | CH₃O |
| Q.644 | CNCH₂ | CH₃CH₂O |
| Q.645 | CNCH₂ | CH₃NH |
| Q.646 | CNCH₂ | CH₃CH₂NH |
| Q.647 | CNCH₂ | (CH₃)₂N |
| Q.648 | CNCH₂ | (CH₃CH₂)₂N |
| Q.649 | CNCH₂ | (CH₃CH₂)CH₃N |
| Q.650 | CNCH₂ | C₆H₅ NH |
| Q.651 | CNCH₂ | (C₆H₅)CH₃N |
| Q.652 | CNCH₂ | cyclopropyl |
| Q.653 | CNCH₂ | cyclobutyl |
| Q.654 | CNCH₂ | cyclopentyl |

TABLE Q-continued

| Q | R² | R³ |
|---|---|---|
| Q.655 | CNCH₂ | cyclohexyl |
| Q.656 | CNCH₂ | CNCH₂ |
| Q.657 | CNCH₂ | CH₃OCH₂ |
| Q.658 | CNCH₂ | CH₃CH₂OCH₂ |
| Q.659 | CNCH₂ | CH₃OCH₂CH₂ |
| Q.660 | CNCH₂ | F₃C—CH₂ |
| Q.661 | CNCH₂ | CH₃OCOCH₂ |
| Q.662 | CNCH₂ | CH₃SCH₂ |
| Q.663 | CNCH₂ | CH₃CH₂SCH₂ |
| Q.664 | CNCH₂ | CH₃SCH₂CH₂ |
| Q.665 | CNCH₂ | C₆H₅CH₂ |
| Q.666 | CNCH₂ | CH₂=CHCH₂ |
| Q.667 | CNCH₂ | CH₂=CH |
| Q.668 | CNCH₂ | CH₃CH=CH |
| Q.669 | CNCH₂ | C₆H₅ |
| Q.670 | CNCH₂ | pyridin-2-yl |
| Q.671 | CNCH₂ | pyridin-3-yl |
| Q.672 | CNCH₂ | pyridin-4-yl |
| Q.673 | CNCH₂ | 2-methyl-pyridin-5-yl |
| Q.674 | CNCH₂ | 3-methyl-pyridin-2-yl |
| Q.675 | CNCH₂ | 2-chloro-pyridin-3-yl |
| Q.676 | CNCH₂ | 2-chloro-pyridin-4-yl |
| Q.677 | CNCH₂ | 2-chloro-pyridin-5-yl |
| Q.678 | CNCH₂ | 2-chloro-pyridin-6-yl |
| Q.679 | CNCH₂ | 4-trifluoromethyl-pyridin-3-yl |
| Q.680 | CNCH₂ | furan-2-yl |
| Q.681 | CNCH₂ | furan-3-yl |
| Q.682 | CNCH₂ | 2-tetrahydrofuranyl |
| Q.683 | CNCH₂ | 3-tetrahydrofuranyl |
| Q.684 | CNCH₂ | thiophen-2-yl |
| Q.685 | CNCH₂ | thiophen-3-yl |
| Q.686 | CNCH₂ | CH₂-A-1 |
| Q.687 | CNCH₂ | CH₂-A-2 |
| Q.688 | CNCH₂ | CH₂-A-3 |
| Q.689 | CNCH₂ | CH₂-A-4 |
| Q.690 | CNCH₂ | CH₂-A-5 |
| Q.691 | CNCH₂ | CH₂-A-6 |
| Q.692 | CNCH₂ | CH₂-A-7 |
| Q.693 | CNCH₂ | CH₂-A-8 |
| Q.694 | CNCH₂ | CH₂-A-9 |
| Q.695 | CNCH₂ | CH₂-A-10 |
| Q.696 | CNCH₂ | CH₂-A-11 |
| Q.697 | CNCH₂ | CH₂-A-12 |
| Q.698 | CNCH₂ | CH₂-A-13 |
| Q.699 | CNCH₂ | CH₂-A-14 |
| Q.700 | CNCH₂ | CH₂-A-15 |
| Q.701 | CNCH₂ | CH₂-A-16 |
| Q.702 | CNCH₂ | CH₂-A-20 |
| Q.703 | CNCH₂ | CH₂-A-21 |
| Q.704 | CNCH₂ | CH₂-A-26 |
| Q.705 | (C=O)OCH₃ | F₃C |
| Q.706 | (C=O)OCH₃ | Cl₃C |
| Q.707 | (C=O)OCH₃ | Cl₂CH |
| Q.708 | (C=O)OCH₃ | ClCH₂ |
| Q.709 | (C=O)OCH₃ | CH₃ |
| Q.710 | (C=O)OCH₃ | CH₃CH₂ |
| Q.711 | (C=O)OCH₃ | (CH₃)₂CH |
| Q.712 | (C=O)OCH₃ | (CH₃)₃C |
| Q.713 | (C=O)OCH₃ | CH₃CH₂CH₂ |
| Q.714 | (C=O)OCH₃ | CH₃CH₂CH₂CH₂ |
| Q.715 | (C=O)OCH₃ | (CH₃)₃CCH₂ |
| Q.716 | (C=O)OCH₃ | CH₃O |
| Q.717 | (C=O)OCH₃ | CH₃CH₂O |
| Q.718 | (C=O)OCH₃ | F₃CCH₂O |
| Q.719 | (C=O)OCH₃ | CH₃NH |
| Q.720 | (C=O)OCH₃ | CH₃CH₂NH |
| Q.721 | (C=O)OCH₃ | (CH₃)₂N |
| Q.722 | (C=O)OCH₃ | (CH₃CH₂)₂N |
| Q.723 | (C=O)OCH₃ | (CH₃CH₂)CH₃N |
| Q.724 | (C=O)OCH₃ | C₆H₅NH |
| Q.725 | (C=O)OCH₃ | (C₆H₅)CH₃N |
| Q.726 | (C=O)OCH₃ | cyclopropyl |
| Q.727 | (C=O)OCH₃ | cyclobutyl |
| Q.728 | (C=O)OCH₃ | cyclopentyl |
| Q.729 | (C=O)OCH₃ | cyclohexyl |
| Q.730 | (C=O)OCH₃ | CNCH₂ |
| Q.731 | (C=O)OCH₃ | CH₃OCH₂ |
| Q.732 | (C=O)OCH₃ | CH₃CH₂OCH₂ |
| Q.733 | (C=O)OCH₃ | CH₃OCH₂CH₂ |
| Q.734 | (C=O)OCH₃ | F₃C CH₂ |
| Q.735 | (C=O)OCH₃ | CH₃OCOCH₂ |
| Q.736 | (C=O)OCH₃ | CH₃SCH₂ |
| Q.737 | (C=O)OCH₃ | CH₃CH₂SCH₂ |
| Q.738 | (C=O)OCH₃ | CH₃SCH₂CH₂ |
| Q.739 | (C=O)OCH₃ | C₆H₅CH₂ |
| Q.740 | (C=O)OCH₃ | CH₂=CHCH₂ |
| Q.741 | (C=O)OCH₃ | CH₂=CH |
| Q.742 | (C=O)OCH₃ | CH₃CH=CH |
| Q.743 | (C=O)OCH₃ | C₆H₅ |
| Q.744 | (C=O)OCH₃ | pyridin-2-yl |
| Q.745 | (C=O)OCH₃ | pyridin-3-yl |
| Q.746 | (C=O)OCH₃ | pyridin-4-yl |
| Q.747 | (C=O)OCH₃ | 2-methyl-pyridin-5-yl |
| Q.748 | (C=O)OCH₃ | 3-methyl-pyridin-2-yl |
| Q.749 | (C=O)OCH₃ | 2-chloro-pyridin-3-yl |
| Q.750 | (C=O)OCH₃ | 2-chloro-pyridin-4-yl |
| Q.751 | (C=O)OCH₃ | 2-chloro-pyridin-5-yl |
| Q.752 | (C=O)OCH₃ | 2-chloro-pyridin-6-yl |
| Q.753 | (C=O)OCH₃ | 2-chloro-pyridin-6-yl |
| Q.754 | (C=O)OCH₃ | 4-trifluoromethyl-pyridin-3-yl |
| Q.755 | (C=O)OCH₃ | furan-2-yl |
| Q.756 | (C=O)OCH₃ | furan-3-yl |
| Q.757 | (C=O)OCH₃ | 2-tetrahydrofuranyl |
| Q.758 | (C=O)OCH₃ | 3-tetrahydrofuranyl |
| Q.759 | (C=O)OCH₃ | thiophen-2-yl |
| Q.760 | (C=O)OCH₃ | thiophen-3-yl |
| Q.761 | (C=O)OCH₃ | CH₂-A-1 |
| Q.762 | (C=O)OCH₃ | CH₂-A-2 |
| Q.763 | (C=O)OCH₃ | CH₂-A-3 |
| Q.764 | (C=O)OCH₃ | CH₂-A-4 |
| Q.765 | (C=O)OCH₃ | CH₂-A-5 |
| Q.766 | (C=O)OCH₃ | CH₂-A-6 |
| Q.767 | (C=O)OCH₃ | CH₂-A-7 |
| Q.768 | (C=O)OCH₃ | CH₂-A-8 |
| Q.769 | (C=O)OCH₃ | CH₂-A-9 |
| Q.770 | (C=O)OCH₃ | CH₂-A-10 |
| Q.771 | (C=O)OCH₃ | CH₂-A-11 |
| Q.772 | (C=O)OCH₃ | CH₂-A-12 |
| Q.773 | (C=O)OCH₃ | CH₂-A-13 |
| Q.774 | (C=O)OCH₃ | CH₂-A-14 |
| Q.775 | (C=O)OCH₃ | CH₂-A-15 |
| Q.776 | (C=O)OCH₃ | CH₂-A-16 |
| Q.777 | (C=O)OCH₃ | CH₂-A-20 |
| Q.778 | (C=O)OCH₃ | CH₂-A-21 |
| Q.779 | (C=O)OCH₃ | CH₂-A-26 |
| Q.780 | CH₂OCH₃ | H |
| Q.781 | CH₂OCH₃ | F₃C |
| Q.782 | CH₂OCH₃ | Cl₃C |
| Q.783 | CH₂OCH₃ | CH₃ |
| Q.784 | CH₂OCH₃ | CH₃CH₂ |
| Q.785 | CH₂OCH₃ | (CH₃)₂CH |
| Q.786 | CH₂OCH₃ | (CH₃)₃C |
| Q.787 | CH₂OCH₃ | CH₃CH₂CH₂ |
| Q.788 | CH₂OCH₃ | CH₃CH₂CH₂CH₂ |
| Q.789 | CH₂OCH₃ | (CH₃)₃CCH₂ |
| Q.790 | CH₂OCH₃ | CH₃O |
| Q.791 | CH₂OCH₃ | F₃CCH₂O |

TABLE Q-continued

| Q | R² | R³ |
|---|---|---|
| Q.792 | CH₂OCH₃ | CH₃NH |
| Q.793 | CH₂OCH₃ | CH₃CH₂NH |
| Q.794 | CH₂OCH₃ | (CH₃)₂N |
| Q.795 | CH₂OCH₃ | (CH₃CH₂)₂N |
| Q.796 | CH₂OCH₃ | C₆H₅NH |
| Q.797 | CH₂OCH₃ | (C₆H₅)CH₃N |
| Q.798 | CH₂OCH₃ | cyclopropyl |
| Q.799 | CH₂OCH₃ | cyclobutyl |
| Q.800 | CH₂OCH₃ | cyclopentyl |
| Q.801 | CH₂OCH₃ | cyclohexyl |
| Q.802 | CH₂OCH₃ | CNCH₂ |
| Q.803 | CH₂OCH₃ | CH₃OCH₂ |
| Q.804 | CH₂OCH₃ | CH₃CH₂OCH₂ |
| Q.805 | CH₂OCH₃ | CH₃OCH₂CH₂ |
| Q.806 | CH₂OCH₃ | F₃C CH₂ |
| Q.807 | CH₂OCH₃ | CH₃OCOCH₂ |
| Q.808 | CH₂OCH₃ | CH₃SCH₂ |
| Q.809 | CH₂OCH₃ | CH₃CH₂SCH₂ |
| Q.810 | CH₂OCH₃ | CH₃SCH₂CH₂ |
| Q.811 | CH₂OCH₃ | C₆H₅CH₂ |
| Q.812 | CH₂OCH₃ | CH₂=CHCH₂ |
| Q.813 | CH₂OCH₃ | CH₂=CH |
| Q.814 | CH₂OCH₃ | CH₃CH=CH |
| Q.815 | CH₂OCH₃ | C₆H₅ |
| Q.816 | CH₂OCH₃ | pyridin-2-yl |
| Q.817 | CH₂OCH₃ | pyridin-3-yl |
| Q.818 | CH₂OCH₃ | pyridin-4-yl |
| Q.819 | CH₂OCH₃ | furan-2-yl |
| Q.820 | CH₂OCH₃ | furan-3-yl |
| Q.821 | CH₂OCH₃ | 2-tetrahydrofuranyl |
| Q.822 | CH₂OCH₃ | 3-tetrahydrofuranyl |
| Q.823 | CH₂OCH₃ | thiophen-2-yl |
| Q.824 | CH₂OCH₃ | thiophen-3-yl |
| Q.825 | CH₂OCH₃ | CH₂-A-1 |
| Q.826 | CH₂OCH₃ | CH₂-A-2 |
| Q.827 | CH₂OCH₃ | CH₂-A-3 |
| Q.828 | CH₂OCH₃ | CH₂-A-4 |
| Q.829 | CH₂OCH₃ | CH₂-A-5 |
| Q.830 | CH₂OCH₃ | CH₂-A-6 |
| Q.831 | CH₂OCH₃ | CH₂-A-7 |
| Q.832 | CH₂OCH₃ | CH₂-A-8 |
| Q.833 | CH₂OCH₃ | CH₂-A-9 |
| Q.834 | CH₂OCH₃ | CH₂-A-10 |
| Q.835 | CH₂OCH₃ | CH₂-A-11 |
| Q.836 | CH₂OCH₃ | CH₂-A-12 |
| Q.837 | CH₂OCH₃ | CH₂-A-13 |
| Q.838 | CH₂OCH₃ | CH₂-A-14 |
| Q.839 | CH₂OCH₃ | CH₂-A-15 |
| Q.840 | CH₂OCH₃ | CH₂-A-16 |
| Q.841 | CH₂OCH₃ | CH₂-A-20 |
| Q.842 | CH₂OCH₃ | CH₂-A-21 |
| Q.843 | CH₂OCH₃ | CH₂-A-26 |
| Q.844 | C(=O)C(CH₃)₃ | CH₂-A-2 |
| Q.845 | C(=O)C(CH₃)₃ | CH₂CF₃ |
| Q.846 | C(=O)CH₂CH₃ | CH₂-A-2 |
| Q.847 | C(=O)CH₂CH₃ | CH₂CF₃ |
| Q.848 | C(=O)N(CH₃)₂ | CH₂-A-2 |
| Q.849 | C(=O)N(CH₃)₂ | CH₂CF₃ |
| Q.850 | C(=S)CH₃ | CH₂-A-2 |
| Q.851 | C(=S)CH₃ | CH₂CF₃ |
| Q.852 | CH₂CH=CH₂ | CH₂-A-2 |
| Q.853 | CH₂CH=CH₂ | CH₂CF₃ | and wherein the variables A in table Q have the same meanings as given for table Z.

Preparation Methods

Compound of formula (I) according to the present invention can be prepared e.g. according the preparation methods and preparation schemes as described below.

Methods for the preparation of substituted amidine compounds of formula (I):

Compounds of formula I can be prepared according to the following methods and variations described in schemes 1-13. $R^1$-$R^5$, $A^1$-$A^4$, $B^1$-$B^3$, X, Y, p and q are defined as above for formula I.

Compounds of formula I can, for example, be prepared by cycloaddition of styrene compounds of formula II with nitrile oxides derived from oximes of formula III as outlined in scheme 1. The reaction typically proceeds through the intermediacy of an in situ generated hydroxamic acid halogenide, normally a chloride, by reaction with a halogenating agent like chlorine, hypochloride, N-succinimide, or chloramine-T. The halogenating agent is combined with the oxime before addition, or in the presence of the styrene II. Depending on the conditions, amine bases such as pyridine or triethylamine may be necessary. The reaction can be run in a wide variety of solvents including DMF, toluene, dichloromethane, chlorobenzene, acetonitrile, tetrahydrofurane, diethylether or the like.

The corresponding styrene compounds of formula II can be prepared as e.g. described in WO 2005085216 or WO 2007094313.

Scheme 1:

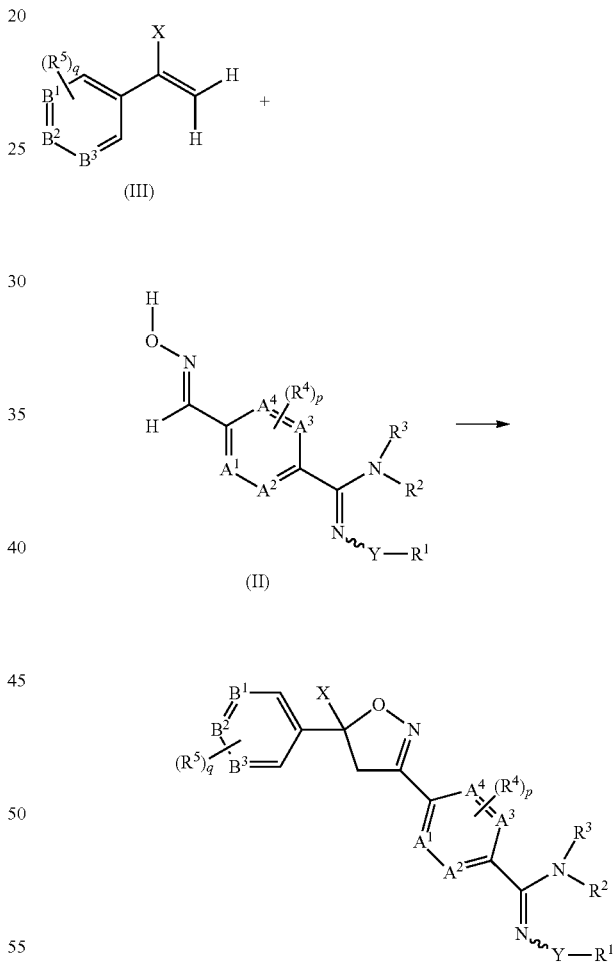

Compounds of formula I, especially the corresponding amidoxime compounds (wherein Y is an oxygen atom) can also be prepared as outlined in scheme 2 by alkylation of substituted imines of formula IV. These corresponding compounds according to formula IV can be prepared starting from the corresponding substances of formula V, (wherein J may be a leaving group like halogen, $OR^{16}$ or $S(O)_nR^{16}$ and wherein n=0-2) as described e.g. by Eloy et al, Chem. Rev. 1962, 62, 155.

Scheme 2:

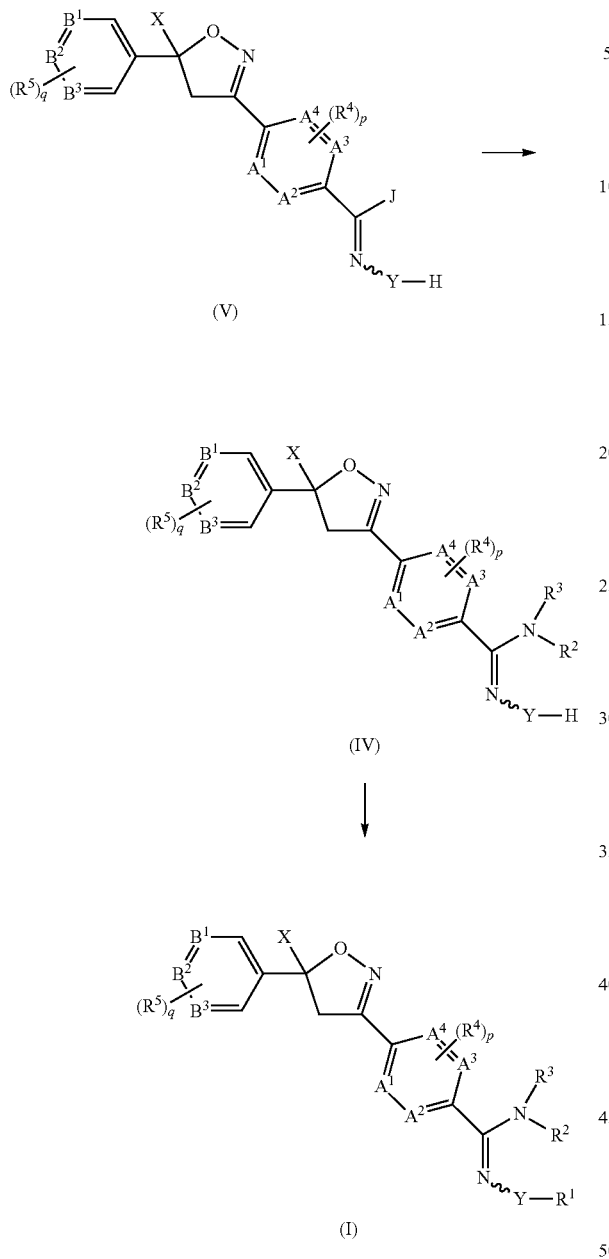

The corresponding intermediate compounds of formula V can be prepared by reaction of a substituted aldimine with a halogenation reagent (for example chlorine, NCS, NBS, NIS, hypochlorite etc) as e.g. described by Kelly et al, Org. & Biomol. Chem. 2008, 6, 787 for the preparation of oximes.

Compounds of formula I can also be prepared as outlined in scheme 3 by condensation of an amide or thioamide of formula VI with a substituted amine, a substituted hydrazine, or an oxygen-substituted oxyl amine, as for example described by Su et al, Organic Letters 2005, 7(13), 2751-2754 for amidoximes, or as for example described by Schmidt et al, Helv. Chim. Acta 1955, 188, 1560 for amidrazones. The preparation of compounds of formula VI is, for example described in WO 2005085216. In formula VI of scheme 3, W may be an oxygen or sulfur atom.

Scheme 3:

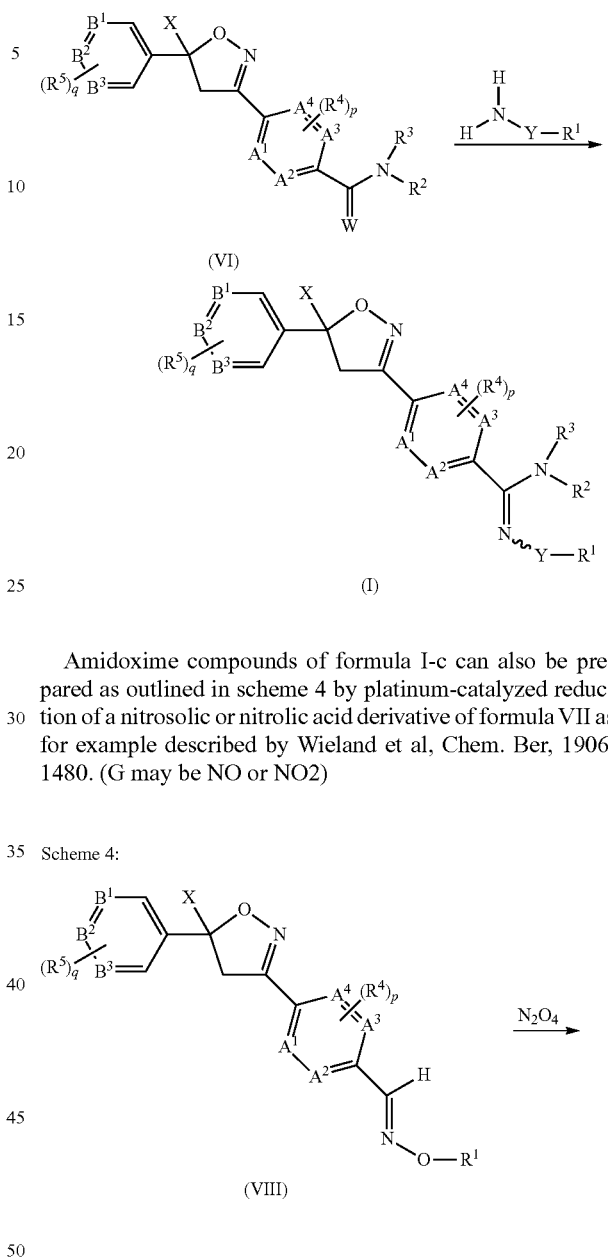

Amidoxime compounds of formula I-c can also be prepared as outlined in scheme 4 by platinum-catalyzed reduction of a nitrosolic or nitrolic acid derivative of formula VII as for example described by Wieland et al, Chem. Ber, 1906, 1480. (G may be NO or NO2)

Scheme 4:

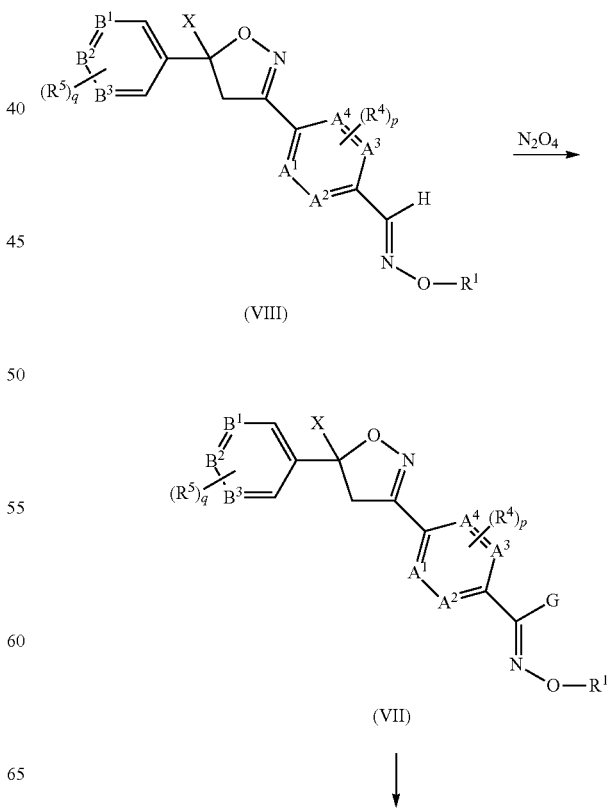

-continued

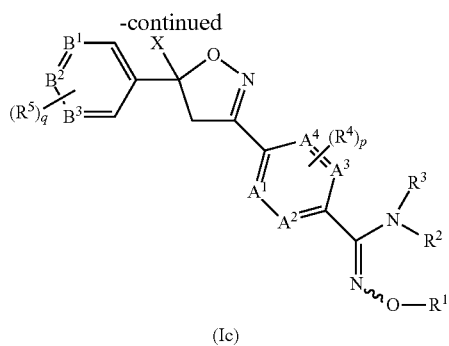

(Ic)

The corresponding compounds of formula VII (G may be NO or NO2) can be prepared as outlined in scheme 4 by nitration of an oxime of formula VIII, as for example described by Boyer et al, J. Am. Chem. Soc. 1959, 81, 4237:

Compounds of formula I, especially the corresponding amidoxime compounds (wherein Y is an oxygen atom) may also be prepared as outlined in scheme 5 by reaction of a nitrile or a thioamide of formula IX (in formula IX of scheme 5, L may be CN or C(=S)NR$^2$R$^3$) with hydroxylamine, as for example described by Stephenson et al, J. Chem. Soc. 1969, 6, 861 or Goldbeck et al, Chem. Ber. 1891, 3658 for amidoximes, or as for example described by Neilson et al, Chem. Rev. 1970, 70, 151 for amidrazones. The corresponding compounds of formula IX can be prepared as described for example in US 2007066617.

Scheme 5:

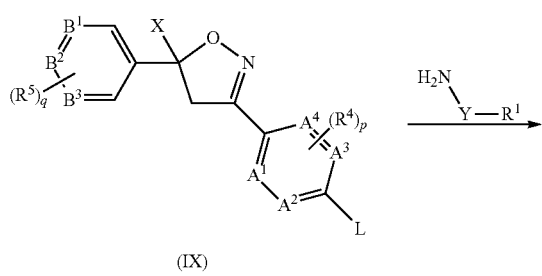

(IX)

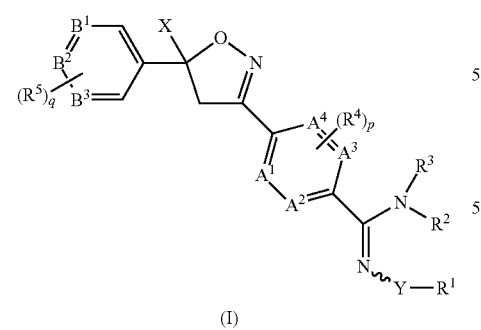

(I)

Compounds of formula I, especially the corresponding amidoxime compounds, wherein Y is an oxygen atom, can also be prepared as outlined in scheme 6 by reaction of an imidate of formula X with for example hydroxylamine, as for example described by Bushey et al, J. Org. Chem. 1980, 45, 4198:

Scheme 6:

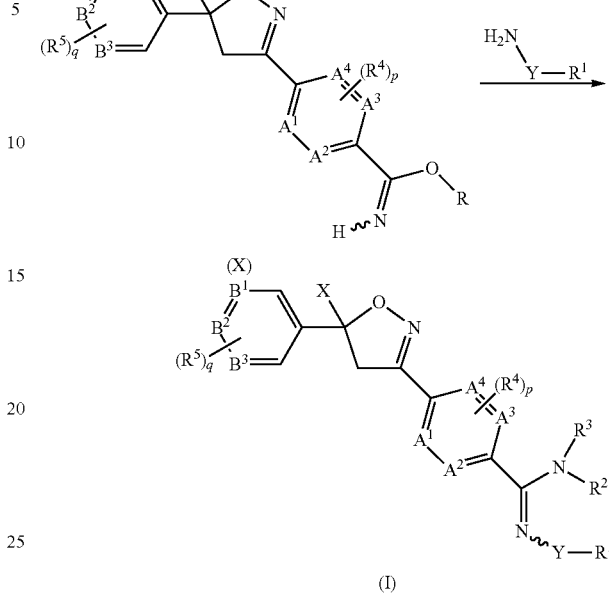

Compounds of formula I can also be prepared as outlined in scheme 7 by cyclization of a compound of formula XI:

Scheme 7:

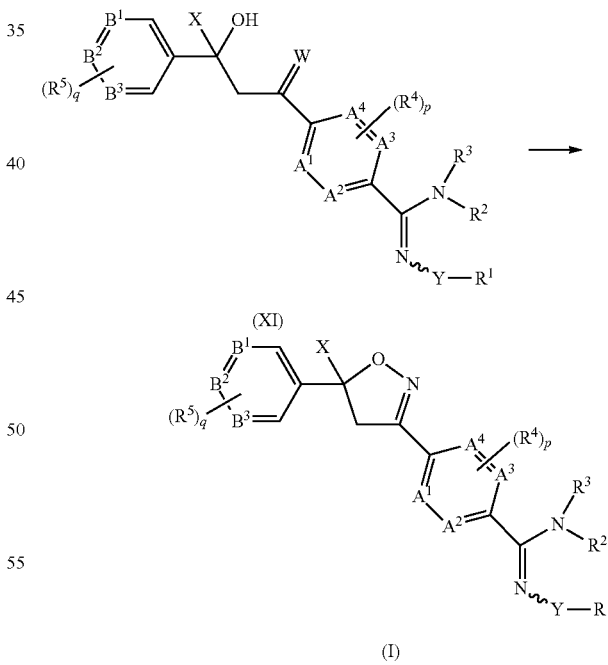

Compounds of formula I can also be prepared as outlined in scheme 8 by reaction of metal organyls of formula XII with N-substituted formamidine derivatives of formula XIII, as for example described by Eloy et al, Chem. Rev. 1962, 62, 155 (in scheme 8, Q may be a metal as for example MgE, Li, Na, K, SnE$_3$; with E being a halogen atom; Z may be a leaving group as for example a halogen or OR$^{16}$ or S(O)$_n$R$^{16}$ and wherein n is 0-2):

Scheme 8:

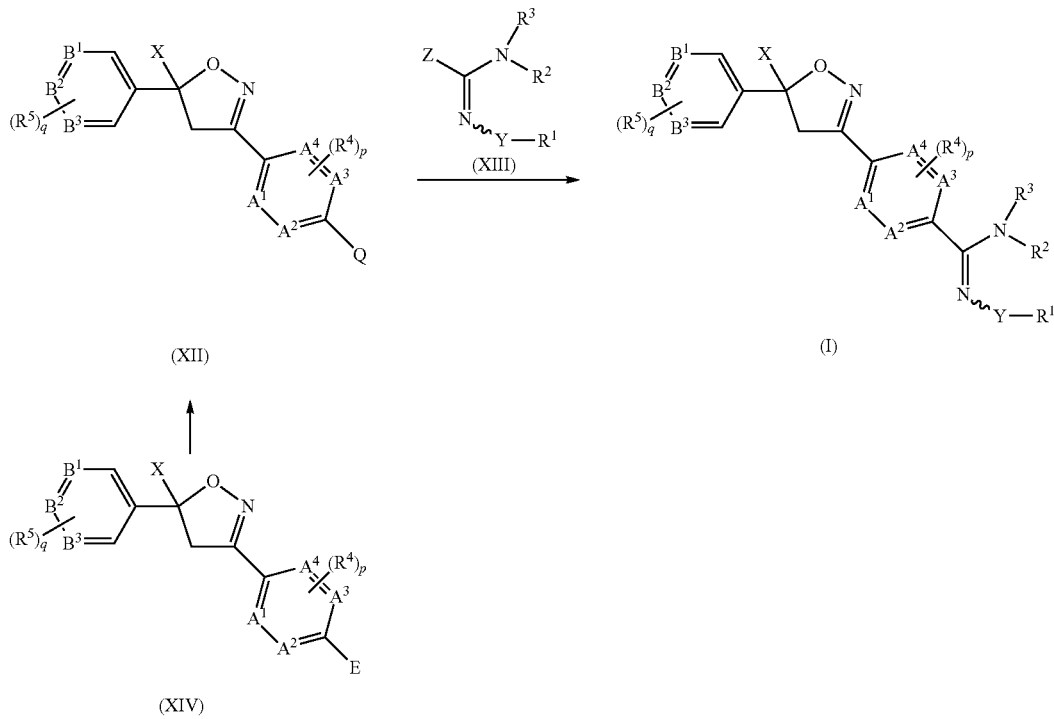

The corresponding metal organyls of formula XII can be prepared by a halogen-metal exchange reaction of halides of formula XIV. The corresponding halides of formula XIV can be prepared as for example described in US 2007066617 (E may be a halogen as for example Cl, Br, I):

Compounds of formula I-d can also be prepared as outlined in scheme 9 by photorearrangement of oxadiazoles of formula XV as for example described by Buscemi et al, J. Het. Chem. 1988, 25, 931-935:

Scheme 9:

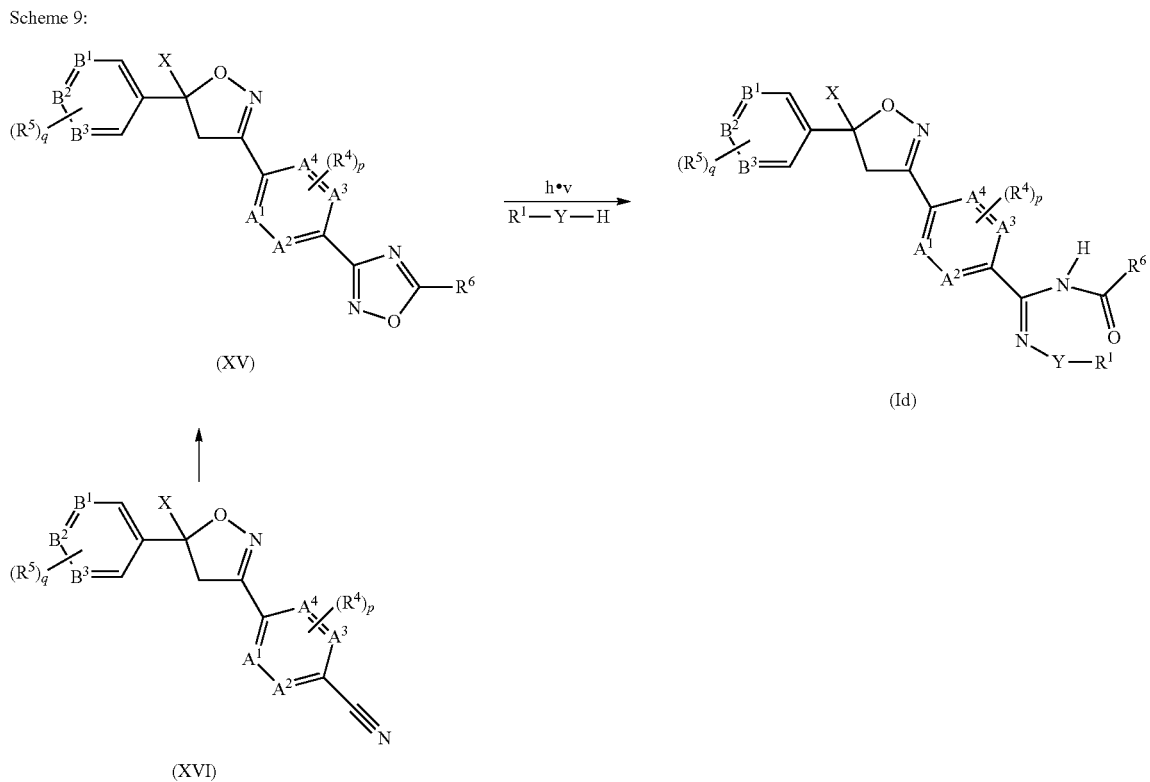

The corresponding oxadiazole compounds of formula XV can be prepared by reaction of a nitrile of formula XVI with hydroxylamine, followed by cyclization with an anhydride as for example described in WO 2006040192. Compounds of formula XVI can be prepared as for example described in US 2007066617.

Compounds of formula III can be prepared as outlined in scheme 10 by reaction of an aldehyde of formula XVIII with hydroxylamine as for example described in WO 2005085216. Aldehyde compounds of formula XVIII can for example be prepared by metalation of a halogenate of formula XIX (E may be a halogen as for example Cl, Br, I) and reaction with a formylation reagent or carbon monoxide as for example described in WO 2005085216. The corresponding compounds of formula XIX can be prepared as for example described in US 2006019998 for compounds with Y=oxygen, or as for example described by Larsen et al, Org. Lett. 2001, 3, 3341-3344 for compounds with Y=substituted nitrogen.

Scheme 10:

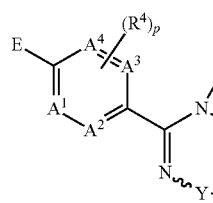

(XIX)

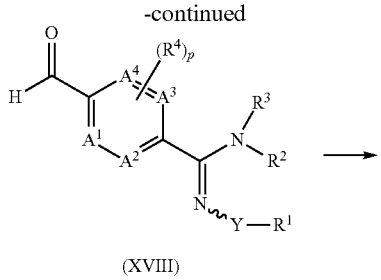

(XVIII)

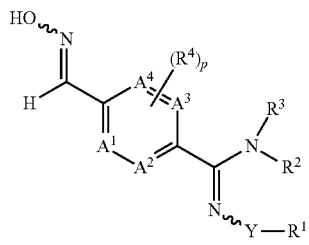

(III)

Amidrazone compounds of formula I-e can be also prepared as outlined in scheme 11 by reaction of an imine derivatives of formula XX (wherein J may be a leaving group like halogen, $OR^{16}$ or $S(O)_n R^{16}$ and wherein n=0-2) with hydrazines as for example described by Weintraub et al, J. Org. Chem. 1968, 33, 1679 or Katritzky et al, J. Chem. Soc., Perkin Trans. 1 1979, 1961.

Scheme 11:

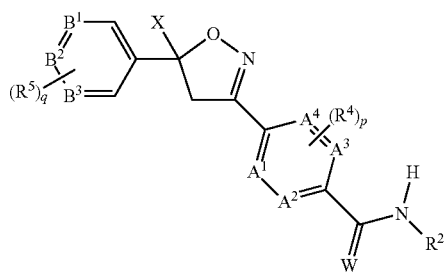

(XXI)

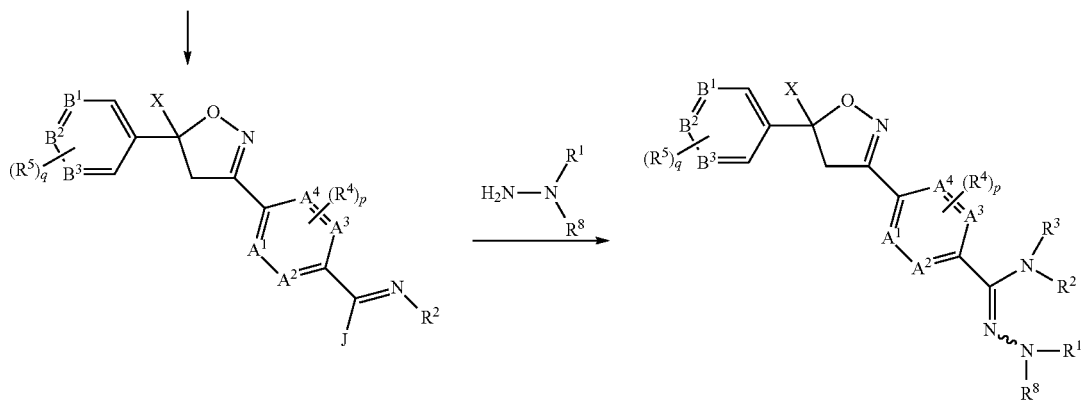

(XX)  (I-e)

The corresponding compounds of formula XX can be prepared as outlined in scheme 11 by reaction of an amide or thioamide of formula VI with a halogenating reagent as for example described by Tanga et al, J. Het. Chem., 2008, 43, 661-665 (W may be an oxygen or sulphur atom). The preparation of the corresponding amide or thioamide compounds of formula XXI is, for example, described in US 2007 0066617.

Amidrazone compounds of formula I-e can be also prepared as outlined in scheme 12 by reaction of a hydrazonoyl halides of formula XXII with amines as for example described by Stevens et al, J. Org. Chem. 1965, 30, 3718-3720 (in formula XXII of scheme 12, wherein J may be a leaving group like halogen, $OR^{16}$ or $S(O)_nR^{16}$ and wherein n=0-2).

Scheme 12:

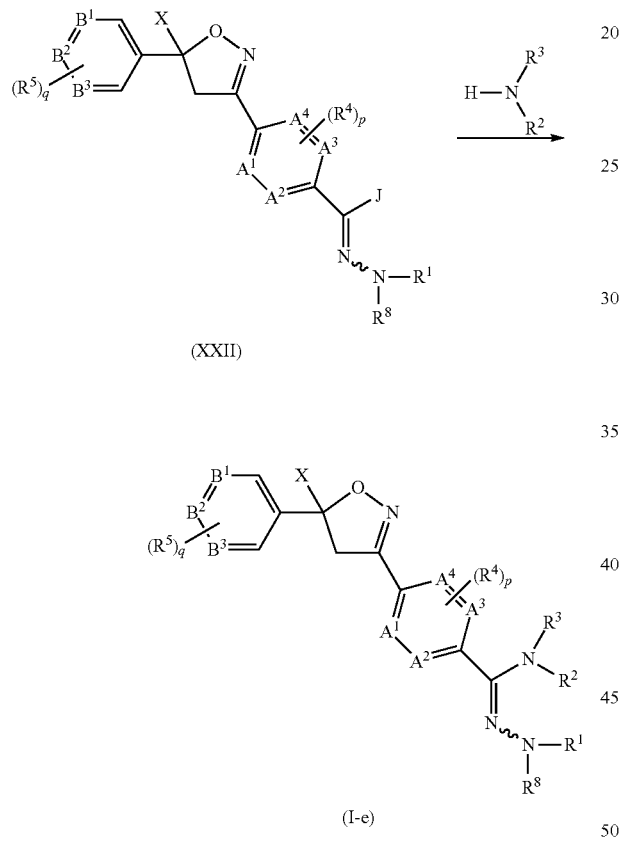

(I-e)

The corresponding compounds of formula XXII can be prepared as outlined in scheme 13 by reaction of a hydrazone compound of formula XXIII with a halogenation reagent as for example described by Danko et al, Pest Management Science 2006, 62, 229-235 (wherein J may be a leaving group like halogen, $OR^{16}$ or $S(O)_nR^{16}$ and wherein n=0-2). Compounds of formula XXIII can be prepared by reaction of an aldehyde XXIV with a hydrazine derivative as for example described by Fattorusso et al, J. Med. Chem. 2008, 51, 1333-1343. Compounds of formula XXIV can be prepared as described for example by Mihara et al, WO 2008122375.

Scheme 13

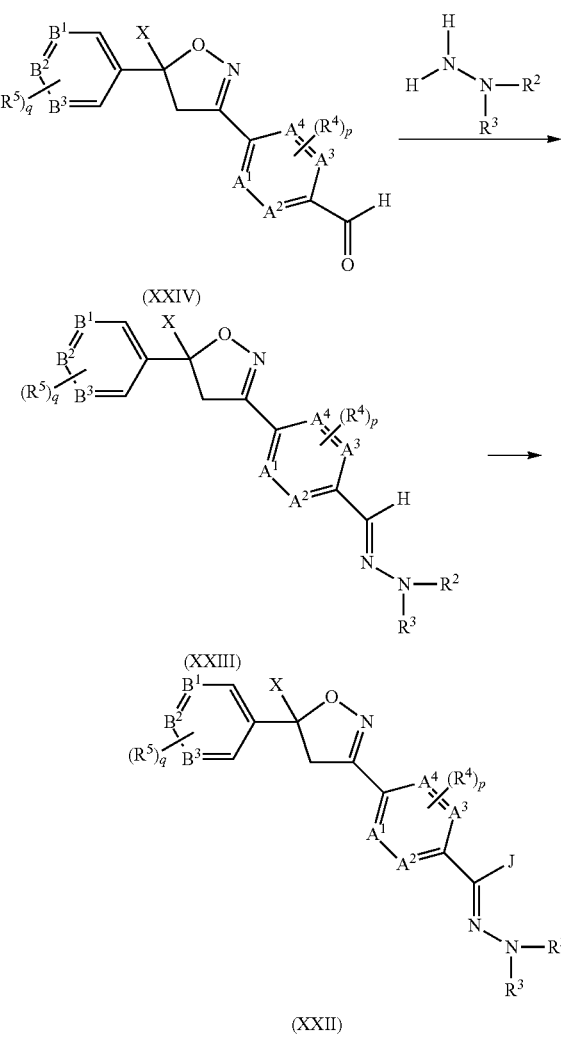

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I, and their salts are in particular suitable for efficiently controlling arthropodal pests such as arachnids, myriapedes and insects as well as nematodes.

The compounds of the formula I are especially suitable for efficiently combating the following pests:

Insects from the order of the lepidopterans (Lepidoptera), for example *Agrotis ypsilon, Agrotis segetum, Alabama argillacea, Anticarsia gemmatalis, Argyresthia conjugella,*

*Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalls, Diatraea grandiosella, Earias insulana, Elasmopalpus lignosellus, Eupoecilia ambiguella, Evetria bouliana Feltia subterranea, Galleria mellonella, Grapholitha funebrana, Grapholitha motesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthor/maea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcate, Cetonia aurata, Ceuthorrhynchus assimilis, Ceuthorrhynchus napi, Chaetocnema Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, lps typographus, Lema bilineata, Lema melanopus, Leptinotarsa decemlineata, Limonius califomicus, Lissorhoptrus oryzophilus, Melanotus communis, Meligethes aeneus, Melolontha hippocastani, Melolontha melolontha, Oulema oryzae, Otiorrhynchus sulcatus, Ot/orrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freebomi, Anopheles leucosphyrus, Anopheles minimus, Anopheles quadrimaculatus, Calliphora vicina, Ceratitis capitata, Chrysomya bezziana, Chrysomya hominivorax, Chrysomya macellafia, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inomata, Culiseta melanura, Dacus cucurbitae, Dacus oleae, Dasineura brassicae, Delia antique, Delia coarctata, Delia platura, Della radicum, Dermatobia hominis, Fannie canicularis, Geomyza Tripunctata, Gasterophilus intestinalis, Glossina motsitans, Glossina palpalis, Glossina fuscipes, Glossina tachinades, Haematobia irritans, Haplodiplosis equestris, Hippelates* spp., *Hylemyia platura, Hypoderma lineata, Leptoconops torrens, Lidomyza sativae, Lidomyza trifolii, Lucilia caprin, Lucilia cuprina, Lucilia sericata, Lycoria pectoralis, Mansonia Mayetiola destructor, Musca autumnalis, Musca domestica, Muscina stabulans, Oestrus ovis, Opomyza tkrum, Oscinella frit, Pegomya hysocyami, Phorbia antiqua, Phorbia brassicae, Phorbia coarctata, Phlebotomus argentipes, Psorophora columbiae, Psfia rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes Leucotermes flavipes, Heterotermes aureus, Reticulitermes fiavipes, Reticulitermes virginicus, Reticulitermes lucifugus, Reticulftermes santonensis, Reticulitermes grassei, Termes natalensis,* and *Coptotermes formosanus;* cockroaches (Blattaria—Blattodea), e.g. *Blattella germanica, Blattella asahinae, Periplaneta americana, Periplaneta japonica, Periplaneta brunnea, Periplaneta fulligginose, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integdceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges Aphidula nasturtii Aphis fabae, Aphis forbesi, Aphis pomi, Aphis gossypfi, Aphis grossulariae, Aphis schneideri, Aphis spfraecola, Aphis sambuci, Acyrthosiphon pisum, Aulacorthum solani, Bemisia argentifolli Brachycaudus cardui, Brachycaudus helichrysi, Brachycaudus persicae, Brachycaudus prunicola, Brevicoryne brassicae, Capitophorus horni, Cerosipha gossypii Chaetosiphon fragaefolii; Cryptomyzus ribis, Dreyfusia nordmannianae, Dreyfusia piceae, Dysaphis radicola, Dysaulacorthum pseudosolani, Dysaphis plantaginea, Dysaphis pyri Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri; Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiliand, Viteus vitifolii Cimex lectularius, Cimex hemipterus, Reduvius senilis,* Triatoma spp., and *Arilus critatus;* ants, bees, wasps, sawflies (Hymenoptera), e.g. *Athalia rosae, Alta cephalotes, Alta capiguara, Atte cephalotes, Atta laevigata, Atta robusta, Alta sexdens, Atta texana,* Crematogaster spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis,* Bombus spp., *Vespula squamosa, Paravespula vulgaris, Paravespula pennsylvanica, Paravespula germanica, Dolichovespula maculata, Vespa crabro, Polistes rubiginosa, Camponotus flondanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melano-* plus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina;

arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophllus annulatus, Boophilus decoloratus, Boophilus microplus, Dermacentor sillvarum, Dermacentor andersoni, Dermacentor variabllis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi Sarcoptes scabiei*, and Eriophyidae spp. such as *Aculus schlechtendali, Phyllocoptrata oleivora* and *Eriophyes sheldoni*, Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis*; Araneida, e.g. *Latrodectus mactans*, and *Loxosceles reclusa*;

fleas (Siphonaptera), e.g. *Ctenocephalides fells, Ctenocephalides canis, Xenopsylla cheopis, Pulex irritans, Tunga penetrans,* and *Nosopsyllus fasciatus*, silverfish, firebrat (Thysanura), e.g. *Lepisma saccharin* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli Bovicola bovis, Menopon gallinae, Menacanthus stramineus and Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii Heterodera trifolii*, and other *Heterodera* species; Seed gall nematodes, Anguina species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemiriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicunous, Ornithodorus moubeta, Otobius megnini, Dermanyssus Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni,* Tarsonemidae spp. such as *Phytonemus pallidus* and *Polyphagotarsonemus latus,* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus* pratensis.

Compounds of the formula I are particularly useful for controlling insects, preferably sucking or piercing insects such as insects from the genera Thysanoptera, Diptera and Hemiptera, in particular the following species:

Thysanoptera: *Frankliniella furca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratthe capitata, Chrysomya bezziana, Chrysomya hominivorax, Chrysomya macellane, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia caniculane Geomyza Tripunctata, Gasterophilus intestinalis, Glossina morsitans, Glossina palpails, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami Phorbia antiqua, Phorbia brassicae, Phorbia coarctata, Phlebotomus argentipes, Psorophora columbiae, Psilia rosae, Psorophora discolor, Prosimulium Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii Aphis grossulariae, Aphis schneideri, Aphis spiraecola, Aphis sambuci Acydhosiphon pisum, Aulacorthum solani, Brachycaudus cardui, Brachy-*

*caudus helichrysi, Brachycaudus persicae, Brachycaudus prunicola, Brevicoryne brassicae, Capitophorus horni, Cerosipha gossypii, Chaetosiphon fragaefolk, Ctyptomyzus ribis, Dreyfusia nordmannianae, Dreyfusia piceae, Dysaphis radicola, Dysaulacorthum pseudosolani Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerast, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiliand*, and *Viteus vitifolii.*

Compounds of the formula I are particularly useful for controlling insects of the orders Hemiptera and Thysanoptera.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP),N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol® 23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:

1. Products for dilution with water. For seed treatment purposes, such products may be applied to the seed diluted or undiluted.

A) Water-soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC) 15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-dispersible Granules and Water-soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-dispersible Powders and Water-soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Other isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl) -methyl]-benzamide (M22.3), 4-[5-(3,5-Dichloro-phenyl)-5-trifluoromethyl-4,5-dihydro-isoxazol-3-A-naphthalene-1-carboxylic acid [(2,2,2-trifluoro-ethylcarbamoyl)-methyl]-amide (M22.4) 4-[5-(3,5-Dichlorophenyl)-5-trifluoromethyl-4,5-dihydro-isoxazol-3-yl]-N(methoxyimino)methyl]-2-methyl-benzamide (M22.5), 4-[5-(3-Chloro-5-trifluoromethylphenyl)-5-trifluoromethyl-4,5-dihydro-isoxazol-3-yl]-2-methyl-N-[(2,2,2-trifluoroethylcarbamoyl)-methyl]-benzamide (M22.6), 4-[5-(3-Chloro-5-trifluoromethylphenyl)-5-trifluoromethyl-4,5-dihydro-isoxazol-3-yl]-naphthalene-1-carboxylic acid [(2,2,2-trifluoroethylcarbamoyl)-methyl]-amide (M22.7) and 5-[5-(3,5-Dichloro-4-fluorophenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H- pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{([5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoropropyl)malononitrile ($CF_2H$—$CF_2$—$CF_2$-$CF_2$—$CH_2$—$C(CN)_2$—$CH_2$—$CH_2$—$CF_3$) (M24.1) and 2-(2,2,3,3,4,4,5,5-octafluoropentyl)-2-(3,3,4,4,4-pentafluorobutyl) -malonodinitrile ($CF_2H$—$CF_2$—$CF_2$-$CF_2$—$CH_2$-$C(CN)_2$—$CH_2$—$CH_2$-$CF_2$—$CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:
4-{[(6-Bromopyrid-3-yl)methyl](2-fluoroethyl)amino}furan-2(5H)-on (M26.1),
4-{[(6-Fluoropyrid-3-yl)methyl](2,2-difluoroethyl)amino}furan-2(5H)-on (M26.2),
4-{[(2-Chloro-1,3-thiazolo-5-yl)methyl](2-fluoroethyl)amino}furan-2(5H)-on (M26.3),
4-{[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on (M26.8),
4-{[(6-Chloropyrid-3-yl)methyl](cyclopropyl)amino}furan-2(5H)-on (M26.9) and
4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N-R'-2,2-dihalo-1-R"cyclopropanecarboxamide-2-(2,6-dichloro-α,α,α-trifluoro-p-tolyl) hydrazone or N—R'-2,2-di(R''')propionamide-2-(2,6-dichloro-α,α,α-trifluoro-p-tolyl) -hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo [3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, potycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metorninostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5):1225-35., Curr Opin Chem. Biol. 2006 October; 10(5): 487-91. Epub 2006 Aug. 28., Biomaterials. 2001 March; 22(5):405-17, Bioconjug Chem. 2005 January-February;16 (1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, ° leyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker /adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/ maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the enantiomers or veterinarily acceptable salts thereof are in particular also suitable for being used for combating parasites in and on animals.

An object of the present invention is therfore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis*, *Ctenocephalides canis*, *Xenopsylla cheopis*, *Pulex irritans*, *Tunga penetrans*, and *Nosopsyllus fasciatus*, cockroaches (Blattaria—Blattodea), e.g. *Blattella germanica*, *Blattella asahinae*, *Periplaneta americana*, *Periplaneta japonica*, *Periplaneta brunnea*, *Periplaneta fuligginosa*, *Periplaneta australasiae*, and *Blatta orientalis*, flies, mosquitoes (Diptera), e.g. *Aedes aegypti*, *Aedes albopictus*, *Aedes vexans*, *Anastrepha ludens*, *Anopheles maculipennis*, *Anopheles crucians*, *Anopheles albimanus*, *Anopheles gambiae*, *Anopheles freeborn*, *Anopheles leucosphyrus*, *Anopheles minimus*, *Anopheles quadrimaculatus*, *Calliphora vicina*, *Chrysomya bezziana*, *Chrysomya hominivorax*, *Chtysomya macel/aria*, *Chrysops discalis*, *Chrysops sllacea*, *Chrysops atlanticus*, *Cochliomyia hominivorax*, *Cordylobia anthropophaga*, *Culicoides furens*, *Culex pipiens*, *Culex nigripalpus*, *Culex quinquefasciatus*, *Culex tarsalis*, *Cultiseta inornata*, *Cultiseta melanura*, *Dermatobia hominis*, *Fannia caniculanis*, *Gasterophilus intestinalis*, *Glossina morsitans*, *Glossina palpalis*, *Glossina fuscipes*, *Glossina tachinoides*, *Haematobia irritans*, *Haplodiplosis equestris*, *Hippelates* spp., *Hypoderma lineata*, *Leptoconops torrens*, *Lucille caprina*, *Lucilia cuprina*, *Lucilia sericata*, *Lycoria pectoralis*, *Mansonia* spp., *Musca domestica*, *Muscina stabulans*, *Oestrus ovis*, *Phlebotomus argentipes*, *Psorophora columbine*, *Psorophora discolor*, *Prosimulium mixtum*, *Sarcophaga haemorrhoidalis*, *Sarcophaga* sp., *Simulium vittatum*, *Stomoxys calcitrans*, *Tabanus bovinus*, *Tabanus atratus*, *Tabanus lineola*, and *Tabanus similis*, lice (Phthiraptera), e.g. *Pediculus humanus capitis*, *Pediculus humanus corporis*, *Pthirus pubis*, *Haematopinus eurysternus*, *Haematopinus suis*, *Linognathus vituli*, *Bovicola bovis*, *Menopon gallinae*, *Menacanthus stramineus* and *Solenopotes capillatus*.

ticks and parasitic mites (Parasitiformes): ticks (Ixodida), e.g. *Ixodes scapularis*, *Ixodes holocyclus*, *Ixodes pacificus*, *Rhiphicephalus sanguineus*, *Dermacentor andersoni*, *Dermacentor variabilis*, *Amblyomma americanum*, *Ambryomma maculatum*, *Ornithodorus hermsi*, *Ornithodorus turicata* and parasitic mites (Mesostigmata), e.g. *Ornithonyssus bacoti* and *Dermanyssus gallinae*, Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp.,*Knemidocoptes* spp., *Cytodites* spp., and *Laminosioptes* spp, Bugs (Heteropterida): *Cimex lectularius*, *Cimex hemipterus*, *Reduvius Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Amblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and Felicola spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus*, *Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*;

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alafia alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations; Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, Nmethyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointmentlike consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

EXAMPLES

The present invention is now illustrated in further details by the following examples, without imposing any limitation thereto.

C. Compound Examples

Compounds can be characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

$^1$H-NMR, respectively $^{13}$C-NMR: The signals are characterized by chemical shift (ppm) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

C.1 Compound Examples 1

Compound Examples 1-1 to 1-46 correspond to compound formula C.1:

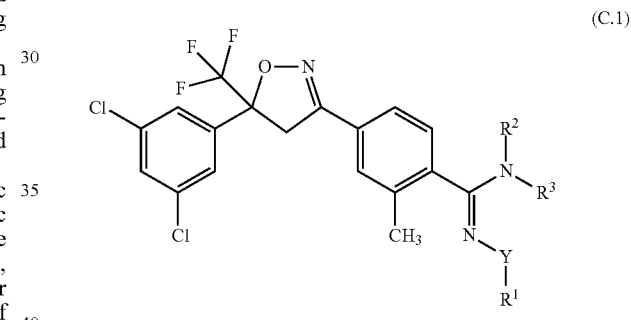

(C.1)

wherein $R^1$, $R^2$, $R^3$ and Y of each compound example is defined table C.1 below.

TABLE C.1

| Compound Ex. | Y—R$^1$ | R$^3$ | R$^2$ | HPLC-MS: R$_t$ (min) and [M + H] |
|---|---|---|---|---|
| 1-1 | OH | H | CH$_3$ | 3.299 446 |
| 1-2 | OH | CH$_3$ | CH$_3$ | 3.431 460 |
| 1-3 | OCH$_3$ | CH$_3$ | CH$_3$ | 3.696 474 |
| 1-4 | OH | H | CH$_2$CF$_3$ | 3.631 514 |
| 1-5 | OCH$_3$ | H | CH$_2$CF$_3$ | 4.399 528 |
| 1-6 | OCH$_3$ | CH$_3$ | CH$_2$CF$_3$ | 3.685 542 |
| 1-7 | O—C(=O)CH$_3$ | H | CH$_2$CF$_3$ | $^1$H-NMR (see ex. S.16) |
| 1-8 | OH | H | CH$_2$-2-pyridyl | 3.266 523 |
| 1-9 | CH$_2$CF$_3$ | H | CH$_2$C(=O)NH-cyclopropyl | 3.648 595 |
| 1-10 | O—C(=O)CH$_3$ | O—C(=O)CH$_3$ | CH$_2$-2-pyridyl | $^{13}$C-NMR (see ex. S.4) |
| 1-11 | OCH$_3$ | H | CH$_2$-2-pyridyl | 3.385 537 |
| 1-12 | OH | H | CH$_2$C(=O)NH—CH$_2$CF$_3$ | 3.463 571 |
| 1-13 | OH | H | CH$_2$C(=O)NH—CH$_2$CH$_3$ | 3.227 517 |
| 1-14 | CH$_3$ | H | CH$_2$CH$_2$CH$_3$ | 3.512 472 |
| 1-15 | N(CH$_3$)$_2$ | H | CH$_2$CH$_2$CH$_3$ | 3.614 501 |
| 1-16 | CH$_3$ | H | CH$_2$CF$_3$ | 3.453 512 |
| 1-17 | CH$_3$ | CH$_3$ | CH$_2$CH$_3$ | 3.506 472 |

TABLE C.1-continued

| Compound Ex. | Y—R¹ | R³ | R² | HPLC-MS: $R_t$ (min) | and [M + H] |
|---|---|---|---|---|---|
| 1-18 | CH₃ | H | CH₂CH₃ | 3.569 | 458 |
| 1-19 | CH₃ | H | CH₂-2-pyridyl | 3.415 | 521 |
| 1-20 | CH₃ | H | CH₂C(=O)NH—CH₂CF₃ | 3.354 | 569 |
| 1-21 | CH₃ | H | CH₂C(=O)NH—CH₂CH₃ | 3.858 | 515 |
| 1-22 | CH₃ | H | CH₂C(=O)NH—C(CH₃)₃ | 3.667 | 543 |
| 1-23 | N(CH₃)₂ | H | CH₃ | 3.410 | 473 |
| 1-24 | cyclopropyl | H | CH₂CH₃ | 3.690 | 484 |
| 1-25 | cyclopropyl | H | CH(CH₃)₂ | 3.737 | 498 |
| 1-26 | cyclopropyl | H | CH₂CH₂CH₃ | 3.766 | 498 |
| 1-27 | cyclopropyl | H | CH₂C(=O)NH—CH₂CH₃ | 3.397 | 541 |
| 1-28 | cyclopropyl | CH₃ | CH₂CH₃ | 3.697 | 498 |
| 1-29 | cyclopropyl | H | CH₂-2-pyridyl | 3.521 | 547 |
| 1-30 | cyclopropyl | H | CH₃ | 3.622 | 470 |
| 1-31 | cyclopropyl | H | CH(CH₃)cyclopropyl | 3.960 | 524 |
| 1-32 | cyclopropyl | H | CH₂C(=O)NH—CH₂CF₃ | 3.605 | 595 |
| 1-33 | cyclopropyl | CH₃ | CH₃ | 3.699 | 484 |
| 1-34 | cyclopropyl | H | CH₂C(=O)NH-cyclopropyl | 3.443 | 553 |
| 1-35 | cyclopropyl | CH₂CH₃ | CH₂CH₃ | 3.828 | 512 |
| 1-36 | cyclopropyl | H | CH₂C(=O)NH—C(CH₃)₃ | 3.751 | 569 |
| 1-37 | N(CH₃)₂ | H | cyclopropyl | 3.659 | 499 |
| 1-38 | CH₂CF₃ | H | CH(CH₃)₂ | 3.855 | 540 |
| 1-39 | CH₂CF₃ | CH₃ | CH₂CH₃ | 3.783 | 540 |
| 1-40 | CH₂CF₃ | H | CH₂CH₂CH₃ | 3.896 | 498 |
| 1-41 | CH₂CF₃ | CH₃ | CH₃ | 3.796 | 526 |
| 1-42 | cyclopropyl | H | cyclopropyl | 3.781 | 496 |
| 1-43 | CH₂CF₃ | H | CH₂-2-pyridyl | 3.771 | 589 |
| 1-44 | CH₂CF₃ | H | CH₂C(=O)NH—CH₂CH₃ | 3.648 | 583 |
| 1-45 | CH₂CF₃ | H | CH₂C(=O)NH—CH₂CF₃ | 3.787 | 637 |
| 1-46 | CH₂CF₃ | H | CH₂C(=O)NH—C(CH₃)₃ | 3.884 | 611 |

C.2 Compound Examples 2

Compound examples 2-8, 2-12 and 2-13 correspond to compound formula C.2:

C.3 Compound Examples 3

Compound examples 3-8, 3-12 and 3-13 correspond to compound formula C.3:

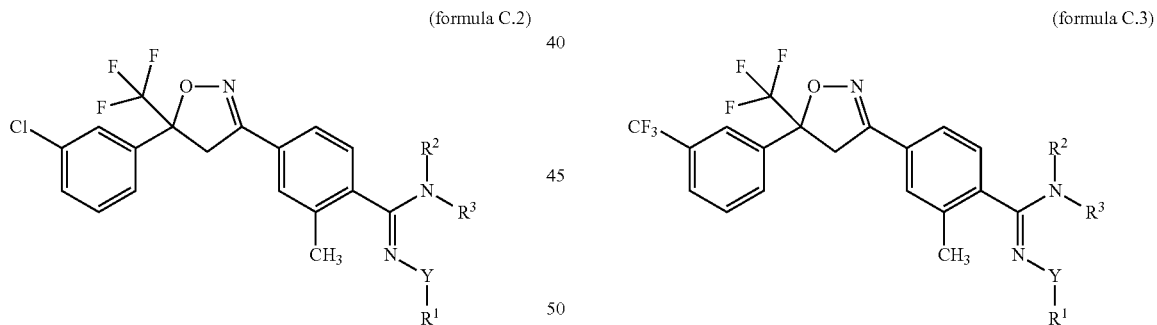

(formula C.2)

(formula C.3)

wherein R¹, R², R³ and Y of each compound example is defined table C.2 below.

wherein R¹, R², R³ and Y of each compound example is defined table C.3 below.

TABLE C.2

| Compound Ex. | Y—R¹ | R³ | R² | HPLC-MS: $R_t$ (min) and [M + H] | |
|---|---|---|---|---|---|
| 2-8 | OH | H | CH₂-2-pyridyl | 2.926 | 489 |
| 2-12 | OH | H | CH₂C(=O)NH—CH₂CF₃ | 3.088 | 537 |
| 2-13 | OH | H | CH₂C(=O)NH—CH₂CH₃ | 2.934 | 483 |

TABLE C.3

| Compound Ex. | Y—R¹ | R³ | R² | HPLC-MS: $R_t$ (min) and [M + H] | |
|---|---|---|---|---|---|
| 3-8 | OH | H | CH₂-2-pyridyl | 3.727 | 523 |
| 3-12 | OH | H | CH₂C(=O)NH—CH₂CF₃ | 3.923 | 571 |
| 3-13 | OH | H | CH₂C(=O)NH—CH₂CH₃ | 3.716 | 517 |

C.4 Compound Examples 4

Compound examples 4-8, 4-12 and 4-13 correspond to compound formula C.4:

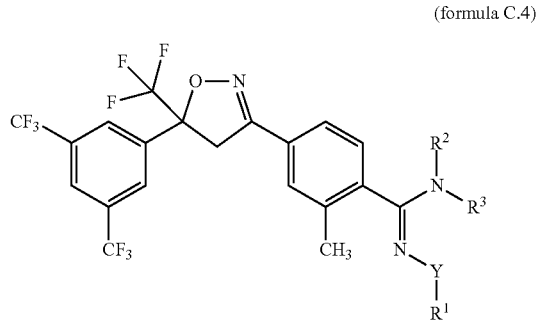

(formula C.4)

wherein $R^1$, $R^2$, $R^3$ and Y of each compound example is defined table C.4 below.

TABLE C.4

| Compound Ex. | Y—$R^1$ | $R^3$ | $R^2$ | HPLC-MS: $R_t$ (min) and [M + H] | |
|---|---|---|---|---|---|
| 4-8 | OH | H | $CH_2$-2-pyridyl | 3.288 | 591 |
| 4-12 | OH | H | $CH_2C(=O)NH—CH_2CF_3$ | 3.465 | 639 |
| 4-13 | OH | H | $CH_2C(=O)NH—CH_2CH_3$ | 3.343 | 585 |

C.5 Compound Examples 5

Compound examples 5-4, 5-8, 5-12 and 5-13 correspond to compound formula C.5:

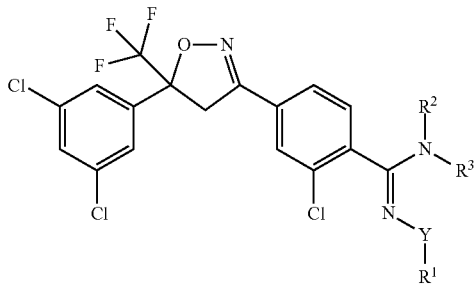

(formula C.5)

wherein $R^1$, $R^2$, $R^3$ and Y of each compound example is defined table C.5 below.

TABLE C.5

| Compound Ex. | Y—$R^1$ | $R^3$ | $R^2$ | HPLC-MS: $R_t$ (min) and [M + H] | |
|---|---|---|---|---|---|
| 5-4 | OH | H | $CH_2CF_3$ | 3.821 | 534 |
| 5-8 | OH | H | $CH_2$-2-pyridyl | 3.597 | 543 |
| 5-12 | OH | H | $CH_2C(=O)NH—CH_2CF_3$ | 3.848 | 591 |
| 5-13 | OH | H | $CH_2C(=O)NH—CH_2CH_3$ | 3.253 | 537 |

C.6 Compound Examples 6

Compound examples 6-8 correspond to compound formula C.6:

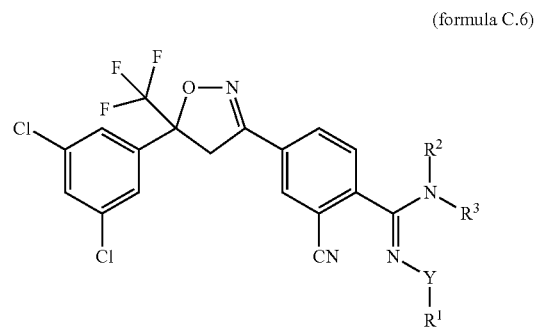

(formula C.6)

wherein $R^1$, $R^2$, $R^3$ and Y of each compound example is defined table C.6 below.

TABLE C.6

| Compound Ex. | Y—$R^1$ | $R^3$ | $R^2$ | HPLC-MS: $R_t$ (min) and [M + H] | |
|---|---|---|---|---|---|
| 6-8 | OH | H | $CH_2$-2-pyridyl | 3.366 | 534 |

C.7 Compound Examples 7

Compound examples 7-8 correspond to compound formula C.7:

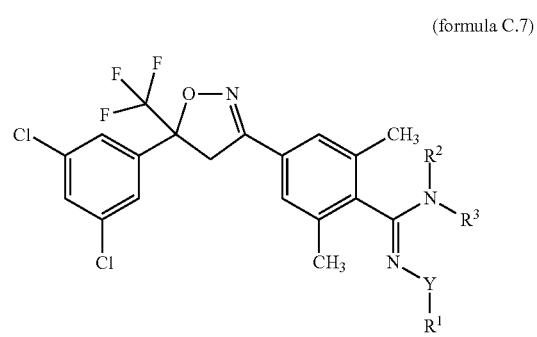

(formula C.7)

wherein $R^1$, $R^2$, $R^3$ and Y of each compound example is defined table C.7 below.

TABLE C.7

| Compound Ex. | Y—$R^1$ | $R^3$ | $R^2$ | HPLC-MS: $R_t$ (min) and [M + H] | |
|---|---|---|---|---|---|
| 7-8 | OH | H | $CH_2$-2-pyridyl | 3.466 | 537 |

C.8 Compound Examples 8

Compound examples 8-8, 8-12, 8-13 correspond to compound formula C.8:

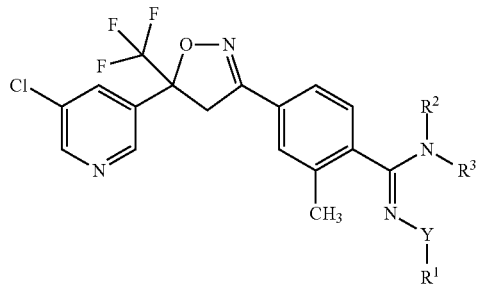

(formula C.8)

wherein $R^1$, $R^2$, $R^3$ and Y of each compound example is defined table C.8 below.

TABLE C.8

| Compound Ex. | Y—$R^1$ | $R^3$ | $R^2$ | HPLC-MS: $R_t$ (min) | and [M + H] |
|---|---|---|---|---|---|
| 8-8 | OH | H | $CH_2$-2-pyridyl | 3.067 | 490 |
| 8-12 | OH | H | $CH_2C(=O)NH-CH_2CF_3$ | 3.297 | 538 |
| 8-13 | OH | H | $CH_2C(=O)NH-CH_2CH_3$ | 3.053 | 484 |

C.9 Compound Examples 9

Compound examples 9-1 to 9-10 correspond to compound formula C.9:

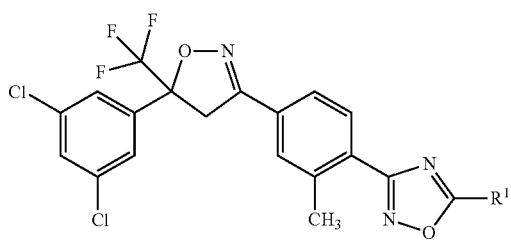

(formula C.9)

wherein $R^1$, $R^2$, $R^3$ and Y of each compound example is defined table C.9 below.

TABLE C.9

| Compound | $R^1$ | HPLC-MS: $R_t$ (min) | and [M + H] |
|---|---|---|---|
| 9-1 | $CH_2CH_2CF_3$ | 4.608 | 538 |
| 9-2 | $CH_3$ | 4.345 | 456 |
| 9-3 | $CH_2CH_3$ | 4.529 | 470 |
| 9-4 | $CH_2CF_3$ | 4.540 | 524 |
| 9-5 | $CF_3$ | 4.743 | 510 |
| 9-6 | $C_6H_5$ | 4.930 | 518 |
| 9-7 | $CH_2-C_6H_5$ | 4.088 | 532 |
| 9-8 | $CH_2-O-C_6H_5$ | 4.683 | 548 |
| 9-9 | $CH_2-O-CH_3$ | 4.347 | 486 |
| 9-10 | $CH(CH_3)_2$ | 4.710 | 484 |

S. SYNTHESIS EXAMPLES

S.1 Synthesis of 4-[5-(3,5-Dichloro-phenyl)-5-trifluoromethyl-4,5-dihydro-isoxazol-3-yl]-N-hydroxy-2,N'-dimethyl-benzamidine (Compound 1-1 of Table C.1)

Step 1: Synthesis of 4-[5-(3,5-Dichloro-phenyl)-5-trifluoromethyl-4,5-dihydro-isoxazol-3-yl]-2-methyl-benzaldehyde A mixture of 4-[5-(3,5-Dichloro-phenyl)-5-trifluoromethyl-4,5-dihydro-isoxazol-3-yl]-2-methyl-benzaldehyde oxime (14.20 g, 31.34 mmol), triethyl silane (10.3 mL, 7.53 g, 62.8 mmol), sodium carbonate (5.43 g, 39.3 mmol), palladium bis(diphenylphosphine)-ferrocene dichloride $CH_2Cl_2$-complex (1.28 g, 1.57 mmol) and DMF (250 mL) were stirred under an atmosphere of carbon monoxide at 65° C. over night. After cooling to room temperature, the solvent was evaporated and the residue taken up in MTBE, filtered and the filtrate was concentrated in vacuum. Purification of the residue on silica gel afforded the title compound (9.60 g, 76%).

Characterization by HPLC-MS: 4.971 min, M=402.0

Step 2: Synthesis of 4-[5-(3,5-Dichloro-phenyl)-5-trifluoromethyl-4,5-dihydro-isoxazol-3-yl]-2-methyl-benzaldehyde oxime A solution of 4-[5-(3,5-Dichloro-phenyl)-5-trifluoromethyl-4,5-dihydro-isoxazol-3-yl]-2-methyl-benzaldehyde (i.e. the product of Step 1, 5.00 g), hydroxylamine hydrochloride (1.30 g) and concentrated hydrochloric acid (1 mL, 1.05 g) in MeOH (37.5 mL) was stirred at 70° C. for 4 h. After cooling, the mixture was evaporated from all volatiles and partitioned between MTBE and water. The organic layer was separated and dried. Chromatography over silica gel yielded the title compound (4.70 g, 91%).

Characterization by HPLC-MS: 4.187 min, M=417.1
Characterization by $^1$H-NMR (400 MHz, $CDCl_3$):
δ [delta]=2.44 (s, 3H), 2.90 (br. s, 1H), 3.81 (d, 1H), 4.15 (d, 1H), 7.47-7.58 (m, 4H), 7.80 (d, 1H), 8.35 (s, 1H), 11.10 (br. s, 1H) ppm.

Step 3: Synthesis of 4-[5-(3,5-Dichloro-phenyl)-5-trifluoromethyl-4,5-dihydro-isoxazol-3-yl]-N-hydroxy-2,N'-dimethyl-benzamidine To a solution of 4-[5-(3,5-Dichloro-phenyl)-5-trifluoromethyl-4,5-dihydro-isoxazol-3-yl]-2-methyl-benzaldehyde oxime (i.e. the product of Step 2, 500 mg) in DMF (25 mL) was added N-chloro succinimide (168 mg) and heated to 75° C. for 1 h. After cooling, the reaction mixture was poured onto water and extracted with MTBE. The combined organic layers were dried ($Na_2SO_4$) and concentrated in vacuo to ¼ of the original volume to obtain the crude hydroxamic acid chloride. This mixture was added to a solution of methylamine (0.66 mL, 41 mg) and triethylamine (0.18 mL, 0.13 g) in THF and stirred at room temperature over night. After concentration in vacuo, the mixture was purified by chromatography on silica gel to obtain the title compound (270 mg, 39%) as a colorless solid.

Characterization by HPLC-MS: 3.299 min, M=446.0
Characterization by $^1$H-NMR (400 MHz, DMSO):
δ [delta]=2.38 (s, 3H), 2.59 (s, 3H), 3.71 (s, 1H), 4.10 (s, 1H), 5.45 (br. s, 1H), 7.32 (m, 1H), 7.45 (s, 1H), 7.48-7.58 (m, 4H) ppm.

S.2 Synthesis of 4-[5-(3,5-Dichloro-phenyl)-5-trifluoromethyl-4,5-dihydro-isoxazol-3-yl]-N-hydroxy-2-methyl-N'-pyridin-2-ylmethyl-benzamidine (Compound 1-8 of Table C.1)

To a solution of 4-[5-(3,5-Dichloro-phenyl)-5-trifluoromethyl-4,5-dihydro-isoxazol-3-yl]-2-methyl-benzaldehyde-oxime ((i.e. the product of Example 1 Step 2, 177 mg, 0.42 mmol) in DMF (4 mL) was added N-chlorosuccinimide (67 mg, 0.50 mmol) and the mixture was stirred at 70° C. bath temperature for 30 min. After cooling to 0° C., picolylamine (85 mg, 0.79 mmol) and triethylamine (145 mg, 1.44 mmol) was added. The mixture was allowed to war to room temperature over night and was then poured on ice water. The pH was adjusted to 7 by addition of NH$_4$Cl and the resulting precipitate was filtered off. The crude product was then purified by column chromatography on SiO$_2$ (CH$_2$Cl$_2$: MeOH=96:4) to give the title compound (75 mg, 42%).

Characterization by HPLC-MS: 3.254 min, M=522.60
Characterization by $^1$H-NMR (400 MHz, CDCl$_3$):
δ [delta]=2.33 (s, 3H), 3.70 (d, 1H), 4.09 (d, 1H), 4.13 (m, 2H), 6.34 (br m, 1H), 7.09 (d, 1H), 7.18 (m, 1H), 7.30 (m, 1H), 7.45 (s, 2H), 7.52 (s, 3H), 7.60 (dt, 1H), 8.52 (m, 1H) ppm.

S.3 Synthesis of 2-({N-hydroxy-2-methyl-4-[5-trifluoromethyl-5-(3-trifluoromethyl-phenyl)-4,5-dihydro-isoxazol-3-yl]-benzimidoyl}-amino)-N-(2,2,2-trifluoro-ethyl)-acetamide (Compound 3-12 of Table C.3)

To a solution of 2-Methyl-4-[5-trifluoromethyl-5-(3-trifluoromethyl-phenyl)-4,5-dihydro-isoxazol-3-yl]-benzaldehyde oxime (250 mg) in DMF (8 mL) was added N-chloro succinimide (84 mg) and heated to 75° C. for 1 h. After cooling, the reaction mixture was poured onto water and extracted with EtOAc. The combined organic layers were dried (Na$_2$SO$_4$) and concentrated in vacuo to ¼ of the original volume to obtain the crude hydroxamic acid chloride. This mixture was added to a solution of 2-amino-N-(2,2,2-trifluoro-ethyl)-acetamide (116 mg) and triethylamine (0.30 mL, 0.21 g) in THF (8 mL) and stirred at room temperature over night. After concentration in vacuo, the mixture was purified by chromatography on silica gel to obtain the title compound (146 mg, 43%).

Characterization by HPLC-MS: 3.923 min, M=571.10

S.4 Synthesis of N-{{4-[5-(3,5-dichloro-phenyl)-5-trifluoromethyl-4,5-dihydro-isoxazol-3-yl]-2-methyl-phenyl}-hydroxyiminoacetyl-methyl}-N-pyridin-2-ylmethyl-acetamide (Compound 1-10 of Table C.1)

To a solution of 4-[5-(3,5-Dichloro-phenyl)-5-trifluoromethyl-4,5-dihydro-isoxazol-3-yl]-N-hydroxy-2-methyl-N'-pyridin-2-ylmethyl-benzamidine (i.e. the product of Example 2, 135 mg) in acetic acid anhydride (5 mL) was added a catalytic amount of N,N-dimethylamino-4-pyridine at 75° C. for 6 h. After cooling, the mixture was poured onto water and extracted with CH$_2$Cl$_2$. Combined organic layers were dried (Na$_2$SO$_4$) and evaporated. Chromatography of the residue on silica gel yielded the title compound (100 mg, 69%)

Characterization by $^{13}$C-NMR (125 MHz, CDCl$_3$): δ [delta]=19.20, 21.05, 22.24, 43.92, 51.00, 87.31, 122.71, 122.90, 124.67, 124.86, 125.31, 129.84, 130.02, 130.26, 130.53, 131.74, 135.68, 136.56, 138.91, 140.45, 149.20, 154.36, 155.39, 155.85, 166.82, 170.25 ppm.

S.5 Synthesis of 4-[5-(3,5-Dichloro-phenyl)-5-trifluoromethyl-4,5-dihydro-isoxazol-3-yl]-N'-methoxy-2,N,N-trimethyl-benzamidine (Compound 1-3 of Table C.1)

To a solution of 4-[5-(3,5-Dichloro-phenyl)-5-trifluoromethyl-4,5-dihydro-isoxazol-3-yl]-N'-hydroxy-2,N,N-trimethyl-benzamidine (200 mg) in DMF (5 mL) was added a solution of LiOH (31 mg) in water (2 mL), before adding dimethyl sulfate (0.21 mL, 0.27 g). The mixture was stirred at room temperature over night and poured onto water. The aqueous layer was extracted with MTBE and the combined organic layers were washed with water, dried (Na$_2$SO$_4$) and evaporated to yield the title compound (170 mg, 83%).

Characterization by HPLC-MS: 3.696 min, M=474.05

S.6 Synthesis of 4-[5-(3,5-Dichloro-phenyl)-5-trifluoromethyl-4,5-dihydro-isoxazol-3-yl]-2,N-dimethyl-N'-propyl-benzamidine (Compound 1-14 of Table C.1)

To a solution of 4-[5-(3,5-Dichloro-phenyl)-5-trifluoromethyl-4,5-dihydro-isoxazol-3-yl]-2,N-dimethyl-benzamide (300 mg) in thionyl chloride (5 mL) was added a catalytic amount of DMF and stirred at reflux for 30 min. All volatiles were removed in vacuum and the residue were taken up in THF (5 mL). This solution was added to a mixture of n-propylamine (247 mg) in THF (5 mL) and stirred at room temperature over night. The solvent was evaporated and the residue was purified by flash chromatography to yield the title compound (74 mg, 22%)

Characterization by HPLC-MS: 3.512, M=472.05

S.7 Synthesis of 4-[5-(3,5-Dichloro-phenyl)-5-trifluoromethyl-4,5-dihydro-isoxazol-3-yl]-2-methyl-benzene-N-propyl-N',N'-dimethyl-amidrazone (Compound 1-15 of Table C.1)

Step 1: Synthesis of 4-[5-(3,5-Dichloro-phenyl)-5-trifluoromethyl-4,5-dihydro-isoxazol-3-yl]-2-methyl-benzoic acid N',N'-dimethyl-hydrazide To a solution of N,N-dimethyl hydrazine (0.55 g) in ether (46 mL) was added 4-[5-(3,5-Dichloro-phenyl)-5-trifluoromethyl-4,5-dihydro-isoxazol-3-yl]-2-methyl-benzoyl chloride (2.00 g) in small portions at 0° C. After 50 min at this temperature, water was added and the pH was adjusted to 7 by addition of NaOH (2 M). The organic layer was separated and the aqueous layer was extracted with ether. Combined organic layers were washed with NaHCO$_3$ solution, dried over Na$_2$SO$_4$ and evaporated to give the title compound (1.50 g, 71%).

Characterization by HPLC-MS: 3.394 min, M=460.05

Step 2: Synthesis of 4-[5-(3,5-Dichloro-phenyl)-5-trifluoromethyl-4,5-dihydro-isoxazol-3-yl]-2-methyl-benzene-N-propyl-N',N'-dimethyl-amidrazone A solution of 4-[5-(3,5-Dichloro-phenyl)-5-trifluoromethyl-4,5-dihydro-isoxazol-3-yl]-2-methyl-benzoic acid N',N'-dimethyl-hydrazide (i.e product of Step 1, 300 mg) in POCl$_3$ (5 mL) was heated at reflux for 10 min, concentrated in vacuum and taken up in THF (5 mL). This was added to a solution of n-propylamine (231 mg) in THF (5 mL) and stirred at room temperature over night. The solvent was removed in vacuum and the residue was purified by flash chromatography on silica gel to yield the title compound (50 mg, 15%).

Characterization by HPLC-MS: 3.614 min, M=501.10

S.8 Synthesis of 3-{4-[5-(3,5-Dichloro-phenyl)-5-trifluoromethyl-4,5-dihydro-isoxazol-3-yl]-2-methyl-phenyl}-5-methyl-[1,2,4]oxadiazole (Compound 9-2 of Table C.9)

Step 1: Synthesis of 4-[5-(3,5-Dichloro-phenyl)-5-trifluoromethyl-4,5-dihydro-isoxazol-3-yl]-N-hydroxy-2-methyl-benzamidine A solution hydroxylamine hydrochloride (8.70 g) in DMSO was cooled to 15° C., before KOtBu was added in small portions. This mixture was added to a solution of 4-[5-(3,5-Dichloro-phenyl)-5-trifluoromethyl-4,5-dihydro-isoxazol-3-yl]-2-methyl-benzonitrile (5.00 g) in DMSO (20 mL) at room temperature and stirred at 80° C. for 5 h. After completion of the reaction, the mixture was poured onto ice-water and the resulting solid was collected by filtration, washed with water and dried. Chromatography on silica gel yielded the title compound (3.3 g, 61%).

Characterization by HPLC-MS: 3.173 min, M=431.95

Step 2: Synthesis of 3-{4-[5-(3,5-Dichloro-phenyl)-5-trifluoromethyl-4,5-dihydro-isoxazol-3-yl]-2-methyl-phenyl}-5-methyl-[1,2,4]oxadiazole To a solution of 4-[5-(3,5-Dichloro-phenyl)-5-trifluoromethyl-4,5-dihydro-isoxazol-3-yl]-N-hydroxy-2-methyl-benzamidine (i.e product of Step 1, 400 mg, 0.93 mmol) in pyridine (10 mL) was added acetyl chloride (0.13 mL, 0.15 g, 1.85 mmol) via syringe and the mixture was stirred at reflux for 30 min. Water and EtOAc were added after cooling and the aqueous layer was extracted with EtOAc. Combined organic layers were dried ($Na_2SO_4$) and concentrated in vacuum. The residue was purified by flash chromatography on silica gel and yielded the title compound (277 mg, 65%).

Characterization by HPLC-MS: 4.345 min, M=456.00
Characterization by $^1$H-NMR (400 MHz, $CDCl_3$):
δ [delta]=2.66 (s, 6H), 3.74 (d, 1H), 4.12 (d, 1H), 7.44 (s, 1H), 7.53 (s, 2H), 7.60 (d, 1H), 7.64 (s, 1H), 8.06 (d, 1H) ppm.

S.9 Synthesis of 3-{4-[5-(3,5-Dichloro-phenyl)-5-trifluoromethyl-4,5-dihydro-isoxazol-3-yl]-2-trifluoroethyl-phenyl}-5-methyl-[1,2,4]oxadiazole (Compound 9-4 of Table C.9)

To a solution of 4-[5-(3,5-Dichloro-phenyl)-5-trifluoromethyl-4,5-dihydro-isoxazol-3-yl]-N-hydroxy-2-methyl-benzamidine (i.e product of Step 1, Example 8, 400 mg, 0.93 mmol) in pyridine (10 mL) was added 3,3,3-trifluoropropionic acid chloride (0.271 g, 1.85 mmol) via syringe and the mixture was stirred at reflux for 30 min and at 140° C. in a microwave oven for 1 h. Water and EtOAc were added after cooling and the aqueous layer was extracted with EtOAc. Combined organic layers were dried ($Na_2SO_4$) and concentrated in vacuum. The residue was purified by flash chromatography on silica gel and yielded the title compound (260 mg, 53%).

Characterization by HPLC-MS: 4.540 min, M=524.00
Characterization by $^1$H-NMR (400 MHz, $CDCl_3$):
δ [delta]=2.68 (s, 3H), 3.73 (d, 1H), 3.90 (q, 2H), 4.12 (d, 1H), 7.43 (s, 1H), 7.53 (s, 2H), 7.56-7.69 (m, 2H), 8.11 (d, 1H) ppm.

S.10 Synthesis of N-Ethyl-2-({N-hydroxy-2-methyl-4-[5-trifluoromethyl-5-(3-trifluoromethyl-phenyl)-4,5-dihydro-isoxazol-3-yl]-benzimidoyl}-amino)-acetamide (Compound 3-13 of Table C.3)

To a solution of 2-Methyl-4-[5-trifluoromethyl-5-(3-trifluoromethyl-phenyl)-4,5-dihydro-isoxazol-3-yl]-benzaldehyde oxime (250 mg) in DMF (8 mL) was added N-chloro succinimide (84 mg) and heated to 75° C. for 1 h. After cooling, the reaction mixture was poured onto ice-water and extracted with EtOAc. The combined organic layers were washed with water, dried ($Na_2SO_4$) and concentrated in vacuo to ¼ of the original volume to obtain the crude hydroxamic acid chloride. This mixture was added to a solution of 2-amino-N-ethyl-acetamide (61 mg) and triethylamine (0.15 mL, 0.11 g) in THF (8 mL) and stirred at room temperature over night. After concentration in vacuo, the mixture was purified by chromatography on silica gel to obtain the title compound (171 mg, 55%).

Characterization by HPLC-MS: 3.716 min, M=517.10

S.11 Synthesis of N-Hydroxy-2-methyl-N'-pyridin-2-ylmethyl-4-[5-trifluoromethyl-5-(3-trifluoromethyl-phenyl)-4,5-dihydro-isoxazol-3-yl]-benzamidine (Compound 3-8 of Table C.3)

To a solution of 2-Methyl-4-[5-trifluoromethyl-5-(3-trifluoromethyl-phenyl)-4,5-dihydro-isoxazol-3-yl]-benzaldehyde oxime (250 mg) in DMF (8 mL) was added N-chloro succinimide (84 mg) and heated to 75° C. for 1 h. After cooling, the reaction mixture was poured onto ice-water and extracted with EtOAc. The combined organic layers were washed with water, dried ($Na_2SO_4$) and concentrated in vacuoto ¼ of the original volume to obtain the crude hydroxamic acid chloride. This mixture was added to a solution of 2-picolylamine (65 mg) and triethylamine (0.15 mL, 0.11 g) in THF (8 mL) and stirred at room temperature over night. After concentration in vacuo, the mixture was purified by chromatography on silica gel to obtain the title compound (138 mg, 44%).

Characterization by HPLC-MS: 3.727 min, M=523.10

S. 12 Synthesis of 2-({2-Chloro-4-[5-(3,5-dichloro-phenyl)-5-trifluoromethyl-4,5-dihydro-isoxazol-3-yl]-N-hydroxy-benzimidoyl}-amino)-N-(2,2,2-trifluoro-ethyl)-acetamide (Compound 5-12 of Table C.5)

Step 1: Synthesis of 2-Chloro-4-[5-(3,5-dichloro-phenyl)-5-trifluoromethyl-4,5-dihydro-isoxazol-3-yl]-benzoic acid methyl ester A mixture of 3-(4-Bromo-3-chloro-phenyl)-5-(3,5-dichloro-phenyl)-5-trifluoromethyl-4,5-dihydro-isoxazole (4.00 g), palladium bis(diphenylphosphine) dichloride $CH_2Cl_2$-complex (0.69 g), palladium acetate (0.14 g), sodium acetate (1.03 g), and methanol (50 mL) was placed in an autoclave, charged with 5 bar of carbon monoxide and stirred at 100° C. for 16 h. After cooling, the autoclave was opened and the reaction mixture was filtered. The filtrate was concentrated in vacuum and the residue was purified by flash chromatography on silica gel to obtain the title compound (2.2 g, 58%).

Characterization by HPLC-MS: 4.285 min, M=451.95

Step 2: Synthesis of 2-Chloro-4-[5-(3,5-dichloro-phenyl)-5-trifluoromethyl-4,5-dihydro-isoxazol-3-yl]-benzaldehyde To a solution of 2-Chloro-4-[5-(3,5-dichloro-phenyl)-5-trifluoromethyl-4,5-dihydro-isoxazol-3-yl]-benzoic acid methyl ester (i.e. the product of Step 1, 2.20 g) in CH$_2$Cl$_2$ was added a solution of diisobutyl aluminium hydride (1 M in CH$_2$Cl$_2$, 10.7 mL) at −78° C. and kept at this temperature for 30 min. MeOH (25 mL) was added carefully and the mixture was allowed to warm to room temp, when aqueous K-Na-tartrate solution was added. The layers were separated and the aqueous phase was extracted with CH$_2$Cl$_2$, combined organic layers were washed with water, dried (Na$_2$SO$_4$) and evaporated. The residue was purified by flash chromatography on silica gel to obtain the title compound (1.35 g, 66%) and 2-Chloro-4-[5-(3,5-dichloro-phenyl)-5-trifluoromethyl-4,5-dihydro-isoxazol-3-yl]-benzyl alcohol (0.49 g, 24%).

Characterization by HPLC-MS: 4.238 min, M=421.85
Characterization by $^1$H-NMR (400 MHz, CDCl$_3$):
δ [delta]=3.73 (d, 1H), 4.10 (d, 1H), 7.43 (m, 1H), 7.50 (s, 2H), 7.62 (d, 1H), 7.76 (s, 1H), 7.98 (d, 1H), 10.48 (s, 1H) ppm.

Step 3: Synthesis of 2-Chloro-4-[5-(3,5-dichloro-phenyl)-5-trifluoromethyl-4,5-dihydro-isoxazol-3-yl]-benzaldehyde Oxime To a solution of 2-Chloro-4-[5-(3,5-dichloro-phenyl)-5-trifluoromethyl-4,5-dihydro-isoxazol-3-yl]-benzaldehyde (i.e. the product of Step 2, 1.20 g) in methanol (5 mL) was added hydroxylamine hydrochloride (296 mg) and a catalytic amount of concentrated hydrochloric acid. The mixture was stirred at 70° C. for 3 h and concentrated in vacuum. Water was added and the mixture was extracted with ethyl acetate. Combined organic layers were dried (Na$_2$SO$_4$) and evaporated to obtain the title compound (1.2 g, 97%).

Characterization by HPLC-MS: 4.090 min, M=436.95

Step 4: Synthesis of 2-({2-Chloro-4-[5-(3,5-dichloro-phenyl)-5-trifluoromethyl-4,5-dihydro-isoxazol-3-yl]-N-hydroxy-benzimidoyl}-amino)-N-(2,2,2-trifluoro-ethyl)-acetamide To a solution of 2-Chloro-4-[5-(3,5-dichloro-phenyl)-5-trifluoromethyl-4,5-dihydro-isoxazol-3-yl]-benzaldehyde oxime (i.e. the product of Step 3, 250 mg) in DMF (5 mL) was added N-chloro succinimide (80 mg) and heated to 75° C. for 1 h. After cooling, the reaction mixture was poured onto ice-water and extracted with EtOAc. The combined organic layers were washed with water, dried (Na$_2$SO$_4$) and concentrated in vacuo to ¼ of the original volume to obtain the crude hydroxamic acid chloride. This mixture was added to a solution of (2,2,2-trifluoro-ethylcarbamoyl)-methyl-ammonium-chloride (110 mg) and triethylamine (0.29 mL, 0.21 g) in THF (10 mL) and stirred at room temperature over night. After concentration in vacuo, the mixture was purified by chromatography on silica gel to obtain the title compound (176 mg, 52%).

Characterization by HPLC-MS: 3.848 min, M=591.00

S.13 Synthesis of 2-Chloro-4-[5-(3,5-dichloro-phenyl)-5-trifluoromethyl-4,5-dihydro-isoxazol-3-yl]-1'-hydroxy-N'-pyridin-2-ylmethyl-benzamidine (Compound 5-8 of Table C.5)

To a solution of 2-Chloro-4-[5-(3,5-dichloro-phenyl)-5-trifluoromethyl-4,5-dihydro-isoxazol-3-yl]-benzaldehyde oxime (i.e. the product of Step 3, 250 mg) in DMF (5 mL) was added N-chloro succinimide (81 mg) and heated to 75° C. for 1 h. After cooling, the reaction mixture was poured onto ice-water and extracted with EtOAc. The combined organic layers were washed with water, dried (Na$_2$SO$_4$) and concentrated in vacuo to ¼ of the original volume to obtain the crude hydroxamic acid chloride. This mixture was added to a solution of 2-picolylamine (62 mg) and triethylamine (0.15 mL, 0.11 g) in THF (10 mL) and stirred at room temperature over night. After concentration in vacuo, the mixture was purified by chromatography on silica gel to obtain the title compound (197 mg, 63%).

Characterization by HPLC-MS: 3.597 min, M=543.00

S.14 Synthesis of 2-({2-Chloro-4-[5-(3,5-dichloro-phenyl)-5-trifluoromethyl-4,5-dihydro-isoxazol-3-yl]-N-hydroxy-benzimidoyl}-amino)-N-ethyl-acetamide (Compound 5-13 of Table C.5)

To a solution of 2-Chloro-4-[5-(3,5-dichloro-phenyl)-5-trifluoromethyl-4,5-dihydro-isoxazol-3-yl]-benzaldehyde Oxime (i.e. the Product of Step 3, 250 mg) in DMF (5 mL) was added N-chloro succinimide (81 mg) and heated to 75° C. for 1 h. After cooling, the reaction mixture was poured onto ice-water and extracted with EtOAc. The combined organic layers were washed with water, dried (Na$_2$SO$_4$) and concentrated in vacuo to ¼ of the original volume to obtain the crude hydroxamic acid chloride. This mixture was added to a solution of 2-amino-N-ethyl-acetamide (58 mg) and triethylamine (0.15 mL, 0.11 g) in THF (10 mL) and stirred at room temperature over night. After concentration in vacuo, the mixture was purified by chromatography on silica gel to obtain the title compound (164 mg, 53%).

Characterization by HPLC-MS: 3.253 min, M=537.05

S.15 Synthesis of 2-Chloro-4-[5-(3,5-dichloro-phenyl)-5-trifluoromethyl-4,5-dihydro-isoxazol-3-yl]-N-hydroxy-N'-(2,2,2-trifluoro-ethyl)-benzamidine (Compound 5-4 of Table C.5)

To a solution of 2-Chloro-4-[5-(3,5-dichloro-phenyl)-5-trifluoromethyl-4,5-dihydro-isoxazol-3-yl]-benzaldehyde oxime (i.e. the product of Step 3, 250 mg) in DMF (5 mL) was added N-chloro succinimide (81 mg) and heated to 75° C. for 1 h. After cooling, the reaction mixture was poured onto ice-water and extracted with EtOAc. The combined organic layers were washed with water, dried (Na$_2$SO$_4$) and concentrated in vacuo to ¼ the original volume to obtain the crude hydroxamic acid chloride. This mixture was added to a solution of 2,2,2-trifluoro ethylamine (57 mg) and triethylamine (0.15 mL, 0.11 g) in THF (10 mL) and stirred at room temperature over night. After concentration in vacuo, the mixture was purified by chromatography on silica gel to obtain the title compound (122 mg, 40%).

Characterization by HPLC-MS: 3.850 min, M=533.95

S.16 Synthesis of 4-[5-(3,5-Dichloro-phenyl)-5-trifluoromethyl-4,5-dihydro-isoxazol-3-yl]-N-hydroxy-acetyl-2-methyl-N'-(2,2,2-trifluoro-ethyl)-benzamidine (Compound 1-7 of Table C.1)

A solution of 4-[5-(3,5-Dichloro-phenyl)-5-trifluoromethyl-4,5-dihydro-isoxazol-3-yl]-N-hydroxy-2-methyl-N'-(2,2,2-trifluoro-ethyl)-benzamidine (250 mg), acetic anhydride (50 pL, 55 mg) and DMAP (5 mg) in CH$_2$Cl$_2$ (10 mL) was stirred at room temperature over night. The mixture was concentrated in vacuum and the residue purified by flash chromatography on silica gel to obtain the title compound (170 mg, 65%).

Characterization by $^1$H-NMR (400 MHz, CDCl$_3$):
δ [delta]=2.24 (s, 3H), 2.39 (s, 3H), 3.46 (br. t, 2H), 3.70 (d, 1H), 4.10 (d, 1H), 5.75 (br t, 1H), 7.39 (d, 1H), 7.43 (m, 1H), 7.52 (s, 2H), 7.54 (s, 1H), 7.62 (s, 1H), ppm.

B. Biological Examples

The activity of the compounds of formula I of the present invention could be demonstrated and evaluated in biological tests described in the following.

If not otherwise specified the test solutions are prepared as follow:

The active compound is dissolved at the desired concentration in a mixture of 1:1 (vol:vol) distilled water:acteon. The test solution is prepared at the day of use and in general at concentrations of ppm (wt/vol).

B.1 Cotton Aphid (*Aphis gossypii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 1-1 and 1-8, respectively, at 300 ppm showed a mortality of at least 75% in comparison with untreated controls.

B.2 Cowpea Aphid (*Aphis craccivora*)

Potted cowpea plants colonized with approximately 100-150 aphids of various stages were sprayed after the pest population has been recorded. Population reduction was assessed after 24, 72, and 120 hours.

In this test, the compounds 1-8, 1-10, 1-11, and 1-13, respectively, at 300 ppm showed a mortality of at least 75% in comparison with untreated controls.

B.3 Diamond Back Moth (*Plutella xylostella*)

Leaves of Chinese cabbage were dipped in test solution and air-dried. Treated leaves were placed in petri dished lined with moist filter paper. Mortality was recorded 24, 72, and 120 hours after treatment.

In this test, the compounds 1-1, 1-2, 1-3, 1-4, 1-5, 1-6, 1-7, 1-8, 1-10, 1-11, 1-12, 1-13, 9-1, 9-2, 9-5, and 9-9, respectively, at 300 ppm showed a mortality of at least 75% in comparison with untreated controls.

B.4 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs. The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-10, 1-11, 1-12, 1-13, 9-2, 9-3, 9-4, 9-9 and 9-10 respectively, at 2500 ppm showed a mortality of at least 75% in comparison with untreated controls.

B.5 Orchid Thrips (*Dichromothrips corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant.

Thrips potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult thrips. The petri dishes are then covered with lids. All test arenas are held under continuous light and a temperature of about 28° C. for duration of the assay. After 4 days, the numbers of live thrips are counted on each flower, and along inner walls of each petri dish. The level of thrips mortality is extrapolated from pre-treatment thrips numbers.

In this test, the compounds 1-1, 1-2, 1-3, 1-4, 1-7, 1-8, 1-10, 1-11, 1-12 and 1-13, respectively, at 300 ppm showed a mortality of at least 75% in comparison with untreated controls.

B.6 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 1-1, 1-3, 1-6 and 1-13, respectively, at 300 ppm showed a mortality of at least 75% in comparison with untreated controls.

B.7 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the $1^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-1, 1-2, 1-3, 1-4, 1-5, 1-6, 1-7, 1-8, 1-10, 1-12, 1-13, 9-1, 9-2, 9-3, 9-4 and 9-10, respectively, at 300 ppm showed a mortality of at least 75% in comparison with untreated controls.

B.8 Red Spider Mite (*Tetranychus kanzawai*)

The active compound was dissolved at the desired concentration in a mixture of 1:1 (v/v) distilled water:acetone. A surfactant (Alkamuls® EL 620) was added at the rate of 0.1% (v/v).

Potted cowpea beans of 7-10 days of age were cleaned with tap water and sprayed with 5 ml of the test solution using air driven hand atomizer. The treated plants were allowed to air dry and afterwards inculated with 20 or more mites by clipping a cassaya leaf section with known mite population. Treated plants were placed inside a holding room at about 25-27° C. and about 50-60% relative humidity.

ortality by counting the live mites 72 HAT. Percent mortality was assessed after 72 h.

In this test, the compounds I-6, and 1-13, respectively, at 500 ppm showed a mortality of at least 75% in comparison with untreated controls.

B.9 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-4, 1-6, 1-8, 1-10, 1-12 and 1-13, respectively, at 2500 ppm showed a mortality of at least 75% in comparison with untreated controls.

B.10 Tobacco Budworm (*Heliothis virescens*)|

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-1, 1-2, 1-3, 1-4, 1-5, 1-6, 1-7, 1-8, 1-10, 1-11, 1-12, 1-13, 9-1, 9-2, 9-3, 9-4, 9-7, 9-8, 9-9 and 9-10, respectively, at 2500 ppm showed a mortality of at least 75% in comparison with untreated controls.

B.11 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, the compounds 1-1, 1-2, 1-3, 1-4, 1-5, 1-6, 1-7, 1-8, 1-10, 1-11, 1-12, 1-13, 9-2 and 9-4, respectively, at 2500 ppm showed a mortality of at least 75% in comparison with untreated controls.

B.12 Western Flower Thrips (*Frankliniella occidentalis*)

Serial dilutions of each technical grade AI were made in pure acetone. 0.5 ml of the treatment solution was deposited into the bottom of a glass vial (scintillation vial). The cap was screwed back onto the vial and inverted for about five seconds. The cap was subsequently removed and the vial laid on its side and rolled constantly, on a hot dog roller, until all the acetone had flashed off and the inner surface of the vial was dry. Cotton leave discs were also dipped simultaneously into the treatment solutions and allowed to dry. After the vials were dried, the leave discs are placed into the vials to serve as a food/water source for the thrips. Each treatment was replicated 5-fold.

Western flower thrips were aspirated into the vials, approximately 5 larvae or adults/vial. Following treatment application the vials were held in a holding room under fluorescent light and constant 26° C. Thrips mortality was assessed at 2 DAT (days after treatment), counting all thrips both dead and alive.

In this test, the compound 1-2 at 300 ppm showed a mortality of at least 75% in comparison with untreated controls.

BA. Animal Health

General Test Conditions of Animal Health Glass Vial Contact Assays

If not otherwise specified, the tests were conducted as glass vial contact assays. Glass vials (20 ml scintillation vials) were used. Treatment solutions were mixed with technical grade chemicals diluted in acetone. Treatment solutions needed for the assays included generally 1 and 10 ppm (0.01 and 0.1 µg/cm$^2$, respectively), but optionally also 100 and/or 1000 ppm for first tier vials. As commercial standard, alphacypermethrin, was run at 1 ppm. As solvent control, acetone was used for the assay. Treatment solution was pipetted into the bottom of each vial. Each vial was turned on its side and placed onto a commercial grade hot dog roller without applying heat. The uncapped vials were allowed to roll to allow for the acetone treatment to vent off. After drying, the vials were placed into the compartmented vial shipping boxes. The workstation was prepared by chilling the table and plastic Petri dishes with the inside wall coated with Fluon. A weigh boat of 10% sugar water saturated cotton dental pellets was also prepared. The animal pests were collected into a tube with a rechargeable insect vacuum. The tube of animal pests was placed in a laboratory refrigerator until the animal pests were incapacitated. The animal pests were emptied into chilled Petri dish. A small cotton dental pellet was soaked in water or in 10 wt % sugar water, whereas the excess solution was gently squeezed out. The cotton dental pellet was placed into the bottom of each vial. For the test, the animal pests were added to each vial and then the cap was loosely put on the vial to allow for ventilation. The test vials were hold at ambient room temperature in compartmented boxes. In general, the animal pests were observed for incapacitation at least at 4, 24, and 48 hours after infestation, or for a longer period if required. Mortality was defined as an insect incapable of coordinated movement when agitated.

BA.1 House Fly Adults (*Musca domestica*)

Treatment solutions were mixed with test compound diluted in acetone at concentrations of 1 and 10 ppm. The small cotton dental pellet added was soaked in 10% sugar water. Flies were observed for incapacitation at 4, 24, and 48 hours after infestation.

In this test, the compounds 1-2 and 1-3, respectively, at 10 ppm showed 48 h after treament a mortality of at least 75% in comparison with untreated controls.

BA.2 Yellowfever Mosquito Adults (*Aedes aegypti*)

BA.2.a Larval Mosquito Water Treatment Assay

The assay was conducted in 6-well polystyrene plates using one plate per treatment rate. Stock solutions were prepared at 100 and 1000 ppm. Screen rates were at 1 and 10 ppm. Distilled water was added to each well, control wells were treated with acetone. Temephos (Abate technical) was used as the standard at 0.1 ppm. Ten late thirdinstar yellowfever mosquito larvae (*Aedes aegypti*) in water were added to each well. One drop of liver powder solution (6 g in 100 ml distilled water) was added to each well as a food source daily. Plates were maintained at 22-25° C. and 25-50% RH (relative humidity) and observed daily for dead larvae and pupae at 1, 2, 3, and 5 days after treatment. Dead larvae and all pupae were removed daily. Mortality was defined as an insect incapable of coordinated movement when agitated.

In this first tier test, the compounds 1-1, 1-2, 1-3, 1-12 and 1-13 respectively, at 1 ppm showed after 5 DAT (days after treatment) a mortality of at least 75% in comparison with untreated controls.

We claim:

1. A compound of formula (I-5)

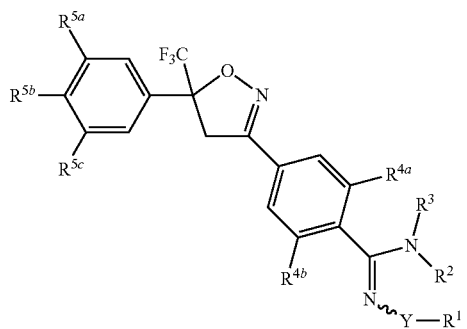

(I-5)

wherein

Y is O, N—$R^8$ or a chemical bond;

$R^1$ is selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $S(O)_nR^7$, $S(O)_nNR^{9a}R^{9b}$, $C(=O)R^6$, $C(=O)NR^{9a}R^{9b}$, $C(=O)OR^7$, $C(=S)R^6$, $C(=S)NR^{9a}R^{9b}$, $C(=S)OR^7$, $C(=S)SR^7$, phenyl, optionally substituted with one or more substituents $R^{10}$, which are independently selected from one another, and a 3-, 4-, 5-, 6- or 7-membered saturated, partly saturated or unsaturated aromatic heterocyclic ring, comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or $R^1$ may be together with $R^2$ a $CH_2CH_2$ or $CH_2$ bridge, forming a 5-membered or 6-membered heterocyclic ring together with the substituted amidine unit they are bond to;

$R^{4a}$, $R^{4b}$ are selected independently from one another from the group consisting of hydrogen, halogen, cyano, azido, nitro, —SCN, $SF_5$, $C_1$-$C_6$-alkyl, $C_3$-$C_8$-cycloalkyl, wherein the carbon atoms of the last two aliphatic and cyclo-aliphatic radicals may optionally be substituted with one or more $R^6$, which are independently selected from one another, $OR^7$, —$OS(O)_nR^7$, $S(O)nR^7$, $NR^{9a}R^{9b}$, $N(R^{9a})C(=O)R^6$, CHO, $C(=O)R^6$, —$C(=O)OR^7$, $C(=NR^{9a})_R^6$, $C(=S)R^6$, phenyl, optionally substituted with one or more substituents independently selected from $R^{10}$, which are selected independently from one another, and a 3-, 4-, 5-, 6- or 7-membered saturated, partly saturated or unsaturated aromatic heterocyclic ring;

$R^{5a}$, $R^{5c}$ are selected independently from one another from the group consisting of hydrogen, halogen, cyano, nitro, SCN, $SF_5$, $C_1$-$C_6$-alkyl, $C_3$-$C_8$-cycloalkyl, wherein the carbon atoms of the two last aliphatic and cyclo-aliphatic radicals may optionally be substituted with one or more $R^6$, selected independently from one another, $OR^7$, $S(O)nR^7$, $NR^{9a}R^{9b}$, $C(=O)R^6$, —$C(=O)OR^7$, $C(=NR^8)R^6$, $C(=S)NR^6$;

$R^{5b}$ is selected from the group consisting of hydrogen, halogen, cyano, nitro, —SCN, $SF_5$, $C_1$-$C_6$-alkyl, $C_1$-$C_6$-alkyl, $C_3$-$C_8$-cycloalkyl, $C_2$-$C_6$-alkenyl, $C_2$-$C_6$-alkinyl, wherein the aliphatic chains of the five last radicals may optionally be substituted with one or more $R^6$, selected independently from one another, $Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^9)R^6$, $C(=S)NR^6$, phenyl, optionally substituted with one or more substituents $R^{10}$, which are selected independently from one another;

and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^6$ is selected from the group consisting of hydrogen, halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $Si(R^{12})_2R^{13}$, $OR^{16}$, $OSO_2R^{16}$, $S(O)_nR^{16}$, $S(O)_nNR^{17a}R^{17b}_2$, $NR^{17a}R^{17b}$, $C(=O)NR^{17aR17b}$, $C(=S)NR^{17a}R^{17b}$, $C(=O)OR^{16}$, phenyl, optionally substituted with one or more substituents $R^{18}$, which are independently selected from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized, or two $R^6$ present on one carbon atom may together form =O, =$CR^{13}R^{14}$; =$S(O)_nR^{16}$; =$S(O)_nNR^{17a}R^{17b}$, =$NR^{17a}$, =$NOR^{16}$; =$NNR^{17a}$;

or two $R^6$ may form a 3-, 4-, 5-, 6-, 7- or 8-membered saturated or partly unsaturated carbocyclic or heterocyclic ring together with the carbon atoms to which the two $R^6$ are bonded to;

$R^7$ is, independent from each other, selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, —$Si(R^{11})_2R^{12}$, $S(O)_nR^{16}$, —$S(O)_nNR^{17a}R^{17b}$, $NR^{17a}R^{17b}$, —$N=CR^{13}R^{14}$, —$C(=O)R^{16}$, $C(=O)NR^{17a}R^{17b}$, $C(=S)NR^{17a}R^{17b}$, $C(=O)OR^{16}$, phenyl, optionally substituted with one or more substituents $R^{18}$; which are selected independently from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^8$ is selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another, $NR^{17a}R^{17b}$, $Si(R^{11})_2R^{12}$, $OR^{16}$, $S(O)nR^{16}$, $S(O)_nNR^{17a}R^{17b}$, $C(=O)R^{15}$, $-C(=O)OR^{16}$, $C(=O)NR^{17a}R^{17b}$, $C(=S)R^{15}$, $C(=S)SR^{16}$, $C(=S)NR^{17aR17b}$; $C(=NR^{17a})R^{15}$;

phenyl, optionally substituted with one or more substituents $R^{18}$, which are selected independently from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, independently selected from one another, and wherein the nitrogen and/or the sulfur atom(s) of the heterocyclic ring may optionally be oxidized;

$R^8$ and $R^1$ may be together a $C_2$-$C_7$ alkylene chain, forming a 3-, 4-, 5-, 6-, 7- or 8-membered saturated, partly saturated, or unsaturated aromatic heterocyclic ring together with the nitrogen atom they are bond to, wherein the alkylene chain may further contain 1 or 2 oxygen atoms, sulfur atoms or nitrogen atoms, and wherein the alkylene chain may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^{9a}$, $R^{9b}$ are selected independent from one another from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $S(O)_nR^{16}$, $-S(O)_nNR^{17a}R^{17b}$, $C(=O)R^{15}$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17a})R^{15}$;

phenyl, optionally substituted with one or more substituents $R^{18}$, which are selected independently from one another, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

or, $R^{9a}$ and $R^{9b}$ are together a $C_2$-$C_7$ alkylene chain and form a 3-, 4-, 5-, 6-, 7- or 8-membered saturated, partly saturated, or unsaturated aromatic ring together with the nitrogen atom they are bonded to, wherein the alkylene chain may contain one or two heteratoms selected from oxygen, sulfur or nitrogen, and may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally substituted with one or more substituents $R^{18}$; which are selected independently from one another, a 3-, 4-, 5-, 6,- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^{10}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another, $Si(R^{11})_2R^{12}$, $OR^{16}$, $OS(O)_nR^{16}$, $-S(O)_nR^{16}$, $S(O)_nNR^{17a}R^{17b}$, $NR^{17a}R^{17b}$, $C(=O)R^{15}$, $C(=O)OR^{16}$, $-C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy, and a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents selected independently from one another from halogen, cyano, $NO_2$, $C_1$-$C_6$-alkyl, $C_1$-$C_6$-haloalkyl, $C_1$-$C_6$-alkoxy or $C_1$-$C_6$-haloalkoxy, and wherein the nitrogen and/or the sulfur atom(s) of the heterocyclic ring may optionally be oxidized;

or two $R^{10}$ present together on one atom of a partly saturated heterocyclic may be =O, $=CR^{13}R^{14}$; $=S(O)_nR^{16}$; $=S(O)_nNR^{17a}R^{17b}$, $=NR^{17a}$, $=NOR^{16}$ or $=NNR^{17a}$, or, two $R^{10}$ on adjacent carbon atoms may be a bridge selected from the group consisting of $CH_2CH_2CH_2CH_2$, $CH=CH-CH=CH$, $N=CH-CH=CH$, $CH=N-CH=CH$, $N=CH-N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^8$, $CH_2CH=N$, $CH=CH-NR^{9a}$, $OCH=N$, and $SCH=N$ and form together with the carbon atoms to which the two $R^{10}$ are bonded to a 5-membered or 6-membered partly saturated or unsaturated, aromatic carbocyclic or heteocyclic ring, wherein the ring may optionally be substituted with one or two substituents selected from the group consisting of =O, OH, CH$^3$, OCH$_3$, halogen, halomethyl and halomethoxy;

R$^{11}$, R$^{12}$ are selected independent from one another from the group consisting of hydrogen, halogen, C$_1$-C$_6$ alkyl, C$_1$-C$_6$ haloalkyl, C$_1$-C$_6$ alkoxyalkyl, C$_2$-C$_6$ alkenyl, C$_2$-C$_6$ haloalkenyl, C$_2$-C$_6$ alkinyl, C$_2$-C$_6$ haloalkinyl, C$_3$-C$_8$ cycloalkyl, C$_3$-C$_8$ halocycloalkyl, C$_1$-C$_6$ alkoxyalkyl, C$_1$-C$_6$ haloalkoxyalkyl, phenyl, optionally substituted with one or more substituents R$^{18}$; which are selected independently from one another, and a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents R$^{18}$, selected independently from one another, and wherein the nitrogen and/or the sulfur atom(s) of the heterocyclic ring may optionally be oxidized;

R$^{13}$, R$^{14}$ are selected independent from one another from the group consisting of C$_1$-C$_4$ alkyl, C$_1$-C$_6$ cycloalkyl, C$_1$-C$_4$ alkoxyalkyl, phenyl and benzyl;

R$^{15}$ is selected from the group consisting of hydrogen, halogen, cyano, azido, nitro, OH, SH, SCN, SF$_5$, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkinyl, C$_3$-C$_8$-cycloalkyl, wherein the four last mentioned aliphatic and cyclo-aliphatic radicals may be unsubstituted, partially or fully halogenated and/or oxgenated and/or may carry 1 or 2 radicals selected from C$_1$-C$_4$ alkoxy, phenyl, benzyl, pyridyl, phenoxy, wherein the last four radicals may be unsubstituted, partially or fully halogenated and/or to carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy, (C$_1$-C$_6$-alkoxy)carbonyl, (C$_1$-C$_6$-alkyl)amino and di-(C$_1$-C$_6$-alkyl)amino, or two R$^{15}$ present on the same carbon atom may together form =O, =CH(C$_1$-C$_4$), =C(C$_1$-C$_4$-alkyl)C$_1$-C$_4$-alkyl, =N(C$_1$-C$_6$-alkyl) or =NO(C$_1$-C$_6$-alkyl);

R$^{16}$ is selected from the group consisting of hydrogen, cyano, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkinyl, C$_3$-C$_8$-cycloalkyl, wherein the four last mentioned radicals may be unsubstituted, partially or fully halogenated and/or oxygenated and/or may carry 1 or 2 radicals selected from C$_1$-C$_4$ alkoxy, phenyl, benzyl, pyridyl, phenoxy, wherein the last four radicals may be unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy and (C$_1$-C$_6$-alkoxy)carbonyl;

R$^{17a}$, R$^{17b}$ is selected from the group consisting of hydrogen, cyano, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkinyl, C$_3$-C$_8$-cycloalkyl, wherein the four last mentioned aliphatic and cyclo-aliphatic radicals may be unsubstituted, partially or fully halogenated and/or oxygenated and/or may carry 1 or 2 radicals selected from C$_1$-C$_4$-alkoxy, phenyl, benzyl, pyridyl, phenoxy, wherein the four last mentioned radicals may be unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy and (C$_1$-C$_6$-alkoxy)carbonyl, or, R$^{17a}$ and R$^{17b}$ may together be a C$_2$-C$_6$ alkylene chain forming a 3- to 7-membered saturated, partly saturated or unsaturated ring together with the nitrogen atom R$^{17a}$ and R$^{17b}$ are bonded to, wherein the alkylene chain may contain 1 or 2 heteroatoms selected from oxygen, sulfur or nitrogen, and may optionally be substituted with halogen, C$_1$-C$_4$-haloalkyl, C$_1$-C$_4$-alkoxy or C$_1$-C$_4$-haloalkoxy, and wherein the nitrogen and/or the sulfur atom(s) of the heterocyclic ring may optionally be oxidized;

R$^{18}$ is selected from the group consisting of hydrogen, cyano, C$_1$-C$_6$-alkoxy, C$_1$-C$_6$-haloalkoxy, C$_1$-C$_6$-alkylthio, C$_1$-C$_6$-alkylsulfinyl, C$_1$-C$_6$-alkylsulfonyl, C$_1$-C$_6$-haloalkylthio, trimethylsilyl, triethylsilyl, tertbutyldimethylsilyl, C$_1$-C$_6$-alkyl, C$_2$-C$_6$-alkenyl, C$_2$-C$_6$-alkinyl, C$_3$-C$_8$-cycloalkyl, wherein the four last mentioned aliphatic and cyclo-aliphatic radicals may be unsubstituted, partially or fully halogenated and/or oxygenated and/or may carry 1 or 2 radicals selected from C$_1$-C$_4$-alkoxy, phenyl, benzyl, pyridyl, phenoxy, wherein the four last mentioned radicals may be unsubstituted, partially or fully halogenated and/or carry 1, 2 or 3 substituents selected from C$_1$-C$_6$-alkyl, C$_1$-C$_6$-haloalkyl, C$_1$-C$_6$-alkoxy, C$_1$-C$_6$ haloalkoxy); and (C$_1$-C$_6$-alkoxy)carbonyl, or two R$^{18}$ present together on one atom of a partly saturated atom may form =O, =N(C$_1$-C$_6$-alkyl), =NO(C$_1$-C$_6$-alkyl), =CH(C$_1$-C$_4$-alkyl) or =C(C$_1$-C$_4$-alkyl)C$_1$-C$_4$-alkyl or, two R$^{18}$ on two adjacent carbon atoms may be together a C$_2$-C$_6$ alkylene chain, which form together with the carbon atom they are bonded to a 3-, 4-, 5-, 6- or 7-membered saturated, partly saturated or unsaturated aromatic, wherein the alkylene chain may contain 1 or 2 heteroatoms selected from the group consisting of oxygen, sulfur and nitrogen, and may optionally be substituted with halogen, C$_1$-C$_4$-haloalkyl, C$_1$-C$_4$-alkoxy or C$_1$-C$_4$-haloalkoxy, and wherein the nitrogen and/or the sulfur atom(s) of the heterocyclic ring may optionally be oxidized;

n is 0, 1 or 2;

k is an integer selected from 0 to 10;

and wherein when Y is N—R$^8$ or a chemical bond;

R$^2$ and R$^3$ are selected independent of each other from the group consisting of hydrogen, cyano, C$_1$-C$_6$-alkyl, C$_3$-C$_8$-cycloalkyl, C$_2$-C$_6$-alkenyl, C$_2$-C$_6$-alkinyl, wherein the carbon atoms of the aforementioned aliphatic and cyclo-aliphatic radicals may optionally be substituted with one or more R$^6$, which are independently selected from one another, NR$^{9a}$R$^{9b}$, S(O)$_n$R$^7$, C(=O)R$^6$, C(=O)NR$^{9a}$R$^{9b}$, C(=O)OR$^7$, C(=S)R$^6$, C(=O)NR$^{9a}$R$^{9b}$, C(=S)SR$^7$, C(=NR$^{9a}$)R$^6$, phenyl, optionally substituted with one or more substituents from R$^{10}$, which are selected independently from one another, and a 5- or 6-membered saturated, partly saturated or unsaturated aromatic heterocyclic ring comprising 1, 2 or 3 heteroatoms selected from the group consisting of oxygen, nitrogen and sulfur, optionally substituted with k substituents R$^{10}$, independently selected from one another, and wherein the nitrogen and/or the sulfur atom(s) of the heterocyclic ring may optionally be oxidized; or R² and R³ may be together a C₄- or C₅-alkylene chain, forming a 5- to 6-membered saturated, partly saturated or unsaturated aromatic heterocyclic ring together with the nitrogen atom they are bond to, wherein the alkylene chain may further contain 1 oxygen atom, sulfur atom or nitrogen atom, and wherein the alkylene chain may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, or a 5 or 6-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

and wherein when Y is O;

R² and R³ are selected independent of each other from the group consisting of cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $NR^{9a}R^{9b}$, $S(O)_nR^7$, $C(=O)R^6$, $C(=O)NR^{9a}R^{9b}$, $C(=O)OR^7$, $C(=S)R^6$, $C(=O)NR^{9a}R^{9b}$, $C(=S)SR^7$, $C(=NR^{9a})R^6$, phenyl, optionally substituted with one or more substituents from $R^{10}$, which are selected independently from one another, and a 5- or 6-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized; or R² and R³ may be together a C₄- or C₅-alkylene chain, forming a 5- to 6-membered saturated, partly saturated or unsaturated aromatic heterocyclic ring together with the nitrogen atom they are bond to, wherein the alkylene chain may further contain 1 oxygen atom, sulfur atom or nitrogen atom, and wherein the alkylene chain may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, or a 5 or 6-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

or an enantiomer, diastereomer, or a salt thereof.

2. The compound of claim 1, wherein $R^1$ is selected from the group consisting of hydrogen, cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $-S(O)_nR^7$, $-S(O)_nNR^{9a}R^{9b}$, $C(=O)R^6$, $C(=O)NR^{9a}R^{9b}$, $C(=O)OR^7$, $-C(=S)R^6$, $C(=S)NR^{9a}R^{9b}$, $C(=S)OR^7$, $-C(=S)SR^7$, phenyl, optionally substituted with one or more substituents $R^{10}$, which are independently selected from one another, and a 5- or 6-membered saturated, partly saturated or unsaturated aromatic heterocyclic ring, comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^{4a}$, $R^{4b}$ are selected independently from one another from the group consisting of hydrogen, halogen, cyano, nitro, SCN, $C_1$-$C_6$-alkyl, $C_3$-$C_8$-cycloalkyl, wherein the carbon atoms of the of the last two aliphatic and cyclo-aliphatic radicals may optionally be substituted with one or more $R^6$, which are independently selected from one another, $OR^7$, $-OS(O)_nR^7$, $S(O)nR^7$, $NR^{9a}R^{9b}$, $N(R^{9a})C(=O)R^6$, $C(=O)R^6$, $-C(=O)OR^7$, $C(=NR^{9a})R^6$, and $C(=S)R^6$, $R^{5a}$, $R^{5c}$ are selected independently from one another from the group consisting of hydrogen, halogen, cyano, $OR^7$, $C_1$-$C_6$-alkyl, and $C_3$-$C_8$-cycloalkyl, wherein the carbon atoms of the two last aliphatic and cyclo-aliphatic radicals may optionally be substituted with one or more $R^6$, selected independently from one another; and $R^{5b}$ is selected from the group consisting of hydrogen, halogen, cyano, $C_1$-$C_6$-alkyl, $C_1$-$C_6$-alkyl, $C_3$-$C_8$-cycloalkyl, wherein the five last aliphatic and cyclo-aliphatic radicals may optionally be substituted with one or more $R^{15}$, selected independently from one another, from the group consisting of $Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^9)R^6$, and $C(=S)R^6$.

3. The compound of claim 1, wherein

Y is oxygen.

4. The compound of claim 1, wherein

Y is a chemical bond.

5. The compound of claim 1, wherein

Y is $NR^8$.

6. The compound of claim 1, wherein the compound is an enantiomer of formula (I-5-S)

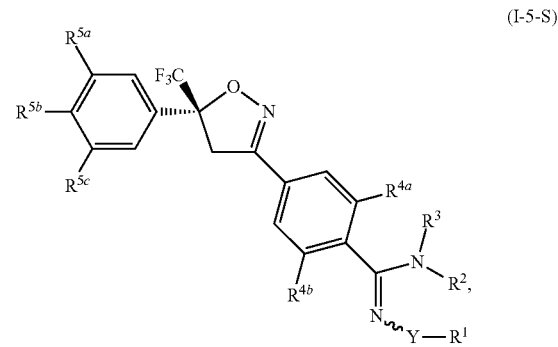

(I-5-S)

having the S-configuration.

7. The compound of claim 1, wherein
the compound is an enantiomer of formula (I-5-R)

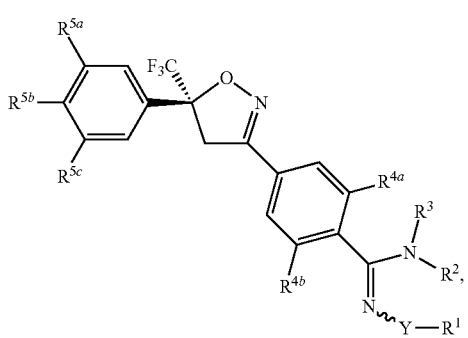

(I-5-R)

having the R-configuration.

8. The compound of claim 1, wherein
$R^2$, $R^3$ are selected independent of each other from the group consisting of hydrogen, cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $NR^{9a}R^{9b}$, $S(O)_nR^7$, $C(=O)R^6$, $C(=O)NR^{9a}R^{9b}$, $C(=O)OR^7$, $C(=S)R^6$, $C(=O)NR^{9a}R^{9b}$, $C(=S)SR^7$, $C(=NR^{9a})R^6$, phenyl, optionally substituted with one or more substituents from $R^{10}$, which are selected independently from one another, and a 5- or 6-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized.

9. The compound of claim 1, wherein
$R^2$ and $R^3$ together form a $C_4$- or $C_5$-alkylene chain, forming a 5- to 6-membered saturated, partly saturated or unsaturated aromatic heterocyclic ring together with the nitrogen atom they are bond to, wherein the alkylene chain may further contain 1 oxygen atom, sulfur atom or nitrogen atom, and wherein the alkylene chain may optionally be substituted with
halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, phenyl, optionally be substituted with one or more substituents $R^{10}$ which are selected independently from one another, or a 5 or 6-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized.

10. An agricultural composition comprising at least one compound of claim 1, or an agriculturally acceptable salt thereof, and at least one inert liquid and/or solid agriculturally acceptable carrier.

11. A veterinary composition comprising at least one compound of claim 1, or a veterinarily acceptable salt thereof, and at least one inert liquid and/or solid veterinarily acceptable carrier.

12. A method for controlling invertebrate pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from invertebrate pest attack or infestation with a pesticidally effective amount of at least one compound of claim 1, an enantiomer, diastereoisomer and/or an agriculturally acceptable salt thereof.

13. The method of claim 12, wherein
$R^1$ is selected from the group consisting of hydrogen, cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $-S(O)_nR^7$, $-S(O)_nNR^{9a}R^{9b}$, $C(=O)R^6$, $C(=O)NR^{9a}R^{9b}$, $C(=O)OR^7$, $-C(=S)R^6$, $C(=S)NR^{9a}R^{9b}$, $C(=S)OR^7$, $-C(=S)SR^7$, phenyl, optionally substituted with one or more substituents $R^{10}$, which are independently selected from one another, and a 5- or 6-membered saturated, partly saturated or unsaturated aromatic heterocyclic ring, comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^{4a}$, $R^{4b}$ are selected independently from one another from the group consisting of hydrogen, halogen, cyano, nitro, SCN, $C_1$-$C_6$-alkyl, $C_3$-$C_8$-cycloalkyl, wherein the carbon atoms of the of the last two aliphatic and cyclo-aliphatic radicals may optionally be substituted with one or more $R^6$, which are independently selected from one another, $OR^7$, $-OS(O)_nR^7$, $S(O)nR^7$, $NR^{9a}R^{9b}$, $N(R^{9a})C(=O)R^6$, $C(=O)R^6$, $-C(=O)OR^7$, $C(=NR^{9a})R^6$, and $C(=S)R^6$, $R^{5a}$, $R^{5c}$ are selected independently from one another from the group consisting of hydrogen, halogen, cyano, $OR^7$, $C_1$-$C_6$-alkyl, and $C_3$-$C_8$-cycloalkyl, wherein the carbon atoms of the two last aliphatic and cyclo-aliphatic radicals may optionally be substituted with one or more $R^6$, selected independently from one another; and $R^{5b}$ is selected from the group consisting of hydrogen, halogen, cyano, $C_1$-$C_6$-alkyl, $C_1$-$C_6$-alkyl, $C_3$-$C_8$-cycloalkyl, wherein the five last aliphatic and cyclo-aliphatic radicals may optionally be substituted with one or more $R^{15}$, selected independently from one another, from the group consisting of $Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^9)R^6$, and $C(=S)R^6$.

14. The method of claim 12, wherein Y is oxygen.

15. The method of claim 12, wherein Y is a chemical bond.

16. The method of claim 12, wherein Y is $NR^8$.

17. The method of claim 12, wherein the compound is an enantiomer of formula (I-5-S)

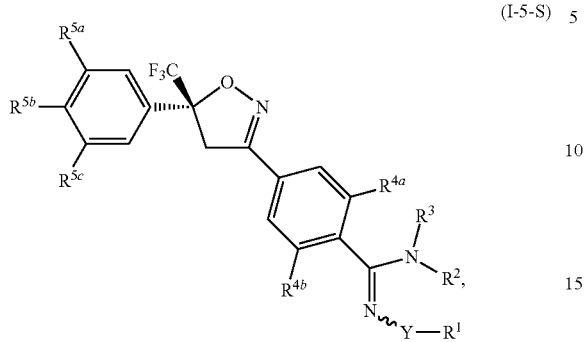

(I-5-S)

having the S-configuration.

18. The method according claim 17, wherein the plant propagation material is seeds.

19. The method of claim 12, wherein the compound is an enantiomer of formula (I-5-R)

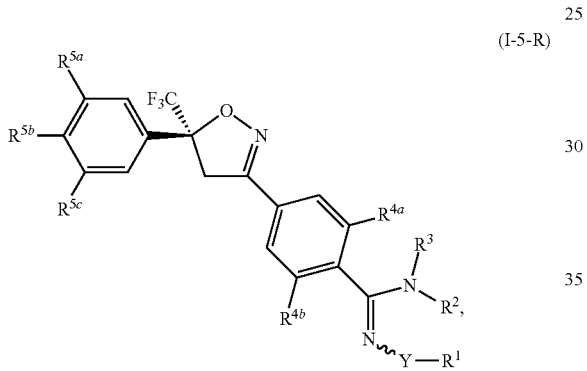

(I-5-R)

having the R-configuration.

20. The method of claim 12, wherein
$R^2$, $R^3$ are selected independent of each other from the group consisting of hydrogen, cyano, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another,
$NR^{9a}R^{9b}$, $S(O)_nR^7$, $C(=O)R^6$, $C(=O)NR^{9a}R^{9b}$, $C(=O)OR^7$, $C(=S)R^6$, $C(=O)NR^{9a}R^{9b}$, $C(=S)SR^7$, $C(=NR^{9a})R^6$,
phenyl, optionally substituted with one or more substituents from $R^{10}$, which are selected independently from one another, and a 5- or 6-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized.

21. The method of claim 12, wherein
$R^2$ and $R^3$ together form a $C_4$- or $C_5$-alkylene chain, forming a 5- to 6-membered saturated, partly saturated or unsaturated aromatic heterocyclic ring together with the nitrogen atom they are bond to,
wherein the alkylene chain may further contain 1 oxygen atom, sulfur atom or nitrogen atom, and wherein the alkylene chain may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl,
phenyl, optionally be substituted with one or more substituents $R^{10}$ which are selected independently from one another,
or a 5 or 6-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized.

22. A method for protecting crops or plants from attack or infestation by invertebrate pests, which method comprises treating the crops or plants with a pesticidally effective amount of at least one compound of claim 1, an enantiomer, diastereoisomer and/or an agriculturally acceptable salt thereof.

23. A method for protecting plant propagation material and/or the plants which grow therefrom from attack or infestation by invertebrate pests, which method comprises treating the plant propagation material with a pesticidally effective amount of at least one compound of claim 1, an enantiomer, diastereoisomer and/or an agriculturally acceptable salt thereof.

24. Plant propagation material treated with a composition comprising at least one compound of claim 1, an enantiomer, diastereoisomer and/or an agriculturally acceptable salt thereof.

25. The plant propagation material according to claim 24, wherein the plant propagation material are seeds.

26. A method for treating or protecting an animal from infestation or infection by invertebrate pests which comprises bringing the animal in contact with a pesticidally effective amount of at least one compound of the formula I-5 as defined in claim 1, an enantiomer, diastereoisomer and/or a veterinarily acceptable salt thereof.

* * * * *